United States Patent
Saphier et al.

(10) Patent No.: US 12,082,904 B2
(45) Date of Patent: Sep. 10, 2024

(54) AUTOMATIC GENERATION OF MULTI-RESOLUTION 3D MODEL INCLUDING RESTORATIVE OBJECT

(71) Applicant: Align Technology, Inc., San Jose, CA (US)

(72) Inventors: Ofer Saphier, Rechovot (IL); Pavel Agniashvili, Moscow (RU); Moti Ben-Dov, Tel Mond (IL); Ran Katz, Hod Hasharon (IL); Avi Kopelman, Palo Alto, CA (US); Maxim Volgin, Moscow (RU); Doron Malka, Tel Aviv (IL); Avraham Zulti, Modiin (IL); Pavel Veryovkin, Krasnogorsk (RU); Maayan Moshe, Ramat Hasharon (IL); Ido Tishel, Kfar Bilu (IL); Adi Levin, Nes Tziona (IL); Shai Farkash, Hod Hasharon (IL); Inna Karapetyan, Modiin (IL); Dina Bova, Shaar Efraim (IL); Edi Fridman, Rishon le Zion (IL); Jonathan Coslovsky, Rehovot (IL)

(73) Assignee: Align Technology, Inc., San Jose, CA (US)

( * ) Notice: Subject to any disclaimer, the term of this patent is extended or adjusted under 35 U.S.C. 154(b) by 429 days.

(21) Appl. No.: 17/390,856

(22) Filed: Jul. 30, 2021

(65) Prior Publication Data
US 2021/0353153 A1 Nov. 18, 2021

Related U.S. Application Data

(63) Continuation of application No. 17/230,825, filed on Apr. 14, 2021.

(Continued)

(51) Int. Cl.
*A61B 5/00* (2006.01)
*G06T 17/20* (2006.01)
(Continued)

(52) U.S. Cl.
CPC ............ *A61B 5/004* (2013.01); *A61B 5/0033* (2013.01); *A61B 5/0088* (2013.01);
(Continued)

(58) Field of Classification Search
None
See application file for complete search history.

(56) References Cited

U.S. PATENT DOCUMENTS

| 6,099,314 A | 8/2000 | Kopelman et al. |
| 6,334,772 B1 | 1/2002 | Taub et al. |

(Continued)

FOREIGN PATENT DOCUMENTS

WO    2018022752 A1    2/2018

OTHER PUBLICATIONS

Isola P., et al., "Image-to-image Translation With Conditional Adversarial Networks", Nov. 26, 2018, 17 pages.

*Primary Examiner* — Rinna Yi
(74) *Attorney, Agent, or Firm* — Lowenstein Sandler LLP

(57) ABSTRACT

A processing device receives a plurality of intraoral scans of a dental arch. The processing device determines, from the plurality of intraoral scans, a first set of intraoral scans that depict a restorative object and a second set of intraoral scans that fail to depict any restorative object. The processing device generates a multi-resolution three-dimensional model of the dental arch, wherein a first portion of the multi-resolution three-dimensional model is generated from the first set of intraoral scans, has a first resolution and represents the restorative object, and wherein a second portion of the multi-resolution three-dimensional model is generated (Continued)

from the second set of intraoral scans, has a second resolution and represents a remainder of the dental arch, wherein the first resolution is greater than the second resolution.

22 Claims, 48 Drawing Sheets

Related U.S. Application Data

(60) Provisional application No. 63/010,667, filed on Apr. 15, 2020.

(51) Int. Cl.
  *G06V 10/764* (2022.01)
  *G06V 10/82* (2022.01)
  *G06V 20/64* (2022.01)

(52) U.S. Cl.
  CPC .......... *A61B 5/7267* (2013.01); *A61B 5/7475* (2013.01); *G06T 17/20* (2013.01); *G06V 10/764* (2022.01); *G06V 10/82* (2022.01); *G06V 20/64* (2022.01); *G06T 2210/41* (2013.01)

(56) References Cited

U.S. PATENT DOCUMENTS

| | | | |
|---|---|---|---|
| 6,334,853 B1 | 1/2002 | Kopelman et al. | |
| 6,463,344 B1 | 10/2002 | Pavlovskaia et al. | |
| 6,540,512 B1 | 4/2003 | Sachdeva et al. | |
| 6,542,249 B1 | 4/2003 | Kofman et al. | |
| 6,633,789 B1 | 10/2003 | Nikolskiy et al. | |
| 6,664,986 B1 | 12/2003 | Kopelman et al. | |
| 6,697,164 B1 | 2/2004 | Babayoff et al. | |
| 6,845,175 B2 | 1/2005 | Kopelman et al. | |
| 6,979,196 B2 | 12/2005 | Nikolskiy et al. | |
| 7,030,383 B2 | 4/2006 | Babayoff et al. | |
| 7,202,466 B2 | 4/2007 | Babayoff et al. | |
| 7,255,558 B2 | 8/2007 | Babayoff et al. | |
| 7,286,954 B2 | 10/2007 | Kopelman et al. | |
| 7,319,529 B2 | 1/2008 | Babayoff | |
| 7,373,286 B2 | 5/2008 | Nikolskiy et al. | |
| 7,507,088 B2 | 3/2009 | Taub et al. | |
| 7,545,372 B2 | 6/2009 | Kopelman et al. | |
| 7,698,068 B2 | 4/2010 | Babayoff | |
| 7,916,911 B2 | 3/2011 | Kaza et al. | |
| 8,108,189 B2 | 1/2012 | Chelnokov et al. | |
| 8,244,028 B2 | 8/2012 | Kuo et al. | |
| 8,587,582 B2 | 11/2013 | Matov et al. | |
| 8,948,482 B2 | 2/2015 | Levin | |
| D742,518 S | 11/2015 | Barak et al. | |
| 9,192,305 B2 | 11/2015 | Levin | |
| 9,261,356 B2 | 2/2016 | Lampert et al. | |
| 9,261,358 B2 | 2/2016 | Atiya et al. | |
| 9,299,192 B2 | 3/2016 | Kopelman | |
| D760,901 S | 7/2016 | Barak et al. | |
| 9,393,087 B2 | 7/2016 | Moalem | |
| 9,408,679 B2 | 8/2016 | Kopelman | |
| 9,431,887 B2 | 8/2016 | Boltanski | |
| 9,439,568 B2 | 9/2016 | Atiya et al. | |
| 9,451,873 B1 | 9/2016 | Kopelman et al. | |
| D768,861 S | 10/2016 | Barak et al. | |
| D771,817 S | 11/2016 | Barak et al. | |
| 9,491,863 B2 | 11/2016 | Boltanski | |
| D774,193 S | 12/2016 | Makmel et al. | |
| 9,510,757 B2 | 12/2016 | Kopelman et al. | |
| 9,660,418 B2 | 5/2017 | Atiya et al. | |
| 9,668,829 B2 | 6/2017 | Kopelman | |
| 9,675,430 B2 | 6/2017 | Verker et al. | |
| 9,693,839 B2 | 7/2017 | Atiya et al. | |
| 9,717,402 B2 | 8/2017 | Lampert et al. | |
| 9,724,177 B2 | 8/2017 | Levin | |
| 9,844,426 B2 | 12/2017 | Atiya et al. | |
| 10,076,389 B2 | 9/2018 | Wu et al. | |
| 10,098,714 B2 | 10/2018 | Kuo | |
| 10,108,269 B2 | 10/2018 | Sabina et al. | |
| 10,111,581 B2 | 10/2018 | Makmel | |
| 10,111,714 B2 | 10/2018 | Kopelman et al. | |
| 10,123,706 B2 | 11/2018 | Elbaz et al. | |
| 10,136,972 B2 | 11/2018 | Sabina et al. | |
| 10,380,212 B2 | 8/2019 | Elbaz et al. | |
| 10,390,913 B2 | 8/2019 | Sabina et al. | |
| 10,453,269 B2 | 10/2019 | Furst | |
| 10,456,043 B2 | 10/2019 | Atiya et al. | |
| 10,499,793 B2 | 12/2019 | Ozerov et al. | |
| 10,504,386 B2 | 12/2019 | Levin et al. | |
| 10,507,087 B2 | 12/2019 | Elbaz et al. | |
| 10,517,482 B2 | 12/2019 | Sato et al. | |
| 10,695,150 B2 | 6/2020 | Kopelman et al. | |
| 10,708,574 B2 | 7/2020 | Furst et al. | |
| 10,772,506 B2 | 9/2020 | Atiya et al. | |
| 10,813,727 B2 | 10/2020 | Sabina et al. | |
| 10,888,399 B2 | 1/2021 | Kopelman et al. | |
| 10,952,816 B2 | 3/2021 | Kopelman | |
| 10,980,613 B2 | 4/2021 | Shanjani et al. | |
| 11,013,581 B2 | 5/2021 | Sabina et al. | |
| D925,739 S | 7/2021 | Shalev et al. | |
| 2010/0036682 A1 | 2/2010 | Trosien et al. | |
| 2010/0159412 A1 | 6/2010 | Moss et al. | |
| 2014/0172392 A1 | 6/2014 | Eldershaw et al. | |
| 2014/0227655 A1* | 8/2014 | Andreiko | G06T 3/14 433/29 |
| 2015/0320320 A1* | 11/2015 | Kopelman | G06T 7/579 433/215 |
| 2016/0256035 A1* | 9/2016 | Kopelman | A61B 1/00045 |
| 2018/0028294 A1 | 2/2018 | Azernikov et al. | |
| 2019/0015177 A1 | 1/2019 | Elazar et al. | |
| 2019/0029784 A1 | 1/2019 | Moalem et al. | |
| 2019/0102880 A1 | 4/2019 | Parpara et al. | |
| 2019/0175314 A1 | 6/2019 | Lagardere et al. | |
| 2019/0348181 A1 | 11/2019 | Jameel | |
| 2019/0388193 A1 | 12/2019 | Saphier et al. | |
| 2019/0388194 A1 | 12/2019 | Atiya et al. | |
| 2020/0066391 A1 | 2/2020 | Sachdeva et al. | |
| 2020/0143541 A1 | 5/2020 | Wang et al. | |
| 2020/0281689 A1 | 9/2020 | Yancey et al. | |
| 2020/0281700 A1 | 9/2020 | Kopelman et al. | |
| 2020/0281702 A1 | 9/2020 | Kopelman et al. | |
| 2020/0315434 A1 | 10/2020 | Kopelman et al. | |
| 2020/0349698 A1 | 11/2020 | Minchenkov et al. | |
| 2020/0349705 A1 | 11/2020 | Minchenkov et al. | |
| 2020/0372705 A1 | 11/2020 | Hershkovich et al. | |
| 2020/0383752 A1 | 12/2020 | Willers et al. | |
| 2020/0404243 A1 | 12/2020 | Saphier et al. | |
| 2021/0030503 A1 | 2/2021 | Shalev et al. | |
| 2021/0059796 A1 | 3/2021 | Weiss et al. | |
| 2021/0068773 A1 | 3/2021 | Moshe et al. | |
| 2021/0121049 A1 | 4/2021 | Rudnitsky et al. | |
| 2021/0128281 A1 | 5/2021 | Peleg | |
| 2021/0137653 A1 | 5/2021 | Saphier et al. | |
| 2021/0196152 A1 | 7/2021 | Saphier et al. | |
| 2021/0353152 A1 | 11/2021 | Saphier et al. | |
| 2022/0117480 A1 | 4/2022 | Kaji et al. | |

* cited by examiner

402

404

406

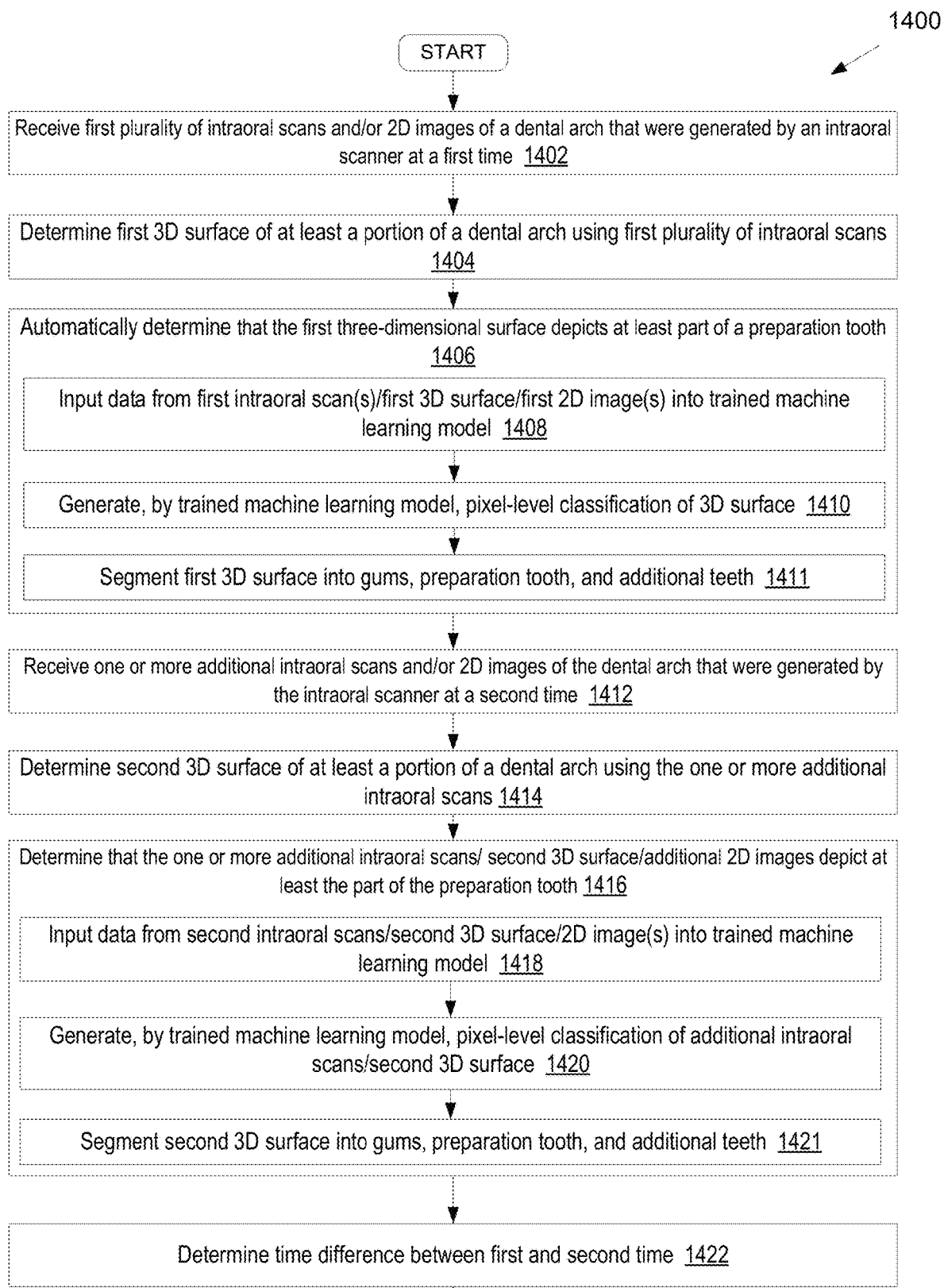

AUTOMATIC GENERATION OF MULTI-RESOLUTION 3D MODEL INCLUDING RESTORATIVE OBJECT

RELATED APPLICATIONS

This patent application is a continuation of U.S. patent application Ser. No. 17/230,825 filed Apr. 14, 2021, which claims the benefit under 35 U.S.C. § 119(e) of U.S. Provisional Application No. 63/010,667, filed Apr. 15, 2020, both of which are incorporated by reference herein.

TECHNICAL FIELD

Embodiments of the present disclosure relate to the field of dentistry and, in particular, to the use of machine learning and/or other techniques to automate the process of performing intraoral scans.

BACKGROUND

For restorative dental work, one or more intraoral scans may be generated of a preparation tooth and/or surrounding teeth on a patient's dental arch using an intraoral scanner. These intraoral scans are then used to generate a virtual three-dimensional (3D) model of a dental site including the preparation tooth and the surrounding teeth. For example, a virtual 3D model of a patient's dental arch may be generated. The virtual 3D model may then be sent to a lab. Similarly, for orthodontic dental work intraoral scans are generated of one or more dental arch, which are used to generate a virtual 3D model of the one or more dental arch and to generate a treatment plan.

The intraoral scanning process involves significant user input, in which a user of an intraoral scanner manually inputs patient information, manually selects a patient to be scanned, manually selects a segment of a dental arch to be scanned, manually indicates whether a scan was successful, manually inputs instructions to transition between stages or modes of intraoral scanning, manually selects prescription details, manually selects a lab to send data to, and so on. Before, during and after intraoral scanning, the user needs to operate different selections and buttons on a screen and on an intraoral scanner. For example, before scanning, a user needs to fill in various prescription (Rx) selections. During scanning, the user needs to press a button to start and stop scanning, the user needs to mark regions that need rescanning in restorative treatment, and the user needs to press a button to begin post processing when scanning has ended.

SUMMARY

In a first aspect of the disclosure, a method comprises: receiving a first one or more intraoral scans of a patient's oral cavity; automatically determining, based on processing of the first one or more intraoral scans, a first scanning role associated with the first one or more intraoral scans, wherein the first scanning role is a first one of an upper dental arch role, a lower dental arch role or a bite role; and determining a first three-dimensional surface associated with the first scanning role.

A second aspect of the disclosure may further extend the first aspect of the disclosure. In the second aspect of the disclosure, the method further comprises: receiving a second one or more intraoral scans of the patient's oral cavity without receiving an indication that the second one or more intraoral scans are associated with a second scanning role; automatically determining, based on processing of the second one or more intraoral scans, a second scanning role associated with the second one or more intraoral scans, wherein the second scanning role is a second one of the upper dental arch role, the lower dental arch role or the bite role; and determining a second three-dimensional surface associated with the second scanning role.

A third aspect of the disclosure may further extend the first aspect of the disclosure or the second aspect of the disclosure. In the third aspect of the disclosure, processing the first scanning role comprises inputting the first one or more intraoral scans into a machine learning model that has been trained to classify intraoral scans as being associated with an upper dental arch role, a lower dental arch role, or a bite role, wherein the machine learning model outputs the first scanning role.

In a fourth aspect of the disclosure, a method comprises: receiving a first one or more intraoral scans of a patient's oral cavity; determining that the first one or more intraoral scans depict a first dental arch of a patient; determining a first identity of the first dental arch of the patient; and determining a first three-dimensional surface of the first dental arch using the first one or more intraoral scans.

A fifth aspect of the disclosure may further extend the fourth aspect of the disclosure. In the fifth aspect of the disclosure, the method further comprises: receiving a user input indicating that the first one or more intraoral scans depict a second dental arch of the patient, the second dental arch having a second identity; determining that the user input is incorrect; and outputting a notification that the first one or more intraoral scans depict the first dental arch having the first identity rather than the second dental arch having the second identity.

A sixth aspect of the disclosure may further extend the fourth or fifth aspect of the disclosure. In the sixth aspect of the disclosure, the method further comprises: determining that the first three-dimensional surface of the first dental arch is complete; and automatically generating a first three-dimensional model of the first dental arch responsive to determining that the first dental arch is complete.

A seventh aspect of the disclosure may further extend the fourth through sixth aspects of the disclosure. In the seventh aspect of the disclosure, the first one or more intraoral scans of the patient's oral cavity are received without first receiving an indication of the identity of the first dental arch or an indication that a new dental arch is being scanned.

An eighth aspect of the disclosure may further extend the fourth through seventh aspects of the disclosure. In the eighth aspect of the disclosure, determining that the first one or more intraoral scans depict the first dental arch of the patient and determining the first identity of the first dental arch of the patient comprises: inputting the first one or more intraoral scans into a machine learning model that has been trained to classify intraoral scans as depicting an upper dental arch, a lower dental arch, or a bite, wherein the machine learning model outputs a first classification indicating the first identity of the first dental arch.

A ninth aspect of the disclosure may further extend the eighth aspect of the disclosure. In the ninth aspect of the disclosure, the first one or more intraoral scans comprises a plurality of intraoral scans, and determining that the first one or more intraoral scans depict the first dental arch of the patient and determining the first identity of the first dental arch of the patient comprises: inputting each intraoral scan of the plurality of intraoral scans into the machine learning model, wherein the machine learning model outputs a plurality of classifications, each of the plurality of classifications being associated with one of the plurality of intraoral scans; and determining that a majority of the classifications output by the machine learning model indicate the first identity of the first dental arch.

A $10^{th}$ aspect of the disclosure may further extend the ninth aspect of the disclosure. In the $10^{th}$ aspect of the disclosure, for at least one of the first three-dimensional surface or an intraoral scan of the first one or more intraoral scans: a lower dental arch is detected if at least a first threshold number of points in the first three-dimensional surface or the intraoral scan depict a tongue; an upper dental arch is detected if at least a second threshold number of points in the first three-dimensional surface or the intraoral scan depict an upper palate; and a bite is detected if at least a third threshold number of points in the first three-dimensional surface or the intraoral scan depict teeth from the lower dental arch and at least the third threshold number of points in the first three-dimensional surface or the intraoral scan depict the upper arch.

An $11^{th}$ aspect of the disclosure may further extend the ninth aspect or $10^{th}$ aspect of the disclosure. In the $11^{th}$ aspect of the disclosure, the first one or more intraoral scans comprises a plurality of intraoral scans, and wherein determining that the first one or more intraoral scans depict the first dental arch of the patient and determining the first identity of the first dental arch of the patient comprises: inputting each intraoral scan of the plurality of intraoral scans into the machine learning model, wherein the machine learning model outputs a plurality of classifications, each of the plurality of classifications being associated with one of the plurality of intraoral scans; and determining a moving average of the plurality of classifications output by the machine learning model, wherein the moving average indicates the first identity of the first dental arch.

A $12^{th}$ aspect of the disclosure may further extend the ninth through $11^{th}$ aspects of the disclosure. In the $12^{th}$ aspect of the disclosure, the first one or more intraoral scans comprise a plurality of intraoral scans received in sequential order, wherein the first one or more intraoral scans are input into the machine learning model in the sequential order, and wherein the machine learning model is a recurrent neural network.

A $13^{th}$ aspect of the disclosure may further extend the ninth through $12^{th}$ aspects of the disclosure. In the $13^{th}$ aspect of the disclosure, for each of the first one or more intraoral scans the machine learning model outputs a confidence value, the method further comprising: for each of the first one or more intraoral scans, determining whether the confidence value associated with an output of the machine learning model for that intraoral scan is below a confidence threshold; and discarding those outputs of the machine learning model having confidence values below the confidence threshold.

A $14^{th}$ aspect of the disclosure may further extend the ninth through $13^{th}$ aspects of the disclosure. In the $14^{th}$ aspect of the disclosure, the first one or more intraoral scans are input into the machine learning model as the first one or more intraoral scans are received and before intraoral scanning of the first dental arch is complete, the method further comprising: generating a height map of the first dental arch by projecting at least a portion of the first three-dimensional surface of the first dental arch onto a plane; and processing data from the height map using the machine learning model or an alternate machine learning model that has been trained to classify height maps as depicting an upper dental arch, a lower dental arch, or a bite, wherein the machine learning model or the alternate machine learning model outputs a second classification indicating the first identity of the first dental arch with a higher level of accuracy as compared to the first classification.

A $15^{th}$ aspect of the disclosure may further extend the fourth through $14^{th}$ aspects of the disclosure. In the $15^{th}$ aspect of the disclosure, the method further comprises: receiving a second intraoral scan that depicts a first bite relation between an upper dental arch and a lower dental arch, the second intraoral scan having been generated at a first time; receiving a third intraoral scan that depicts a second bite relation between the upper dental arch and the lower dental arch, the third intraoral scan having been generated at a second time; determining a first difference between the first bite relation and the second bite relation; determining a second difference between the first time and the second time; and determining, based at least in part on the first difference and the second difference, whether the second intraoral scan and the third intraoral scan depict a same bite of the patient or a different bite of the patient.

A $16^{th}$ aspect of the disclosure may further extend the fourth through $15^{th}$ aspects of the disclosure. In the $16^{th}$ aspect of the disclosure, determining that the first one or more intraoral scans depict the first dental arch of the patient and determining the first identity of the first dental arch of the patient comprises: determining whether at least one of the first three-dimensional surface or some of the first one or more intraoral scans include a representation of a tongue or an upper palette; and determining that the first identity of the first dental arch of the patient is for a lower jaw responsive to determining that at least one of the first three-dimensional surface or some of the one or more intraoral scans include a representation of a tongue; or determining that the first identity of the first dental arch of the patient is for an upper jaw responsive to determining that at least one of the first three-dimensional surface or some of the first one or more intraoral scans include a representation of an upper palette.

A $17^{th}$ aspect of the disclosure may further extend the fourth through $16^{th}$ aspects of the disclosure. In the $17^{th}$ aspect of the disclosure, determining that the first one or more intraoral scans depict the first dental arch of the patient and determining the first identity of the first dental arch of the patient comprises: determining whether at least one of the first one or more intraoral scans was generated before an intraoral scanner was inserted into the patient's oral cavity depicts a nose or a chin; and determining that the first identity of the first dental arch of the patient is for a lower dental arch responsive to determining that at least one of the first one or more intraoral scans include a representation of a chin; or determining that the first identity of the first dental arch of the patient is for an upper dental arch responsive to determining that at least one of the first one or more intraoral scans include a representation of a nose.

An $18^{th}$ aspect of the disclosure may further extend the $17^{th}$ aspect of the disclosure. In the $18^{th}$ aspect of the disclosure, the method further comprises: detecting, based on data from an inertial measurement unit of an intraoral scanner that generated the first one or more intraoral scans, that the intraoral scanner was rotated about a longitudinal axis of the intraoral scanner after the first one or more intraoral scans were generated; receiving a second one or more intraoral scans of the patient's oral cavity after the intraoral scanner was rotated about the longitudinal axis; determining that the second one or more intraoral scans depict the lower dental arch if the first identity of the first dental arch is the upper dental arch; and determining that the second one or more intraoral scans depict the upper dental arch if the first identity of the first dental arch is the lower dental arch.

A 19th aspect of the disclosure may further extend the fourth through 18th aspects of the disclosure. In the 19th aspect of the disclosure, determining that the first one or more intraoral scans depict the first dental arch of the patient and determining the first identity of the first dental arch of the patient comprises: generating an image of the first dental arch, the image comprising a height map; and processing data from the image using a machine learning model that has been trained to classify images of dental arches as depicting an upper dental arch, a lower dental arch, or a bite, wherein the machine learning model outputs a classification indicating the first identity of the first dental arch.

A 20th aspect of the disclosure may further extend the 19th aspect of the disclosure. In the 20th aspect of the disclosure, the first three-dimensional surface is generated prior to determining the first identity of the first dental arch, and wherein the image of the first dental arch is generated by projecting at least a portion of the first three-dimensional surface of the first dental arch onto a two-dimensional surface.

A 21st aspect of the disclosure may further extend the fourth through 20th aspects of the disclosure. In the 21st aspect of the disclosure, the method further comprises: labeling the first one or more intraoral scans as belonging to a first segment of the first dental arch; receiving a second one or more intraoral scans of the patient's oral cavity; determining that the second one or more intraoral scans depict the first dental arch of the patient having the first identity; and labeling the second one or more intraoral scans as belonging to a second segment of the first dental arch.

A 22nd aspect of the disclosure may further extend the fourth through 21st aspects of the disclosure. In the 22nd aspect of the disclosure, the method further comprises: determining whether the first one or more intraoral scans depict a lingual view, a buccal view or an occlusal view of the first dental arch.

A 23rd aspect of the disclosure may further extend the first through 22nd aspects of the disclosure. In the 23rd aspect of the disclosure, a computer readable medium comprising instructions that, when executed by a processing device, cause the processing device to perform the method of any of the first through 22nd aspects of the disclosure.

A 24th aspect of the disclosure may further extend the first through 22nd aspects of the disclosure. In the 24th aspect of the disclosure, a system comprises: an intraoral scanner to generate the one or more intraoral scans; and a computing device connected to the intraoral scan via a wired or wireless connection, the computing device to perform the method of any of the first through 22nd aspects of the disclosure.

In a 25th aspect of the disclosure, a method comprises: receiving a first one or more intraoral scans of a patient's oral cavity; processing the first one or more intraoral scans; determining, based on the processing of the first one or more intraoral scans, a first one of an upper dental arch or a lower dental arch that is depicted in the first one or more intraoral scans; automatically generating a first three-dimensional surface of the first one of the upper dental arch or the lower dental arch using the first one or more intraoral scans; receiving a second one or more intraoral scans of the patient's oral cavity; processing the second one or more intraoral scans; determining, based on the processing of the second one or more intraoral scans, a second one of the upper dental arch or the lower dental arch that is depicted in the second one or more intraoral scans; and automatically generating a second three-dimensional surface of the second one of the upper dental arch or the lower dental arch using the second one or more intraoral scans.

A 26th aspect of the disclosure may further extend the 25th aspect of the disclosure. In the 26th aspect of the disclosure, the method further comprises: receiving a third one or more intraoral scans of the patient's oral cavity; processing the third one or more intraoral scans; and determining, based on the processing of the third one or more intraoral scans, that a patient bite is depicted in the third one or more intraoral scans.

A 27th aspect of the disclosure may further extend the 25th or 26th aspect of the disclosure. In the 27th aspect of the disclosure, the first three-dimensional surface is generated as the first one or more intraoral scans are received, the method further comprising: automatically determining that a user has transitioned from scanning of the first one of the upper dental arch or the lower dental arch to scanning of the second one of the upper dental arch or the lower dental arch; and switching from generation of the first three-dimensional surface to generation of the second three-dimensional surface responsive to determining that the second one or more intraoral scans depict the second one of the upper dental arch or the lower dental arch.

A 28th aspect of the disclosure may further extend the 25th through 27th aspects of the disclosure. In the 28th aspect of the disclosure, a computer readable medium comprises instructions that, when executed by a processing device, cause the processing device to perform the method of any of the 25th through 27th aspects of the disclosure.

A 29th aspect of the disclosure may further extend the 25th through 27th aspects of the disclosure. In the 29th aspect of the disclosure, a system comprises: an intraoral scanner to generate the first one or more intraoral scans and the second one or more intraoral scans; and a computing device connected to the intraoral scan via a wired or wireless connection, the computing device to perform the method of any of the 25th through 27th aspects of the disclosure.

In a 30th aspect of the disclosure, a method comprises: receiving a first plurality of intraoral scans of a dental arch; automatically determining, based on processing of the first plurality of intraoral scans, that the first plurality of intraoral scans depict a restorative dental object; determining a first resolution to use for a first portion of a three-dimensional model of the dental arch that is to be generated from the first plurality of intraoral scans; receiving a second plurality of intraoral scans of the dental arch; automatically determining, based on processing of the second plurality of intraoral scans, that the second plurality of intraoral scans fail to depict a restorative dental object; determining a second resolution to use for a second portion of the three-dimensional model of the dental arch that is to be generated from the second plurality of intraoral scans; and generating the three-dimensional model of the dental arch having the first portion and the second portion, wherein the first portion comprises a depiction of the restorative dental object and is generated from the first plurality of intraoral scans and has the first resolution, and wherein the second portion is generated from the second plurality of intraoral scans and has the second resolution, wherein the first resolution is greater than the second resolution.

A 31st aspect of the disclosure may further extend the 30th aspect of the disclosure. In the 31st aspect of the disclosure, the three-dimensional model comprises a single variable resolution three-dimensional surface, wherein the first portion of the single variable resolution three-dimensional surface has the first resolution and the second portion of the variable resolution three-dimensional surface has the second resolution.

A 32$^{nd}$ aspect of the disclosure may further extend the 30$^{th}$ or 31$^{st}$ aspect of the disclosure. In the 32$^{nd}$ aspect of the disclosure, the method further comprises: receiving the first plurality of intraoral scans and the second plurality of intraoral scans based on an uninterrupted continuous scan of the dental arch, wherein no user input is received that indicates a transition from scanning of the dental arch to scanning of the restorative dental object or that indicates a transition from scanning of the restorative dental object to scanning of the dental arch.

A 33$^{rd}$ aspect of the disclosure may further extend the 30$^{th}$ through 32$^{nd}$ aspects of the disclosure. In the 33$^{rd}$ aspect of the disclosure, automatically determining, based on processing of the first plurality of intraoral scans, that the first plurality of intraoral scans depict a restorative dental object comprises: processing data from the first plurality of intraoral scans using a trained machine learning model that has been trained to identify restorative dental objects, wherein for each intraoral scan the trained machine learning model generates an output classifying the intraoral scan as containing a restorative dental object or as not containing a restorative dental object.

A 34$^{th}$ aspect of the disclosure may further extend the 30$^{th}$ through 33$^{rd}$ aspects of the disclosure. In the 34$^{th}$ aspect of the disclosure, for each intraoral scan the trained machine learning model outputs a map comprising, for each pixel in the intraoral scan, an indication as to whether or not that pixel depicts a restorative dental object.

A 35$^{th}$ aspect of the disclosure may further extend the 30$^{th}$ through 34$^{th}$ aspects of the disclosure. In the 35$^{th}$ aspect of the disclosure, the method further comprises: determining a first region of the second portion that depicts a tooth to gum boundary or a tooth to tooth boundary; determining a second region of the second portion that fails to depict the tooth to gum boundary or the tooth to tooth boundary; and updating the three-dimensional model to cause the second portion of the second region to have a third resolution that is lower than the second resolution.

A 36$^{th}$ aspect of the disclosure may further extend the 30$^{th}$ through 35$^{th}$ aspects of the disclosure. In the 35$^{th}$ aspect of the disclosure, the method further comprises: automatically determining, based on the processing of the first plurality of intraoral scans, whether the first plurality of intraoral scans depict an upper dental arch, a lower dental arch or a bite; and automatically determining, based on the processing of the second plurality of intraoral scans, whether the second plurality of intraoral scans depict the upper dental arch, the lower dental arch, or the bite.

A 37$^{th}$ aspect of the disclosure may further extend the 30$^{th}$ through 36$^{th}$ aspects of the disclosure. In the 37$^{th}$ aspect of the disclosure, a computer readable medium comprises instructions that, when executed by a processing device, cause the processing device to perform the method of any of the 30$^{th}$ through 36$^{th}$ aspects of the disclosure.

A 38$^{th}$ aspect of the disclosure may further extend the 30$^{th}$ through 36$^{th}$ aspects of the disclosure. In the 38$^{th}$ aspect of the disclosure, a system comprises: an intraoral scanner to generate the first plurality of intraoral scans and the second plurality of intraoral scans; and a computing device connected to the intraoral scan via a wired or wireless connection, the computing device to perform the method of any of the 30$^{th}$ through 36$^{th}$ aspects of the disclosure.

In a 39$^{th}$ aspect of the disclosure, a method comprises: receiving one or more intraoral scans of a patient's oral cavity; processing an input comprising data from the one or more intraoral scans using a trained machine learning model that has been trained to classify dental sites represented in intraoral scans, wherein the trained machine learning model generates an output comprising one or more dental classification, the one or more dental classification comprising an indication as to whether or not the one or more intraoral scans comprise a depiction of one or more types of restorative dental object; determining, based on the dental classification output by the trained machine learning model, that the one or more intraoral scans depict a restorative dental object; and determining a three-dimensional surface of the restorative dental object using at least portions of the one or more intraoral scans.

A 40$^{th}$ aspect of the disclosure may further extend the 39$^{th}$ aspect of the disclosure. In the 40$^{th}$ aspect of the disclosure, the trained machine learning model outputs a map comprising, for each pixel in an intraoral scan, an indication as to whether or not that pixel depicts a restorative dental object.

A 41$^{st}$ aspect of the disclosure may further extend the 39$^{th}$ or 40$^{th}$ aspect of the disclosure. In the 41$^{st}$ aspect of the disclosure, the one or more types of restorative dental object comprise a preparation, a scan body and a dental implant, and wherein the one or more dental classification comprises a preparation classification, a scan body classification and a dental implant classification.

A 42$^{nd}$ aspect of the disclosure may further extend the 41$^{st}$ aspect of the disclosure. In the 42$^{nd}$ aspect of the disclosure, the trained machine learning model outputs a probability map comprising, for each pixel in an intraoral scan, at least one of a first probability that the pixel depicts a preparation, a second probability that the pixel depicts a scan body or a third probability that the pixel depicts a dental implant.

A 43$^{rd}$ aspect of the disclosure may further extend the 42$^{nd}$ aspect of the disclosure. In the 43$^{rd}$ aspect of the disclosure, the probability map further comprises, for each pixel in the one or more intraoral scans, at least one of a probability that the pixel belongs to a dental class representing gums, a probability that the pixel belongs to a dental class representing attachments to teeth, a probability that the pixel belongs to a dental class representing brackets on teeth, or a probability that the pixel belongs to a dental class representing excess material, the excess material comprising material other than teeth, gums, scan bodies, or dental implants.

A 44$^{th}$ aspect of the disclosure may further extend the 41$^{st}$ through 43$^{rd}$ aspects of the disclosure. In the 44$^{th}$ aspect of the disclosure, the trained machine learning model is capable of distinguishing between a plurality of different types of scan bodies, and wherein the output of the trained machine learning model comprises, for each type of scan body of the plurality of different types of scan bodies, a probability that the one or more intraoral scans comprise a depiction of that type of scan body.

A 45$^{th}$ aspect of the disclosure may further extend the 39$^{th}$ through 44$^{th}$ aspects of the disclosure. In the 45$^{th}$ aspect of the disclosure, the one or more intraoral scans are processed during an intraoral scanning session as the one or more intraoral scans are received and while additional intraoral scans are being generated.

A 46$^{th}$ aspect of the disclosure may further extend the 39$^{th}$ through 45$^{th}$ aspects of the disclosure. In the 46$^{th}$ aspect of the disclosure, the trained machine learning model divides the one or more intraoral scans into a plurality of zones, and wherein the output comprises, for each zone, an indication as to whether that zone contains a depiction of a restorative dental object.

A 47th aspect of the disclosure may further extend the 39th through 46th aspects of the disclosure. In the 47th aspect of the disclosure, the method further comprises: determining a central zone of the one or more intraoral scans, wherein the data from the one or more intraoral scans comprises data from the central zone and excludes data outside of the central zone.

A 48th aspect of the disclosure may further extend the 39th through 47th aspects of the disclosure. In the 48th aspect of the disclosure, the method further comprises: receiving one or more color images of the patient's oral cavity, wherein the one or more color images are associated with an intraoral scan of the one or more intraoral scans and was taken by an intraoral scanner at approximately a same position and orientation as the intraoral scan; and generating an input for the trained machine learning model, the input comprising data from the intraoral scan and data from the one or more color images, wherein the trained machine learning model uses the data from the one or more color images as well as the data from the intraoral scan to generate the output.

A 49th aspect of the disclosure may further extend the 39th through 48th aspects of the disclosure. In the 49th aspect of the disclosure, the method further comprises: receiving an additional image generated under lighting conditions in which the patient's oral cavity is illuminated with at least one of infrared light or ultraviolet light, wherein the additional image is associated with an intraoral scan of the one or more intraoral scans and was taken by an intraoral scanner at approximately a same position and orientation as the intraoral scan; and generating an input for the trained machine learning model, the input comprising data from the intraoral scan and data from the additional image, wherein the trained machine learning model uses data from the additional image as well as the data from the intraoral scan to generate the output.

A 50th aspect of the disclosure may further extend the 49th aspect of the disclosure. In the 50th aspect of the disclosure, the one or more dental classification further comprising at least one of an indication as to whether the one or more intraoral scans comprise a depiction of a real tooth or an indication as to whether the one or more intraoral scans comprise a depiction of an artificial tooth.

A 51st aspect of the disclosure may further extend the 39th through 50th aspects of the disclosure. In the 51st aspect of the disclosure, the method further comprises: receiving a plurality of additional intraoral scans that depict the restorative dental object, wherein the three-dimensional surface of the restorative dental object is determined using the one or more intraoral scans and the plurality of additional intraoral scans; generating a height map by projecting the three-dimensional surface onto a plane; and processing the height map using the trained machine learning model or an additional trained machine learning model that has been trained to identify restorative dental objects in height maps, wherein the trained machine learning model generates an output comprising an indication as to whether the height map comprises a depiction of a restorative dental object.

A 52nd aspect of the disclosure may further extend the 51st aspect of the disclosure. In the 52nd aspect of the disclosure, the height map depicts an occlusal view of a dental arch comprising the restorative dental object.

A 53rd aspect of the disclosure may further extend the 52nd aspect of the disclosure. In the 53rd aspect of the disclosure, the method further comprises: determining a tooth position on the dental arch at which the restorative dental object is located; and labeling the restorative object with the determined tooth position in the three-dimensional surface.

A 54th aspect of the disclosure may further extend the 39th through 53rd aspects of the disclosure. In the 54th aspect of the disclosure, the one or more intraoral scans is received without first receiving a user input indicating that a restorative object is to be scanned.

A 55th aspect of the disclosure may further extend the 39th through 54th aspects of the disclosure. In the 55th aspect of the disclosure, the method further comprises: prompting a user to identify a tooth position on the dental arch at which the restorative dental object is located.

A 56th aspect of the disclosure may further extend the 39th through 55th aspects of the disclosure. In the 56th aspect of the disclosure, a computer readable medium comprises instructions that, when executed by a processing device, cause the processing device to perform the method of any of the 39th through 55th aspects of the disclosure.

A 57th aspect of the disclosure may further extend the 39th through 55th aspects of the disclosure. In the 57th aspect of the disclosure, a system comprises: an intraoral scanner to generate the one or more intraoral scans; and a computing device connected to the intraoral scan via a wired or wireless connection, the computing device to perform the method of any of the 39th through 55th aspects of the disclosure.

In a 58th aspect of the disclosure, a method comprises: determining a first three-dimensional surface of at least a portion of a dental arch using a first plurality of intraoral scans generated by an intraoral scanner at a first time; determining that the first three-dimensional surface depicts at least part of a preparation tooth or at least part of a surrounding region of the preparation tooth; receiving one or more additional intraoral scans of the dental arch that were generated by the intraoral scanner at a second time; determining that the one or more additional intraoral scans depict at least the part of the preparation tooth or the part of the surrounding region of the preparation tooth; determining a time difference between the first time and the second time; determining a change to at least one of the preparation tooth or the surrounding region of the preparation tooth between the first three-dimensional surface and the one or more additional intraoral scans; determining, based at least in part on the time difference and the change to at least one of the preparation tooth or the surrounding region of the preparation tooth, whether to use a) the first three-dimensional surface, b) data from the one or more additional intraoral scans or c) a combination of the first three-dimensional surface and the data from the one or more additional intraoral scans to depict the part of the preparation tooth or the surrounding region of the preparation tooth; and generating a three-dimensional model of the dental arch, wherein a) the first three-dimensional surface, b) the data from the one or more additional intraoral scans or c) the combination of the first three-dimensional surface and the data from the one or more additional intraoral scans is used to depict the part of the preparation tooth or the part of the surrounding region of the preparation tooth in the three-dimensional model.

A 59th aspect of the disclosure may further extend the 58th aspect of the disclosure. In the 59th aspect of the disclosure, the one or more additional intraoral scans comprises a second plurality of intraoral scans, the method further comprising: determining a second three-dimensional surface of at least the portion of the dental arch using the second plurality of intraoral scans; determining that the second three-dimensional surface comprises a representation of at least the part of the preparation tooth or the part of the surrounding region of the preparation tooth; and determining the change to at least one of the preparation tooth or the surrounding region of the preparation tooth based on comparing the first three-dimensional surface and the second three-dimensional surface; wherein determining whether to use a) the first three-dimensional surface, b) data from the one or more additional intraoral scans or c) a combination of the first three-dimensional surface and the data from the one or more additional intraoral scans to depict the part of the preparation tooth or the part of the surrounding region of the preparation tooth comprises determining whether to use a) the first three-dimensional surface, b) the second three-dimensional surface or c) a combination of the first three-dimensional surface and the second three-dimensional surface to depict the part of the preparation tooth or the part of the surrounding region of the preparation tooth; and wherein a) the first three-dimensional surface, b) the second three-dimensional surface or c) the combination of the first three-dimensional surface and the second three-dimensional surface is used to depict the part of the preparation tooth or the part of the surrounding region of the preparation tooth in the three-dimensional model.

A $60^{th}$ aspect of the disclosure may further extend the $59^{th}$ aspect of the disclosure. In the $60^{th}$ aspect of the disclosure, the method further comprises: determining that the time difference exceeds a time difference threshold; determining that the change to the preparation tooth exceeds a change threshold; and determining to use a) the first three-dimensional surface or b) the second three-dimensional surface based on the time difference exceeding the time difference threshold and the change to at least one of the preparation tooth or the surrounding region of the preparation tooth exceeding the change threshold.

A $61^{st}$ aspect of the disclosure may further extend the $59^{th}$ or $60^{th}$ aspect of the disclosure. In the $61^{st}$ aspect of the disclosure, the method further comprises: determining that the second time is at least a threshold amount of time after the first time; identifying a retraction cord depicted in the first three-dimensional surface; determining that the second three-dimensional surface does not include a representation of the retraction cord; and determining to use the second three-dimensional surface rather than the first three-dimensional surface for a region where insertion and subsequent removal of the retraction cord exposed a margin line of the preparation tooth.

A $62^{nd}$ aspect of the disclosure may further extend the $59^{th}$ through $61^{st}$ aspects of the disclosure. In the $62^{nd}$ aspect of the disclosure, the method further comprises: determining that the second time is after the first time; determining that the preparation tooth comprises less material in the part of the preparation tooth from the second three-dimensional surface than in the part of the preparation tooth from the first three-dimensional surface; and determining to use the second three-dimensional surface for the part of the preparation tooth.

A $63^{rd}$ aspect of the disclosure may further extend the $59^{th}$ through $62^{nd}$ aspects of the disclosure. In the $63^{rd}$ aspect of the disclosure, the second time is later than the first time, the method further comprising: receiving audio data, the audio data having been generated at a third time that is between the first time and the second time; determining that the audio data comprises sounds associated with a dental drill; and determining to use the second three-dimensional surface.

A $64^{th}$ aspect of the disclosure may further extend the $59^{th}$ through $63^{rd}$ aspects of the disclosure. In the $64^{th}$ aspect of the disclosure, the method further comprises: determining, based on inertial measurement data for the intraoral scanner, an inertial state of the intraoral scanner between generation of the first plurality of intraoral scans and the second plurality of intraoral scans; wherein the inertial state of the intraoral scanner is used to determine whether to use a) the first three-dimensional surface, b) the second three-dimensional surface or c) the combination of the first three-dimensional surface and the second three-dimensional surface to depict the part of the preparation tooth or the part of the surrounding region of the preparation tooth.

A $65^{th}$ aspect of the disclosure may further extend the $59^{th}$ through $64^{th}$ aspects of the disclosure. In the $65^{th}$ aspect of the disclosure, the method further comprises: identifying a liquid obscuring the part of the preparation tooth in the second three-dimensional surface based on processing the one or more additional intraoral scans using at least one of color image processing or a trained machine learning model; and determining to use the first three-dimensional surface and not the second three-dimensional surface to depict the part of the preparation tooth.

A $66^{th}$ aspect of the disclosure may further extend the $65^{th}$ aspect of the disclosure. In the $66^{th}$ aspect of the disclosure, the liquid comprises at least one of blood or saliva.

A $67^{th}$ aspect of the disclosure may further extend the $59^{th}$ through $66^{th}$ aspects of the disclosure. In the $67^{th}$ aspect of the disclosure, the method further comprises: outputting to a display an indication of whether a) the first three-dimensional surface, b) the second three-dimensional surface or c) the combination of the first three-dimensional surface and the second three-dimensional surface was determined for depicting the part of the preparation tooth or the part of the surrounding region of the preparation tooth; receiving a user input indicating that the determination of whether to use a) the first three-dimensional surface, b) the second three-dimensional surface or c) the combination of the first three-dimensional surface and the second three-dimensional surface to depict the part of the preparation tooth or the part of the surrounding region of the preparation tooth was incorrect, wherein the user input indicates a correct one of a) the first three-dimensional surface, b) the second three-dimensional surface or c) the combination of the first three-dimensional surface and the second three-dimensional surface to use to depict the part of the preparation tooth or the part of the surrounding region of the preparation tooth; and updating the three-dimensional model of the dental arch using the correct one of a) the first three-dimensional surface, b) the second three-dimensional surface or c) the combination of the first three-dimensional surface and the second three-dimensional surface to depict the part of the preparation tooth or the part of the surrounding region of the preparation tooth.

A $68^{th}$ aspect of the disclosure may further extend the $59^{th}$ through $67^{th}$ aspects of the disclosure. In the $68^{th}$ aspect of the disclosure, the method further comprises: segmenting the first three-dimensional surface into gums and one or more teeth, wherein one of the one or more teeth is the preparation tooth; and segmenting the second three-dimensional surface into gums and one or more additional teeth, wherein one of the one or more additional teeth is the preparation tooth.

A $69^{th}$ aspect of the disclosure may further extend the $58^{th}$ through $68^{th}$ aspects of the disclosure. In the $69^{th}$ aspect of the disclosure, the method further comprises: outputting to a display an indication of whether a) the first version of the three-dimensional surface, b) the data from the one or more additional intraoral scans or c) the combination of the first version of the three-dimensional surface and the data from the one or more additional intraoral scans was determined for depicting the part of the preparation tooth or the part of the surrounding region of the preparation tooth.

A 70th aspect of the disclosure may further extend the 58th through 69th aspects of the disclosure. In the 70th aspect of the disclosure, the method further comprises: determining that intraoral scanning of the preparation tooth is complete; automatically determining a contour of a margin line of the preparation tooth; and highlighting the contour of the margin line on the three-dimensional model.

A 71st aspect of the disclosure may further extend the 58th through 70th aspects of the disclosure. In the 71st aspect of the disclosure, the method further comprises: automatically processing data from the three-dimensional model to identify an area for which an additional intraoral scan is recommended; and notifying a user to generate one or more additional intraoral scans depicting the area.

A 72nd aspect of the disclosure may further extend the 71st aspect of the disclosure. In the 72nd aspect of the disclosure, automatically processing the data from the three-dimensional model to identify an area for which an additional intraoral scan is recommended comprises: determining, for a tooth represented in the three-dimensional model, an amount of imaged gum tissue surrounding the tooth; and determining that the amount of imaged gum tissue surrounding the tooth at the area is less than a threshold.

A 73rd aspect of the disclosure may further extend the 71st and 72nd aspects of the disclosure. In the 73rd aspect of the disclosure, the area for which an additional intraoral scan is recommended comprises at least one of a missing palatal area, an unscanned tooth, an incomplete scan of a tooth, a void in a scan of a tooth, an unclear margin line, or an area having insufficient color information.

A 74th aspect of the disclosure may further extend the 58th through 73rd aspects of the disclosure. In the 74th aspect of the disclosure, the method further comprises: after generating the three-dimensional model of the dental arch, generating a trajectory of a virtual camera showing the three-dimensional model of the dental arch from a plurality of view settings and a plurality of zoom settings, wherein one or more zoomed in views of the preparation tooth are included in the trajectory; and automatically executing the trajectory to display the three-dimensional model from the plurality of view settings and the plurality of zoom settings.

A 75th aspect of the disclosure may further extend the 74th aspect of the disclosure. In the 75th aspect of the disclosure, the method further comprises: determining the trajectory of the virtual camera based on one or more zoom operations and one or more rotation operations manually performed by a user for one or more previous three-dimensional models of dental arches.

A 76th aspect of the disclosure may further extend the 58th through 75th aspects of the disclosure. In the 76th aspect of the disclosure, a computer readable medium comprises instructions that, when executed by a processing device, cause the processing device to perform the method of any of the 58th through 75th aspects of the disclosure.

A 77th aspect of the disclosure may further extend the 58th through 75th aspects of the disclosure. In the 77th aspect of the disclosure, a system comprises: an intraoral scanner to generate the first plurality of intraoral scans and the one or more additional intraoral scans; and a computing device connected to the intraoral scan via a wired or wireless connection, the computing device to perform the method of any of the 58th through 75th aspects of the disclosure.

In a 78th aspect of the disclosure, a method of automatically generating a prescription for treating one or more teeth in a dental arch of a patient comprises: receiving a plurality of intraoral scans of the patient that were generated by an intraoral scanner; determining a three-dimensional surface of at least a portion of one or more dental arch of the patient using the plurality of intraoral scans; automatically determining whether a restorative dental object is represented in at least one of the three-dimensional surface or one or more intraoral scans of the plurality of intraoral scans; and automatically generating a prescription for treating the one or more teeth based at least in part on at least one of a) a presence or absence of a restorative dental object in at least one of the three-dimensional surface or the one or more intraoral scans or b) a location of the restorative dental object in the one or more dental arch of the patient.

A 79th aspect of the disclosure may further extend the 78th aspect of the disclosure. In the 79th aspect of the disclosure, the method further comprises: comparing the three-dimensional surface of at least the portion of the one or more dental arch of the patient to a previously generated three-dimensional surface of the one or more dental arch of the patient; determining one or more differences between the three-dimensional surface and the previously generated three-dimensional surface based on a result of the comparing; and determining the one or more teeth to be treated based on the one or more differences.

An 80th aspect of the disclosure may further extend the 79th aspect of the disclosure. In the 80th aspect of the disclosure, the restorative dental object is a preparation tooth, and the plurality of intraoral scans of the patient depict the preparation tooth, the method further comprising: generating a first portion of a three-dimensional model of the one or more dental arch comprising the preparation tooth using the three-dimensional surface; and generating a remainder of the three-dimensional model using the previously generated three-dimensional surface.

An 81st aspect of the disclosure may further extend the 79th or 80th aspect of the disclosure. In the 81st aspect of the disclosure, the restorative dental object is a preparation tooth, and wherein the one or more teeth to be treated comprises the preparation tooth, the method further comprising: automatically determining an exterior surface of a crown to be placed on the preparation tooth based at least in part on a portion of the previously generated three-dimensional surface depicting a tooth before the tooth was ground to become the preparation tooth; and automatically determining an interior surface of the crown based at least in part on the representation of the preparation tooth in the three-dimensional surface.

An 82nd aspect of the disclosure may further extend the 79th through 81st aspects of the disclosure. In the 82nd aspect of the disclosure, the restorative dental object is a preparation tooth, and the one or more teeth to be treated comprises the preparation tooth, the method further comprising: determining one or more changed regions of the preparation tooth between the three-dimensional surface and the previously generated three-dimensional surface based on a result of the comparing, wherein the one or more differences are included in the one or more changed regions; determining one or more unchanged regions of the preparation tooth between the three-dimensional surface and the previously generated three-dimensional surface based on a result of the comparing; determining a border between the one or more unchanged regions and the one or more changed regions; and automatically determining a margin line based at least in part on the border.

An 83rd aspect of the disclosure may further extend the 78th through 82nd aspects of the disclosure. In the 83rd aspect of the disclosure, the restorative dental object comprises a scan body, a dental implant or a preparation tooth.

An 84$^{th}$ aspect of the disclosure may further extend the 78$^{th}$ through 83$^{rd}$ aspects of the disclosure. In the 84$^{th}$ aspect of the disclosure, the method further comprises: segmenting the three-dimensional surface of at least the portion of the one or more dental arch into a plurality of separate teeth; determining a tooth number for each of the one or more teeth to be treated; and automatically adding the tooth number for each of the one or more teeth to be treated to the prescription.

An 85$^{th}$ aspect of the disclosure may further extend the 78$^{th}$ through 84$^{th}$ aspects of the disclosure. In the 85$^{th}$ aspect of the disclosure, the method further comprises: determining a type of dental prosthesis to be used to treat the one or more teeth; and adding an identifier of the type of dental prosthesis to the prescription.

An 86$^{th}$ aspect of the disclosure may further extend the 85$^{th}$ aspect of the disclosure. In the 86$^{th}$ aspect of the disclosure, determining the type of dental prosthesis comprises: determining, based at least in part on a geometry of the preparation, whether an inlay, an onlay, a crown, a denture, a veneer or a bridge is appropriate to treat the one or more teeth.

An 87$^{th}$ aspect of the disclosure may further extend the 85$^{th}$ through 86$^{th}$ aspects of the disclosure. In the 87$^{th}$ aspect of the disclosure, the method further comprises: determining an identity of a dentist treating the patient; determining, based on at least one of the preparation, the type of dental prosthesis, or historical statistics of dental labs used by the dentist, a recommended dental lab to send the prescription to; and adding the recommended dental lab to the prescription.

An 88$^{th}$ aspect of the disclosure may further extend the 87$^{th}$ aspect of the disclosure. In the 88$^{th}$ aspect of the disclosure, the method further comprises: determining at least one of a) historical statistics of materials used for dental prosthetics by the dentist, b) historical statistics of materials used for dental prosthetics by the recommended dental lab or c) materials available at the recommended dental lab; selecting a material to use for the dental prosthesis based on at least one of a) the historical statistics of the materials used for dental prosthetics by the dentist, b) the historical statistics of the materials used for dental prosthetics by the recommended dental lab or c) the materials available at the recommended dental lab; and adding the selected material to the prescription.

An 89$^{th}$ aspect of the disclosure may further extend the 87$^{th}$ through 88$^{th}$ aspect of the disclosure. In the 89$^{th}$ aspect of the disclosure, the method further comprises: receiving color images of the dental arch, the color images having been generated by the intraoral scanner; determining colors of teeth adjacent to the preparation based on the color images; determining a color for the dental prosthesis based at least in part on the colors of the teeth adjacent to the preparation; and automatically adding the color of the dental prosthesis to the prescription.

A 90$^{th}$ aspect of the disclosure may further extend the 78$^{th}$ through 89$^{th}$ aspects of the disclosure. In the 90$^{th}$ aspect of the disclosure, the method further comprises: receiving one or more two-dimensional images generated by the intraoral scanner; determining whether the one or more two-dimensional images depict an interior of a mouth; and causing, without user input, the intraoral scanner to begin generating the plurality of intraoral scans or to stop generating intraoral scans based on whether the one or more two-dimensional images depict an interior of a mouth.

A 91$^{st}$ aspect of the disclosure may further extend the 90$^{th}$ aspect of the disclosure. In the 91$^{st}$ aspect of the disclosure, determining that the one or more two-dimensional images depict an interior of a mouth comprises: inputting the one or more two-dimensional images into a machine learning model trained to classify images as intraoral images, wherein the machine learning model outputs a classification for the one or more two-dimensional images indicating that the one or more two-dimensional images depict an interior of a mouth.

A 92$^{nd}$ aspect of the disclosure may further extend the 78$^{th}$ through 91$^{st}$ aspects of the disclosure. In the 92$^{nd}$ aspect of the disclosure, the method further comprises: inputting at least one of an intraoral scan or a height map generated from the three-dimensional surface into a machine learning model trained to classify height maps as an upper dental arch view, a lower dental arch view, or a bite view, wherein the machine learning model outputs a classification of one of the upper dental arch view, the lower dental arch view or the bite view; and indicating the determined one of the upper dental arch view, the lower dental arch view or the bite view in a graphical user interface.

A 93$^{rd}$ aspect of the disclosure may further extend the 78$^{th}$ through 92$^{nd}$ aspects of the disclosure. In the 93$^{rd}$ aspect of the disclosure, the method further comprises: determining that a first three-dimensional surface of an upper dental arch, a second three-dimensional surface of a lower dental arch and a third three-dimensional surface of a bite depicting a relation of the upper dental arch to the lower dental arch have been generated; responsive to determining that the first three-dimensional surface of the upper dental arch, the second three-dimensional surface of the lower dental arch and the third three-dimensional surface of the bite have been generated, automatically determining occlusal contact areas on the upper dental arch and the lower dental arch based on the first three-dimensional surface of the upper dental arch, the second three-dimensional surface of the lower dental arch and the third three-dimensional surface of the bite; and automatically generating an occlusal map depicting the occlusal contact areas on the upper dental arch and the lower dental arch without first receiving a user request to generate the occlusal map.

A 94$^{th}$ aspect of the disclosure may further extend the 78$^{th}$ through 93$^{rd}$ aspects of the disclosure. In the 94$^{th}$ aspect of the disclosure, the method further comprises: receiving a first intraoral scan that depicts a first bite relation between an upper dental arch and a lower dental arch, the first intraoral scan having been generated at a first time; receiving a second intraoral scan that depicts a second bite relation between the upper dental arch and the lower dental arch, the second intraoral scan having been generated at a second time; determining a first difference between the first bite relation and the second bite relation; determining a second difference between the first time and the second time; and determining, based at least in part on the first difference and the second difference, whether the first intraoral scan and the second intraoral scan depict a same bite of the patient or a different bite of the patient.

A 95$^{th}$ aspect of the disclosure may further extend the 94$^{th}$ aspect of the disclosure. In the 95$^{th}$ aspect of the disclosure, the method further comprises: responsive to determining that the first intraoral scan and the second intraoral scan depict the same bite, merging data from the first intraoral scan and the second intraoral scan to generate a three-dimensional surface depicting the bite.

A 96$^{th}$ aspect of the disclosure may further extend the 94$^{th}$ through 95$^{th}$ aspects of the disclosure. The 96$^{th}$ aspect of the disclosure includes performing the following responsive to determining that the first intraoral scan and the second intraoral scan depict different bites: generating a first three-dimensional surface depicting a first bite from the first intraoral scan; and generating a second three-dimensional surface depicting a second bite from the second intraoral scan.

A 97th aspect of the disclosure may further extend the 78th through 96th aspects of the disclosure. In the 97th aspect of the disclosure, the method further comprises: receiving biometric data of a user of the intraoral scanner; and automatically determining an identity of the user of the intraoral scanner using the biometric data.

A 98th aspect of the disclosure may further extend the 97th aspect of the disclosure. In the 98th aspect of the disclosure: receiving the biometric data comprises receiving an image of a face of the user generated by the intraoral scanner; and automatically determining the identity of the user of the intraoral scanner using the biometric data comprises processing the image of the face using a trained machine learning model trained to perform facial recognition, wherein the identity of the user is determined from a list of possible users associated with a particular dental office.

A 99th aspect of the disclosure may further extend the 97th or 98th aspects of the disclosure. In the 99th aspect of the disclosure, the method further comprises: determining whether the user a) only performs orthodontic dental procedures or b) only performs restorative dental procedures based on historical data about the user; responsive to determining that the user only performs restorative dental procedures, automatically initiating a restorative dental procedure workflow, wherein the prescription is for a dental prosthesis; and responsive to determining that the user only performs orthodontic dental procedures, automatically initiating an orthodontic dental procedure workflow, wherein the prescription is for orthodontia.

A 100th aspect of the disclosure may further extend the 78th through 99th aspects of the disclosure. In the 100th aspect of the disclosure, the patient is an unknown patient, the method further comprising: determining a current date and time; determining a known patient scheduled for the current date and time; comparing the three-dimensional surface of the dental arch of the unknown patient to a three-dimensional surface of a dental arch of the known patient scheduled for the current date and time; determining a match between the three-dimensional surface of the dental arch of the unknown patient and the three-dimensional surface of the dental arch of the known patient; and verifying the unknown patient as the known patient.

A 101st aspect of the disclosure may further extend the 78th through 100th aspects of the disclosure. In the 101st aspect of the disclosure, the method further comprises, responsive to determining that a restorative dental object is included in the dental arch of the patient: determining that a restorative dental procedure is to be performed; and initiating a restorative dental procedure workflow.

A 102nd aspect of the disclosure may further extend the 78th through 101st aspects of the disclosure. In the 102nd aspect of the disclosure, the method further comprises, after determining that no restorative dental object is included in the dental arch of the patient: determining that an orthodontic dental procedure is to be performed; and initiating an orthodontic dental procedure workflow.

A 103rd aspect of the disclosure may further extend the 78th through 102nd aspects of the disclosure. In the 103rd aspect of the disclosure, the patient is an unknown patient, the method further comprising: comparing the three-dimensional surface of the dental arch of the unknown patient to a plurality of three-dimensional surfaces of dental arches of known patients; determining a match between the three-dimensional surface of the dental arch of the unknown patient and a three-dimensional surface of a dental arch of a known patient; and identifying the unknown patient as the known patient.

A 104th aspect of the disclosure may further extend the 78th through 103rd aspects of the disclosure. In the 104th aspect of the disclosure, a computer readable medium comprises instructions that, when executed by a processing device, cause the processing device to perform the method of any of the 78th through 103rd aspects of the disclosure.

A 105th aspect of the disclosure may further extend the 78th through 103rd aspects of the disclosure. In the 105th aspect of the disclosure, a system comprises: an intraoral scanner to generate the plurality of intraoral scans; and a computing device connected to the intraoral scan via a wired or wireless connection, the computing device to perform the method of any of the 78th through 103rd aspects of the disclosure.

In a 106th aspect of the disclosure, a method comprises: receiving an intraoral scan of an oral cavity, the intraoral scan having been generated by an intraoral scanner comprising a probe inserted into the oral cavity; determining, from the intraoral scan, an area in the intraoral scan that represents a dirty region of an optical surface associated with the intraoral scanner; determining whether the area that represents a dirty region of the optical surface satisfies one or more criteria; and responsive to determining that the area that represents a dirty region of the optical surface satisfies the one or more criteria, performing the following: determining that the optical surface is obscured; and generating a notification indicating that the optical surface is obscured.

A 107th aspect of the disclosure may further extend the 106th aspect of the disclosure. In the 107th aspect of the disclosure, the intraoral scan was generated based on non-coherent light output by the intraoral scanner and reflected off of an object in the oral cavity back into the intraoral scanner.

A 108th aspect of the disclosure may further extend the 106th through 107th aspects of the disclosure. In the 108th aspect of the disclosure, the probe is inserted into a disposable sleeve, wherein the optical surface is a window of the disposable sleeve, and wherein the notification comprises at least one of a first notification to replace the disposable sleeve or a second notification indicating a percentage of the window of the disposable sleeve that is dirty.

A 109th aspect of the disclosure may further extend the 106th through 108th aspects of the disclosure. In the 109th aspect of the disclosure, the optical surface is a window or mirror of the probe, and wherein the notification comprises a notification to clean the probe of the intraoral scanner.

A 110th aspect of the disclosure may further extend the 106th through 109th aspects of the disclosure. In the 110th aspect of the disclosure, the method further comprises: rejecting the intraoral scan, wherein the rejected intraoral scan is not used during generation of a three-dimensional model of a dental arch in the oral cavity.

A 111th aspect of the disclosure may further extend the 106th through 110th aspects of the disclosure. In the 111th aspect of the disclosure, each of the points corresponds to a pixel in the intraoral scan, the method further comprising: responsive to determining that the area that represents a dirty region of the optical surface satisfies the one or more criteria, using the intraoral scan to determine a three-dimensional surface of a dental site in the oral cavity, wherein those pixels associated with points that in the area that represents a dirty region of the optical surface are not used in the determination of the three-dimensional surface.

A 112$^{th}$ aspect of the disclosure may further extend the 106$^{th}$ through 111$^{th}$ aspects of the disclosure. In the 112$^{th}$ aspect of the disclosure, the method further comprises: responsive to determining that the area that represents a dirty region of the optical surface satisfies the one or more criteria, discarding data for those points associated with the area that represents the dirty region of the optical surface.

A 113$^{th}$ aspect of the disclosure may further extend the 106$^{th}$ through 112$^{th}$ aspects of the disclosure. In the 113$^{th}$ aspect of the disclosure, the method further comprises: identifying a cluster of points that represent a dirty region of the optical surface; determining at least one of a size or a shape of the cluster of points; determining whether the size or shape is indicative of a dental site; and responsive to determining that the size or shape is indicative of a dental site, using the intraoral scan to determine a three-dimensional surface of the dental site, wherein those pixels associated with points that are associated with a dirty region of the optical surface are used in the determination of the three-dimensional surface.

A 114$^{th}$ aspect of the disclosure may further extend the 106$^{th}$ through 113$^{th}$ aspects of the disclosure. In the 114$^{th}$ aspect of the disclosure, the method further comprises: processing at least one of the intraoral scan or data from a three-dimensional surface generated from the intraoral scan and one or more additional intraoral scans using a trained machine learning model that has been trained to identify regions in intraoral scans obscured by a dirty probe or a dirty sleeve over the probe, wherein the trained machine learning model outputs a map comprising, for each pixel in at least one of the intraoral scan or the data from the three-dimensional surface, an indication as to whether or not that pixel represents a dirty region of the optical surface, each of the pixels being associated with one of the points.

A 115$^{th}$ aspect of the disclosure may further extend the 106$^{th}$ through 114$^{th}$ aspects of the disclosure. In the 115$^{th}$ aspect of the disclosure, the method further comprises: receiving a plurality of intraoral scans generated by the intraoral scanner, wherein the intraoral scan is one of the plurality of intraoral scans; determining, for each intraoral scan of the plurality of intraoral scans, those points that represent a dirty region of the optical surface; and determining points that represent a dirty region of the optical surface for at least a threshold amount of the plurality of intraoral scans; wherein the one or more criteria comprise a criterion that an amount of points that represent a dirty region of the optical surface for at least the threshold amount of the plurality of intraoral scans meet or exceed a dirty region size threshold.

A 116$^{th}$ aspect of the disclosure may further extend the 106$^{th}$ through 115$^{th}$ aspects of the disclosure. In the 116$^{th}$ aspect of the disclosure, the one or more criteria comprises a threshold, wherein the one or more criteria are satisfied when an amount of points that represent a dirty region of the optical surface exceeds the threshold.

A 117$^{th}$ aspect of the disclosure may further extend the 106$^{th}$ through 116$^{th}$ aspects of the disclosure. In the 117$^{th}$ aspect of the disclosure, the determining, from the intraoral scan, the area in the intraoral scan that represents a dirty region of the optical surface of the probe comprises: determining distances of points depicted in the intraoral scan from the probe of the intraoral scanner; and determining points having a distance that is less than or equal to a distance threshold, wherein those points having a distance that is less than or equal to the distance threshold are points that represent a dirty region of the optical surface.

A 118$^{th}$ aspect of the disclosure may further extend the 117$^{th}$ aspect of the disclosure. In the 118$^{th}$ aspect of the disclosure, the probe of the intraoral scanner comprises a window and is inserted into a sleeve, wherein the sleeve comprises a second window that aligns with the window of the probe, and wherein the distance threshold is approximately a measured distance to the second window of the sleeve.

A 119$^{th}$ aspect of the disclosure may further extend the 117$^{th}$ through 118$^{th}$ aspects of the disclosure. In the 119$^{th}$ aspect of the disclosure, the method further comprises: identifying a cluster of points having distances that are less than or equal to the distance threshold; determining at least one of a size or a shape of the cluster of points; determining whether the size or shape is indicative of a dental site; and responsive to determining that the size or shape is indicative of a dental site, using the intraoral scan to determine a three-dimensional surface of the dental site, wherein those pixels associated with points having distances that are less than or equal to the distance threshold are used in the determination of the three-dimensional surface.

A 120$^{th}$ aspect of the disclosure may further extend the 117$^{th}$ through 118$^{th}$ aspects of the disclosure. The 120$^{th}$ aspect of the disclosure includes, for each point having a distance that is less than or equal to the distance threshold, performing the following: determining a plurality of surrounding points that are within a threshold proximity to the point on a plane; determining distances of those points that are within the threshold proximity to the point on the plane; determining an amount of those points that are within the threshold proximity to the point on the plane that have distances that exceed the distance threshold; determining whether the amount of the points that are within the threshold proximity to the point on the plane that have distances that exceed the distance threshold exceeds an additional threshold; and responsive to determining that the amount of the points that are within the threshold proximity to the point on the plane that have distances that exceed the distance threshold exceeds the additional threshold, classifying the point as an obscured point.

A 121$^{st}$ aspect of the disclosure may further extend the 117$^{th}$ through 120$^{th}$ aspects of the disclosure. In the 121$^{st}$ aspect of the disclosure, the method further comprises: receiving a second intraoral scan generated by the intraoral scanner; determining distances of points depicted in the second intraoral scan from the probe of the intraoral scanner; determining those points in the second intraoral scan having a distance that is less than or equal to the distance threshold; comparing those points in the second intraoral scan having distances that are less than or equal to the distance threshold to those points in the intraoral scan having distances that are less than or equal to the distance threshold; and determining, based on the comparing, points that have distances that are less than or equal to the distance threshold in both the intraoral scan and the second intraoral scan; wherein the one or more criteria comprise a criterion that the amount of points that have distances that are less than or equal to the distance threshold are shared by a plurality of intraoral scans.

A 122$^{nd}$ aspect of the disclosure may further extend the 106$^{th}$ through 121$^{st}$ aspects of the disclosure. In the 122$^{nd}$ aspect of the disclosure, the method further comprises: receiving an additional intraoral scan of the oral cavity, wherein determining, from the intraoral scan, an area in the intraoral scan that represents a dirty region of an optical surface associated with the intraoral scanner comprises: determining one or more unchanged points between the intraoral scan and the additional intraoral scan; and determining that the one or more unchanged points are the area in the intraoral scan that represents the dirty region of the optical surface.

A 123$^{rd}$ aspect of the disclosure may further extend the 106$^{th}$ through 122$^{nd}$ aspects of the disclosure. In the 123$^{rd}$ aspect of the disclosure, a computer readable medium comprises instructions that, when executed by a processing device, cause the processing device to perform the method of any of the 106$^{th}$ through 121$^{st}$ aspects of the disclosure.

A 124$^{th}$ aspect of the disclosure may further extend the 106$^{th}$ through 122$^{nd}$ aspects of the disclosure. In the 124$^{th}$ aspect of the disclosure, a system comprises: an intraoral scanner to generate the intraoral scan; and a computing device connected to the intraoral scan via a wired or wireless connection, the computing device to perform the method of any of the 106$^{th}$ through 121$^{st}$ aspects of the disclosure.

In a 125$^{th}$ aspect of the disclosure, a method comprises: receiving an intraoral scan of an oral cavity, the intraoral scan having been generated by an intraoral scanner comprising a probe inserted into the oral cavity; receiving one or more two-dimensional (2D) images generated by the intraoral scanner, wherein the one or more 2D images are associated with the intraoral scan; determining, from at least one of the intraoral scan or the one or more 2D images, an amount of points in the intraoral scan that represent a dirty region of an optical surface associated with the intraoral scanner; determining whether the amount of points that represent a dirty region of the optical surface satisfies one or more criteria; and responsive to determining that the amount of points that represent a dirty region of a the optical surface satisfies the one or more criteria, performing the following: determining that the optical surface is obscured; and generating a notification indicating that the optical surface is obscured.

A 126$^{th}$ aspect of the disclosure may further extend the 125$^{th}$ aspect of the disclosure. In the 126$^{th}$ aspect of the disclosure, the one or more 2D images are a color 2D images.

A 127$^{th}$ aspect of the disclosure may further extend the 125$^{th}$ or 126$^{th}$ aspect of the disclosure. In the 127$^{th}$ aspect of the disclosure, a system may comprise: an intraoral scanner to generate the intraoral scan and the 2D image; and a computing device connected to the intraoral scan via a wired or wireless connection, the computing device to perform the method of any of the 125$^{th}$ or 126$^{th}$ aspect of the disclosure. Alternatively, in the 127$^{th}$ aspect of the disclosure, a computer readable medium may comprise instructions that, when executed by a processing device, cause the processing device to perform the method of any of the 125$^{th}$ or 126$^{th}$ aspect of the disclosure.

In a 128$^{th}$ aspect of the disclosure, a method comprises: receiving a first plurality of scans of a preparation tooth; determining a first three-dimensional surface of the preparation tooth using the first plurality of scans; receiving a second plurality of scans of an intaglio surface of a temporary dental prosthetic designed for the preparation tooth or of an impression of the preparation tooth; determining a second three-dimensional surface representing the intaglio surface of the temporary dental prosthetic or of the impression of the preparation tooth using the second plurality of scans; automatically making a determination, for one or more segments of a margin line of the preparation tooth, whether to use the first three-dimensional surface, the second three dimensional surface, or a combination of the first three-dimensional surface and the second three-dimensional surface for a three-dimensional model of the preparation tooth; and generating a three-dimensional model of the preparation tooth based at least in part on the determination, for the one or more segments of the margin line, whether to use the first three-dimensional surface, the second three dimensional surface, or the combination of the first three-dimensional surface and the second three-dimensional surface for the three-dimensional model.

A 129$^{th}$ aspect of the disclosure may further extend the 128$^{th}$ aspect of the disclosure. In the 129$^{th}$ aspect of the disclosure, the method further comprises: determining the one or more segments of the margin line; for each segment of the one or more segments, determining a first quality rating of the segment if the first three-dimensional surface is used, a second quality rating of the segment if the second three-dimensional surface is used, and a third quality rating of the segment if a combination of the first three-dimensional surface and the second three-dimensional surface is used; wherein for each segment the determination of whether to use the first three-dimensional surface, the second three dimensional surface, or a combination of the first three-dimensional surface and the second three-dimensional surface is made by selecting an option associated with a highest quality rating from the first quality rating, the second quality rating and the third quality rating.

A 130$^{th}$ aspect of the disclosure may further extend the 129$^{th}$ aspect of the disclosure. In the 130$^{th}$ aspect of the disclosure, the method further comprises: inverting the second three-dimensional surface; registering the inverted second three-dimensional surface with the first three-dimensional surface; and for each segment of the one or more segments, performing the following: determining a first depth of the segment from the first three-dimensional surface; determining a second depth of the segment from the second three-dimensional surface; and determining whether to use the first three-dimensional surface or the second three-dimensional surface based at least in part on a comparison of the first depth to the second depth.

A 131$^{st}$ aspect of the disclosure may further extend the 130$^{th}$ aspect of the disclosure. In the 131$^{st}$ aspect of the disclosure, the method further comprises: determining which of the first depth or the second depth is a greater depth; and selecting whichever of the first three-dimensional surface or the second three-dimensional surface has the greater depth.

A 132$^{nd}$ aspect of the disclosure may further extend any of the 128$^{th}$ through 131$^{st}$ aspects of the disclosure. In the 132$^{nd}$ aspect of the disclosure, the method further comprises: inverting the second three-dimensional surface; registering the inverted second three-dimensional surface with the first three-dimensional surface; and for each segment of the one or more segments, performing the following: determining a first curvature of the segment from the first three-dimensional surface; determining a second curvature of the segment from the second three-dimensional surface; and determining whether to use the first three-dimensional surface or the second three-dimensional surface based at least in part on a comparison of the first curvature to the second curvature.

A 133$^{rd}$ aspect of the disclosure may further extend the 128$^{th}$ through 132$^{nd}$ aspects of the disclosure. In the 133$^{rd}$ aspect of the disclosure, the method further comprises: automatically identifying the margin line of the preparation tooth in the three-dimensional model; and marking the margin line on the three-dimensional model.

A 134th aspect of the disclosure may further extend the 128th through 133rd aspects of the disclosure. In the 134th aspect of the disclosure, the method further comprises: comparing the second three-dimensional surface to the first three dimensional surface; determining, based on a result of the comparing, that the second three-dimensional surface mates with the first three-dimensional surface; and determining that the second three-dimensional surface is of the intaglio surface of the temporary dental prosthetic or the impression of the preparation tooth.

A 135th aspect of the disclosure may further extend the 128th through 134th aspects of the disclosure. In the 135th aspect of the disclosure, no user input is received linking the second three-dimensional surface to the first three-dimensional surface, wherein the second three-dimensional surface is compared with a plurality of three-dimensional surfaces, where each of the plurality of three-dimensional surfaces is for a different preparation tooth of a same patient or of different patients.

A 136th aspect of the disclosure may further extend the 128th through 135th aspects of the disclosure. In the 136th aspect of the disclosure, the method further comprises: determining that the second three-dimensional surface is the intaglio surface of the a temporary dental prosthetic designed for the preparation tooth or of an impression of the preparation tooth based on a shape of the second three-dimensional surface.

A 137th aspect of the disclosure may further extend the 128th through 136th aspects of the disclosure. In the 136th aspect of the disclosure, the method further comprises: automatically identifying the margin line in the first three-dimensional surface; and automatically identifying the margin line in the second three-dimensional surface.

A 138th aspect of the disclosure may further extend the 137th aspect of the disclosure. In the 138th aspect of the disclosure: the margin line is automatically identified in the first three-dimensional surface by inputting at least one of the first three-dimensional surface or projections of the first three-dimensional surface onto one or more planes into a trained machine learning model that outputs an indication of the margin line for the first three-dimensional surface; and the margin line is automatically identified in the second three-dimensional surface by inputting at least one of the second three-dimensional surface or projections of the second three-dimensional surface onto one or more planes into the trained machine learning model that outputs an indication of the margin line for the second three-dimensional surface.

A 139th aspect of the disclosure may further extend the 128th through 138th aspects of the disclosure. In the 139th aspect of the disclosure, a computer readable medium comprises instructions that, when executed by a processing device, cause the processing device to perform the method of any of the 128th through 138th aspects of the disclosure.

A 140th aspect of the disclosure may further extend the 128th through 138th aspects of the disclosure. In the 140th aspect of the disclosure, a system comprises: an intraoral scanner to generate the first plurality of scans and the second plurality of scans; and a computing device connected to the intraoral scan via a wired or wireless connection, the computing device to perform the method of any of the 128th through 138th aspects of the disclosure.

In a 141st aspect of the disclosure, a method comprises: receiving a first plurality of scans of an edentulous dental arch; receiving a second plurality of scans of an intaglio surface of a first denture designed for the edentulous dental arch or of an impression taken of at least a portion of the edentulous dental arch; determining a three-dimensional surface of the edentulous dental arch using the first plurality of scans and the second plurality of scans; and generating a virtual three-dimensional model using the three-dimensional surface, wherein the virtual three-dimensional model is usable to manufacture a second denture for the edentulous dental arch.

A 142nd aspect of the disclosure may further extend the 141st aspect of the disclosure. In the 142nd aspect of the disclosure, the method further comprises: determining a first three-dimensional surface using the first plurality of scans; determining a second three-dimensional surface using the second plurality of scans; comparing the second three-dimensional surface to the first three dimensional surface; and determining, based on a result of the comparing, that the second three-dimensional surface mates with the first three-dimensional surface.

A 143rd aspect of the disclosure may further extend the 141st through 142nd aspects of the disclosure. In the 143rd aspect of the disclosure, the three-dimensional surface comprises one or more mucco-dynamic borders.

A 144th aspect of the disclosure may further extend the 141st through 143rd aspects of the disclosure. In the 144th aspect of the disclosure, the method further comprises: receiving a user input associating the second plurality of scans with the first plurality of scans.

A 145th aspect of the disclosure may further extend the 141st through 144th aspects of the disclosure. In the 145th aspect of the disclosure, the impression is of only a portion of the edentulous dental arch.

A 146th aspect of the disclosure may further extend the 141st through 145th aspects of the disclosure. In the 146th aspect of the disclosure, a computer readable medium comprises instructions that, when executed by a processing device, cause the processing device to perform the method of any of the 141st through 145th aspects of the disclosure.

A 147th aspect of the disclosure may further extend the 141st through 145th aspects of the disclosure. In the 147th aspect of the disclosure, a system comprises: an intraoral scanner to generate the first plurality of scans and the second plurality of scans; and a computing device connected to the intraoral scan via a wired or wireless connection, the computing device to perform the method of any of the 141st through 145th aspects of the disclosure.

BRIEF DESCRIPTION OF THE DRAWINGS

Embodiments of the present disclosure are illustrated by way of example, and not by way of limitation, in the figures of the accompanying drawings.

FIGS. 14A-B illustrate a flow chart of an embodiment for a method of automatically generating and updating a 3D model of a preparation tooth as the preparation tooth is modified.

DETAILED DESCRIPTION

Figure 1:
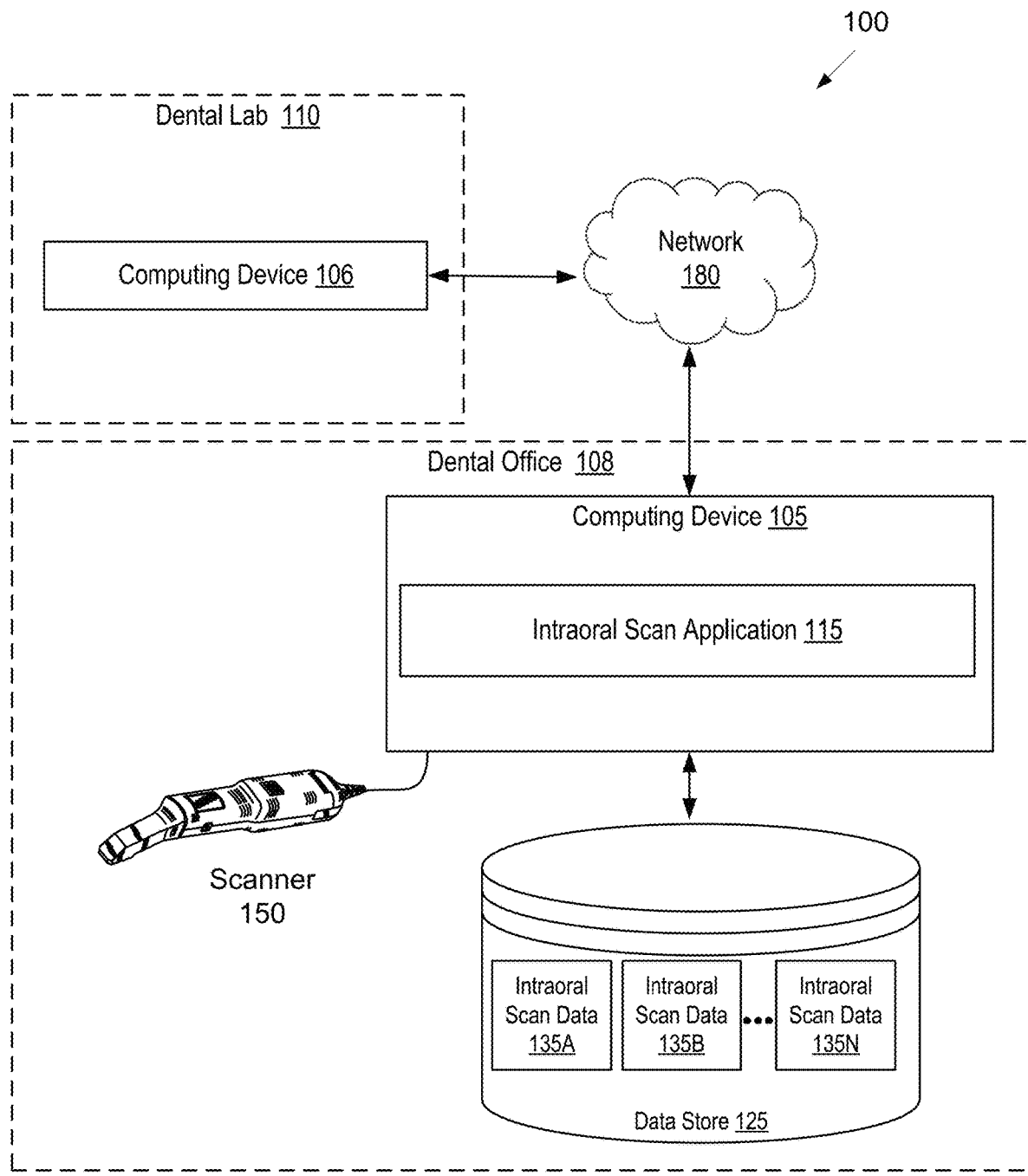
FIG. 1 illustrates one embodiment of a system for performing intraoral scanning and/or generating a virtual three-dimensional model of an intraoral site.

Described herein are methods and systems for simplifying and automating the process of performing intraoral scanning. In some embodiments, user input is minimized. For example, user input of patient information, user input to select a patient to be scanned, user input selecting a segment of a dental arch to be scanned, user input indicating whether scanning was successful, user input manually inputting instructions to transition between stages or modes of intraoral scanning, user input selecting prescription details, user input selecting a lab to send data to, and so on may be reduced or eliminated in embodiments.

Embodiments disclosed herein provide automated systems and methods for automatically identifying a segment and/or role associated with received intraoral scans, for automatically identifying, classifying and/or determining positions of restorative objects in intraoral scans, for automatically generating a prescription for treating a patient's dental arch, for automatically determining whether a restorative or orthodontic workflow is to apply for a patient, and so on. Additionally, embodiments disclosed herein provide a system and method for automatically detecting whether a surface of an intraoral scanner is dirty. Additionally, embodiments disclosed herein provide a system and method for determining a margin line or other information using data from an intaglio surface of a denture, elastomeric impressions or temporary crown.

With application of one or more of the embodiments described herein, a doctor is able to perform orthodontic and/or restorative dental operations with much less training, as opposed to traditional workflows. Additionally, embodiments enable a quicker full scan (e.g., since there may be no need to go through a lengthy prescription (Rx) generation process, and since there may be no need to erase or mark regions, resulting in less chair time with a patient). Additionally, embodiments reduce or eliminate a need for a doctor to transition back and forth between scanning a patient and interfacing with a computer to review scan results, which minimizes cross contamination (since there is less or no need to touch a screen or keyboard).

In an example, a common sequence for generating a prescription for orthodontic treatment is (1) select case definition drop down menu, (2) select orthodontic case type, (3) type in a patient name, (4) select whether or not brackets will be used, and (5) select number of bite scans (e.g., two bite scans). Additionally, the doctor performs a scan for the patient, which includes (1) press a button to initiate scan mode, (2) manually select the upper dental arch to scan, (3) scan the upper dental arch, (4) manually select the lower dental arch to scan, (5) scan the lower dental arch, (6) select a bite to scan, (7) scan the bite, (8) perform occlusal clearance review, (9) delete and rescan if needed, and (10) indicate that scanning is done and that a 3D model is to be generated. In contrast, a simplified sequence for generating a prescription for orthodontic treatment and performing scanning in embodiments includes (1) start scanning. All other operations may be automated. For example, the system may automatically identify a current role (e.g., lower dental arch, upper dental arch, bite) being scanned, and generate the proper model accordingly, and may automatically determine when scanning is complete (e.g., for a particular role or overall) and initiate post processing (e.g., this may start when enough data was accumulated and a new scan region is started or a doctor has removed the intraoral scanner from the patient's oral cavity). The system may automatically perform occlusal clearance review, and notify the doctor if there are any problems. The system may also automatically determine that a current case type is an orthodontic case type. Additionally, the system may automatically determine an identity of the patient being scanned (e.g., based on a calendar system indicating a patient appointment corresponding to a current time and/or based on comparison of intraoral scans to stored records of patient scans).

In another example, a common sequence for generating a prescription for restorative dental treatment is (1) select case definition drop down menu, (2) select restorative case type, (3) type in a patient name, (4) select which teeth are preparation teeth and/or implants, (5) define types of implants, (6) manually select materials to be used for implants (prosthodontics), (7) manually set the preparation type (e.g., bridge, crown, etc.), (8) manually set the color definition for the prosthodontic, and (9) manually select a lab to use. Additionally, the doctor performs a scan for the patient, which includes (1) press a button to initiate scan mode, (2) manually select the upper dental arch to scan, (3) scan the upper dental arch, (4) manually select the lower dental arch to scan, (5) scan the lower dental arch, (6) manually select a bite to scan, (7) scan the bite, (8) manually select a preparation tooth to be scanned, (9) scan the preparation tooth, (10) perform occlusal clearance review, (11) manually delete and rescan if needed, (12) indicate that scanning is done and that a 3D model is to be generated, (13) review 3D model, (14) manually mark the margin line in the 3D model, and send the 3D model to the selected lab. In contrast, a simplified sequence for generating a prescription for restorative treatment and performing scanning in embodiments includes (1) start scanning. All other operations may be automated. For example, the system may automatically identify a current role (e.g., lower dental arch, upper dental arch, bite) being scanned and identify whether or not a preparation tooth is being scanned, and generate the proper model accordingly, and may automatically determine when scanning is complete (e.g., for a particular role or overall) and initiate post processing (e.g., this may start when enough data was accumulated and a new scan region is started or a doctor has removed the intraoral scanner from the patient's intraoral cavity). The system may automatically perform occlusal clearance review, and notify the doctor if there are any problems. The system may also automatically determine that a current case type is a restorative case type. Additionally, the system may automatically determine an identity of the patient being scanned (e.g., based on a calendar system indicating a patient appointment corresponding to a current time and/or based on comparison of intraoral scans to stored records of patient scans). With each automated identification and/or operation, processing logic may provide visual and/or audio feedback to a user of an intraoral scanner letting the user know that the system understands a current state of the scanning process. For example, the system may notify the user when the upper dental arch is detected, when a preparation tooth is detected, when a lower dental arch is detected, when a patient bite is detected, when scanning is determined to be complete, and so on. Processing logic may also notify the doctor when 3D models are automatically generated, when occlusal clearance review is automatically performed, when one or more details of a prescription are automatically determined, and so on. From this information a user can know where they are in a scanning workflow without a need to manually input information.

Additionally, for restorative treatment a doctor often needs to modify a preparation tooth (e.g., by performing additional drilling/grinding or by adding/removing a retraction cord) and then rescan the preparation tooth. In embodiments the system identifies what was changed after each rescan, and shows a region where the change was made, identifying changes in teeth (e.g., to the margin line and/or preparation shape) and/or changes in gums (e.g., between images taken before and after a retraction cord was used to expose the margin line). The system includes logic to determine what portions of data to use from each scan to generate a highest quality 3D model. Additionally, after each scan/rescan, the system may compute and show occlusal surfaces, margin lines, insertion path (including any insertion path problems), and so on. Additionally, the system may automatically determine a color to use for a prosthodontic based on the color/shade of neighboring teeth, and may also automatically determine material type, lab selection, and so on based on usage patterns of the doctor.

Various embodiments are described herein. It should be understood that these various embodiments may be implemented as stand-alone solutions and/or may be combined. Accordingly, references to an embodiment, or one embodiment, may refer to the same embodiment and/or to different embodiments. Additionally, some embodiments are discussed with reference to restorative dentistry, and in particular to preparation teeth. However, it should be understood that embodiments discussed with reference to restorative dentistry (e.g., prosthodontics) may also apply to corrective dentistry (e.g., orthodontia). Additionally, embodiments discussed with reference to preparation teeth may also apply to teeth generally, and not just preparation teeth. Furthermore, embodiments discussed with reference to margin lines may also apply to other dental features, such as cracks, chips, gum lines, caries, and so on.

Some embodiments are discussed herein with reference to intraoral scans and intraoral images. However, it should be understood that embodiments described with reference to intraoral scans also apply to lab scans or model/impression scans. A lab scan or model/impression scan may include one or more images of a dental site or of a model or impression of a dental site, which may or may not include height maps, and which may or may not include color images.

FIG. 1 illustrates one embodiment of a system 100 for performing intraoral scanning and/or generating a virtual three-dimensional model of an intraoral site. System 100 includes a dental office 108 and optionally one or more dental lab 110. The dental office 108 and the dental lab 110 each include a computing device 105, 106, where the computing devices 105, 106 may be connected to one another via a network 180. The network 180 may be a local area network (LAN), a public wide area network (WAN) (e.g., the Internet), a private WAN (e.g., an intranet), or a combination thereof.

Computing device 105 may be coupled to one or more intraoral scanner 150 (also referred to as a scanner) and/or a data store 125 via a wired or wireless connection. In one embodiment, multiple scanners 150 in dental office 108 wirelessly connect to computing device 105. In one embodiment, scanner 150 is wirelessly connected to computing device 105 via a direct wireless connection. In one embodiment, scanner 150 is wirelessly connected to computing device 105 via a wireless network. In one embodiment, the wireless network is a Wi-Fi network. In one embodiment, the wireless network is a Bluetooth network, a Zigbee network, or some other wireless network. In one embodiment, the wireless network is a wireless mesh network, examples of which include a Wi-Fi mesh network, a Zigbee mesh network, and so on. In an example, computing device 105 may be physically connected to one or more wireless access points and/or wireless routers (e.g., Wi-Fi access points/routers). Intraoral scanner 150 may include a wireless module such as a Wi-Fi module, and via the wireless module may join the wireless network via the wireless access point/router. Computing device 106 may also be connected to a data store (not shown). The data stores may be local data stores and/or remote data stores. Computing device 105 and computing device 106 may each include one or more processing devices, memory, secondary storage, one or more input devices (e.g., such as a keyboard, mouse, tablet, touchscreen, microphone, camera, and so on), one or more output devices (e.g., a display, printer, touchscreen, speakers, etc.), and/or other hardware components.

In embodiments, scanner 150 includes an inertial measurement unit (IMU). The IMU may include an accelerometer, a gyroscope, a magnetometer, a pressure sensor and/or other sensor. For example, scanner 150 may include one or more micro-electromechanical system (MEMS) IMU. The IMU may generate inertial measurement data, including acceleration data, rotation data, and so on.

Computing device 105 and/or data store 125 may be located at dental office 108 (as shown), at dental lab 110, or at one or more other locations such as a server farm that provides a cloud computing service. Computing device 105 and/or data store 125 may connect to components that are at a same or a different location from computing device 105 (e.g., components at a second location that is remote from the dental office 108, such as a server farm that provides a cloud computing service). For example, computing device 105 may be connected to a remove server, where some operations of intraoral scan application 115 are performed on computing device 105 and some operations of intraoral scan application 115 are performed on the remote server.

Some additional computing devices may be physically connected to the computing device 105 via a wired connection. Some additional computing devices may be wirelessly connected to computing device 105 via a wireless connection, which may be a direct wireless connection or a wireless connection via a wireless network. In embodiments, one or more additional computing devices may be mobile computing devices such as laptops, notebook computers, tablet computers, mobile phones, portable game consoles, and so on. In embodiments, one or more additional computing devices may be traditionally stationary computing devices, such as desktop computers, set top boxes, game consoles, and so on. The additional computing devices may act as thin clients to the computing device 105. In one embodiment, the additional computing devices access computing device 105 using remote desktop protocol (RDP). In one embodiment, the additional computing devices access computing device 105 using virtual network control (VNC). Some additional computing devices may be passive clients that do not have control over computing device 105 and that receive a visualization of a user interface of intraoral scan application 115. In one embodiment, one or more additional computing devices may operate in a master mode and computing device 105 may operate in a slave mode.

Intraoral scanner 150 may include a probe (e.g., a hand held probe) for optically capturing three-dimensional structures. The intraoral scanner 150 may be used to perform an intraoral scan of a patient's oral cavity. An intraoral scan application 115 running on computing device 105 may communicate with the scanner 150 to effectuate the intraoral scan. A result of the intraoral scan may be intraoral scan data 135A, 135B through 135N that may include one or more sets of intraoral scans, which may include intraoral images. Each intraoral scan may include a two-dimensional (2D) or 3D image that may include depth information (e.g., a height map) of a portion of a dental site. In embodiments, intraoral scans include x, y and z information. In one embodiment, the intraoral scanner 150 generates numerous discrete (i.e., individual) intraoral scans.

In some embodiments, sets of discrete intraoral scans are merged into a smaller set of blended intraoral scans, where each blended scan is a combination of multiple discrete scans. The intraoral scan data 135A-N may include raw scans and/or blended scans, each of which may be referred to as intraoral scans (and in some instances as intraoral images). While scanning, the intraoral scanner may generate multiple (e.g., tens) of scans (e.g., height maps) per second (referred to as raw scans). In order to improve the quality of the data captured, a blending process may be used to combine a sequence of raw scans into a blended scan by some averaging process. Additionally, intraoral scanner 150 may generate many scans per second. This may be too much data to process using a machine learning model in real time. Accordingly, groups of similar scans may be combined into the blended scans, and the blended scans may be input into one or more trained machine learning model. This may vastly reduce the computation resources used to process the intraoral scans without degrading quality. In one embodiment, each blended scan includes data from up to 20 raw scans, and further includes scans that differ by less than a threshold angular difference from one another and/or by less than a threshold positional difference from one another. Accordingly, some blended scans may include data from 20 scans, while other blended scans may include data from fewer than 20 scans. In one embodiment, the intraoral scan (which may be a blended scan) includes height values and intensity values for each pixel in the image.

Intraoral scan data 135A-N may also include color 2D images and/or images of particular wavelengths (e.g., near-infrared (NIRI) images, infrared images, ultraviolet images, etc.) of a dental site in embodiments. In embodiments, intraoral scanner 150 alternates between generation of 3D intraoral scans and one or more types of 2D intraoral images (e.g., color images, NIRI images, etc.) during scanning. For example, one or more 2D color images may be generated between generation of a fourth and fifth intraoral scan. For example, some scanners may include multiple image sensors that generate different 2D color images of different regions of a patient's dental arch concurrently. These 2D color images may be stitched together to form a single color representation of a larger field of view that includes a combination of the fields of view of the multiple image sensors.

The scanner 150 may transmit the intraoral scan data 135A, 135B through 135N to the computing device 105. Computing device 105 may store the intraoral scan data 135A-135N in data store 125.

According to an example, a user (e.g., a practitioner) may subject a patient to intraoral scanning. In doing so, the user may apply scanner 150 to one or more patient intraoral locations. The scanning may be divided into one or more segments (also referred to as roles). As an example, the segments may include a lower dental arch of the patient, an upper dental arch of the patient, one or more preparation teeth of the patient (e.g., teeth of the patient to which a dental device such as a crown or other dental prosthetic will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with the scan being directed towards an interface area of the patient's upper and lower teeth). Via such scanner application, the scanner 150 may provide intraoral scan data 135A-N to computing device 105. The intraoral scan data 135A-N may be provided in the form of intraoral scan data sets, each of which may include 2D intraoral images (e.g., color 2D images) and/or 3D intraoral scans of particular teeth and/or regions of an intraoral site. In one embodiment, separate intraoral scan data sets are created for the maxillary arch, for the mandibular arch, for a patient bite, and/or for each preparation tooth. Alternatively, a single large intraoral scan data set is generated (e.g., for a mandibular and/or maxillary arch). Intraoral scans may be provided from the scanner 150 to the computing device 105 in the form of one or more points (e.g., one or more pixels and/or groups of pixels). For instance, the scanner 150 may provide an intraoral scan as one or more point clouds. The intraoral scans may each comprise height information (e.g., a height map that indicates a depth for each pixel).

The manner in which the oral cavity of a patient is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes an edentulous region, the neighboring preparation teeth (e.g., abutment teeth) and the opposing arch and dentition. Alternatively, full scans of upper and/or lower dental arches may be performed if a bridge is to be created.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity (intraoral site), or a real or virtual model thereof, or directed to the design and preparation of the intraoral site to receive such a prosthesis. A prosthesis may include any restoration such as crowns, veneers, inlays, onlays, implants and bridges, for example, and any other artificial partial or complete denture. The term orthodontic procedure refers, inter alia, to any procedure involving the oral cavity and directed to the design, manufacture or installation of orthodontic elements at a intraoral site within the oral cavity, or a real or virtual model thereof, or directed to the design and preparation of the intraoral site to receive such orthodontic elements. These elements may be appliances including but not limited to brackets and wires, retainers, clear aligners, or functional appliances.

In embodiments, intraoral scanning may be performed on a patient's oral cavity during a visitation of dental office 108. The intraoral scanning may be performed, for example, as part of a semi-annual or annual dental health checkup. The intraoral scanning may also be performed before, during and/or after one or more dental treatments, such as orthodontic treatment and/or prosthodontic treatment. The intraoral scanning may be a full or partial scan of the upper and/or lower dental arches, and may be performed in order to gather information for performing dental diagnostics, to generate a treatment plan, to determine progress of a treatment plan, and/or for other purposes. The dental information (intraoral scan data 135A-N) generated from the intraoral scanning may include 3D scan data, 2D color images, NIRI and/or infrared images, and/or ultraviolet images, of all or a portion of the upper jaw and/or lower jaw. The intraoral scan data 135A-N may further include one or more intraoral scans showing a relationship of the upper dental arch to the lower dental arch. These intraoral scans may be usable to determine a patient bite and/or to determine occlusal contact information for the patient. The patient bite may include determined relationships between teeth in the upper dental arch and teeth in the lower dental arch.

For many prosthodontic procedures (e.g., to create a crown, bridge, veneer, etc.), an existing tooth of a patient is ground down to a stump. The ground tooth is referred to herein as a preparation tooth, or simply a preparation. The preparation tooth has a margin line (also referred to as a finish line), which is a border between a natural (unground) portion of the preparation tooth and the prepared (ground) portion of the preparation tooth. The preparation tooth is typically created so that a crown or other prosthesis can be mounted or seated on the preparation tooth. In many instances, the margin line of the preparation tooth is subgingival (below the gum line).

After a preparation tooth is created, a practitioner typically performs operations to ready that preparation tooth for scanning. Readying the preparation tooth for scanning may include wiping blood, saliva, etc. off of the preparation tooth and/or separating a patient's gum from the preparation tooth to expose the finish line. In some instances, a practitioner will insert a cord (also referred to as a dental wire) around the preparation tooth between the preparation tooth and the patient's gum. The practitioner will then remove the cord before generating a set of intraoral scans of the preparation tooth. The soft tissue of the gum will then revert back to its natural position, and in many cases collapses back over the finish line, after a brief time period. Accordingly, some of intraoral scan data 135A-N may include intraoral scans that were taken before the gum has collapsed over the margin line, and other intraoral scan data 135A-N may include intraoral scans that were taken after the gum has collapsed over the margin line. As a result, some intraoral scan data is superior to other intraoral scan data in depicting the preparation tooth, and in particular in depicting the margin line.

Intraoral scanners may work by moving the scanner 150 inside a patient's mouth to capture all viewpoints of one or more tooth. During scanning, the scanner 150 is calculating distances to solid surfaces in some embodiments. These distances may be recorded as images called 'height maps'. Each scan (e.g., optionally height map) is overlapped algorithmically, or 'stitched', with the previous set of scans to generate a growing 3D surface. As such, each scan is associated with a rotation in space, or a projection, to how it fits into the 3D surface.

During intraoral scanning, intraoral scan application 115 may register and stitch together two or more intraoral scans generated thus far from the intraoral scan session. In one embodiment, performing registration includes capturing 3D data of various points of a surface in multiple scans, and registering the scans by computing transformations between the scans. One or more 3D surfaces may be generated based on the registered and stitched together intraoral scans during the intraoral scanning. The one or more 3D surfaces may be output to a display so that a doctor or technician can view their scan progress thus far. As each new intraoral scan is captured and registered to previous intraoral scans and/or a 3D surface, the one or more 3D surfaces may be updated, and the updated 3D surface(s) may be output to the display. In embodiments, separate 3D surfaces are generated for the upper jaw and the lower jaw. This process may be performed in real time or near-real time to provide an updated view of the captured 3D surfaces during the intraoral scanning process.

When a scan session or a portion of a scan session associated with a particular scanning role (e.g., upper jaw role, lower jaw role, bite role, etc.) is complete (e.g., all scans for an intraoral site or dental site have been captured), intraoral scan application 115 may automatically generate a virtual 3D model of one or more scanned dental sites (e.g., of an upper jaw and a lower jaw). The final 3D model may be a set of 3D points and their connections with each other (i.e. a mesh). To generate the virtual 3D model, intraoral scan application 115 may register and stitch together the intraoral scans generated from the intraoral scan session that are associated with a particular scanning role. The registration performed at this stage may be more accurate than the registration performed during the capturing of the intraoral scans, and may take more time to complete than the registration performed during the capturing of the intraoral scans. In one embodiment, performing scan registration includes capturing 3D data of various points of a surface in multiple scans, and registering the scans by computing transformations between the scans. The 3D data may be projected into a 3D space of a 3D model to form a portion of the 3D model. The intraoral scans may be integrated into a common reference frame by applying appropriate transformations to points of each registered scan and projecting each scan into the 3D space.

In one embodiment, registration is performed for adjacent or overlapping intraoral scans (e.g., each successive frame of an intraoral video). In one embodiment, registration is performed using blended scans. Registration algorithms are carried out to register two adjacent or overlapping intraoral scans (e.g., two adjacent blended intraoral scans) and/or to register an intraoral scan with a 3D model, which essentially involves determination of the transformations which align one scan with the other scan and/or with the 3D model. Registration may involve identifying multiple points in each scan (e.g., point clouds) of a scan pair (or of a scan and the 3D model), surface fitting to the points, and using local searches around points to match points of the two scans (or of the scan and the 3D model). For example, intraoral scan application 115 may match points of one scan with the closest points interpolated on the surface of another scan, and iteratively minimize the distance between matched points. Other registration techniques may also be used.

Intraoral scan application 115 may repeat registration for all intraoral scans of a sequence of intraoral scans to obtain transformations for each intraoral scan, to register each intraoral scan with previous intraoral scan(s) and/or with a common reference frame (e.g., with the 3D model). Intraoral scan application 115 may integrate intraoral scans into a single virtual 3D model by applying the appropriate determined transformations to each of the intraoral scans. Each transformation may include rotations about one to three axes and translations within one to three planes.

In many instances, data from one or more intraoral scans does not perfectly correspond to data from one or more other intraoral scans. Accordingly, in embodiments intraoral scan application 115 may process intraoral scans (e.g., which may be blended intraoral scans) to determine which intraoral scans (or which portions of intraoral scans) to use for portions of a 3D model (e.g., for portions representing a particular dental site). Intraoral scan application 115 may use data such as geometric data represented in scans and/or time stamps associated with the intraoral scans to select optimal intraoral scans to use for depicting a dental site or a portion of a dental site (e.g., for depicting a margin line of a preparation tooth). In one embodiment, images are input into a machine learning model that has been trained to select and/or grade scans of dental sites. In one embodiment, one or more scores are assigned to each scan, where each score may be associated with a particular dental site and indicate a quality of a representation of that dental site in the intraoral scans.

Additionally, or alternatively, intraoral scans may be assigned weights based on scores assigned to those scans. Assigned weights may be associated with different dental sites. In one embodiment, a weight may be assigned to each scan (e.g., to each blended scan) for a dental site (or for multiple dental sites). During model generation, conflicting data from multiple intraoral scans may be combined using a weighted average to depict a dental site. The weights that are applied may be those weights that were assigned based on quality scores for the dental site. For example, processing logic may determine that data for a particular overlapping region from a first set of intraoral scans is superior in quality to data for the particular overlapping region of a second set of intraoral scans. The first intraoral scan data set may then be weighted more heavily than the second intraoral scan data set when averaging the differences between the intraoral scan data sets. For example, the first intraoral scans assigned the higher rating may be assigned a weight of 70% and the second intraoral scans may be assigned a weight of 30%. Thus, when the data is averaged, the merged result will look more like the depiction from the first intraoral scan data set and less like the depiction from the second intraoral scan data set.

Intraoral scan application 115 may generate one or more 3D models from intraoral scans, and may display the 3D models to a user (e.g., a doctor) via a user interface. The 3D models can then be checked visually by the doctor. The doctor can virtually manipulate the 3D models via the user interface with respect to up to six degrees of freedom (i.e., translated and/or rotated with respect to one or more of three mutually orthogonal axes) using suitable user controls (hardware and/or virtual) to enable viewing of the 3D model from any desired direction. The doctor may review (e.g., visually inspect) the generated 3D model of an intraoral site and determine whether the 3D model is acceptable (e.g., whether a margin line of a preparation tooth is accurately represented in the 3D model). In some embodiments, the intraoral scan application 115 automatically generates a sequence of views of the 3D model and scrolls through the views in the generated sequence. This may include zooming in, zooming out, panning, rotating, and so on.

Intraoral scan application 115 may include logic for automatically performing one or more operations traditionally performed manually by a user, referred to herein as smart scanning. A user may enter a smart scanning mode by making a selection to perform a smart scan from a user interface of intraoral scan application 115. Alternatively, intraoral scan application 115 may default to the smart scanning mode. At any time a user may select to exit the smart scanning mode. Multiple stages and work flows of intraoral scanning are provided, along with descriptions for each stage/work flow on how a user need to add input (apart from scanning) is removed.

Automatic User Identification (Scanner Login)

In some embodiments, one or more forms of automatic user identification is performed to determine an identity of a doctor (or other user) of scanner 150 and/or to log the doctor into intraoral scan application 115 prior to commencement of intraoral scanning or at another time. Examples of automatic user identification that may be used include face identification, fingerprint identification, voice identification, other biometric information, and/or scanner motion identification. For face identification, a user may use the scanner 150 to generate one or more images of their face. Alternatively, computing device 105 may include a separate camera (not shown) that may capture one or more image of the user's face. Computing device 105 may have images of faces of users of scanner 150 and/or a trained machine learning model trained to identify faces of users of scanner 150, and may then perform facial recognition to identify the user (e.g., by inputting the captured image into the trained machine learning model).

For voice identification, scanner 150 and/or computing device 105 may include a microphone. The one or more microphone may capture audio of a user of scanner 150 speaking (e.g., saying a particular login phrase). Computing device 105 may have recorded spoken audio of users of scanner 150 and/or a trained machine learning model trained to identify voices of users of scanner 150, and may then perform voice recognition to identify the user (e.g., by inputting the captured audio into the trained machine learning model and/or comparing the captured audio to stored audio).

Scanner 150 may include one or more motion sensors (e.g., gyroscopes and/or accelerometers). Users may set scanner motion passwords by choosing a record scanner motion password option in intraoral scan application 115, and then moving the scanner 150 as they see fit (e.g., moving the scanner up, down, left, right, forward, backward, rotating the scanner, and so on). Once a scanner motion password is recorded, an unknown user may log into their user ID or account on intraoral scan application 115 by moving the scanner 150 according to their recorded scanner motion password. Intraoral scan application 115 may compare a received scanner motion (e.g., which may include a sequence of accelerations and/or rotations) and compare it to a set of recorded scanner motions. If a match is identified between the received scanner motion and a stored scanner motion associated with a user account, scanner motion identification may be successful and the user may be identified and logged into their account.

Intraoral scanner 150 may include a touchpad or other touch-sensitive input device which may function as a fingerprint reader in embodiments. For fingerprint identification, a user may press a finger (e.g., a thumb) onto the touchpad or other touch-sensitive input device. A fingerprint of the user may be determined based on the user pressing the touchpad or other touch-sensitive input device. The fingerprint may be compared to one or more stored fingerprints. If a match is identified between the detected fingerprint and a fingerprint associated with a user account, then the doctor associated with that user account may be identified, and the doctor may automatically be logged into their user account.

Automatic Patient Identification

As set forth above, intraoral scan application 115 may automatically determine an identity of a user of scanner 150 and log that user into their account on intraoral scan application 115 using one or more identification techniques. Additionally, or alternatively, intraoral scan application 115 may automatically determine an identity of a patient. Such identification of the patient may be performed before, during, or after intraoral scanning of the patient.

For a first time patient, user name and details are manually or automatically added to a patient record. For manual entry, the doctor or a technician may input patient details into intraoral scan application 115. For automatic entry, intraoral scan application 115 may access practice management software, calendar software and/or other software containing patient information, and may retrieve that patient information and automatically populate a patient entry in intraoral scan application 115 with the retrieved patient information.

For example, information for a patient assigned to a current dental chair at a current time may automatically be retrieved from practice management software and/or calendar software.

Once user information has been added once, a doctor may just start scanning, and the intraoral scan application may automatically identify the patient based on his teeth shape. For example, a patient may have previously undergone an intraoral scan, and one or more 3D models of the patient's dental arches may be associated with an entry for the patient. A doctor may start scanning the patients oral cavity during a later visit without first inputting information identifying the patient. Intraoral scan application 115 may register and stitch together intraoral scans to generate a 3D surface and/or 3D model of a dental arch as set forth above, and may compare the 3D surface or 3D model to stored 3D models of dental arches of one or more patients. If a match or approximate match is found between the 3D surface or 3D model and a stored 3D model of a dental arch of a patient on file, then the patient may be automatically identified based on the match or approximate match. A 3D model generated based on the current visit may then be automatically associated with the patient and stored in the patient's file, and/or a prescription may be started for the patient, and patient information may automatically be added to the prescription.

Automatic Start and Stop of Scanning

Images (e.g., color images) without or with illumination (e.g., with minimal illumination) may be taken by scanner 150 at some frequency (e.g., at a frequency of approximately 10 Hz) in embodiments. The system may detect when the scanner 150 is starting to enter the oral cavity based on the generated images. In some embodiments, intraoral scan application 115 or scanner 150 processes received images to determine whether objects typically found in or around a mouth are identified (e.g., such as teeth, lips, tongue, etc.). For example, intraoral scan application 115 or scanner 150 may include a trained machine learning model trained to perform object classification of images and to detect the presence of certain objects associated with a face, mouth and/or oral cavity, such as teeth, lips, tongue, etc. When a transition from images in which no intraoral objects are detected to images in which intraoral objects are detected takes place, intraoral scan application 115 or scanner 150 may determine that scanner 150 has been inserted into a patient mouth. When the system detects that the scanner 150 has been inserted into an oral cavity, intraoral scanner 150 may automatically begin generating intraoral scans. This may include intraoral scan application 115 sending an instruction to begin scanning to scanner 150.

When a transition from images in which intraoral objects are detected to images in which no intraoral objects are detected takes place, intraoral scan application 115 or scanner 150 may determine that scanner 150 has been removed from a patient mouth. When the system detects that the scanner 150 has been removed from an oral cavity, intraoral scanner 150 may automatically stop generating intraoral scans. This may include intraoral scan application 115 sending an instruction to stop scanning to scanner 150. In some instances, intraoral scan application 115 may automatically begin generating one or more 3D models of dental arches and/or performing post processing and/or diagnostics on generated 3D models of dental arches responsive to detecting removal of the intraoral scanner 150 from a patient mouth.

Intraoral objects will start appearing in a field of view (FOV) of the scanner 150 (e.g., in the FOV of front cameras of the scanner 150 or a front of a FOV of the scanner 150), and will then be shown to move towards a back of the camera when the scanner 150 enters an oral cavity. For example, images of intraoral objects will initially appear first in the FOV of the front cameras of scanner 150 (if scanner includes multiple cameras) or in the front of the FOV of the scanner (e.g., if scanner includes just a single camera and/or a single FOV) and then in the FOV of back cameras of the scanner 150 or a back of the FOV of scanner 150 when the scanner is entering the oral cavity. Additionally, when the scanner 150 is removed from an oral cavity, intraoral objects will be shown to move in a reverse direction to the direction shown when the scanner 150 is inserted into an oral cavity. For example, images of intraoral objects will first stop appearing in the FOV of the back cameras of scanner 150 (if scanner includes multiple cameras) or in the back of the FOV of the scanner (e.g., if scanner includes just a single camera and/or a single FOV) and then will stop appearing in the FOV of front cameras of the scanner 150 or a front of the FOV of scanner 150 when the scanner is being removed from the oral cavity. Intraoral scan application 115 may detect movement of intraoral objects and/or the transition between detecting and not detecting intraoral objects, and may use this information to improve accuracy of a start and stop decision for scanning.

In addition to automatically starting and stopping scanning, the system can automatically start and stop one or more light sources based on the determination as to whether or not the scanner 150 is in an oral cavity. For example, for scanners 150 that use structured light (SL) projectors, the intraoral scan application 115 and/or intraoral scanner 150 can automatically turn on and off the structured light (SL) projectors. This can reduce or eliminate disorienting light projection onto objects in a room of a dental office when the scanner 150 is removed from a patient's mouth (referred to as a disco effect).

In embodiments, intraoral scan application 115 provides in a graphic user interface (GUI) feedback to show that the system understands where it is. This can include providing an indication (e.g., a visual indication) as to whether the intraoral scan application 115 has detected that the scanner 150 is inside of or outside of a patient's mouth. Additionally, or alternatively, intraoral scan application 115 may provide in the GUI an indication (e.g., a visual indication) of whether an upper dental arch is being scanned presently, whether a lower dental arch is being scanned presently, whether a patient bite is being scanned presently, whether a restorative object is detected, and so on.

Automatic Role Identification

A scanning process usually has several stages—so-called roles (also referred to as scanning roles). Three major roles are upper jaw role (also referred to as upper dental arch role), lower jaw role (also referred to as lower dental arch role) and bite role. The bite role refers to a role for a relative position of the upper jaw and lower jaw while the jaw is closed. Traditionally a user of scanner 150 chooses a target role by means of the user interface of intraoral scan application 115, and only after such a user input does scanning proceed. In embodiments, the intraoral scan application is configured to eliminate such user input and identify the role automatically while scanning. In embodiments, intraoral scan application 115 automatically determines whether a user is currently scanning teeth on an upper jaw (upper jaw role), teeth on a lower jaw (lower jaw role), or scanning both teeth on the upper and lower jaw while the patient's jaw is closed (bite role). Intraoral scan application 115 may then assign a detected role to intraoral scan data, 3D surfaces and/or 3D models from which the role was detected. Thus, intraoral scan application 115 may automatically determine whether a user is scanning an upper jaw, a lower jaw, or a bite, and label intraoral scans appropriately based on such determination. Additionally, or alternatively, 3D surfaces and/or 3D models generated from such intraoral scans may also be labeled with a determined role.

In some embodiments, a separate role is assigned to each preparation tooth and/or other restorative object on a dental arch. Thus, roles may include an upper jaw role, a lower jaw role, a bite role, and one or more preparation roles, where a preparation role may be associated with a preparation tooth or another type of preparation or restorative object. In addition to automatically identifying the upper jaw role, lower jaw role, and bite role, intraoral scan application 115 may also automatically identify preparation roles from intraoral scan data, 3D surfaces and/or 3D models. A preparation may be associated with both a jaw role (e.g., an upper jaw role or a lower jaw role) and a preparation role in some embodiments.

In some embodiments, intraoral scan application 115 uses machine learning to detect whether intraoral scans depict an upper dental arch (upper jaw role), a lower dental arch (lower jaw role), or a bite (bite role). In some embodiments, intraoral scan application 115 uses machine learning to detect whether intraoral scans depict an upper dental arch (upper jaw role), a lower dental arch (lower jaw role), a bite (bite role), and/or a preparation (preparation role). As intraoral scan data is generated, intraoral scans from the intraoral scan data and/or 2D images from the intraoral scan data may be input into a trained machine learning model that has been trained to identify roles. The trained machine learning model may then output a classification of a role (or roles) for the intraoral scan data. In some embodiments, intraoral scan application 115 generates a 3D surface by stitching together multiple intraoral scans, and inputs data from the 3D surface into a trained machine learning model that outputs a classification of a role (or roles) for the 3D surface. The same ML model may be used both for processing intraoral scan data and for processing data from a generated 3D surface. Alternatively, different ML models may be used for processing intraoral scan data and data from a 3D surface. The one or more ML models may process 3D data (e.g., 3D surfaces) or 2D data (e.g., height maps or projections of 3D surfaces onto a 2D plane). Intraoral scan application 115 may provide feedback via a graphical user interface (GUI) to show that the system understands where it is (e.g., whether a current role is an upper dental arch, a lower dental arch, a bite, or a preparation tooth).

Embodiments use machine learning to classify 2D images, intraoral scans, 3D surfaces, and/or height maps into their relevant scanning roles. One implementation uses a deep neural network to learn how to map an input image, intraoral scan, 3D surface and/or height map to human labeled scanning roles. The result of this training is a function that can predict labels of scanning roles directly from input images, intraoral scans, 3D surfaces, and/or height maps. Possible inputs can be individual height maps or intraoral scans, 3D surfaces, an occlusal view of a jaw generated from stitching together multiple height maps or intraoral scans and/or multiple jaw views (e.g., generated from stitching together multiple height maps and/or intraoral scans).

Use of individual intraoral scans and/or images (e.g., individual height maps) and/or data of 3D surfaces from multiple intraoral scans and/or images (referred to as multiple jaw views) to determine roles may enable choosing or identifying a moment when one role is changed to another role. For example, intraoral scan application 115 may automatically determine when a doctor has transitioned from scanning a bottom dental arch to scanning a top dental arch, or when the doctor has transitioned from scanning the top dental arch to scanning the bottom dental arch. Processing logic may additionally determine when a scan of a dental arch is complete, and may automatically proceed with generating a 3D model of the dental arch and/or perform one or more other operations responsive to such a determination. For example, intraoral scan application 115 may compute and show occlusal clearance information (e.g., such as via an occlusion map) and/or perform occlusal clearance calculations automatically (e.g., in another part of a screen than where a 3D surface or 3D model is shown) when the upper, lower and bite roles are all finished.

In some embodiments, intraoral scan application 115 continually or periodically determines roles associated with intraoral scans and/or 3D surfaces as the intraoral scans are received and the 3D surfaces are generated. Role classifications determined based on a single scan may be less accurate than role classifications determined based on data from multiple intraoral scans (e.g., from 3D surfaces or multiple jaw views). Since errors may be inevitable for individual predictions (e.g., based on a single intraoral scan), an aggregated solution may be used in some embodiments. For example, intraoral scan application 115 may make an initial classification for an intraoral scan, and may then make further classifications for additional intraoral scans that stitch to the initial intraoral scan and/or for a 3D surface generated from stitching of the initial intraoral scan to the additional intraoral scans. The further classifications may be more accurate than the initial classification. Accordingly, the accuracy of the role classification may continually improve as further intraoral scans are generated. Thus, a role associated with a segment of a dental arch may be correctly classified in real time, and can be further combined with corresponding segments of the same role/dental arch.

In an example, stitching may be incorporated so that classification is performed on an entire 3D surface (e.g., a segment of stitched scans). In another example, to achieve better accuracy intraoral scan application 115 can use a statistical approach based on classifications of multiple intraoral scans. For example, intraoral scan application 115 may classify a sequence of intraoral scans, and may then assign a classification to the entire sequence based on a majority of the classifications of the individual intraoral scans in the sequence. In one embodiment, intraoral scan application 115 uses a moving average of predictions, where the predominant classification among some number (e.g., 5, 10, 20, 50, 100, etc.) of the most recent intraoral scans is determined to be the role for those most recent intraoral scans.

Each prediction or classification of a role for an intraoral scan may be accompanied by an uncertainty value. The higher the uncertainty value, the lower the certainty that the prediction is correct. In one embodiment, the intraoral scan application 115 discards the most uncertain predictions. This may include discarding predictions that have an uncertainty that fails to satisfy some criterion (e.g., fails to meet a threshold, such as a 50% certainty threshold) and/or discarding a set number of predications with highest uncertainty values. Accordingly, a moving average of predications may be used to determine a role, where one or more predictions in the moving average have been discarded.

Usually it is better to remove moving tissues (lips, cheeks, tongue, etc.) from the inputs to make the final model cleaner. But in the context of scanning role identification it can be better to use the original data with moving tissues since moving tissues can provide additional information that can help to identify roles. For example, a tongue is generally associated with the lower jaw role, and the shape of lips is different for upper and lower jaws. All such specific features can give much better accuracy for role identification compared to a cleaned input (in which moving tissues have been removed from the scans). Thus, in embodiments the scan data that is input into the machine learning model to determine a role has not been processed by a moving tissue removal algorithm and/or has not had moving tissue removed.

A scanning role is only one of many possible features that can be identified given an input as described above. Other features could be identified as well. For example, intraoral scan application 115 may determine one or more additional classifications for intraoral scans, 3D surfaces, height maps, 2D images, and so on. Such determinations may be made using one or more trained machine learning models in embodiments. In one embodiment, a single machine learning model may be trained to assign multiple types of classifications to input intraoral scan data (e.g., including role classification as well as one or more additional types of classification). In one embodiment, different trained machine learning models are used to determine different types of classification. In one embodiment, intraoral scan application 115 determines for input intraoral scan data and/or intraoral 3D surface data whether the intraoral scan data depicts a lingual or buccal side of a jaw. In one embodiment, intraoral scan application 115 determines for input intraoral scan data and/or intraoral 3D surface data whether orthodontic treatment and/or restorative treatment is to be performed. In one embodiment, intraoral scan application 115 determines for input intraoral scan data and/or intraoral 3D surface data whether there any brackets and/or attachments detected on patient teeth, and optionally locations (e.g., segmentation) of such brackets and/or attachments. All such features can be identified concurrently from a single model and even support each other in terms of prediction accuracy in embodiments.

The accuracy of the identification of roles and/or other features such as those set forth above can be improved by segmentation of intraoral scan data and/or intraoral 3D surface data into dental classes, such as teeth, gums, excess material, and so on. One or more trained machine learning model may be trained to perform such segmentation of intraoral scan data and/or intraoral 3D surface data. The same machine learning model may perform such segmentation as well as one or more of the classifications set forth above. Alternatively, one or more separate machine learning model may perform such segmentation.

In embodiments, soft tissue classification (e.g., of tongue, cheek, lips, upper palate, etc.) is additionally performed using a trained machine learning model by inputting intraoral scans, height maps, images, 3D surfaces, projections of 3D models, etc. into one or more trained machine learning model.

In some embodiments, input intraoral scan data/3D surface data is limited to intraoral scans (e.g., height maps) and/or 3D surfaces (or projections of 3D surfaces onto one or more plane) generated by stitching together such intraoral scans. In further embodiments, input layers/data that are used (e.g., that is input one or more trained machine learning model) include color images (e.g., color 2D images) and/or images generated under specific lighting conditions (e.g., NIRI images). Scanner 150 may separately generate intraoral scans (which include height information) and color 2D images and/or other 2D images. The intraoral scans and 2D images may be generated close enough in time that they depict the same or close to the same surface. The 2D images (e.g., color 2D images) may provide additional data that improves distinction between teeth and gums, tongue, and so on due to differences in color between these objects.

To better account for multiple inputs, in some embodiments a recurrent neural network (RNN) is used to classify roles and/or one or more additional features as set forth above. Use of an RNN allows the system to identify features on the basis of a sequence of scans, and can improve accuracy. In some embodiments, one or more trained machine learning models (which may or may not be an RNN) include multiple input layers, where each of the multiple input layers may receive a separate intraoral scan. The trained ML model may then make a prediction or classification (e.g., of a scanning role) based on the multiple scans. This may be combined with input layers for additional information such as color 2D images and/or NIRI images.

In some embodiments, as set forth above, processing logic automatically identifies scanning roles and automatically assigns such automatically identified scanning roles to 3D surfaces, intraoral scans and/or 3D models of dental arches. Alternatively, in embodiments a user may manually select a scanning role for one or more intraoral scans, a 3D surface of a dental arch and/or a 3D model of a dental arch. In such an embodiment, processing logic may automatically perform role classification as described herein, and may output a warning if a different role is detected than a role that was input by the doctor. In one embodiment, processing logic outputs a notice stating that an alternative role was detected, and asking if the doctor would like the alternative role to be assigned to the intraoral scan(s) 3D surface and/or 3D model.

Multi-Bite Detection

Related to detection of a bite role, the intraoral scan application 115 in embodiments can also detect a multi-bite scenario. In a multi-bite scenario, different bites may be recorded, which show a different relation between the upper and lower jaw. In addition to classifying a bite role, intraoral scan application 115 may compare scan data and/or analysis of scan data for different intraoral scans classified as bites. Alternatively, or additionally, intraoral scan application 115 may apply machine learning to classify multi-bite scenarios. Intraoral scan application 115 may detect discrepancies between bites, and determine whether such discrepancies merely represent variations of a single bite or whether such discrepancies represent multiple different bites (referred to as multi-bite detection). In some instances, the multiple bites are at the direction of the doctor, who may have instructed a patient to bite in different ways. The system in embodiments can automatically detect, using the application of machine learning or based on comparison of multiple bite scans, such a multi-bite scenario.

In an example, a doctor may need to go in and out of the oral cavity with the scanner 150 and wait a few seconds. Scans of bite parts may be recorded separately. Sometimes unintended motion can create discrepancies in the scans of the bites. To understand if this is an intended multi-bite, or an error, the system may output an indication of a potential multi-bite, and ask the doctor for confirmation. Alternatively, the system may automatically make a determination as to whether or not a multi-bite is present. Intraoral scan application 115 may take into consideration the bite locations (e.g., the difference between the different bites) and/or times of taking the scans associated with the bites when making such a determination. This feature may be useful in cases that include bite elevation.

With regards to multi-bite detection, a few possible scenarios include: (a) both sides of the mouth give the same bite relation, indicating that everything is okay and that it is not a multi-bite case; and (b) both sides of the mouth give different bite relation, indicating a need to determine if it is a distortion or a multi-bite case. In embodiments, to decide whether a detected discrepancy is due to distortion or a multi-bite case, the system may take into consideration both time lag between two bite scans and a magnitude of the change or difference in the bite between the two scans. In on embodiment, a time lag (e.g., which may be measured in seconds) between two bite scans is determined, and the time lag is compared to a time lag threshold. The time lag threshold may be, for example, 1 second, 2 seconds, 4 seconds, 10 seconds, and so on. In one embodiment, the two bite scans are compared, and a difference in the bite between the two scans is computed (e.g., which may be measured in microns). The bite difference may then be compared to a bite difference threshold. The bite difference threshold may be, for example, 50 microns, 75 microns, 100 microns, 150 microns, 200 microns, and so on. In one embodiment, if the time lag exceeds the time lag threshold and the bite difference exceeds the bite difference threshold, intraoral scan application 115 determines that the two bite scans represent a multi-bite scenario.

Automatic Identification of Restorative Objects

In some embodiments, intraoral scan application 115 is able to automatically identify intraoral scans and/or 3D surfaces that depict a restorative object. The restorative object may be a preparation or a scan body, for example. Restorative objects may also include, for example, dental prosthetics such as implants, crowns, inlays, onlays, caps, veneers, and so on. While the term preparation typically refers to the stump of a preparation tooth, including the margin line and shoulder that remains of the tooth, the term preparation herein also includes artificial stumps, pivots, cores and posts, or other devices that may be implanted in the intraoral cavity so as to receive a crown or other prosthesis. Embodiments described herein with reference to a preparation tooth also apply to other types of preparations, such as the aforementioned artificial stumps, pivots, and so on. In some embodiments, processing logic automatically identifies restorative objects in intraoral scans, images, 3D surfaces and/or 3D models. For example, processing logic may perform pixel-level classification of intraoral scans, images, 3D surfaces and/or 3D models, where at least one of the classes is for a restorative object.

In some embodiments, intraoral scan application 115 includes one or more trained machine learning models (e.g., a neural network) trained to perform classification of dental sites, where at least one class is for a restorative object. The trained machine learning model(s) may perform image level classification/scan level classification, may perform pixel-level classification, or may perform classification of groups of pixels. Traditionally, a doctor manually identifies restorative objects. Embodiments provide an improved user experience by eliminating the need to for a doctor to manually identify restorative objects. In embodiments, multiple features (e.g., types of restorative objects) can be identified concurrently from a single trained machine learning model.

Restorative treatment cases include very specific objects such as implants, scan bodies and so-called preparations. The identification of such objects is useful for further processing and treatment. Manual identification is very time consuming and error prone. Embodiments eliminate manual identification/input of restorative objects.

In one embodiment, the intraoral scan application 115 uses machine learning to classify intraoral scan data/intraoral 3D surface data into relevant dental classes, which can include preparations, scan bodies, regular teeth, and so on. One implementation uses a deep neural network to learn how to map an input image to human labeled dental classes, where the dental classes include regular teeth and one or more restorative objects. The result of this training is a trained machine learning model that can predict labels directly from input scan data and/or 3D surface data. Input data may be individual intraoral scans (e.g., height maps), 3D surface data (e.g., a 3D surface from multiple scans or a projection of such a 3D surface onto a plane) and/or or other images (e.g., color images and/or NIRI images). Such data may be available in real time while scanning. Additionally, intraoral scan data associated with an individual scan may be large enough (e.g., scanner may have a large enough FOV) as to include at least one tooth and its surroundings. Given an input based on a single intraoral scan, the trained neural network can predict if the scan (e.g., height map) contains any of the dental classes described above. The nature of such prediction may be probabilistic: for every class there is a probability of it being presented on the intraoral scan. Such approach allows the system to identify areas on a 3D surface and/or a 3D model generated from the intraoral scan that relate to restorative objects and thus should be treated differently than natural teeth. For example, such areas can be scanned with higher resolution than other areas not including restorative objects and/or a higher resolution may be used for 3D surfaces generated from scans including restorative objects. Accordingly, the system may automatically determine whether a scan depicts a restorative object, and when a 3D model is generated using that scan further processing may be performed to generate a higher resolution for that region of the model. As a result, the restorative object in that 3D model may have a higher resolution than other objects (e.g., other teeth) in that 3D model. Thus, a 3D model with variable resolution may be generated in embodiments.

In some embodiments, intraoral scan application 115 uses a higher resolution to depict other types of dental objects in addition to or instead of using a higher resolution to depict restorative objects. For example, intraoral scan application 115 may identify a boundary of a gum and a tooth (or multiple teeth and surrounding gingiva), and may use a higher resolution for such a boundary in a 3D model. In another example, intraoral scan application may identify an interproximal region between teeth (e.g., a tooth to tooth boundary), and may use a higher resolution to depict the interproximal region in a 3D model. In another example, intraoral scan application can detect a margin line and depict the margin line in a 3D model using a higher resolution.

In one embodiment, a 3D model is initially generated at a first resolution (or portions of the 3D model are initially generated at the first resolution), and a smoothing and/or simplifying operation is performed to reduce the first resolution to a lower second resolution for one or more regions of the 3D model or of one or more of the portions of the 3D model (e.g., by reducing a number of points, vertices and/or polygons per unit area). Two techniques that may be used to simplify a 3D surface are point removal (in which a percentage of points in a region are deleted) and edge contraction (in which two endpoints of a triangle edge are replaced with a single point, and triangles are then redrawn). For example, intraoral scan application 115 may identify restorative objects, tooth to gum borders, margin lines and/or tooth to tooth borders in a 3D model. Processing logic may then reduce a resolution of those areas that do not include the identified restorative objects, tooth to gum borders, margin lines and/or tooth to tooth borders in the 3D model. In some embodiments, the multi-resolution 3D model may include more than two different resolutions. For example, gums may be represented with a first resolution that is a lowest resolution, natural teeth other than regions of the teeth that border other teeth or gums may be represented with a second resolution that is a higher resolution than the first resolution, and tooth to gum borders, restorative objects and tooth to tooth borders may be represented with a third resolution that is higher than the second resolution. In some instances, a margin line of a preparation tooth may be represented with a fourth resolution that is higher still than the third resolution.

In some embodiments, intraoral scan application 115 generates a multi-resolution 3D model of a dental arch using the determination of whether or not intraoral scans/3D surfaces depict a restorative object and/or another type of object to be represented using a higher resolution. Intraoral scan application 115 may use a first resolution for portions of the 3D model that depict restorative objects, margin lines, interproximal areas, tooth to gum boundaries and/or other regions identified for higher resolution and may use a second resolution for portions of the 3D model that do not depict restorative objects or other regions identified for higher resolution. Restorative objects in a 3D model of a dental arch may benefit from increased resolution since these regions may be used, for example, to determine a size and/or shape of an interior surface of a prosthodontic to be placed on the restorative object. Similarly, a margin line, interproximal region, and/or tooth to gum boundary may benefit from increased resolution. However, increasing resolution of other regions of a 3D model may not be beneficial, and may unnecessarily increase processor utilization, memory utilization, and so on. Multi-resolution 3D models of dental arches provide the advantages of high resolution for restorative objects and optionally other regions such as a margin line, interproximal region and/or tooth to gum boundary and the advantages of lower resolution for a remainder of a 3D model of a dental arch.

After an intraoral scanning process is complete, the resulting 3D model may have a surface that appears rough and/or a file size of the 3D model may be too large, creating problems with saving to storage and/or transmitting the file containing the 3D model. As set forth above, in some embodiments, a higher resolution is initially used to depict one or more of the types of dental objects in a 3D model and a lower resolution is initially used to depict one or more other types of dental objects in the 3D model. Alternatively, a 3D model with a single resolution may be initially generated. In either case, after the 3D model is generated, a smoothing and/or simplification operation may be performed on one or more regions of the 3D model to reduce a resolution of the 3D model at the one or more regions. This enables the intraoral scan application 115 to avoid over-smoothing or over-simplifying of areas of interest (thereby hiding dental features such as a margin line, tooth to gum border, tooth to tooth border, tooth features, and so on) and/or of under-smoothing or under-simplifying other areas. Thus, a high resolution may be preserved in areas of interest, while smoothing and/or simplifying may be performed for areas not of interest to reduce the resolution at those areas not of interest. Areas of interest may be identified by inputting the 3D model, portions of the 3D model, projections of the 3D model onto one or more planes and/or intraoral scans used to generate the 3D model into a trained ML model that has been trained to perform dental object classification (e.g., pixel-level classification of dental objects) and/or by applying a cost function to the outputs of the trained ML model. This may include identifying restorative objects, natural teeth, gingiva, tooth to tooth borders, tooth to gum borders, margin lines, and/or other dental objects or classes.

In some embodiments, different regions may have their resolutions reduced by different amounts. For example, areas comprising representations of gums (which may not be areas of interest) may have a resolution reduced by a maximum amount, while areas comprising representations of natural teeth (which may also not be areas of interest) may have a resolution reduced by a lesser amount. Areas of interest (AOIs) may include restorative objects, tooth to tooth borders, tooth to gingiva borders, and/or margin lines, for example. In embodiments, AOIs are user selectable. For example, a user may select from a drop-down menu which types of dental objects or classes correspond to AOIs.

For better localization of target objects, the system can divide a height map into zones (grid-like) and detect restorative objects for every such zone. A zone may include a patch of pixels, or example. As a variation of such an approach, a central zone can be used so that an object will be identified only if it fully presented on the intraoral scan and was not just partially viewed in the intraoral scan. For example, if a restorative object is identified in a central region of an intraoral scan, then the intraoral scan may be classified as a scan of a restorative object. However, if the central region of the intraoral scan does not include a restorative object (even if some other region of the intraoral scan does include a restorative object), then the intraoral scan may not be classified as a scan of a restorative object.

In some embodiments, the system can not only identify presence of restorative objects on an intraoral scan and/or 3D surface (e.g., on a height map), but also can also make segmentation of the intraoral scan and/or 3D surface according to any of the dental classes discussed herein. Thus, every pixel of the intraoral scan and/or 3D surface can be classified as belonging to a specific dental class. This approach allows for better localization of restorative objects and eventually performs a full segmentation of the 3D model by combining segmentations of intraoral scans.

For better accuracy, additional inputs can be used, such as a color layer, a NIRI layer, layers for multiple scans, and so on as discussed elsewhere herein. The restorative objects identification can be combined with other identification problems like teeth/gums/excess material segmentation, brackets/attachments detection, role detection, and so on.

Automatic Prescription (Rx)

In embodiments, as set forth in further detail below, intraoral scan application 115 may automatically generate prescriptions for treating patients. Intraoral scan application 115 may automatically generate prescriptions for orthodontic treatment and/or restorative treatment. Prescriptions for orthodontic treatment may include a treatment plan to apply a sequence of aligners to a patients teeth to correct malocclusions, for example, Prescriptions for restorative treatment may include information for a cap, bridge, denture, crown, and so on.

Different clinics may specialize in just orthodontic treatment, in just restorative treatment, or in both orthodontic and restorative treatment. The dental practice information may be used to automatically determine whether to generate an orthodontic treatment prescription or a restorative treatment prescription. For example, for orthodontic clinics a determination may be made automatically to generate an orthodontic treatment prescription. For a clinic that performs just restorative treatment or both restorative and orthodontic treatment, further information may be used to automatically generate a prescription.

In some instances, a doctor may take a pre-scan of a patient's dental arch (e.g., before any treatment is performed). A pre-scan 3D model of the patient's dental arch may be generated based on the pre-scan. The intraoral scan application 115 may save the pre-scan and/or pre-scan 3D model to a patient record, and may identify that saved scan/3D model as a pre-scan/pre-scan 3D model. In an example, a pre-scan 3D model may be generated before a tooth is ground to form a preparation tooth. The pre-scan 3D model may provide information for a shape, coloration, position, etc. of a tooth before that tooth is ground to form a preparation tooth. The pre-scan 3D model may then be used for various purposes, such as to determine how much tooth has been ground to generate the preparation, to determine a shape of a prosthodontic, and so on.

In some instances the intraoral scan application 115 (or a doctor or clinic) may have access to older patient scans and/or 3D models of dental arches for a patient. When the system has access to an old patient scan/3D model, the system can use this older scan and/or 3D model for multiple purposes. A non-exhaustive list of uses for the older scan and/or 3D model include: (a) detecting patient name (as described above), (b) detecting which tooth is being treated, (c) eliminating a need for a pre-scan, and/or (d) computing a target crown structure, and simplifying a margin line (where the new shape and old tooth have identical shape). For b and c, a fine local registration of the specific tooth may be wanted to improve difference accuracy (e.g., if the older scan is from significant past time).

In an example, intraoral scan application 115 may compare a current intraoral scan (or a 3D surface or 3D model generated from current intraoral scans) to previous intraoral scans (or 3D surfaces or 3D models generated from previous intraoral scans) of the patient. Based on the comparison, intraoral scan application 115 may determine differences between the current teeth of the patient and the previous teeth of the patient. These differences may indicate which tooth or teeth are being treated. This information on teeth being treated may be added to a prescription.

In another example, intraoral scan application 115 may provide an indication to a doctor that previous scans (or 3D models) of a patient's dental arch are existent. Based on such an indication, the doctor may choose not to perform a pre-scan. In such a scenario, the previously generated scans and/or 3D model of the patient's dental arch may be used for the same purposes that a pre-scan 3D model would normally be used for. For example, a doctor may skip performing a pre-scan prior to forming a preparation tooth.

In another example, intraoral scan application 115 may use one or more older patient scans (or 3D models generated from older patient scans) to compute a target crown structure and/or a margin line. For example, the one or more older 3D models may provide an outer shape for a crown.

Once an intraoral scan is received, a basic analysis of the scan may be performed. Intraoral scan application 115 may search for one or more different types of issues. Types of issues that may be searched for include: (a) search for preparation teeth and/or other preparation objects and (b) search for scan bodies. The search for preparation teeth and/or preparation objects may be performed via 3D image processing and/or via application to machine learning (ML) classification, which is described in greater detail below. The search for scan bodies may be performed via ML classification, as further described below.

A prescription (Rx) may be generated and/or filled automatically with recommendations based on detection of preparation teeth (e.g., including determination of location and/or shape of preparation teeth) and/or detection of scan bodies (e.g., including determination of location, spacing, angles, shape, type, etc. of scan bodies). The prescription may include a suggestion of an appropriate dental appliance to order from a lab based on the preparations. Examples of dental appliances that may automatically be added to a prescription include a crown, a bridge, an inlay, a veneer, and a denture. The appropriate dental appliance (e.g., prosthodontic) may be determined based on a geometry, location and/or number of restorative objects (e.g., preparation teeth) in embodiments. Clinical decisions for the determined prescription, such as single crowns or bridge, for example, may be rule based or can also be learned (e.g., using machine learning). For example, a machine learning model may be trained using a training dataset including inputs of 3D surfaces and/or projections of 3D surfaces and types of dental prosthetics that were placed at preparation teeth and/or other restorative objects in the 3D surfaces. The machine learning model may be trained to receive as an input a 3D surface/3D model or one or more projections of a 3D surface/3D model and to output a prediction of a dental prosthetic to be used.

The system may recommend a material for a dental prosthetic based on previous history (general statistics, doctor past statistics, lab material availability, etc.), and may recommend color based on contra-lateral and neighboring teeth. The prescription may include one or more color for a crown, bridge, etc. Color may be decided based on best estimates of neighboring teeth and/or on a pre-treatment scan and/or previously generated scan. A determined color may automatically be added to a prescription.

The system may recommend a lab (e.g., dental lab 110) to use based on labs previously used by the doctor. Information on a lab to use, a material to use, a color to use, and so on may automatically be added to the prescription in embodiments. Once a prescription is generated, the prescription may automatically be sent to a dental lab 110 indicated in the prescription. The prescription may be reviewed and approved by a doctor before it is sent to the dental lab 110.

The system may automatically generate a prescription for restorative treatment and/or orthodontic treatment, which may be a prescription for a crown, cap, bridge, aligners, etc. The prescription may include an automatic selection of particular materials and/or dental labs, for example. Decisions on materials and/or a dental lab may be based on historical statistics and/or based on application of machine learning. For example, a machine learning model may be trained using training data including 3D surfaces/models of dental arches and/or preparations with labels of materials and/or labs that were used. The machine learning model may be trained to receive a 3D surface or one or more projections of a 3D surface of a dental arch or preparation, and to output a prediction of a material and/or lab to use. Preferences may be related to case type, user name, type of treatment, area of treatment, etc. The system may learn doctor preferences associated with these properties, and get a default decision right a majority of the time based on such learning. When the system sees that there is no one right choice, the system may show multiple (e.g., two) options for the doctor to choose between.

A doctor may review the generated 3D model and/or other properties of the automatically generated prescription. The doctor may make any changes that they deem appropriate to the 3D model and/or to other aspects of the prescription. This may include generating one or more additional intraoral scans and updating the 3D model using the additional intraoral scans, changing materials for a prosthodontic, changing a lab to send the prescription to, changing a color of a prosthodontic, and so on. Every decision by the doctor may go into a learning data base of the specific doctor and used to update one or more machine learning models that may be trained specifically to the preferences of that doctor. Once the doctor (e.g., dentist) has determined that the 3D model and/or prescription is acceptable, the doctor may instruct computing device 105 to send the prescription to computing device 106 of dental lab 110. Alternatively, such instructions may automatically be generated and sent.

Intraoral scan application 115 and/or a separate dental modeling application may analyze the 3D model to determine if it is adequate for manufacture of a dental prosthetic. Intraoral scan application or the dental modeling application may include logic to identify the margin line and/or to modify the surface of one or more dental sites and/or to modify a margin line. If the 3D model is deemed suitable (or can be modified such that it is placed into a condition that is deemed suitable), then the dental prosthetic may be manufactured from the 3D model.

In embodiments, intraoral scan application 115 analyzes a generated 3D surface or 3D model and determines one or more quality ratings for the 3D model or surface. Different quality ratings may be assigned to different portions of the 3D model, such as to portions of a margin line, areas of a preparation tooth, areas surrounding a preparation tooth, and so on. Intraoral scan application 115 may provide feedback on areas that fail to meet certain quality criteria and that might benefit from rescanning to generate a better quality 3D model of a dental site. For example, intraoral scan application 115 may determine an amount of scanned gums or gingiva around teeth, and in particular around a preparation tooth. The amount of scanned gums may be compared to a scanned gums threshold, and if the detected amount of scanned gums surrounding a tooth is less than the threshold, then intraoral scan application 115 may flag that tooth for receiving further scans of gums. In an example, it may be beneficial to scan at least 3 mm of gingival tissue surrounding every tooth. Accordingly, if an outer border of any scanned region of gum tissue around a tooth is less than 3 mm from the tooth, then that region of the gum tissue and/or the tooth may be flagged to the doctor for further scanning.

In another example, intraoral scan application 115 may detect missing areas for which intraoral scan data was not generated. This can include missing scan data of a palate, unscanned teeth, incomplete scanning of teeth, holes or voids in scanning information (e.g., voids above a threshold size), and so on. Such missing areas may be flagged to the doctor for further scanning. In another example, intraoral scan application 115 may detect whether a scanning protocol was followed, and may flag one or more deviations from the scanning protocol. For example, intraoral scan application may determine whether one or more occlusal scans are missing. In another example, intraoral scan application 115 determines whether any portion of a margin line is unclear, poorly formed, or obscured, as discussed above. In another example, intraoral scan application determines a color quality of an area based on 2D color images generated of the area. If insufficient 2D color images of an area have been generated, then the color quality for that area may be low.

Accordingly, intraoral scan application 115 may flag an area for further scanning to receive additional color information for that area. In another example, surface quality (e.g., number of known points on a surface) may depend on a number of scans that have been received for that surface. With a few number of scans for a surface at a particular area, the area may be produced but with low certainty or low quality. Intraoral scan application 115 may flag such areas that have too few data points for further scanning.

Generally after a doctor completes an intraoral scan and a virtual 3D model has been generated, the doctor manually moves the model in 3D to determine whether the model is adequate. In embodiments, the system automatically determines and generates a rotation path and/or a zoom sequence as the doctor would have done after scanning, and after completion of a preparation. This may then be played back to the doctor automatically. The system may learn expected moves, zooms, rotations, etc., and create a trajectory. The system may possibly additionally or alternatively show multiple views on the screen at once with or without motion. If problem areas have been identified, then the system may generate arrows or other identifiers pointing to and/or emphasizing those problem areas (e.g., like unclear margin line or small distance from opposing jaw). The automatically generated trajectory may additionally or alternatively zoom in on the identified problem areas.

Restorative Workflow

In some embodiments, the intraoral scan application 115 automatically performs or follows a restorative workflow. The restorative workflow is one of the most complex workflows to operate (manually or automatically) in dentistry, and typically it takes significant time for a doctor to learn how to perform a restorative workflow. In embodiments, may aspects of the restorative workflow are automated, which saves considerable time and reduces complexity for the doctor. Additionally, the automated restorative workflow can reduce training time for training doctors to use the intraoral scan application 115.

In embodiments, a restorative workflow may work with pre-scanning or without pre-scanning. In some embodiments, a doctor may generate a pre-scan 3D model of a patient's oral cavity prior to performing one or more restorative operations, such as grinding a tooth to form a preparation, pulling a tooth, inserting an implant, and so on. In some embodiments, a previous 3D model of a patient's dental arch may already be existent, which may be used for the same purposes that a pre-scan 3D model is used for.

The intraoral scan application 115 may have a full segmentation ability and identification ability of teeth and gums, scan bodies and other common elements in the oral cavity, as set forth above. Intraoral scan application 115 can perform these identifications and/or segmentations from intraoral scans and/or from 3D surfaces as set forth above. In one embodiment, to perform the automatic restorative workflow, segmentation of teeth, gums, scan bodies and preparation teeth is automatically performed.

One complication with a restorative workflow is that the doctor may scan a tooth or other dental site multiple times over the course of preparing the tooth or other dental site, and between each scan the doctor may make changes to the dental site. A 3D surface and/or 3D model may be generated based on an initial set of intraoral scans. Then a second set of intraoral scans may be generated after the doctor has made some changes to the dental site (e.g., by grinding a tooth). Traditionally, the doctor needs to mark on the 3D model or 3D surface that includes the dental site in some way to identify what parts of the 3D model/3D surface to keep and what parts should be overwritten using data from the new set of intraoral scans. The system may assume that the change between sets of intraoral scans (e.g., rework of a preparation, removal of a dental wire, addition of a dental wire, etc.) all happens between scans.

In embodiments, one or more criteria may be used to determine that a possible change has been made to a 3D model or 3D surface of a dental site. In one embodiment, each time the doctor takes out the scanner 150 from the patient's mouth and stops the scanning, the intraoral scan application 115 will measure the amount of time passed between scans. The elapsed time between scans may be compared to a time threshold. The time threshold may be, for example, 10 seconds, 30 seconds, 1 minute, or other time threshold). If the elapsed time exceeds the time threshold, intraoral scan application 115 may determine that a 3D surface/3D model has potentially been modified.

In some embodiments, the scanner 150 and/or computing device 150 includes a microphone. The microphone may receive audio between scans and assess the audio to determine whether particular sounds are detected from the audio, such as the sound of a drill, which is a distinctive loud sound. In one embodiment, audio features (e.g., an audio fingerprint) of the received audio is compared to stored audio features (e.g., an audio fingerprint) associated with a drill or other tool used to modify a dental site. This may include generating an audio fingerprint from the audio using an audio fingerprinting algorithm. If the audio features of the received audio match stored audio features associated with modification of a dental site (e.g., of a dental drill), intraoral scan application 115 may determine that a 3D surface/3D model has potentially been modified.

Intraoral scanner 150 may include one or more motion sensors (e.g., an accelerometer and/or gyroscope) usable to detect motion of the scanner 150. Data from the motion sensors may be assessed to determine whether the scanner 150 leaves the hand of the doctor (e.g., is placed on a surface or in a cradle) between scans. In one embodiment, a particular motion profile may be indicative of removal of the scanner from a patient's mouth and/or placement on a surface. Additionally, lack of any motion for a threshold time duration may be indicative that the scanner 150 has been put down by the doctor (e.g., on a surface or in a cradle). Thus, the received motion data may be compared to one or more motion criteria to determine whether the scanner 150 has been set down between scans. Data from the motion sensors may additionally or alternatively be used to determine whether scanner 150 remained still in the doctors hand between scans (e.g., if the doctor had a short rest). The received motion data may be compared to one or more additional motion criteria to determine whether the scanner 150 remained at rest in the doctor's hand. Such criteria may include, for example a second threshold time duration that is shorter than the threshold time duration usable to determine that scanner 150 has been set down by the doctor. Such criteria may further include a negative rule, where if a motion profile indicative of removal of the scanner from a patient's mouth and/or placement on a surface is identified, then the rule for resting in hand is not satisfied.

Assuming scanning has stopped, and some time has passed between scans (e.g., one or more of the criteria set forth above are satisfied), the system may assume a possible change in the 3D surface/model. The changes can be related, for example, to a gum line, to margin line, and/or to a shape of a preparation. For each preparation tooth, the system decides if there was a change to a 3D surface associated with the preparation tooth. This determination can be made easier by finding an exact position of the preparation tooth represented in the new scan relative to the already generated 3D surface/model from the surrounding unchanged features (e.g., unchanged tissue). The system knows what pixels in the 3D surface/model depict a preparation and which pixels depict surrounding features as well as which pixels in the new intraoral scan depict the preparation and which pixels depict surrounding features based on an earlier performed classification and segmentation.

The system can review the new region of the preparation tooth and compare the specific parts of the preparation tooth from the new scan to the specific parts of the preparation tooth in the 3D surface/model. For example, a dental wire taken out will change the gum shape of the surrounding area of a preparation tooth. The system does this by 3D comparisons between the 3D surface and the new intraoral scan in an embodiment. Intraoral scan application 115 may then update the 3D surface or 3D model by replacing data associated with some portions of the preparation tooth or an area surrounding a preparation tooth with data from one or more new intraoral scans. Intraoral scan application 115 may then display the modified 3D model or 3D surface of the dental arch. In some embodiments a GUI of the intraoral scan application 115 shows a current surface post change as well as a previous surface as it existed pre-change. The differences between the post-change surface and the pre-change surface may be shown, for example, with dashed lines, a see-through mesh, or other visualization that is different from a visualization of the current post-change surface.

In one embodiment, the system will take the shape of the tooth as revealed by the new parts of the scan, under where the gum line used to be. But the system can also keep a representation of where the gum line used to be. This may be a better representation of a surface (note that it may not be a single surface but multiple surfaces), and the system may check if it can give a better clinical outcome if used. The system can also detect a change between intraoral scans (as opposed to a change between a scan and a 3D surface or 3D model) of the region (assuming near same angle of view between the scans). In some cases, the system can observe that a dental wire is already in between a gum and a tooth. For this case, the system may expect one or more next scans to be without the dental wire. The system can also detect changes based on bleeding from the gums and/or excess saliva.

In some embodiments, intraoral scan application 115 detects margin lines and/or dental retraction lines on the scans and/or 3D surface/model. Intraoral scan application 115 may determine that a region within a margin line and/or dental retraction line is to be modified and that regions outside of the margin line and/or dental retraction line is not to be modified. Another change that a doctor may make to a preparation tooth is to rework the preparation tooth, such as by further grinding of the preparation tooth. Sometimes this is performed after occlusal clearance shows a too small distance between the preparation tooth and an opposing tooth on an opposing dental arch. The preparation tooth may also be reworked after a shape analysis of the preparation tooth indicates that the shape should be modified, after reports of a problematic insertion path for a prosthodontic over the preparation tooth (e.g., if an insertion path is blocked), or when the system reports a low-quality margin line. For each of these cases, the doctor will usually rework the preparation tooth.

With each change, the system will need to understand what part of a dental site changed, and remove that changed part from the previous 3D representation, and replace that changed part with information from the new scan data. In some embodiments, this may be facilitated with the aid of the scanner 150 knowing where it is accurately based, for example, on motion data and/or assessment of intraoral scans to determine movements of the scanner 150 between scans.

In an example, intraoral scan application 115 may include logic for automatically identifying (e.g., highlighting) a margin line in an image and/or 3D model of a preparation tooth. This may make it easier for the doctor to inspect the margin line for accuracy. Intraoral scan application 115 may additionally mark and/or highlight specific segments of the margin line that are unclear, uncertain, and/or indeterminate. Additionally, or alternatively, intraoral scan application 115 may mark and/or highlight specific areas (e.g., a surface) that is unclear, uncertain and/or indeterminate. For example, segments of the margin line that are acceptable may be shown in a first color (e.g., green), while segments of the margin line that are unacceptable may be shown in a second color (e.g., red). In one embodiment, a trained machine learning model is used to identify a margin line in a preparation tooth.

Intraoral scan application 115 may additionally or alternatively include logic for automatically correcting a surface of a tooth in an image and/or 3D model of the tooth and/or for modifying a margin line of a preparation tooth that is unacceptable. This may be referred to as "virtual cleanup" or "sculpting" of the margin line. In one embodiment, intraoral scan application 115 includes logic for performing such virtual cleanup or sculpting as set forth in US Publication No. 2021/0059796, entitled "Automated detection, generation and/or correction of dental features in digital models," which is incorporated by reference herein.

In one embodiment, a trained machine learning model is used to modify an image and/or 3D model of a preparation tooth, such as to correct a margin line of the preparation tooth (e.g., to sculpt or perform virtual cleanup of the margin line). An updated margin line (e.g., a virtually cleaned up or sculpted margin line) may be indicated in the modified image and/or the modified 3D model. A doctor may inspect the modified margin line to determine if it is accurate.

In an example, a part of a real margin line of a scanned preparation tooth may not be sufficiently clearly defined in the 3D model. For example, during the initial 3D data collection step, for example via scanning, that resulted in the first 3D virtual model being generated, a part of the physical dental surface may have been covered with foreign material, such as for example saliva, blood, or debris. The part of the physical dental surface may also have been obscured by another element such as for example part of the gums, cheek, tongue, dental instruments, artifacts, etc. Alternatively, for example, during the initial 3D data collection step (e.g., via scanning) that resulted in the first virtual 3D model being generated, the region may have been distorted or otherwise defective and may not properly correspond to a physical dental surface (e.g., due to some defect in the actual scanning process). Automatic correction may be performed to remove the representation of the foreign material and show the underlying tooth surface and/or margin line. If automatic correction of the dental surface and/or margin line was performed, then the obscured region may be created, and the obscuring object may be removed in the 3D model.

When a change to a dental site is small (e.g., a few tens of microns to a few hundred microns) it may be difficult to detect the change and determine how to update the 3D surface and/or 3D model. On the other hand, when a change to a dental site is larger (e.g., on the order of millimeters), there is no place to confuse and it is easy to make a replacement to the 3D surface and/or 3D model. Such small changes may be when 3D changes are on the scale of a few tens of microns, up to few hundred microns. Changes of this magnitude can sometimes be in the range of noise, and averaging with previous scans (as common during scanning) would mix up and merge together the changes with previous depictions of the changed dental site. Due to this, in some embodiments each scan will not average with previous scans, until a decision can be made as to whether a change has been made to the dental site. Additionally, even after a decision is made, recordings of the different scans may be retained, so that the decision can be changed if new information or user guidance is given indicating that a change occurred where no change was detected or that a change did not occur where a change was detected.

A small difference at a dental site between earlier scans generated before a modification of the dental site and later scans generated after the modification of the dental site may be at an error level per surface point of the scans. However, differences will generally be detected for an area that includes multiple points rather than at a single point. Such differences of an area of a dental site can be represented by creating a difference map between the earlier scans (generated prior to the modification) and the later scans (generated after the modification). A low pass filter may be applied to the difference map to determine if differences are point differences or area differences. Point differences are generally noise, and area differences have a high probability of being actual differences in the dental site.

Additionally, intraoral scan application 115 may be able to detect particular types of common differences between a 3D model or 3D surface and intraoral scans generated after a change to a dental site depicted in the 3D model or 3D surface. For example, differences in some areas (like when taking out a dental retraction cord) will have a specific place and be around the tooth. Intraoral scan application may include one or more rules for detecting signs of such common differences and/or may include one or more machine learning models that have been trained to receive data from two intraoral scans (or data from two sets of intraoral scans) and to identify particular types of differences between the data from the two intraoral scans or from the two sets of intraoral scans.

In one embodiment, in cases where the intraoral scan application 115 automatically makes a decision as to whether detected differences are associated with modifications to a dental site or with noise and/or an error, a GUI of intraoral scan application 115 will show these results (e.g., in some highlighted manner). This may include showing a first 3D surface that results from a decision made by intraoral scan application 115 and optionally showing changes from a previous 3D surface or 3D model. Intraoral scan application 115 may also show a second 3D surface that would result from a different decision alongside the first 3D surface. Intraoral scan application 115 may output a request for an approval or rejection of the automatic determination. Such approval or rejection may be in the form of a voice approval or rejection, a press of one or more button on scanner 150 and/or an input device (e.g., touch screen, touchpad, mouse, etc.) of computing device 105, a gesture detected based on motion data of scanner 150, and/or some other type of input.

In embodiments, intraoral scan application 115 may detect transitions between different modes or stages of a restorative workflow. For example, intraoral scan application 115 may detect when a dental wire (also referred to as a dental cord or retraction cord) is inserted between a tooth and gum around a preparation tooth and/or when the dental wire is removed from between the tooth and gum. Additionally, intraoral scan application 115 may detect stages or rounds of grinding of a preparation tooth during the formation of the preparation tooth. When stages of the restorative workflow/treatment are recognized, and when transitions between "modes" or stages of treatment are recognized, intraoral scan application can output a notification, so that the doctor knowns the intraoral scan application is accurately tracking the restorative workflow or treatment. If the intraoral scan application 115 has incorrectly identified a stage of the workflow or treatment, the doctor may provide an input indicating that the intraoral scan application 115 is wrong and/or indicating a correct stage or more. This input may be used to perform further training of the intraoral scan application 115 (e.g., of one or more machine learning models of the intraoral scan application 115) to improve accuracy.

In embodiments, each intraoral scan is recorded separately and may be processed separately, and these intraoral scans may be re-processed after one or more additional scans are received and/or after scanning of a dental arch or dental site is complete. The re-processing may be performed using the intraoral scan and additional intraoral scans (and/or a 3D surface or 3D model), which provides improved accuracy. Accordingly, even if the system did not accurately identify stages of the workflow or treatment in real time and/or did not detect correct scanning roles in real time, the system can update and correct earlier errors in classification of the stage or mode of treatment and/or errors in classification of scanning mode after scanning. This can possibly eliminate any need for rescanning.

During repeated scanning some scans may be discarded, as it is not always possible to know a doctors intentions in advance and some decisions of the intraoral scan application may be wrong. In embodiments, the intraoral scan application 115 maintains (e.g., stores) all scan data of a scanning session. If the intraoral scan application 115 is wrong in a decision, and it receives correction from a doctor, it can always use the stored but previously unused data to perform a re-computation, without a need to rescan the patient. The re-computation may include re-determining a 3D surface and/or 3D model using different scans than were previously used and/or using a different weighting for combining scans than was previously used. Such re-computations can be performed to determine updates for segmentation, role identification, restorative workflow identification, orthodontic workflow identification, determinations of changes to dental sites, and/or any of the other predictions, classifications or determinations discussed herein.

In some instances, a doctor may provide an ambiguous or unclear input that can be interpreted in multiple ways, where each interpretation may lead to a different result. Additionally, in some instances intraoral scan application determines that there is an equal likelihood (or approximately equal likelihood) that two different outcomes are correct (e.g., that a modification was made to a dental site and that a modification was not made to the dental site). In such cases where the intraoral scan application receives ambiguous or unclear input or cannot determine a correct output automatically, the intraoral scan application 115 may suggest two or three options for the doctor to decide between. In embodiments, a separate 3D surface or 3D model may be shown for each of the options. The doctor may then select the correct option. Once the correct option is selected, retraining may be performed using the knowledge of the correct option. This may include retraining one or more machine learning models.

Use of Intaglio Surface for Restorative Cases

In some embodiments, a 3D model generated based on a scan of a dental site in a patient's mouth is inaccurate or of sub-optimal quality because there are insufficient features at the dental site to perform registration and stitching of scans and/or to generate an accurate depiction of the dental site. In such instances, additional scans may be generated of an intaglio surface of a dental prosthetic that was manufactured for the dental site and/or of an impression taken of the dental site. Scan data from the intaglio surface of the impression or dental prosthetic may then be used together with the scan data of the dental site to generate a more accurate 3D model of the dental site. Additionally, an intraoral scan of a preparation tooth may include an unclear or obscured or poorly defined margin line. In such instances, scan data from the intaglio surface of an impression of the preparation tooth of a dental prosthetic for the preparation tooth may improve a quality, definition and/or clarity of the margin line in a 3D model of the preparation tooth. Thus, scans of intaglio surfaces can improve, for example, a depiction of a margin line around a preparation tooth, a depiction of an edentulous region of a dental arch, and so on.

In some instances a doctor does not need to provide any input to intraoral scan application 115 indicating that they are taking a scan of an intaglio surface, or that they are taking the scan of the intaglio surface for a particular patient. In some embodiments, when one or more scans of an intaglio surface of a dental prosthetic (e.g., a temporary dental prosthetic) or impression are generated, those scans are automatically analyzed. Based on such analysis, intraoral scan application 115 may determine that a scan is of an intaglio surface rather than of a dental site in an oral cavity. For example, scans of dental sites have a generally mound-like shape with a predominantly convex surface. On the other hand, scans of an intaglio surface generally have a valley-like shape with a predominantly concave surface. Based on such information, intraoral scan application may automatically determine whether a received scan is of an object in an oral cavity or is of an intaglio surface of a dental prosthetic or impression. In one embodiment, a trained machine learning model outputs a classification of a scan as being of an object in an oral cavity or of an intaglio surface.

In some embodiments, intraoral scan application 115 generates a 3D surface and/or 3D model of the intaglio surface, and compares the 3D surface and/or 3D model to stored 3D models of one or more patients. Intraoral scan application 115 may additionally compare intraoral scans to stored 3D models of one or more patients. For intraoral scans and/or 3D surfaces of an intaglio surface, intraoral scan application may invert the data from the intraoral scans and/or the 3D surface before comparing to stored 3D models. Comparisons may then be made to various 3D models until a match is identified. A match may be made between the intaglio surface and a surface of a particular preparation tooth on a dental arch of a particular 3D model of a particular patient, for example. Once a match is identified, intraoral scan application 115 may automatically identify a patient associated with the intaglio scan data and/or a particular preparation tooth associated with the intaglio scan data. Intraoral scan application 115 may additionally automatically determine a 3D model and/or a particular region of the 3D model (e.g., the region associated with an identified preparation tooth) to combine with the 3D surface and/or intaglio scan data to generate an updated 3D model (e.g., with an improved margin line).

For example, a temporary crown may be manufactured for placement on a preparation tooth. The intaglio surface of the temporary crown may be scanned using scanner 150, and scans of the intaglio surface of the temporary crown may be used together with scans of the preparation tooth to determine a margin line around the preparation tooth. Intraoral scan application 115 in embodiments may automatically take intaglio scan data and combine it with the scan data of the preparation tooth to determine where the margin line is with no dental wire being used. This may include determining portions of the intaglio scan data to use for some regions of the margin line (e.g., such as those regions that are obscured by a gum in the intraoral scan data of the preparation tooth) and determining portions of the intraoral scan data of the preparation tooth to use for other regions of the margin line. In other instances, intraoral scan application 115 may determine to use only data from the scans of the preparation tooth for the margin line or to use only data from scans of the intaglio surface of the temporary crown for the margin line. Intraoral scan application 115 may automatically determine what data to use from the intraoral scans and what data to use from the scans of the intaglio surface to determine the margin line. For example, 90% of the margin line may be determined based on intraoral scan data of the preparation tooth (e.g., because these portions of the margin line are exposed in the intraoral scan data), and 10% of the margin line may be determined based on scan data of the intaglio surface of the temporary crown (e.g., because these portions of the margin line are obscured in the intraoral scan data).

Scanning of a dental site is complicated by regions in which a patient is missing teeth, referred to as edentulous regions. For example, in cases where two or more adjacent teeth are missing, there may be a large span of soft tissue that needs to be scanned. Scanning of edentulous areas of a dental arch are particularly challenging because there may be insufficient geometric reference points to perform registration and stitching of scans. Additionally, soft gum tissue may move or deform between scans, reducing an accuracy of a generated 3D model. Moreover, for soft gum tissue it may be advantageous to capture a full range of possible positions and/or shapes of the soft gum tissue, which cannot typically be captured merely by intraoral scanning of an edentulous area. Accordingly, systems are generally incapable of accurately capturing a full envelope of an edentulous region.

Accordingly, in embodiments an impression of an edentulous region may be taken (e.g., using an elastomeric impression material), where the impression captures an envelope of movement of the soft tissue at the edentulous region. An intaglio surface of the impression may then be scanned using scanner 150. Alternatively, or additionally, an intaglio surface of a previously manufactured denture may be scanned using scanner 150. The scans of the intaglio surface 150 may capture the full movement envelope of the soft tissue. Scans of the edentulous region may additionally be generated. The scans of the edentulous region may automatically be combined with the scans of the intaglio surface of the impression or denture to generate a 3D model usable to manufacture a new denture for the patient. The combined scans may be used, for example, to determine the intaglio surface of a new denture to be manufactured.

Automatic Detection of Dirty Optical Surfaces

The intraoral scanner 150 operates in a non-sterile environment. Saliva, blood and other material can accumulate on an optical surface of the scanner head, obstructing the optical path of light traveling into and out of scanner 150. The optical surface may be, for example, a window or a mirror in a head of the scanner 150. Most intraoral scanners 150 have an exit window above which the scanner is composed and below which the system expects to scan teeth and other dental objects. Additionally, most intraoral scanners 150 include a folding mirror in a head of the scanner 150 that reflects light such that the light exits the scanner at an angle to a longitudinal axis of the scanner 150 (e.g., at a right angle, an acute angle or an obtuse angle to the longitudinal axis). For scanners that include an exit window, the exit window may become dirty. For scanners that lack an exit window, the folding mirror may become dirty. Obstruction or dirtying of the optical surface (e.g., exit window and/or mirror) can have a negative impact on the accuracy of intraoral scan data such as intraoral scans, intraoral color images, and NIRI images generated by scanner 150. For a closed tip scanner (e.g. the iTero® scanner or the Cerec® scanner), dirt and grime accumulates on the scanner head's exit window and/or on the exit window of a protective sleeve that covers at least a portion of the scanner head. For an open tip scanner (e.g. the 3Shape® scanner, the CareStream® scanner, or Medit® scanner), dirt and grime accumulates on a folding mirror and/or lens in the scanner head and/or on a folding mirror inside a sleeve or attachment to the scanner head. The disturbance or obstruction on an optical surface can include but not be limited to dirt, blood or grime on an exit window, on a folding mirror, on glass, on a lens, or on any other object or surface in the optical path (referred to as an optical surface) of the scanner 150.

In embodiments, the intraoral scan application 115 and/or intraoral scanner 150 automatically detects obstructions (e.g., dirt, grime, blood, saliva, etc.) on an optical surface of the scanner 150. Obstructions may be detected using image processing and/or the application of machine learning. In some embodiments, a dirty optical surface is detected by generating and/or analyzing a depth map/height map. In other embodiments, a dirty optical surface is identified without use of depth maps or determination of depths.

Intraoral scan application 115 may determine a level of obstruction of the optical surface. If the level of obstruction exceeds an obstruction threshold (e.g., a dirtiness threshold), then intraoral scan application 115 may generate a warning message to clean the optical surface and/or to change a protective sleeve or attachment on the scanner 150. In embodiments, a threshold amount of obstruction on an optical surface that qualifies as "dirty" may be set. A default threshold may be set automatically, and a doctor may adjust the threshold via user input. When the system detects that an optical surface (e.g., a sleeve, lens, window and/or mirror) has reached the threshold, a message can be generated and/or scanning can be stopped. The system can decide to output a pop-up warning to the dentist to "please change the sleeve" in an embodiment. If the dentist ignores the notice, the system can automatically pause scanning and/or can prevent the sending of the virtual 3D model to a lab (e.g., in an extremely dirty sleeve/mirror/window situation). This can also prevent reuse of sleeves by doctors, which reduces the risk of cross contamination between patients.

In one embodiment, a dirty optical surface (i.e. obstructions on an optical surface) is detected using depth information. This may include generating a depth map or height map, and then comparing heights/depths in the depth map/height map to a depth threshold. A depth of the optical surface (e.g., distance of the optical surface from focusing optics) may be known, and the depth threshold (also referred to as a distance threshold) may be set based on the known depth of the optical surface. Intraoral scan application 115 may determine which, if any, of the depths from the depth map is equal to or less than the depth threshold. Every point or pixel associated with depth value that is less than or equal to the depth threshold may be identified as obscured. Depth detection capabilities are not limited to the exit window and continues into the scanner. In one embodiment, every depth detected inside the scanner 150 (e.g., at a depth of the mirror, lenses, etc.) is considered a disturbance or obstruction on an optical surface as the optical path inside the scanner 150 should be clear.

In an example, intraoral scanner 150 includes known distances of a sleeve's exit window (or inner mirror or probe exit window). These values may be determined by calibration or by design, and may be stored by intraoral scan application 115 and/or by scanner 150. Intraoral scan application 115 may receive a depth map with one or more candidates for distance. For each candidate in the depth map, intraoral scanner 115 may check if it is close to the exit window (or mirror) using a threshold. A different threshold may be used to decide whether the candidate is below or above the exit window. Intraoral scan application 115 may count the number of candidates close to the exit window. If the number of candidates is larger than a threshold, the system may output a notification that the sleeve could be dirty. Alternatively, or additionally, processing logic may output a notification indicating a percentage of an optical surface that is dirty. This notification may be updated as the optical surface becomes dirtier and/or is cleaned. Additionally, or alternatively, intraoral scan application 115 may determine a size of a dirty region (a number of adjacent points that qualify as dirty), and determine whether the size of the dirty region exceeds a size threshold. If so, intraoral scanner 115 may determine that scanner 150 has a dirty optical surface. Additionally, or alternatively, intraoral scan application 115 may determine whether a threshold number of scans (e.g., consecutive scans) have dirty regions with sizes that exceed a threshold. If so, intraoral scanner 115 may determine that scanner 150 has a dirty optical surface.

In one embodiment, intraoral scan application 115 compares two or more intraoral scans to determine unchanged pixels/points between the two or more intraoral scans. If a majority or some of the points/pixels between the scans differ but some remain unchanged, then intraoral scan application 115 may determine that those unchanged points/pixels are obscured by a dirty optical surface. In one embodiment, intraoral scan application generates a color image that is an average of multiple color images. This average may then be analyzed (e.g., using a trained ML model) to identify moving objects and unmoving objects. The moving objects may appear as smeared objects in the combined image and may be associated with clean regions of the optical surface, while the unmoving objects may appear as sharp or clear objects in the combined image and may be associated with dirty regions of the optical surface.

In embodiments, intraoral scan application 150 is able to distinguish between a dirty lens, a dirty mirror, a dirty exit window of scanner 150 and a dirty sleeve on scanner 150. In embodiments, intraoral scan application 150 may output an indication as to which optical component (or optical components) are detected to be dirty. If a protective sleeve (e.g., a window of a protective sleeve) or a protective attachment (e.g., a mirror of a protective attachment) is detected to be dirty, then a user may correct the issue by replacing the dirty sleeve or attachment with a clean sleeve or attachment. If an exit window of the scanner 150 is detected to be dirty, then a doctor may need to clean the exit window before continuing a scanning procedure. Typically there is nothing that prevents a dentist from using a dirty sleeve, dirty attachment, dirty lens, and so on. In embodiments, the system automatically detects a dirty sleeve or dirty attachment and prevents further scanning until the dirty sleeve or dirty attachment is replaced or cleaned.

Dirty sleeves and other dirty optical surfaces cause significant waste of time in the modeling phase of generating a dental appliance. For example, it takes a computer aided drafting (CAD) designer an average of 8 minutes to process a virtual 3D model generated using an intraoral scanner that is clean vs. about 12 minutes to process a virtual 3D model generated using a dirty scanner. Thus, CAD designer work time may be reduced by applying the dirty sleeve/dirty scanner detection methodology. Additionally, numbers of rejected cases may be reduced, and numbers of clinical escalations may be reduced.

In some embodiments, one or more optical surface of the intraoral scanner 150 may become fogged when the scanner head of the intraoral scanner 150 is inserted into an oral cavity. This may occur, for example, if a protective sleeve is replaced and/or a cold sleeve is inserted into a patient's mouth before the sleeve has had a chance to heat up to around the patient's body temperature. In some instances the fogging may be interpreted as a dirty optical surface. In some instances, color images generated by the intraoral scanner 150 may be used to detect a color, opacity and/or transparency of the area that has been identified as dirty. For example, the color image(s) and/or intraoral scans may be input into a trained ML model that has been trained to identify dirty optical surfaces and to identify fogged optical surfaces. The ML model may output an indication as to whether an optical surface is dirty or whether it is fogged. In one embodiment, intraoral scanner 150 determines a temperature of one or more regions of the scanner 150, and outputs a notification indicating that a detected dirty surface is possibly due to fogging and to wait to determine if the occlusion of the optical surface clears automatically (e.g., to wait a few seconds).

For any of the automated decision made by the intraoral scan application 115, such as automatic scanning role determination, automatic prescription generation, automatic selection of portions of intraoral scans to use for 3D surfaces, automatic classification of dental objects, and so on, a doctor may override the automatic decisions. In each instance of an automatic decision that is made by the intraoral scan application 115, intraoral scan application 115 may provide an indication of the automatic decision that was made and an option for the doctor to change the automatic decision to a different decision. When such a manual override occurs, the original decision, the details that led to the original decision, and the doctor's manual decision are recorded. This data may then be used to retrain one or more components (e.g., one or more trained ML models) of the intraoral scan application 115 in order to improve the accuracy of the system.

Figure 2A:
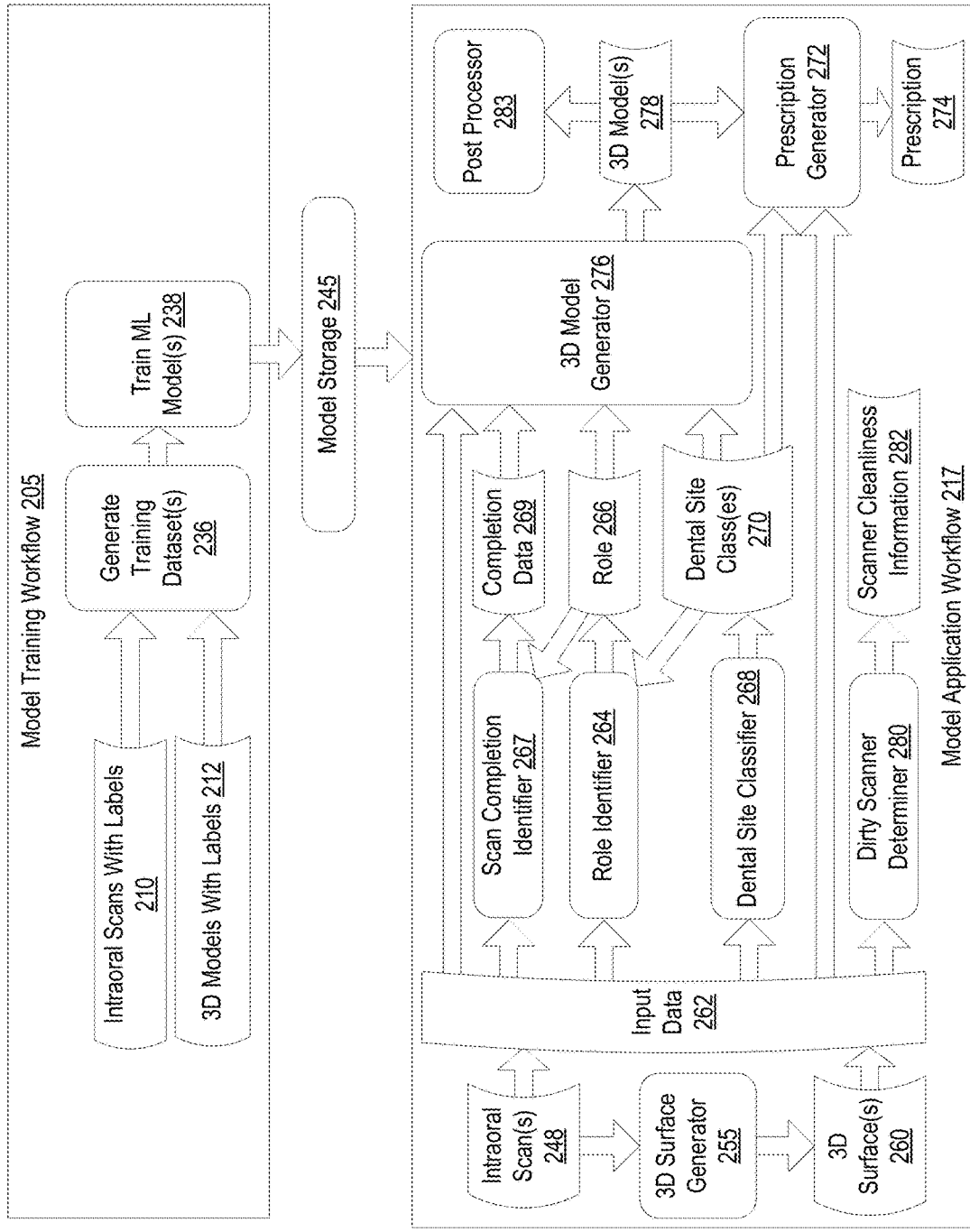
FIG. 2A illustrates a model training workflow and a model application workflow for an intraoral scanning application, in accordance with an embodiment of the present disclosure.

FIG. 2A illustrates a model training workflow 205 and a model application workflow 217 for an intraoral scanning application, in accordance with an embodiment of the present disclosure. In embodiments, the model training workflow 205 may be performed at a server which may or may not include an intraoral scan application, and the trained models are provided to an intraoral scan application (e.g., on computing device 105 of FIG. 1), which may perform the model application workflow 217. The model training workflow 205 and the model application workflow 217 may be performed by processing logic executed by a processor of a computing device. One or more of these workflows 205, 217 may be implemented, for example, by one or more machine learning modules implemented in an intraoral scan application 115 or other software and/or firmware executing on a processing device of computing device 4200 shown in FIG. 42.

The model training workflow 205 is to train one or more machine learning models (e.g., deep learning models) to perform one or more classifying, segmenting, detection, recognition, etc. tasks for intraoral scan data (e.g., 3D scans, height maps, 2D color images, NIRI images, etc.) and/or 3D surfaces generated based on intraoral scan data. The model application workflow 217 is to apply the one or more trained machine learning models to perform the classifying, segmenting, detection, recognition, etc. tasks for intraoral scan data (e.g., 3D scans, height maps, 2D color images, NIRI images, etc.) and/or 3D surfaces generated based on intraoral scan data. One or more of the machine learning models may receive and process 3D data (e.g., 3D point clouds, 3D surfaces, portions of 3D models, etc.). One or more of the machine learning models may receive and process 2D data (e.g., 2D images, height maps, projections of 3D surfaces onto planes, etc.).

Many different machine learning outputs are described herein. Particular numbers and arraignments of machine learning models are described and shown. However, it should be understood that the number and type of machine learning models that are used and the arrangement of such machine learning models can be modified to achieve the same or similar end results. Accordingly, the arrangements of machine learning models that are described and shown are merely examples and should not be construed as limiting.

In embodiments, one or more machine learning models are trained to perform one or more of the below tasks. Each task may be performed by a separate machine learning model. Alternatively, a single machine learning model may perform each of the tasks or a subset of the tasks. Additionally, or alternatively, different machine learning models may be trained to perform different combinations of the tasks. In an example, one or a few machine learning models may be trained, where the trained ML model is a single shared neural network that has multiple shared layers and multiple higher level distinct output layers, where each of the output layers outputs a different prediction, classification, identification, etc. The tasks that the one or more trained machine learning models may be trained to perform are as follows:

I) Scanning role classification—this can include classifying intraoral scans, sets of intraoral scans, 3D surfaces generated from multiple intraoral scans, 3D models generated from multiple intraoral scans, etc. as associated with an upper jaw role, a lower jaw role, or a bite role. This can also include classifying intraoral scans as associated with a preparation role.

II) Scan view classification—this can include classifying intraoral scans or sets of intraoral scans as depicting a lingual side of a jaw, a buccal side of a jaw, or an occlusal view of a jaw. Other views may also be determinable, such as right side of jaw, left side of jaw, and so on.

III) Dental object segmentation—this can include performing point-level classification (e.g., pixel-level classification or voxel-level classification) of different types of dental objects from intraoral scans, sets of intraoral scans, 3D surfaces generated from multiple intraoral scans, 3D models generated from multiple intraoral scans, etc. The different types of dental objects may include, for example, teeth, gingiva, an upper palate, a preparation tooth, a restorative object other than a preparation tooth, an implant, a bracket, an attachment to a tooth, soft tissue, a retraction cord (dental wire), blood, saliva, and so on. In some embodiments, different types of restorative objects may be identified, different types of implants may be identified, different types of brackets may be identified, different types of attachments may be identified, different types of soft tissues (e.g., tongue, lips, cheek, etc.) may be identified, and so on.

IV) Scanning success determination and/or scanning quality ranking—this can include assigning a quality value to individual scans, 3D surfaces, 3D models, etc. Quality values above a threshold may be determined to be a scanning success. This can also include assigning quality values to portions or regions of 3D surfaces or 3D models. Portions or regions with quality values that are below a threshold may be flagged for rescanning.

V) Prescription generation—this can include predicting parameters for a prescription based on intraoral scans, sets of intraoral scans, 3D surfaces generated from multiple intraoral scans, 3D models generated from multiple intraoral scans, and so on. Examples of prescription parameters that may be predicted include whether a prescription is for orthodontic treatment or restorative treatment, one or more teeth to be treated, a type of prosthodontic to be used, a color to be used for a prosthodontic, a material to be used for a prosthodontic, a lab to be used, and so on. Each of the different types of predictions/classifications associated with prescription generation may be determined by a separate ML model or by a ML model trained to generate multiple different outputs. For example, separate ML models may be trained to determine a dental lab, a type of dental prosthetic, a material for a dental prosthetic, a color for a dental prosthetic, and so on.

VI) Case type classification—this can include determining whether orthodontic treatment and/or restorative treatment will be performed for a patient based on intraoral scans, sets of intraoral scans, 3D surfaces generated from multiple intraoral scans, 3D models generated from multiple intraoral scans, and so on.

VII) Dental surface change detection—this can include determining whether a doctor has made any changes to one or more dental sites between intraoral scans, such as by grinding a tooth, adding a dental wire, removing a dental wire, etc. as well as whether changes such as accumulation of blood, removal of blood, accumulation of saliva, removal of saliva, and so on has occurred between scans. Such determinations can be made based on an input of one or more first scans or a 3D surface/3D model generated from the one or more first scans and one or more second scans or a 3D surface generated from the one or more second scans. The machine learning model may identify a region of change and any changes that were made, and may determine which portions of an earlier 3D surface/3D model to replace with data from the second one or more scans.

VIII) Dirty optical surface detection—this can include classifying an intraoral scanner or protective sleeve/attachment as dirty based on one or more intraoral scans. Additionally, this can include performing pixel-level classification of regions of a scan as dirty and/or can include determining which portions of a scanner are dirty (e.g., a window of a protective sleeve, a window of a scanner head, a lens, a folding mirror, etc.).

IX) Scanning completion identification—this can include determining when scanning of an upper jaw is complete, when scanning of a lower jaw is complete and/or when scanning of a bite is complete based on intraoral scans, sets of intraoral scans, and/or 3D surfaces generated from multiple intraoral scans. This can also include determining when scanning is complete overall. Once scanning of a segment is complete, processing logic may automatically generate a 3D model of the segment (e.g., a dental arch). Once scanning of all segments is complete (e.g., upper dental arch, lower dental arch and bite), processing logic may automatically perform post processing, perform occlusal contact analysis, perform diagnosis, and so on.

X) Detecting insertion into/withdrawal from oral cavity—this can include determining based on one or more 2D images whether or not a scanner is in an oral cavity, whether a scanner is being inserted into an oral cavity and/or whether a scanner is being withdrawn from an oral cavity.

XI) Margin line identification/marking—this can include performing pixel-level identification/classification of a margin line around a preparation tooth based on intraoral scans, sets of intraoral scans, 3D surfaces generated from multiple intraoral scans, 3D models generated from multiple intraoral scans, and so on. This can also include marking the identified margin line. Margin line identification and marking is described in US Publication No. 2021/0059796.

XII) Tooth number classification—this can include performing pixel level identification/classification and/or group/patch-level identification/classification of each tooth from 3D surface data. Teeth can be classified using one or more standard tooth numbering schemes, such as the American Dental Association (ADA) teeth numbering.

XIII) Moving tissue (excess tissue) identification/removal—this can include performing pixel-level identification/classification of moving tissue (e.g., tongue, finger, lips, etc.) from intraoral scans and optionally removing such moving tissue from intraoral scans. Moving tissue identification and removal is described in US Publication No. 2020/0349698, entitled "Excessive material removal using machine learning," which is incorporated by reference herein.

XIV) Insertion path prediction—this can include predicting an insertion path for a dental prosthesis based on a 3D surface, 3D model, etc.

XV) Multi-bite detection—this can include identifying the presence or absence of a multi-bite scenario based on multiple intraoral scans (e.g., each depicting a slightly different bite) and/or 3D surfaces generated from intraoral scans.

XVI) Intaglio surface detection/usage—this can include classifying intraoral scans, sets of intraoral scans, 3D surfaces generated from multiple intraoral scans, 3D models generated from multiple intraoral scans, etc. as depicting or not depicting an intaglio surface of an impression or prosthodontic. This can also include determining a match between an intaglio surface and a preparation associated with the intaglio surface.

XVII) Doctor voice recognition—this can include identifying a voice as belonging to a particular doctor (e.g., one of a set of possible doctors) based on audio of the doctor.

XVIII) Doctor facial recognition—this can include identifying a face as belonging to a particular doctor (e.g., one of a set of possible doctors) based on an image of a face of the doctor.

XIX) Motion pattern recognition—this can include identifying a user of a scanner as a particular doctor (e.g., one of a set of possible doctors) based on motion data generated by the scanner.

XX) 3D model viewing trajectory generation—this can include determining from a 3D model of a dental arch (or one or more projections of the 3D model) a viewing trajectory for the 3D model.)

XXI) Tooth to gum border identification/marking—this can include performing pixel-level identification/classification of a tooth to gum border around one or more tooth based on intraoral scans, sets of intraoral scans, 3D surfaces generated from multiple intraoral scans, 3D models generated from multiple intraoral scans, and so on.)

XXII) Tooth to tooth (interproximal region) border identification/marking—this can include performing pixel-level identification/classification of a tooth to tooth border for one or more interproximal regions between teeth based on intraoral scans, sets of intraoral scans, 3D surfaces generated from multiple intraoral scans, 3D models generated from multiple intraoral scans, and so on.

Note that for any of the above identified tasks associated with intraoral scans/3D surfaces/3D models, though they are described as being performed based on an input of intraoral scans, 3D surface and/or 3D models, it should be understood that these tasks may also be performed based on 2D images such as color images, NIRI images, and so on. Any of these tasks may be performed using ML models with multiple input layers or channels, where a first layer may include an intraoral scan/3D surface (or projection of a 3D surface)/3D model (or projection of a 3D model), a second layer may include a 2D color image, a third layer may include a 2D NIRI image, and so on. In another example, a first layer or channel may include a first 3D scan, a second layer or channel may include a second 3D scan, and so on.

One type of machine learning model that may be used to perform some or all of the above asks is an artificial neural network, such as a deep neural network. Artificial neural networks generally include a feature representation component with a classifier or regression layers that map features to a desired output space. A convolutional neural network (CNN), for example, hosts multiple layers of convolutional filters. Pooling is performed, and non-linearities may be addressed, at lower layers, on top of which a multi-layer perceptron is commonly appended, mapping top layer features extracted by the convolutional layers to decisions (e.g. classification outputs). Deep learning is a class of machine learning algorithms that use a cascade of multiple layers of nonlinear processing units for feature extraction and transformation. Each successive layer uses the output from the previous layer as input. Deep neural networks may learn in a supervised (e.g., classification) and/or unsupervised (e.g., pattern analysis) manner. Deep neural networks include a hierarchy of layers, where the different layers learn different levels of representations that correspond to different levels of abstraction. In deep learning, each level learns to transform its input data into a slightly more abstract and composite representation. In an image recognition application, for example, the raw input may be a matrix of pixels; the first representational layer may abstract the pixels and encode edges; the second layer may compose and encode arrangements of edges; the third layer may encode higher level shapes (e.g., teeth, lips, gums, etc.); and the fourth layer may recognize a scanning role. Notably, a deep learning process can learn which features to optimally place in which level on its own. The "deep" in "deep learning" refers to the number of layers through which the data is transformed. More precisely, deep learning systems have a substantial credit assignment path (CAP) depth. The CAP is the chain of transformations from input to output. CAPs describe potentially causal connections between input and output. For a feedforward neural network, the depth of the CAPs may be that of the network and may be the number of hidden layers plus one. For recurrent neural networks, in which a signal may propagate through a layer more than once, the CAP depth is potentially unlimited.

In one embodiment, a U-net architecture is used for one or more machine learning model. A U-net is a type of deep neural network that combines an encoder and decoder together, with appropriate concatenations between them, to capture both local and global features. The encoder is a series of convolutional layers that increase the number of channels while reducing the height and width when processing from inputs to outputs, while the decoder increases the height and width and reduces the number of channels. Layers from the encoder with the same image height and width may be concatenated with outputs from the decoder. Any or all of the convolutional layers from encoder and decoder may use traditional or depth-wise separable convolutions.

In one embodiment, one or more machine learning model is a recurrent neural network (RNN). An RNN is a type of neural network that includes a memory to enable the neural network to capture temporal dependencies. An RNN is able to learn input-output mappings that depend on both a current input and past inputs. The RNN will address past and future scans and make predictions based on this continuous scanning information. RNNs may be trained using a training dataset to generate a fixed number of outputs (e.g., to classify time varying data such as video data as belonging to a fixed number of classes). One type of RNN that may be used is a long short term memory (LSTM) neural network.

A common architecture for such tasks is LSTM (Long Short Term Memory). Unfortunately, LSTM is not well suited for images since it does not capture spatial information as well as convolutional networks do. For this purpose, one can utilize ConvLSTM—a variant of LSTM containing a convolution operation inside the LSTM cell. ConvLSTM is a variant of LSTM (Long Short-Term Memory) containing a convolution operation inside the LSTM cell. ConvLSTM replaces matrix multiplication with a convolution operation at each gate in the LSTM cell. By doing so, it captures underlying spatial features by convolution operations in multiple-dimensional data. The main difference between ConvLSTM and LSTM is the number of input dimensions. As LSTM input data is one-dimensional, it is not suitable for spatial sequence data such as video, satellite, radar image data set. ConvLSTM is designed for 3-D data as its input. In one embodiment, a CNN-LSTM machine learning model is used. A CNN-LSTM is an integration of a CNN (Convolutional layers) with an LSTM. First, the CNN part of the model processes the data and a one-dimensional result feeds an LSTM model.

In one embodiment, a class of machine learning model called a MobileNet is used for one or more neural networks. A MobileNet is an efficient machine learning model based on a streamlined architecture that uses depth-wise separable convolutions to build light weight deep neural networks. MobileNets may be convolutional neural networks (CNNs) that may perform convolutions in both the spatial and channel domains. A MobileNet may include a stack of separable convolution modules that are composed of depth-wise convolution and pointwise convolution (conv 1×1). The separable convolution independently performs convolution in the spatial and channel domains. This factorization of convolution may significantly reduce computational cost from $HWNK^2M$ to $HWNK^2$ (depthwise) plus HWNM (conv 1×1), $HWN(K^2+M)$ in total, where N denotes the number of input channels, $K^2$ denotes the size of convolutional kernel, M denotes the number of output channels, and H×W denotes the spatial size of the output feature map. This may reduce a bottleneck of computational cost to conv 1×1.

In one embodiment, a generative adversarial network (GAN) is used for one or more machine learning models. A GAN is a class of artificial intelligence system that uses two artificial neural networks contesting with each other in a zero-sum game framework. The GAN includes a first artificial neural network that generates candidates and a second artificial neural network that evaluates the generated candidates. The GAN learns to map from a latent space to a particular data distribution of interest (a data distribution of changes to input images that are indistinguishable from photographs to the human eye), while the discriminative network discriminates between instances from a training dataset and candidates produced by the generator. The generative network's training objective is to increase the error rate of the discriminative network (e.g., to fool the discriminator network by producing novel synthesized instances that appear to have come from the training dataset). The generative network and the discriminator network are co-trained, and the generative network learns to generate images that are increasingly more difficult for the discriminative network to distinguish from real images (from the training dataset) while the discriminative network at the same time learns to be better able to distinguish between synthesized images and images from the training dataset. The two networks of the GAN are trained once they reach equilibrium. The GAN may include a generator network that generates artificial intraoral images and a discriminator network that segments the artificial intraoral images. In embodiments, the discriminator network may be a MobileNet.

In one embodiment, one or more machine learning model is a conditional generative adversarial (cGAN) network, such as pix2pix. These networks not only learn the mapping from input image to output image, but also learn a loss function to train this mapping. GANs are generative models that learn a mapping from random noise vector z to output image y, $G: z \rightarrow y$. In contrast, conditional GANs learn a mapping from observed image x and random noise vector z, to y, $G: \{x, z\} \rightarrow y$. The generator G is trained to produce outputs that cannot be distinguished from "real" images by an adversarially trained discriminator, D, which is trained to do as well as possible at detecting the generator's "fakes". The generator may include a U-net or encoder-decoder architecture in embodiments. The discriminator may include a MobileNet architecture in embodiments. An example of a cGAN machine learning architecture that may be used is the pix2pix architecture described in Isola, Phillip, et al.

"Image-to-image translation with conditional adversarial networks." *arXiv preprint* (2017).

Training of a neural network may be achieved in a supervised learning manner, which involves feeding a training dataset consisting of labeled inputs through the network, observing its outputs, defining an error (by measuring the difference between the outputs and the label values), and using techniques such as deep gradient descent and back-propagation to tune the weights of the network across all its layers and nodes such that the error is minimized. In many applications, repeating this process across the many labeled inputs in the training dataset yields a network that can produce correct output when presented with inputs that are different than the ones present in the training dataset. In high-dimensional settings, such as large images, this generalization is achieved when a sufficiently large and diverse training dataset is made available.

For the model training workflow 205, a training dataset containing hundreds, thousands, tens of thousands, hundreds of thousands or more intraoral scans, images and/or 3D models should be used to form a training dataset. In embodiments, up to millions of cases of patient dentition that may have underwent a prosthodontic procedure and/or an orthodontic procedure may be available for forming a training dataset, where each case may include various labels of one or more types of useful information. Each case may include, for example, data showing a 3D model, intraoral scans, height maps, color images, NIRI images, etc. of one or more dental sites, data showing pixel-level segmentation of the data (e.g., 3D model, intraoral scans, height maps, color images, NIRI images, etc.) into various dental classes (e.g., tooth, restorative object, gingiva, moving tissue, upper palate, etc.), data showing one or more assigned classifications for the data (e.g., scanning role, in mouth, not in mouth, lingual view, buccal view, occlusal view, anterior view, left side view, right side view, etc.), and so on. This data may be processed to generate one or multiple training datasets 236 for training of one or more machine learning models. The machine learning models may be trained, for example, to automate the one or more processes that traditionally require doctor input during intraoral scanning, such as processes of inputting a scanning role, of inputting instructions to start or stop scanning, of identifying which regions of a 3D surface or 3D model to update after modifying a preparation tooth, of generating an orthodontic or restorative prescription, and so on. Such trained machine learning models can be added to an intraoral scan application, and can be applied to significantly reduce a level of user input associated with intraoral scanning and/or to simplify the scanning process.

In one embodiment, generating one or more training datasets 236 includes gathering one or more intraoral scans with labels 210 and/or one or more 3D models with labels 212. The labels that are used may depend on what a particular machine learning model will be trained to do. For example, to train a machine learning model to perform classification of dental sites (e.g., dental site classifier 268), a training dataset 236 may include pixel-level labels of various types of dental sites. Training datasets may also be generated that include voice data of doctors, facial images of doctors, and/or other information.

Processing logic may gather a training dataset 236 comprising 2D or 3D images, intraoral scans, 3D surfaces, 3D models, height maps, etc. of dental sites (e.g., of dental arches) having one or more associated labels (e.g., pixel-level labeled dental classes in the form of maps (e.g., probability maps), image level labels of scanning roles, etc.). One or more images, scans, surfaces, and/or models and optionally associated probability maps in the training dataset 236 may be resized in embodiments. For example, a machine learning model may be usable for images having certain pixel size ranges, and one or more image may be resized if they fall outside of those pixel size ranges. The images may be resized, for example, using methods such as nearest-neighbor interpolation or box sampling. The training dataset may additionally or alternatively be augmented. Training of large-scale neural networks generally uses tens of thousands of images, which are not easy to acquire in many real-world applications. Data augmentation can be used to artificially increase the effective sample size. Common techniques include random rotation, shifts, shear, flips and so on to existing images to increase the sample size.

To effectuate training, processing logic inputs the training dataset(s) 236 into one or more untrained machine learning models. Prior to inputting a first input into a machine learning model, the machine learning model may be initialized. Processing logic trains the untrained machine learning model(s) based on the training dataset(s) to generate one or more trained machine learning models that perform various operations as set forth above.

Training may be performed by inputting one or more of the images, scans or 3D surfaces (or data from the images, scans or 3D surfaces) into the machine learning model one at a time. Each input may include data from an image, intraoral scan or 3D surface in a training data item from the training dataset. The training data item may include, for example, a height map and an associated probability map, which may be input into the machine learning model. As discussed above, training data items may also include color images, images generated under specific lighting conditions (e.g., UV or IR radiation), and so on. Additionally, pixels of images may include height values or may include both height values and intensity values. The data that is input into the machine learning model may include a single layer (e.g., just height values from a single image) or multiple layers. If multiple layers are used, then one layer may include the height values from the image/scan/surface, and a second layer may include intensity values from the image/scan/surface. Additionally, or alternatively, additional layers may include three layers for color values (e.g., a separate layer for each color channel, such as an R layer, a G layer and a B layer), a layer for pixel information from an image generated under specific lighting conditions, and so on. In some embodiments, data from multiple images/scans/surfaces is input into the machine learning model together, where the multiple images/scans/surfaces may all be of the same dental site. For example, a first layer may include height values from a first scan of a dental site, a second layer may include height values from a second scan of the dental site, a third layer may include height values from a scan of the dental site, and so on. In some embodiments, an RNN is used. In such an embodiment, a second layer may include a previous output of the machine learning model (which resulted from processing a previous input).

The machine learning model processes the input to generate an output. An artificial neural network includes an input layer that consists of values in a data point (e.g., intensity values and/or height values of pixels in a height map). The next layer is called a hidden layer, and nodes at the hidden layer each receive one or more of the input values. Each node contains parameters (e.g., weights) to apply to the input values. Each node therefore essentially inputs the input values into a multivariate function (e.g., a non-linear mathematical transformation) to produce an output value. A next layer may be another hidden layer or an output layer. In either case, the nodes at the next layer receive the output values from the nodes at the previous layer, and each node applies weights to those values and then generates its own output value. This may be performed at each layer. A final layer is the output layer, where there is one node for each class, prediction and/or output that the machine learning model can produce. For example, for an artificial neural network being trained to perform dental site classification, there may be a first class (excess material), a second class (teeth), a third class (gums), a fourth class (restorative objects) and/or one or more additional dental classes. Moreover, the class, prediction, etc. may be determined for each pixel in the image/scan/surface, may be determined for an entire image/scan/surface, or may be determined for each region or group of pixels of the image/scan/surface. For pixel level segmentation, for each pixel in the image/scan/surface, the final layer applies a probability that the pixel of the image/scan/surface belongs to the first class, a probability that the pixel belongs to the second class, a probability that the pixel belongs to the third class, and/or one or more additional probabilities that the pixel belongs to other classes.

Accordingly, the output may include one or more prediction and/or one or more a probability map. For example, an output probability map may comprise, for each pixel in an input image/scan/surface, a first probability that the pixel belongs to a first dental class, a second probability that the pixel belongs to a second dental class, and so on. For example, the probability map may include probabilities of pixels belonging to dental classes representing a tooth, gingiva, or a restorative object. In further embodiments, different dental classes may represent different types of restorative objects.

Processing logic may then compare the generated probability map and/or other output to the known probability map and/or label that was included in the training data item. Processing logic determines an error (i.e., a classification error) based on the differences between the output probability map and/or label(s) and the provided probability map and/or label(s). Processing logic adjusts weights of one or more nodes in the machine learning model based on the error. An error term or delta may be determined for each node in the artificial neural network. Based on this error, the artificial neural network adjusts one or more of its parameters for one or more of its nodes (the weights for one or more inputs of a node). Parameters may be updated in a back propagation manner, such that nodes at a highest layer are updated first, followed by nodes at a next layer, and so on. An artificial neural network contains multiple layers of "neurons", where each layer receives as input values from neurons at a previous layer. The parameters for each neuron include weights associated with the values that are received from each of the neurons at a previous layer. Accordingly, adjusting the parameters may include adjusting the weights assigned to each of the inputs for one or more neurons at one or more layers in the artificial neural network.

Once the model parameters have been optimized, model validation may be performed to determine whether the model has improved and to determine a current accuracy of the deep learning model. After one or more rounds of training, processing logic may determine whether a stopping criterion has been met. A stopping criterion may be a target level of accuracy, a target number of processed images from the training dataset, a target amount of change to parameters over one or more previous data points, a combination thereof and/or other criteria. In one embodiment, the stopping criteria is met when at least a minimum number of data points have been processed and at least a threshold accuracy is achieved. The threshold accuracy may be, for example, 70%, 80% or 90% accuracy. In one embodiment, the stopping criteria is met if accuracy of the machine learning model has stopped improving. If the stopping criterion has not been met, further training is performed. If the stopping criterion has been met, training may be complete. Once the machine learning model is trained, a reserved portion of the training dataset may be used to test the model.

As an example, in one embodiment, a machine learning model (e.g., dental site classifier 268) is trained to segment intraoral images by classifying regions of those intraoral images into one or more dental classes. A similar process may be performed to train machine learning models to perform other tasks such as those set forth above. A set of many (e.g., thousands to millions) 3D models and/or intraoral scans of dental arches with labeled dental classes may be collected. In an example, each point in 3D models may include a label having a first value for a first label representing natural teeth, a second value for a second label representing restorative objects, and a third value for a third label representing gums/gingiva. One of the three values may be 1, and the other two values may be 0, for example.

Dental site classifier 268 may include one or more machine learning models that operate on 3D data or may include one or more machine learning models that operate on 2D data. If dental site classifier 268 includes a machine learning model that operates on 2D data, then for each 3D model with labeled dental classes, a set of images (e.g., height maps) may be generated. Each image may be generated by projecting the 3D model (or a portion of the 3D model) onto a 2D surface or plane. Different images of a 3D model may be generated by projecting the 3D model onto different 2D surfaces or planes in some embodiments. For example, a first image of a 3D model may be generated by projecting the 3D model onto a 2D surface that is in a top down point of view, a second image may be generated by projecting the 3D model onto a 2D surface that is in a first side point of view (e.g., a buccal point of view), a third image may be generated by projecting the 3D model onto a 2D surface that is in a second side point of view (e.g., a lingual point of view), and so on. Each image may include a height map that includes a depth value associated with each pixel of the image. For each image, a probability map or mask may be generated based on the labeled dental classes in the 3D model and the 2D surface onto which the 3D model was projected. The probability map or mask may have a size that is equal to a pixel size of the generated image. Each point or pixel in the probability map or mask may include a probability value that indicates a probability that the point represents one or more dental classes. For example, there may be four dental classes, including a first dental class representing excess material, a second dental class representing teeth, a third dental class representing gums, and a fourth dental class representing restorative objects. Points that have a first dental class may have a value of (1,0,0,0) (100% probability of first dental class and 0% probability of second, third and fourth dental classes), points that have a second dental class may have a value of (0,1,0,0), points that have a third dental class may have a value of (0,0,1,0), and points that have a fourth dental class may have a value of (0,0,0,1) for example. If a machine learning model is being trained to perform image-level classification/prediction as opposed to pixel-level classification/segmentation, then a single value or label may be associated with a generated image as opposed to a map having pixel-level values.

A training dataset may be gathered, where each data item in the training dataset may include an image (e.g., an image comprising a height map) or a 3D surface and an associated probability map (which may be a 2D map if associated with an image or a 3D map if associated with a 3D surface) and/or other label. Additional data may also be included in the training data items. Accuracy of segmentation can be improved by means of additional classes, inputs and multiple views support. Multiple sources of information can be incorporated into model inputs and used jointly for prediction. Multiple dental classes can be predicted concurrently from a single model or using multiple models. Multiple problems can be solved simultaneously: role classification, teeth/gums/restorative object segmentation, view determination, etc. Accuracy is higher than traditional image and signal processing approaches.

Additional data may include color image data. For example, for each intraoral scan or image (which may be monochrome), there may also be a corresponding color image. Each data item may include the scan (e.g., a height map) as well as the color image. Two different types of color images may be available. One type of color image is a viewfinder image, and another type of color image is a scan texture. A scan texture may be a combination or blending of multiple different viewfinder images. Each intraoral scan may be associated with a corresponding viewfinder image generated at about the same time that the intraoral image was generated. If blended scans are used, then each scan texture may be based on a combination of viewfinder images that were associated with the raw scans used to produce a particular blended scan.

A default method may be based on depth info only and still allows distinguishing several dental classes such as teeth, gums, excess material (e.g., moving tissues), restorative objects, and so on. However, sometimes depth info is not enough for good accuracy. For example, a partially scanned tooth may look like gums or even excess material in monochrome. In such cases color info may help. In one embodiment, color info is used as an additional 3 layers (e.g., RGB), thus, getting 4 layers input for the network. Two types of color info may be used, which may include viewfinder images and scan textures. Viewfinder images are of better quality but need alignment with respect to height maps. Scan textures are aligned with height maps, but may have color artifacts.

Another type of additional data may include an image generated under specific lighting conditions (e.g., an image generated under ultraviolet or infrared lighting conditions). The additional data may be a 2D or 3D image, and may or may not include a height map.

In some embodiments, sets of data points are associated with the same dental site, and are sequentially labeled. In some embodiments a recurrent neural network is used, and the data points are input into a machine learning model during training in ascending order.

In some embodiments, each image or scan includes two values for each pixel in the image, where the first value represents height (e.g., provides a height map), and where the second value represents intensity. Both the height values and the intensity values may be used to train a machine learning model.

In an example, a confocal intraoral scanner may determine the height of a point on a surface (which is captured by a pixel of an intraoral image) based on a focus setting of the intraoral scanner that resulted in a maximum intensity for that point on the surface. The focus setting provides a height or depth value for the point. Typically the intensity value (referred to as a grade) is discarded. However, the intensity value (grade) associated with the height or depth value may be kept, and may be included in the input data provided to the machine learning model.

Once one or more trained ML models 238 are generated, they may be stored in model storage 245, and may be added to an intraoral scan application (e.g., intraoral scan application 115). Intraoral scan application 115 may then use the one or more trained ML models 238 as well as additional processing logic to implement a "smart scanning" mode, in which user manual input of information is minimized or even eliminated in some instances.

In one embodiment, model application workflow 217 includes one or more trained machine learning models that function as a dental site classifier 268, a scan completion identifier 267 and a role identifier 264. These logics may be implemented as separate machine learning models or as a single combined machine learning model in embodiments. For example, role identifier 264, scan completion identifier 267 and dental site classifier 268 may share one or more layers of a deep neural network. However, each of these logics may include distinct higher level layers of the deep neural network that are trained to generate different types of outputs. The illustrated example is shown with only some of the functionality that is set forth in the list of tasks above for convenience. However, it should be understood that any of the other tasks may also be added to the model application workflow 217.

For model application workflow 217, according to one embodiment, an intraoral scanner generates a sequence of intraoral scans 248. A 3D surface generator 255 may perform registration between these intraoral scans, stitch the intraoral scans together, and generate a 3D surface 260 from the intraoral scans. As further intraoral scans are generated, these may be registered and stitched to a 3D surface 260, increasing a size of the 3D surface 260 and an amount of data for the 3D surface 260. Input data 262 may include one or more of the intraoral scans 248 and/or a generated 3D surface 260.

Input data 262 may be input into dental site classifier 268, which may include a trained neural network. Based on the input data 262, dental site classifier 268 outputs information on dental site classes 270, which may be point-level (e.g., pixel-level) classification of the input data. This may include outputting a set of classification probabilities for each pixel and/or a single classification for each pixel. The output dental site classes 270 may be, for example, a mask or map of classes and/or of class probabilities. In one embodiment, dental site classifier 268 identifies for each pixel whether it represents a tooth, gingiva, or a restorative object. Dental site classifier 268 may additionally classify pixels as "other" if they are below a probability threshold for a tooth, gingiva, or restorative object. In one embodiment, dental site classifier 268 additionally classifies pixels that represent moving tissue (excess tissue), an upper palate, a preparation tooth, a restorative object other than a preparation tooth, an implant, a bracket, an attachment to a tooth, a tongue, soft tissue, and so on. The dental site classifier 268 may be trained to classify any one or more of the described types of dental classes. In some embodiments, different types of restorative objects may be identified, different types of implants may be identified, different types of brackets may be identified, different types of attachments may be identified, different types of soft tissues (e.g., tongue, lips, cheek, etc.) may be identified, and so on.

When a single intraoral scan 248 has been generated, input data 262 for dental site classifier 268 may include that single scan. Once multiple scans 248 have been generated, input data 262 for dental site classifier 268 may include the multiple scans. Classifications based on multiple scans may be more accurate than classifications based on a single scan. Once a 3D surface 260 has been generated, input data 262 to dental site classifier 268 may include the 3D surface (e.g., one or more projections of the 3D surface onto one or more planes), which may result in still more accurate segmentation.

Input data 262 may be input into role identifier 264, which may include a trained neural network. Based on the input data 262, role identifier 264 outputs a classification of a scanning role 266 associated with the input data 262. For example, role identifier 264 may classify input data 262 as being associated with an upper jaw role, a lower jaw role, or a bite role. When a single intraoral scan 248 has been generated, input data 262 for role identifier 264 may include that single scan. Once multiple scans 248 have been generated, input data 262 for role identifier 264 may include the multiple scans. Classifications based on multiple scans may be more accurate than classifications based on a single scan. Once a 3D surface 260 has been generated, input data 262 to role identifier 264 may include the 3D surface or a plurality of projections of the 3D surface onto planes, which may result in still more accurate classifications of roles.

Optionally, segmentation information (e.g., pixel-level dental site classes 270) can be input as an additional layer into role identifier 264. This may improve an accuracy of role identifier 264. For example, pixel-level dental site classes 270 may include information on pixels or points that are classified as an upper palate and pixels or points that are classified as a tongue. Generally, scans with at least a threshold number of pixels/points with an upper palate classification are of an upper dental arch. Similarly, scans with at least a threshold number of pixels/points with a tongue classification are generally of a lower dental arch. Accordingly, the dental site classification information may help to improve an accuracy of the role identifier.

In one embodiment, a lower dental arch is detected if at least a first threshold number of points in the first three-dimensional surface or the intraoral scan depict a tongue. The first threshold number may be, for example, 2%, 5%, 10%, 15%, 20%, 25%, 30%, 35%, or some other percentage of a total number of pixels/points in a scan, set of scans, or 3D surface. In one embodiment, an upper dental arch is detected if at least a second threshold number of points in the first three-dimensional surface or the intraoral scan depict an upper palate. The second threshold number may be, for example, 2%, 5%, 10%, 15%, 20%, 25%, 30%, 35%, or some other percentage of a total number of pixels/points in a scan, set of scans, or 3D surface. In one embodiment, a bite is detected if at least a third threshold number of points in the first three-dimensional surface or the intraoral scan depict teeth from the lower dental arch and at least the third threshold number of points in the first three-dimensional surface or the intraoral scan depict the upper arch. The third threshold number may be, for example, 2%, 5%, 10%, 15%, 20%, 25%, 30%, 35%, or some other percentage of a total number of pixels/points in a scan, set of scans, or 3D surface.

Role identifier 264 may further include logic that performs one or more operations based on an output of a trained ML model. For example, a trained ML model may process each intraoral scan 248 to determine a role classification for that scan. Additional logic of role identifier 264 may then determine a moving median or average of outputs of the ML model for a window of intraoral scans, and determine a role classification based on the moving median or average.

Input data 262 may be input into scan completion identifier 267, which may include a trained neural network. Based on the input data 262, scan completion identifier 267 may output a prediction as to whether scanning of a particular segment (e.g., upper dental arch or lower dental arch) is complete, referred to as completion data 269. Scan completion identifier 267 may additionally determine whether scanning of all segments is complete. Optionally, scan completion identifier 267 may receive role classification data 266 output by role identifier 264 as an additional input layer. Role classification information 266 may improve an accuracy of determination of completion of a segment and/or of all segments. For example, when a role changes from an upper jaw role to a lower jaw role, this may increase a probability that the upper jaw segment is complete. Similarly, when a role changes from a lower jaw role to an upper jaw role, this may increase a probability that the lower jaw segment is complete. Additionally, when a role changes from an upper or lower jaw role to a bite role, this information may indicate that the upper and lower segments are likely complete.

When scanning of a segment (e.g., upper or lower dental arch) is complete, 3D model generator 276 performs a more accurate registration and stitching of intraoral scans 248 from input data 262 to generate a 3D model 278 of the completed segment. In embodiments, 3D model generator 276 automatically generates a 3D model of a segment responsive receiving completion data 269 indicating that scanning of the segment is complete. 3D model generator 276 may additionally receive role classification information 266 from role identifier 264, and may automatically label the generated 3D model appropriately (e.g., as the upper dental arch or lower dental arch) based on the role classification information 266. 3D model generator 276 may additionally receive dental site class information 270 from dental site classifier 268, and may optionally apply the dental site classifications to the generated 3D model. For example, 3D model generator 276 may label teeth, gingiva, preparation teeth and other restorative objects, brackets, attachments to teeth, and so on in the 3D model.

Once 3D models of the upper and lower dental arches are complete, and scanning of a bite role is complete, post processor 283 may automatically perform one or more post-processing operations. This may include generating an occlusion map, analyzing occlusal contacts between the upper dental arch and the lower dental arch, determining a margin line of a preparation tooth, determining a quality of the margin line, and so on. Numerous other post-processing operations may also be performed.

Prescription generator 272 can automatically start a prescription 274 for a patient and fill in some or all of the information for the prescription 274. Prescription generator 272 may receive input data 262 and/or a 3D model, and may determine an identity of a patient based on inputting the input data 262 and/or 3D model into a machine learning model trained to identify past patients based on their dentition and/or may compare the input data 262 and/or 3D model to stored 3D models of known patients. If the trained ML model outputs a recognition of a particular patient or if there is a match between the input data and a portion of a stored 3D model of a patient's dental arch, then prescription generator 272 may determine an identity of the patient associated with the input data 262 and/or 3D model, and may fill in one or more patient details in the prescription 274 based on stored information about the identified patient. Such information may include a patient name, gender, age, allergies, and so on.

Prescription generator 272 may additionally receive information on dental classes 270 in the input data 262 and/or may receive one or more 3D models of dental arches of a patient. The 3D models may include point-level labels of dental classes. The dental classes may include information such as identification of natural teeth, identification of one or more restorative objects (e.g., preparation teeth), identification of gingiva, and so on.

Prescription generator 272 may automatically predict whether a patient needs orthodontic treatment and/or restorative treatment based on input data 262, dental class information 270 and/or 3D model(s) 278. Prescription generator 272 may include information associated with a particular dental office at which model application workflow 217 is performed. Such information may include historical information on a number of restorative treatments that have been performed at the dental office and/or a number of orthodontic treatments that have been performed at the dental office. If only restorative treatments have been performed, then prescription generator 272 may automatically determine that a restorative treatment will be performed, and may start a restorative workflow. If only orthodontic treatments have been performed, then prescription generator 272 may automatically determine that an orthodontic treatment will be performed, and start an orthodontic workflow. If the dental office performs both restorative and orthodontic treatments, then prescription generator 272 may use input data 262, dental classes 270 and/or 3D model(s) 278 to determine whether an orthodontic or restorative treatment is to be performed. In one embodiment, if no restorative objects are identified and one or more other cues indicate that orthodontic treatment is to be performed (e.g., such as a detected malocclusion), then prescription generator 272 may determine that an orthodontic treatment is to be performed, and start an orthodontic workflow. In some embodiments, if no restorative objects are detected, processing logic may determine that input data (e.g., from a scanning session) is from a patient scheduled visit (e.g., a checkup). Such a determination may be made, for example, based on comparing a current date associated with the input data with dates of one or more previously generated 3D models. If the dates indicate some periodic or regular timing of scanning sessions, then processing logic may determine that the current input data is associated with a scheduled patient visit, and not necessarily with an orthodontic treatment or restorative treatment. Additionally, if a first 3D model is generated with no restorative objects, and then in the same day a second 3D model or 3D surface with one or more restorative objects is generated, then processing logic may determine that the first 3D model is a pre-treatment 3D model. In some embodiments, if no restorative object is detected, processing logic may determine that some medical treatment workflow other than an orthodontic workflow or a restorative workflow is to be performed. In one embodiment, if one or more restorative objects are identified, then prescription generator 272 may determine that a restorative treatment is to be performed, and may start a restorative workflow.

Prescription generator 272 may identify tooth numbers (e.g., optionally according to the American Dental Association (ADA) teeth numbering system) associated with the restorative objects based on the input data 262, dental class data 270 and/or 3D models 278. In one embodiment, prescription generator 272 includes a trained machine learning model that has been trained to determine tooth numbers associated with restorative objects. The prescription 274 may then be populated with information on which teeth are to receive prosthodontics.

Prescription generator 272 may include a trained machine learning model that has been trained to determine a type of dental prosthesis to be applied to each restorative object. The machine learning model may have been trained using training data including scans, images, 3D models, 3D surfaces, etc. of dental arches with restorative objects and labels indicating what types of dental prosthetics were applied to those restorative objects. The input data 262, dental classes 270 and/or 3D model(s) 278 may be input into the trained ML model, which may output, for each restorative object, a prediction of a type of dental prosthesis to be applied to that restorative object. The prescription 274 may be automatically populated with an indication of what dental prosthesis to use for each tooth number that has a restorative object.

Prescription generator 272 may include a trained machine learning model that has been trained to determine a type of material to be used for each dental prosthesis included in the prescription 274. The machine learning model may have been trained using training data including scans, images, 3D models, 3D surfaces, etc. of dental arches with restorative objects and labels indicating what types of materials were used for dental prosthetics applied to those restorative objects. The input data 262, dental classes 270 and/or 3D model(s) 278 may be input into the trained ML model, which may output, for each restorative object, a prediction of a type of material to use for the dental prosthesis to be applied to that restorative object. The prescription 274 may be automatically populated with an indication of what material to use for each dental prosthesis included in the prescription 274.

Prescription generator 272 may include a trained machine learning model that has been trained to determine a lab to be used to manufacture each dental prosthesis included in the prescription 274. The machine learning model may have been trained using training data including scans, images, 3D models, 3D surfaces, etc. of dental arches with restorative objects and labels indicating what labs were used to manufacture dental prosthetics applied to those restorative objects. The input data 262, dental classes 270 and/or 3D model(s) 278 may be input into the trained ML model, which may output, for each restorative object, a prediction of a dental lab to use for the dental prosthesis to be applied to that restorative object. The prescription 274 may be automatically populated with an indication of what lab to use for each dental prosthesis included in the prescription 274.

One or more of the above identified ML models of the prescription generator 272 may be combined into a single trained ML model (e.g., a single deep neural network) in embodiments.

In some implementations of model application workflow 217, a dirty scanner determiner 280 automatically detects one or more dirty optical surfaces of a scanner. Dirty scanner determiner 280 may or may not use a trained ML model to detect dirty optical surfaces. In one embodiment, dirty scanner determiner 280 includes a trained ML model that has been trained to receive input data 262 (e.g., intraoral scans and/or color images) and to output a classification of a dirty optical surface or a clean optical surface. In on embodiment, the trained ML model outputs a pixel-level classification of clean and dirty regions of a field of view (FOV) of the scanner.

Instead of, or in addition to, the use of an ML model to identify dirty regions of optical surfaces, dirty scanner determiner 280 may use image processing techniques to identify dirty regions of optical surfaces. In one embodiment, dirty scanner determiner 280 determines dirty regions of optical surfaces based on depth information from intraoral scans. If a region of an optical surface is marred by grime, dirt, blood, and so on, then a detected depth of pixels associated with that region will generally be much less than depths of pixels that are not associated with dirty regions. Detected depths (or heights) may be compared to one or more depth thresholds (or one or more height thresholds), and dirty regions may be detected for depths that are at or below the one or more depth thresholds (or at or above one or more height thresholds).

Dirty scanner determiner 280 may determine sizes of dirty regions and/or a percentage of an optical surface that is dirty. If dirty regions have sizes that exceed a size threshold are detected and/or a percentage of the optical surface that is dirty exceeds a threshold, then dirty scanner determiner 280 may determine that the scanner (or a sleeve or attachment on the scanner) is dirty. Scanner cleanliness information 282 may be output by dirty scanner determiner 280, for example. If scanner cleanliness information 282 is of a dirty scanner, then dirty scanner determiner 280 may output a notification to replace a sleeve or attachment on the scanner, or to clean the scanner. Alternatively, or additionally, processing logic may output an indication of an amount or percentage of an optical surface (e.g., a window of a sleeve) that is dirty. This indication may appear once a threshold amount of the optical surface is dirty, and may be updated as the optical surface becomes dirtier and/or cleaner. In some embodiments, different dirtiness thresholds are used. If an amount obscured pixels exceeds a first dirtiness threshold, then a notification may be output. If the amount of obscured pixels exceeds a second, greater, dirtiness threshold, then scanning may be automatically paused and/or a prescription 274 generated using intraoral scans with the dirty scanner may be blocked from being sent to a dental lab.

In embodiments, dirty scanner determiner 280 can determine which optical surface or surfaces are dirty. Dirty scanner determiner 280 may output different notifications depending on which surfaces are dirty. For example, if a window of a sleeve is dirty, then dirty scanner determiner 280 may output a notice to replace the sleeve. However, if a window or mirror of the scanner are dirty, then dirty scanner determiner 280 may output a notice to clean the window or mirror.

Figure 2B:
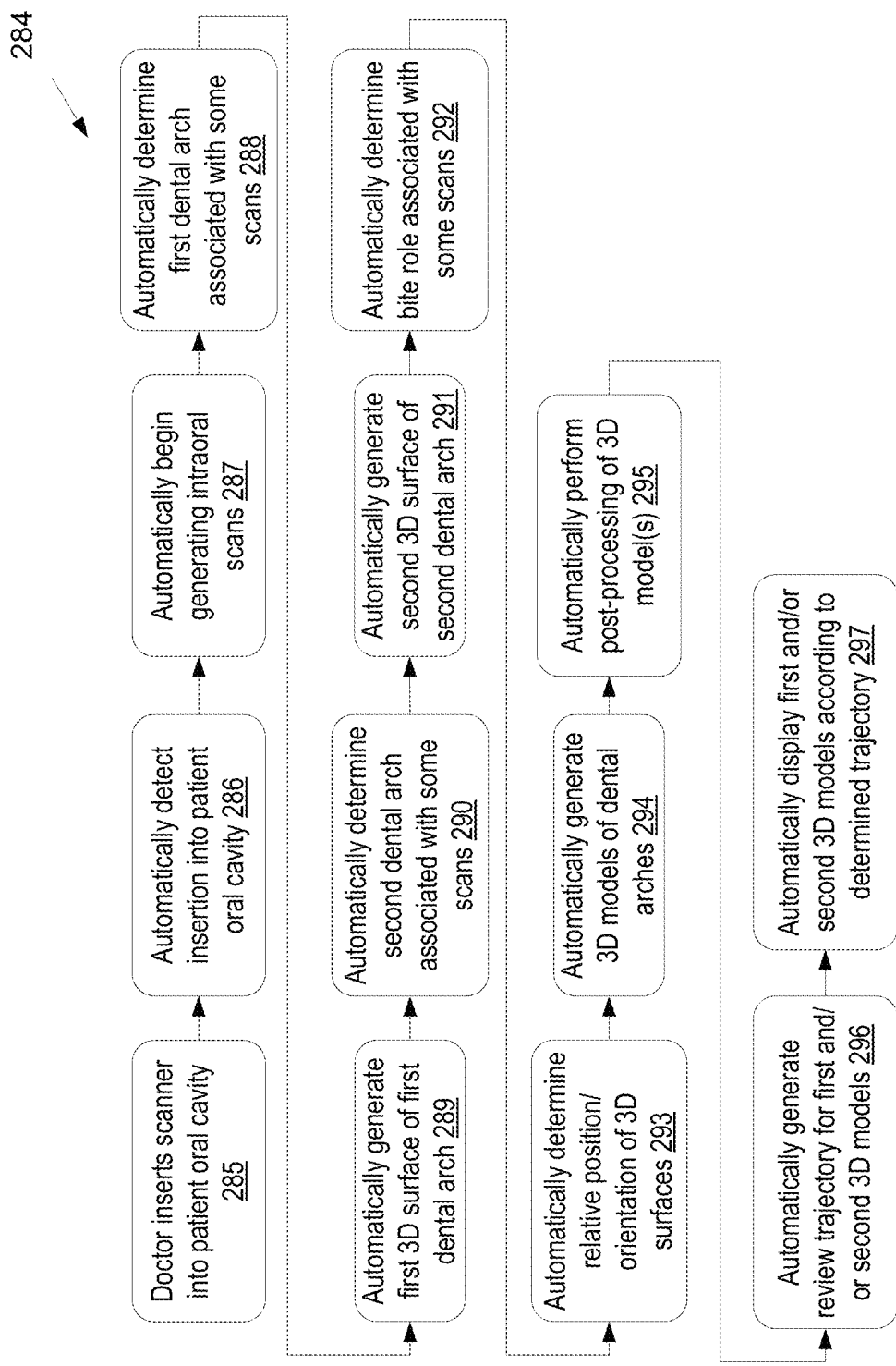
FIG. 2B illustrates an example intraoral scanning workflow, in accordance with an embodiment of the present disclosure.

FIG. 2B illustrates an example intraoral scanning workflow 284, in accordance with an embodiment of the present disclosure. Intraoral scanning workflow 284 may be performed, for example, by system 100 of FIG. 1. The example intraoral scanning workflow 284 starts with a doctor turning on an intraoral scanner and inserting the intraoral scanner into a patient's oral cavity (block 285). Processing logic (e.g., executing on scanner 150 and/or computing device 105) then automatically detects when the scanner is inserted into the patient's oral cavity (block 286). In one embodiment, the scanner begins generating periodic images (e.g., color 2D images) when it is turned on, and these images are input into a trained ML model that has been trained to detect insertion into an oral cavity. Processing logic may detect that the scanner is input into the patient's oral cavity responsive to the ML model outputting an indication that one or more images depict objects in an oral cavity. At block 287, processing logic automatically begins generating intraoral scans. This may also include automatically outputting structured light if the scanner uses structured light to determine depth information for scans.

At block 288, processing logic automatically determines a first dental arch (e.g., upper dental arch or lower dental arch) associated with one or more generated intraoral scans. In one embodiment, intraoral scans are input into a trained ML model trained to determine a scanning role associated with the scans. Processing logic may detect that the scanner is scanning the first dental arch responsive to the ML model outputting an indication that one or more scans depict the first dental arch. At block 289, processing logic automatically generates a first 3D surface of the first dental arch by registering and stitching together the scans of the dental arch. As additional scans are received and classified as being scans of the first dental arch, these scans may be stitched to the first 3D surface. The 3D surface, or one or more views or portions of the 3D surface, may be input into the trained ML model or another trained ML model trained to determine a scanning role associated with 3D surfaces. Processing logic may confirm that the scanner is scanning the first dental arch responsive to the ML model outputting an indication that the 3D surface is of the first dental arch. Alternatively, if the ML model determines that the 3D surface is of a second dental arch, then a classification of the first dental arch may change to a classification of the second dental arch for the 3D surface and the associated intraoral scans used to generate the 3D surface.

As the doctor continues scanning of the patient's oral cavity, eventually the doctor will finish scanning the first dental arch, and will start scanning the second dental arch (e.g., will switch from scanning the upper dental arch to the lower dental arch, or from scanning the lower dental arch to the upper dental arch). At block 290, processing logic automatically detects the switch from scanning the first dental arch to the second dental arch, and determines that one or more recent intraoral scans are of the second dental arch. In one embodiment, the intraoral scan(s) are input into a trained ML model trained to determine a scanning role associated with the scans. Processing logic may detect that the scanner is scanning the second dental arch (and has switched from scanning of the first dental arch to scanning of the second dental arch) responsive to the ML model outputting an indication that one or more scans depict the second dental arch. At block 290, processing logic automatically generates a second 3D surface of the second dental arch by registering and stitching together the scans of the second dental arch. As additional scans are received and classified as being scans of the second dental arch, these scans may be stitched to the second 3D surface. The second 3D surface, or one or more views or portions of the second 3D surface, may be input into the trained ML model or another trained ML model trained to determine a scanning role associated with 3D surfaces. Processing logic may confirm that the scanner is scanning the second dental arch responsive to the ML model outputting an indication that the 3D surface is of the second dental arch. Alternatively, if the ML model determines that the 3D surface is of a first dental arch, then a classification of the second dental arch may change to a classification of the first dental arch for the second 3D surface and the associated intraoral scans used to generate the second 3D surface.

Once the doctor finishes scanning the first dental arch and the second dental arch (e.g., the upper and lower dental arches of the patient), the doctor may transition to scanning of the patient's bite. The doctor may instruct the patient to close their mouth, and may generate one or more scans of the closed mouth, showing the relation of the upper dental arch to the lower dental arch. At block 292, processing logic automatically detects the switch from scanning the second dental arch to the scanning of the bite, and determines that one or more recent intraoral scans are of the patient's bite (bite role). In one embodiment, the intraoral scan(s) are input into a trained ML model trained to determine a scanning role associated with the scans. Processing logic may detect that the scanner is scanning the patient bite (and has switched from scanning of the second dental arch to scanning of the bite) responsive to the ML model outputting an indication that one or more scans depict a patient bite.

At block 292, processing logic automatically determines a relative position and orientation of the first 3D surface to the second 3D surface based on the one or more scans of the patient bite. At block 294, processing logic may automatically generate a 3D model of the first dental arch (e.g., upper dental arch) and a 3D model of the second dental arch (e.g., lower dental arch). Alternatively, the 3D model of the first dental arch may be automatically generated after block 290 if a determination can be made at that stage that the whole first dental arch is complete in the first 3D surface. Additionally, the 3D model of the second dental arch may be automatically generated after block 292 if a determination can be made at that stage that the whole second dental arch is complete in the second 3D surface.

At block 295, processing logic automatically performs one or more post-processing operations of the first and/or second 3D models. This may include, for example, automatically determining occlusal clearance information for teeth in the first and second dental arches, and performing an occlusal clearance analysis to determine if there are any problem contact points between the teeth of the upper and lower dental arches.

At block 296, processing logic automatically generates a review trajectory for the first and/or second dental arches. This may include determining a sequence of views of the first and/or second dental arches and transitions between the views. The trajectory may include rotating the 3D model(s), panning the 3D model(s), zooming in or out on certain areas of the 3D model(s) (e.g., for potential problem areas such as areas identified from the occlusal clearance analysis), and so on. The trajectory may automatically be determined based on historical reviews of 3D models of dental arches by the doctor. In one embodiment, the one or more 3D models are input into a trained ML model that has been trained to generate a review trajectory for a 3D surface/3D model based on an input of the 3D surface/3D model. At block 297, processing logic automatically displays the first and/or second 3D models according to the automatically determined review trajectory. At any time during the display of the 3D models, the doctor may instruct processing logic to pause the trajectory, rewind the trajectory, speed up the trajectory, slow down the trajectory, and so on. The doctor may also cancel the automatically determined review trajectory and manually manipulate a view of the first and/or second 3D models at any time.

FIGS. 3, 7-11, 14A-18, 20-31, 35-38 and 41 are flow charts illustrating various methods that are may be performed to implement "smart scanning", which reduces an amount of user input and streamlines the scanning process. The methods may be performed by a processing logic that may comprise hardware (e.g., circuitry, dedicated logic, programmable logic, microcode, etc.), software (e.g., instructions run on a processing device to perform hardware simulation), firmware, or a combination thereof. In one embodiment, at least some operations of the methods are performed by a computing device of a scanning system and/or by a server computing device (e.g., by computing device 105 of FIG. 1 or computing device 4200 of FIG. 42).

Figure 3:
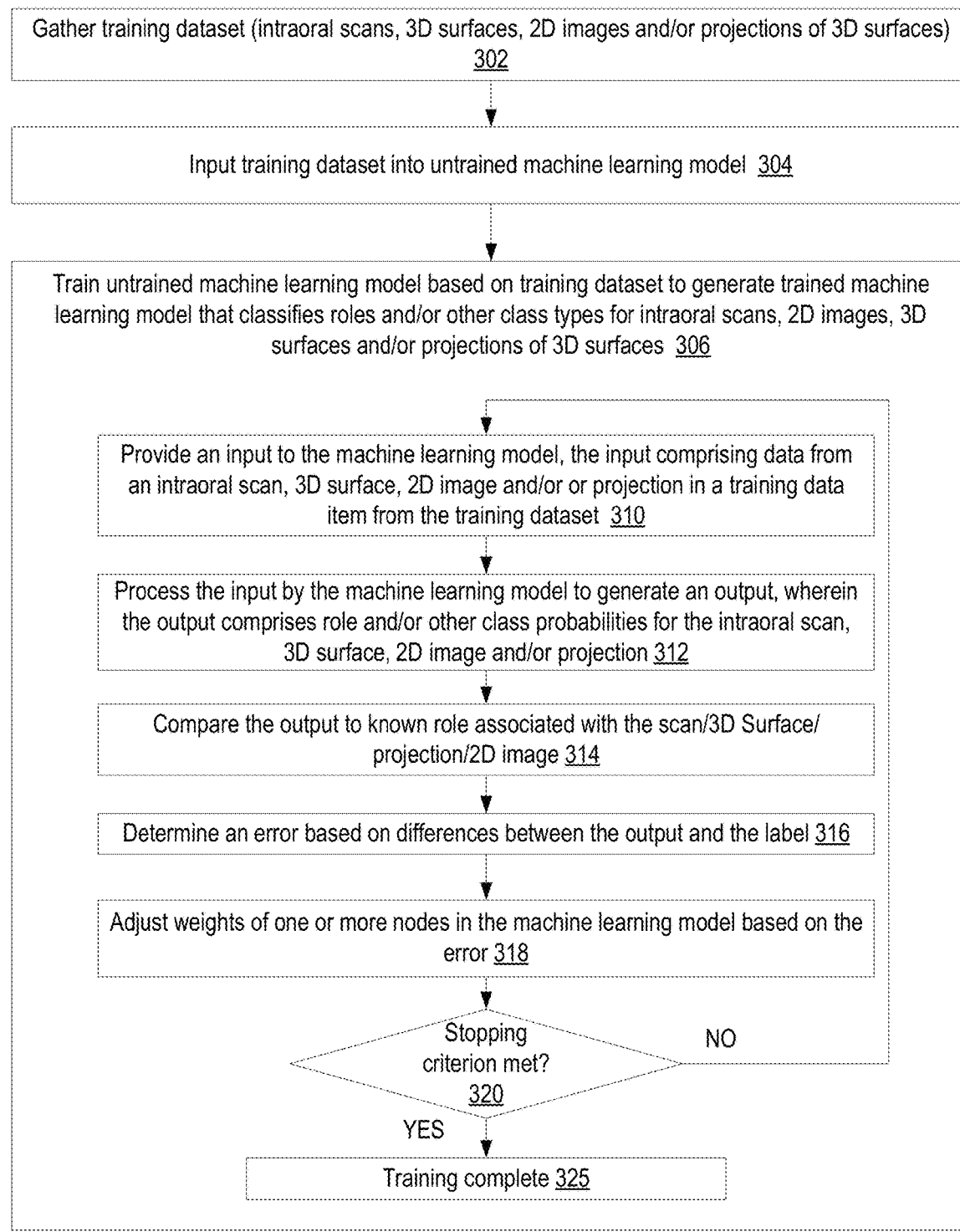
FIG. 3 is a flow chart illustrating an embodiment for a method of training a machine learning model to identify scanning roles.

FIG. 3 is a flow chart illustrating an embodiment for a method 300 of training a machine learning model to identify scanning roles. At block 302 of method 300, processing logic gathers a training dataset, which may include intraoral scans (e.g., height maps) of dental sites, 3D surfaces of dental sites, 2D images of dental sites and/or projections of 3D surfaces of dental sites. Each data item (e.g., intraoral scan, image, 3D surfaces, etc.) of the training dataset may include one or more labels. The data items in the training dataset may include image-level labels that indicate a scanning role. For example, some intraoral scans may include a label of a lower dental arch, some intraoral scans may include a label of a upper dental arch, and some intraoral scans may include a label of a bite. The data items in the training dataset may also include other labels, such as pixel-level classifications of dental classes, such as teeth, gingiva, restorative objects, and so on. Training of an ML model to perform pixel-level classification of dental classes is described in greater detail with reference to FIG. 9. The data items may also include other labels, such as labels of a lingual view, a buccal view, a left side of dental arch, a right side of dental arch, an occlusal view, and so on. Multiple other types of labels may also be associated with the data items in the training dataset, as set forth above.

At block 304, data items from the training dataset are input into the untrained machine learning model. At block 306, the machine learning model is trained based on the training dataset to generate a trained machine learning model that classifies scanning roles from intraoral scans, images and/or 3D surfaces (or projections of 3D surfaces). The machine learning model may also be trained to output one or more other types of predictions, image-level classifications, pixel-level classifications, patch-level classifications (where a patch is a group of pixels), decisions, and so on. For example, the machine learning model may also be trained to perform pixel-level classification of intraoral scans, images, 3D surfaces, etc. into dental classes.

In one embodiment, at block 310 an input of a training data item is input into the machine learning model. The input may include data from an intraoral scan (e.g., a height map), a 3D surface, a 2D image and/or a projection of a 3D surface. At block 312, the machine learning model processes the input to generate an output. The output may include a first probability that the input belongs to an upper dental arch role, a second probability that the input belongs to a lower dental arch role, and a third probability that the input belongs to a bite role. The output may additionally include a probability of the input containing a depiction of a restorative object. The output may additionally include a pixel-level classification of the input into dental classes.

At block 314, processing logic compares the output probabilities of the upper dental arch role, the lower dental arch role and the bite role to a role associated with the input. At block 316, processing logic determines an error based on differences between the output scanning role probabilities and the label of the role associated with the input. At block 318, processing logic adjusts weights of one or more nodes in the machine learning model based on the error.

Additionally, at block 314, processing logic may compare output probabilities of other predictions, classifications, etc. to one or more other labels associated with the input. At block 316, processing logic may determine errors for each of the comparisons. At block 318, processing logic may adjust weights of one or more nodes in the machine learning model based on these errors. Thus, the machine learning model may be trained to perform scanning role classification as well as dental object segmentation and/or one or more other classification, prediction and/or segmentation operations.

At block 320, processing logic determines if a stopping criterion is met. If a stopping criterion has not been met, the method returns to block 310, and another training data item is input into the machine learning model. If a stopping criterion is met, the method proceeds to block 325, and training of the machine learning model is complete.

In one embodiment, multiple different ML models are trained to perform scanning role classification. Each of the ML models may be trained to perform scanning role classification for a different type of input data. For example, a first ML model may be trained to perform scanning role classification for intraoral scans, a second ML model may be trained to perform scanning role classification for relatively small 3D surfaces generated from multiple intraoral scans or projections of such 3D surfaces onto planes, and a third ML model may be trained to perform scanning role classification from relatively large 3D surfaces generated from a large number of scans or projections of such 3D surfaces onto one or more planes (e.g., a projection of a 3D surface of an entire dental arch onto an occlusal plane, which may be a horizontal plane). The first ML model may determine a scanning role for intraoral scans almost immediately after the scans are generated, but without high accuracy. As further intraoral scans are generated, the second ML model may determine a scanning role for the multiple scans (e.g., for a 3D surfaces generated by stitching together the multiple scans) with higher accuracy. As still further scans are generated, the third ML model may determine a scanning role for the 3D surface with still higher accuracy. In one embodiment, a single ML model is trained to perform the operations of the above discussed first, second and third ML models.

Figure 4:
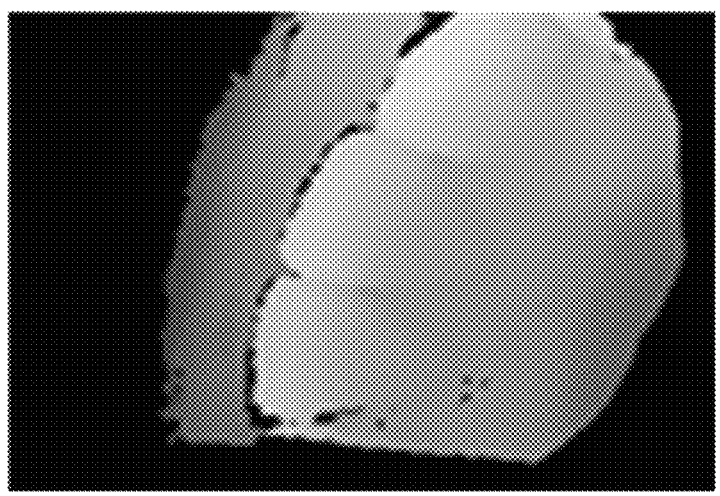
FIG. 4 illustrates example individual height maps used to train a machine learning model to determine scanning roles.
Figure 4:
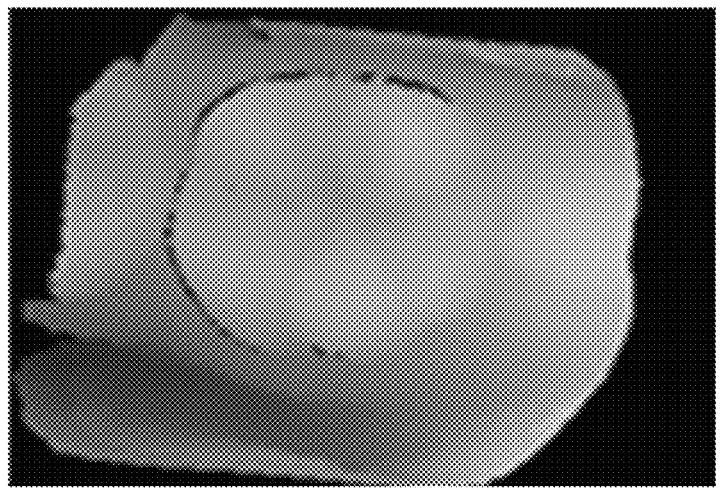
Figure 4:
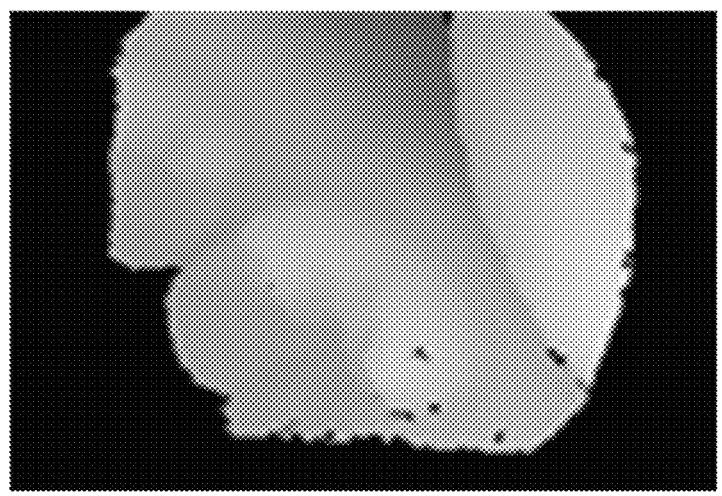

FIG. 4 illustrates example intraoral scans 402, 404, 406 that may be used to train a machine learning model to determine scanning roles and/or may be input into a trained ML model in order for the trained ML model to classify a scanning role for the intraoral scans. A solution that uses individual height maps (or other intraoral scans) to determine a scanning role as those height maps and/or scans are generated can provide a real time or near-real time determination of scanning roles. The intraoral scans 402, 404, 406 may be discrete or raw intraoral scans or may be blended intraoral scans. In one embodiment, the intraoral scans 402, 404, 406 are blended intraoral scans. Use of blended intraoral scans to determine scanning role during scanning can reduce computational resource usage as compared to use of raw intraoral scans. Individual intraoral scans are small due to a field of view (FOV) of the scanner, and are noisy, which makes it challenging to accurately classify scanning role from intraoral scans.

Figure 5:
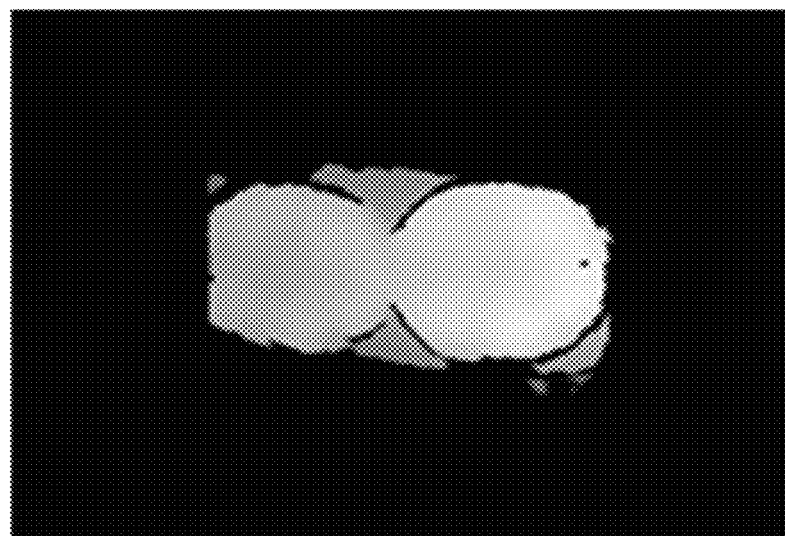
FIG. 5 illustrates an example occlusal view of a jaw used to train a machine learning model to determine scanning roles.
Figure 5:
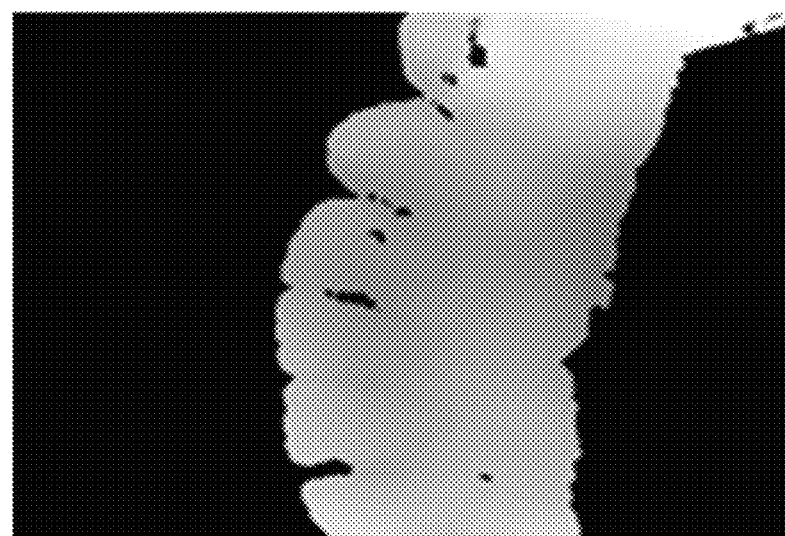
Figure 5:
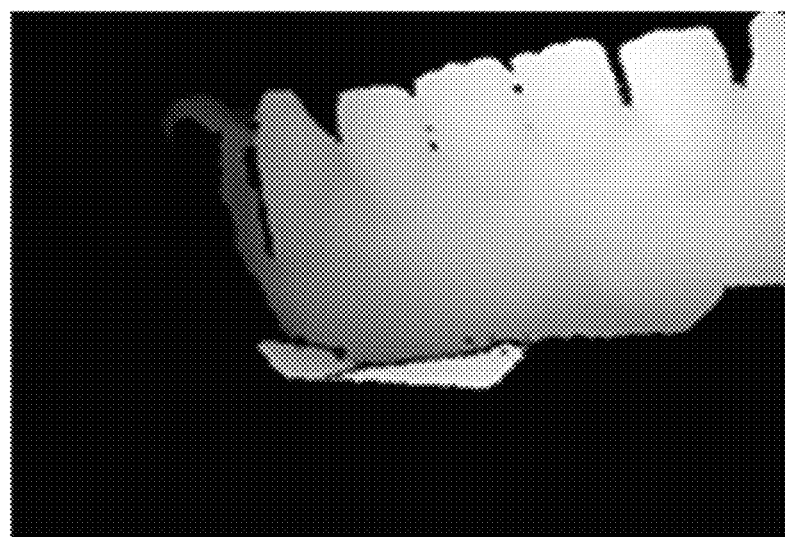

FIG. 5 illustrates example projections of 3D surfaces 500, 505, 510 (referred to as multiple jaw views since they combine data from multiple intraoral scans and project that data onto multiple planes to generate a set of views (e.g., height maps)) that may be used to train a machine learning model to determine scanning roles and/or may be input into a trained ML model in order for the trained ML model to classify a scanning role for the 3D surfaces (and the associated intraoral scans used to generate the 3D surfaces). In embodiments, 3D surfaces may be projected onto multiple planes to generate projections with height information (e.g., height maps) that contain information associated with multiple intraoral scans. Processing logic can use a set of projections of a jaw from different directions that are available during a scanning from a partially stitched 3D surface. For example, the multiple projections may be input into different input layers or channels of a trained neural network. Such projections give more information than individual height maps or intraoral scans (approaching occlusal view richness) and, at the same time, are available in or near-real time from near the very beginning of scanning. This approach gives high accuracy along with a real time nature.

Figure 6:
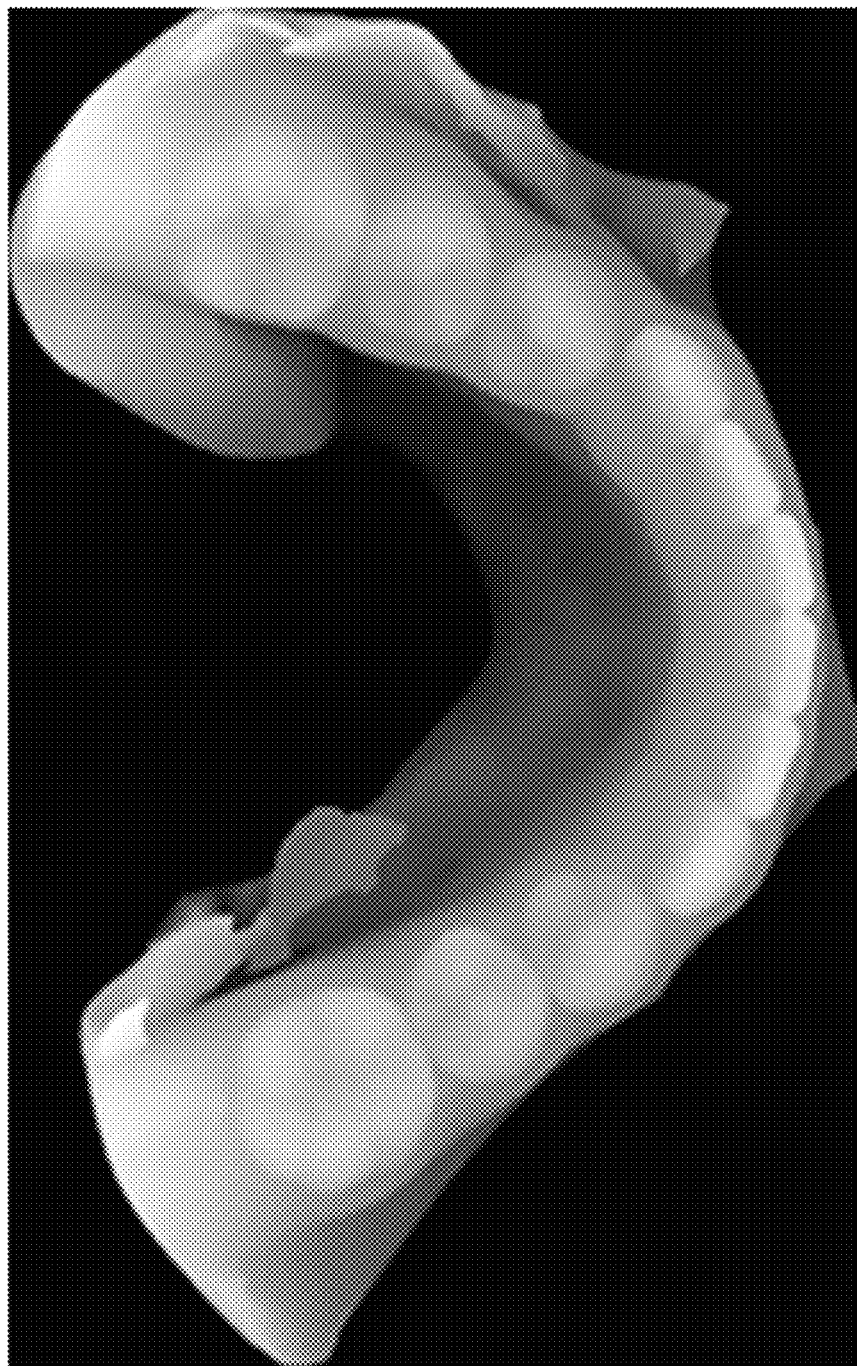
FIG. 6 illustrates example multiple jaw views used to train a machine learning model to determine scanning roles.

FIG. 6 illustrates an example occlusal view 600 of a jaw that may be used to train a machine learning model to determine scanning roles and/or that may be input into a trained ML model in order for the trained ML model to classify a scanning role for the jaw (and the associated intraoral scans used to generate the 3D surface of the jaw). Use of the occlusal view to determine the role is the most accurate solution since an occlusal view of a jaw is usually of good quality and has many features that provide easy classification. On the other hand, the occlusal view of a jaw is available only after some scanning has already happened and thus cannot be used for a real time solution. However, use of the occlusal view 600 can be an additional check of the less accurate solution (like scanning roles determined from individual height maps) that improves overall accuracy of the prediction.

Figure 7:
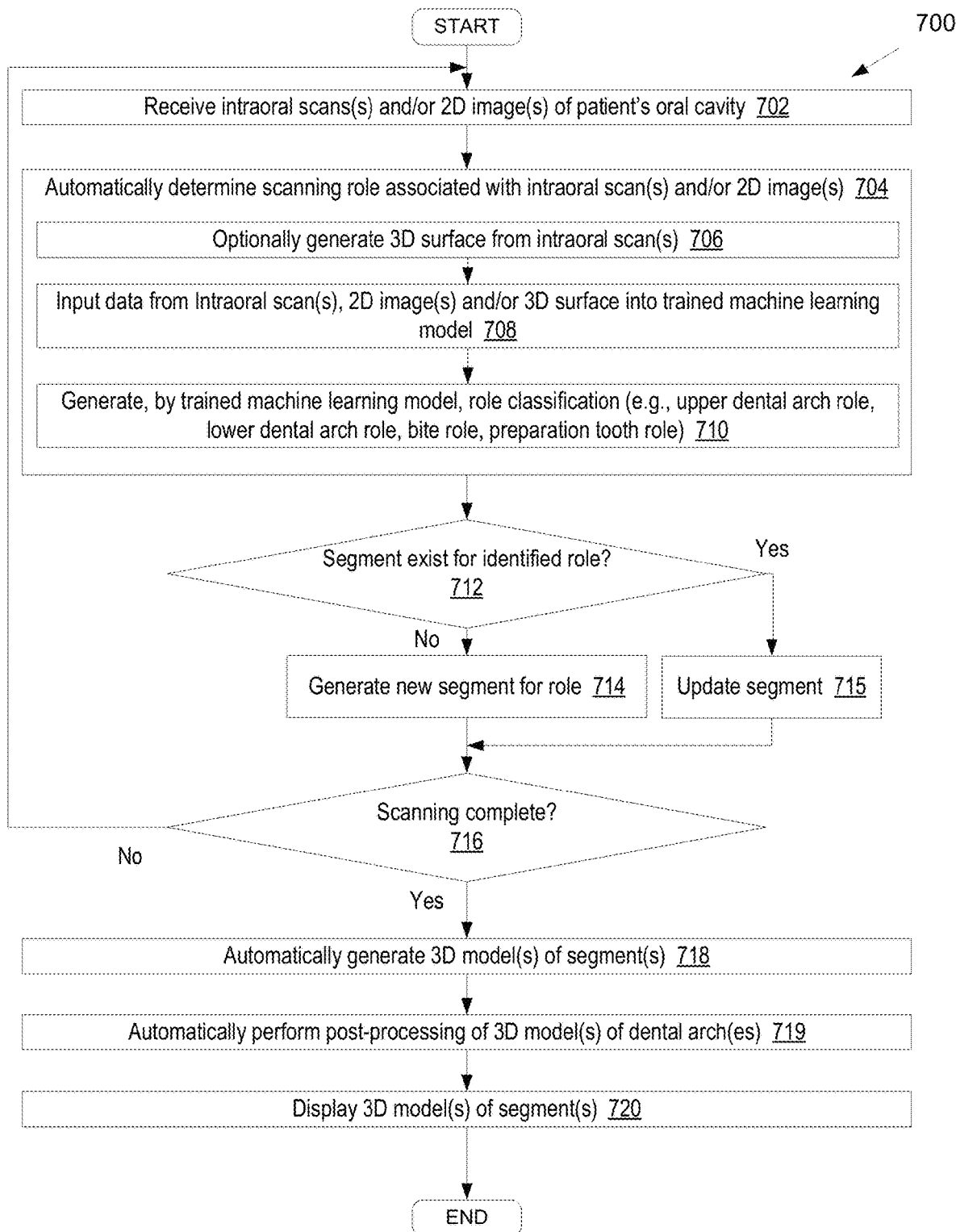
FIG. 7 is a flow chart illustrating an embodiment for a method of automatically determining a scanning role for intraoral scans.

FIG. 7 is a flow chart illustrating an embodiment for a method 700 of automatically determining a scanning role for intraoral scans. At block 702 of method 700, processing logic receives one or more intraoral scans (e.g., height maps) and/or 2D images (e.g., color images, NIRI images, etc.) of a patient's oral cavity. In one embodiment, one or more sequence of intraoral scans is received, where the sequence of intraoral scans were generated close in time to one another and form a group. During scanning of even a single dental arch, multiple groups of intraoral scans may be generated. A group of intraoral scans may be intraoral scans that are taken within a threshold time from one another, that have a threshold amount of overlap with one another, that are taken between a start button and a stop button of a scanner being pressed, or a group that shares some other commonality. In one embodiment, as intraoral scans are generated, they are stitched to one another if possible. A value may be assigned to a 3D surface, and that value may be applied to all intraoral scans that were used to generate that 3D surface. In one embodiment, intraoral scans that have the same assigned 3D surface value are part of a group. In one embodiment, intraoral scans from groups of intraoral scans are processed together, either simultaneously, in parallel, or in sequence.

At block 704, processing logic automatically determines a scanning role associated with the intraoral scans and/or 2D images. In one embodiment, the scanning role is determined using one or more ML models that have been trained to determine a scanning role based on an input of data from an intraoral scan and/or a 2D image associated with the intraoral scan. The ML model may receive one or a set of intraoral scans as an input. If multiple intraoral scans are input into the ML model at a time, then those multiple intraoral scans would be from a same group of intraoral scans. In some instances the intraoral scans may be resized before they are input into the ML model.

In one embodiment, the scanning role is determined using one or more ML models that have been trained to determine a scanning role based on an input of a 3D surface generated by stitching together multiple intraoral scans. The 3D surface may be a segment of a larger 3D surface, where the segment was generated from stitching together multiple intraoral scans from a group of intraoral scans. The 3D surface may be sized to a size that the ML model is configured to receive. This may include adjusting a scale of the 3D surface.

In one embodiment, the scanning role is determined by projecting a 3D surface onto multiple planes to provide multiple different 2D views of the 3D surface, where each projection may include height information along an axis normal to the plane onto which the 3D surface is projected, and inputting the multiple projections into one or more trained ML model that have been trained to determine a scanning role based on an input of a set of projections of a 3D surface of a dental site. The 3D surface may be a segment of a larger 3D surface, where the segment was generated from stitching together multiple intraoral scans from a group of intraoral scans. The projections of the 3D surface may be sized to a size that the ML model is configured to receive. This may include adjusting a scale of the projections of the 3D surface.

In one embodiment, the scanning role is determined by projecting a 3D surface of a full jaw (or a portion of a jaw) onto an occlusal plane (which may be a horizontal plane), and inputting the projection onto the occlusal plane into one or more trained ML model that have been trained to determine a scanning role based on an input of an occlusal view of a jaw (or portion of a jaw). The projection may have a size that can be accepted by the ML model, or may be resized and/or scaled so that is of a size that can be accepted by the ML model.

In one embodiment, at block 706 processing logic generates a 3D surface by stitching together multiple intraoral scans. Processing logic may then project the 3D surface onto multiple different planes to provide multiple views of the 3D surface. For example, processing logic may project the 3D surface onto a lingual side plane, onto a buccal side plane, and onto an occlusal plane.

At block 708, processing logic may input data from the intraoral scans (e.g., height maps) and/or color images associated with the intraoral scans into a trained ML model. Additionally, or alternatively, processing logic may input one or more projections of the 3D surface generated at block 706 into a trained ML model, optionally with one or more color images. Additionally, or alternatively, processing logic may input the 3D surface into a trained ML model (e.g., for an ML model trained to operate on 3D data).

In one embodiment, inertial measurement data (e.g., rotation data and/or acceleration data) may be used to determine a scanning role or to aid in the determination of a scanning role. For example, if an upper jaw role was determined for a first scan, and a rotation of the intraoral scanner about a horizontal axis (or a relatively or approximately horizontal axis) was detected between the first scan and a second scan, then this may be an indication that the second scan is of a lower jaw. However, if scanning was stopped between the first and second scans, then inertial measurement data may not improve detection of the scanning role. Generally when the intraoral scanner is angled such that the field of view of the intraoral scanner is above the intraoral scanner (facing upwards) generated scans are of the upper jaw. Similarly, generally when the intraoral scanner is angled such that the field of view of the intraoral scanner is below the intraoral scanner (facing downwards) generated scans are of the lower jaw. An accelerometer may be used to generate acceleration data that is usable to determine a direction of gravity, and the determined direction of gravity may be used to determine whether the intraoral scanner is facing upwards or downwards or sideways. The determined direction of gravity relative to the scanner and/or relative to detected teeth sides may be used to increase an accuracy of role detection. Accordingly, inertial measurement data generated by an inertial measurement unit that may include a gyroscope and/or an accelerometer may be input into a model such as a trained ML model along with intraoral scans, 3D surfaces, projections of 3D surfaces, etc. to improve an accuracy of role identification.

At block 710, the trained ML model(s) may output a role classification based on processing of the input data (e.g., intraoral scan(s), projections, images, 3D surface, etc.). The output role classification may include an upper dental arch role, a lower dental arch role, or a bite role. In one embodiment, the output includes a first probability of the role being an upper dental arch role, a second probability of the role being a lower dental arch role, and a third probability of the role being a bite role. In one embodiment, the ML model(s) further outputs an indication as to whether or not a preparation tooth role is associated with the input. In some instances, an output may include a first classification of one of the upper dental arch role, the lower dental arch role, or the bite role and a second classification of a preparation tooth role or no preparation tooth role.

For some intraoral scanners (e.g., those with large fields of view) and/or some intraoral scans, portions of an upper dental arch and portions of a lower dental arch may both be represented in the intraoral scans even though the scans are not patient bite scans. Accordingly, in some embodiments processing logic is capable of determining multiple different scanning roles for a single input (e.g., a single intraoral scan), where a first scanning role is determined for a first region of the input and a second scanning role is determined for a second region of the input. For example, processing logic may classify a first region of an intraoral scan as being of the upper dental arch and a second region of the intraoral scan as being of the lower dental arch. Accordingly, in some embodiments, processing logic outputs a pixel-level or zone/patch-level role classification for input data. For example, processing logic may classify each pixel as belonging to an upper dental arch role, a lower dental arch role, a bite role and/or a preparation role.

At block 712, processing logic determines whether a segment has been created for the identified role or roles (e.g., whether an upper dental arch segment or 3D surface or a lower dental arch segment or 3D surface have been created). If a segment has not yet been created for the identified role or roles, the method continues to block 714 and processing logic generates a new segment for the identified role(s). This may include starting a 3D surface associated with the identified role. If at block 712 processing logic determines that a segment already exists for the identified role, then at block 715 processing logic may add data to the segment based on the intraoral scan(s). This may include stitching the intraoral scan(s) to an already generated 3D surface. If an intraoral scan includes a first region or zone with a first role classification and a second region or zone with a second role classification, then processing logic may stitch the first region of the intraoral scan to a first 3D surface associated with the first role and may stitch the second region of the intraoral scan to a second 3D surface associated with the second role. Accordingly, in embodiments, two 3D surfaces (one for an upper dental arch and one for a lower dental arch) may be determined and generated concurrently.

At block 716, processing logic determines whether scanning is complete. Such a determination may be made based on analysis of a completeness of the segments for the upper and lower dental arches and existence of one or more intraoral scans associated with a bite role, based on detection of removal of a scanner from a patient's mouth, based on detection of the scanner being placed on a surface or in a cradle, and/or on other information. In one embodiment, processing logic automatically determines whether scanning is complete. Such a determination may be made based on the output of one or more trained ML models. For example, a first ML model may have previously output classifications of all scanning roles, and the first ML model or a second ML model may have previously output a prediction that a 3D surface of an upper dental arch is complete and a prediction that a lower dental arch is complete, and a third ML model may output an indication that the scanner has been removed from a patient's mouth. Processing logic may receive such outputs from one or more ML models and determine based on one or more of the outputs that scanning is complete. If scanning is complete, the method continues to block 718. If scanning is not complete, the method returns to block 702.

In embodiments, processing logic can automatically determine scanning roles and transitions between scanning roles without any push of a button by a user. For example, a user starts scanning, an upper dental arch is detected, then at some point a lower dental arch is detected. The system determines that the upper dental arch is complete. The user continues scanning the lower dental arch, and then at some point a bite is detected. The system then determines that the lower dental arch is complete. After additional scans, the scanner is withdrawn from a patient's mouth, and the system determines that scanning of the patient bite is complete. As each of the upper dental arch, lower dental arch, and bite are complete, processing logic may provide a visual and/or audible indication that the respective scanning role or segment is complete.

At block 718, processing logic may automatically generate a first 3D model of the upper dental arch and a second 3D model of the lower dental arch. Alternatively, the first 3D model may automatically be generated after scanning of an upper dental arch is complete but before scanning as a whole is complete and. Similarly, the second 3D model may automatically be generated after scanning of the lower dental arch is complete but before scanning as a whole is complete.

At block 719, processing logic automatically performs post-processing of the upper and/or lower dental arches. At block 720, processing logic displays the upper and/or lower dental arches.

Figure 8A:
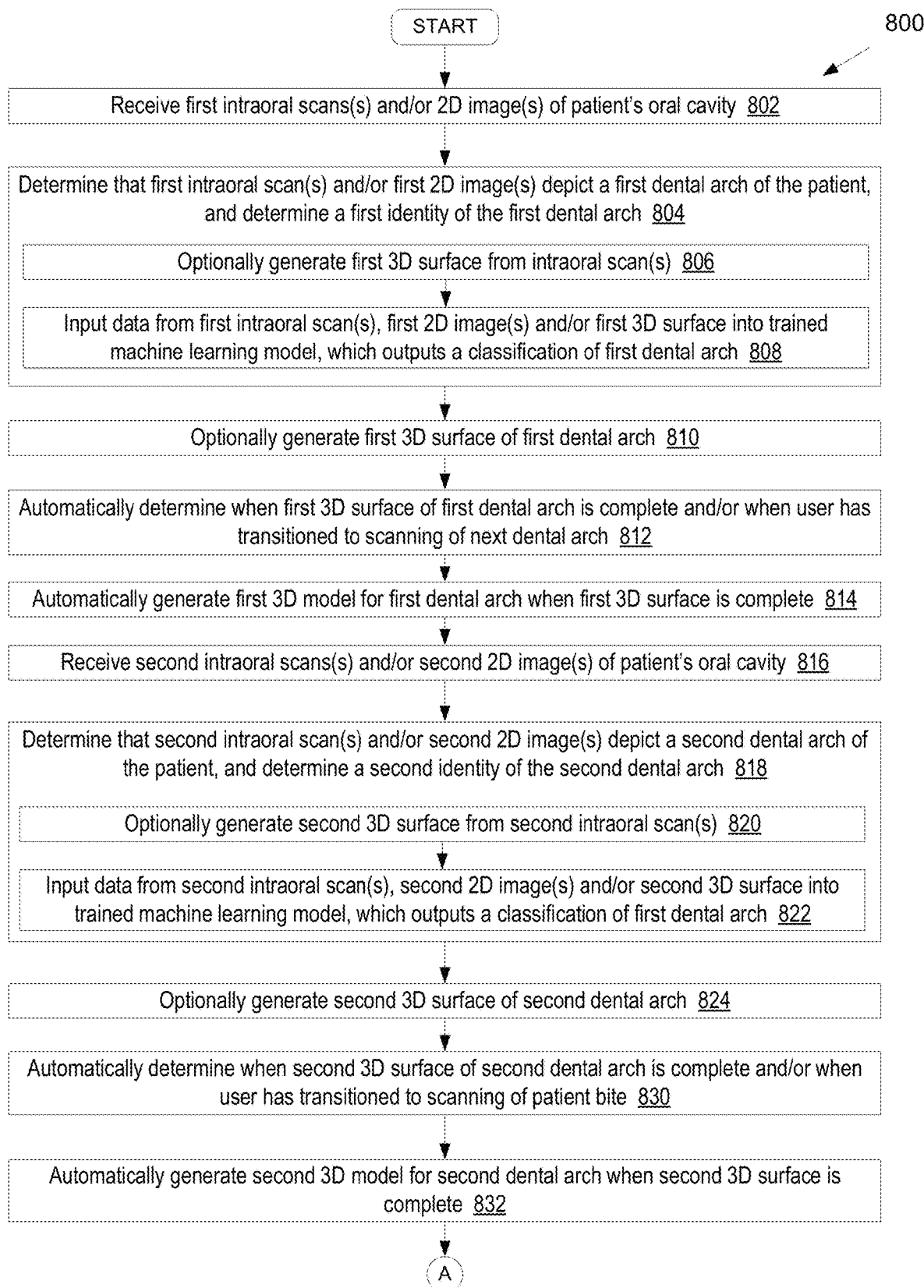
FIGS. 8A-B illustrate a flow chart of an embodiment for a method of performing intraoral scanning without receiving user input specifying scanning roles.
Figure 8B:
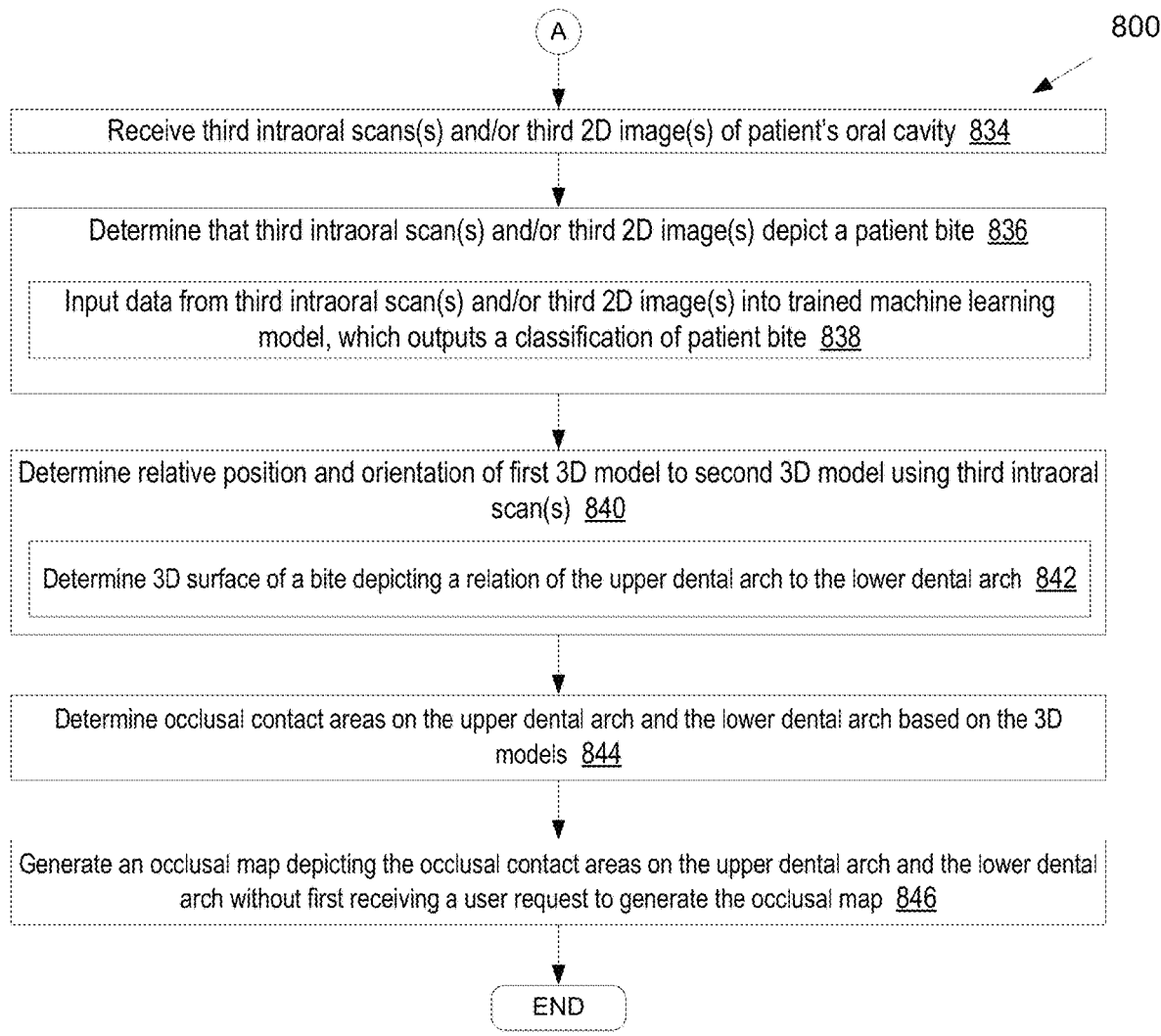

FIGS. 8A-B illustrate a flow chart of an embodiment for a method 800 of performing intraoral scanning without receiving user input specifying scanning roles. At block 802 of method 800, processing logic receives one or more first intraoral scans and/or associated 2D images of a patient's oral cavity. At block 804, processing logic determines that the first intraoral scan(s) and/or first 2D image(s) depict a first dental arch of the patient, and determines a first identity of the first dental arch (e.g., identifies the first dental arch as being the upper dental arch or the lower dental arch). This may include generating a first 3D surface from the intraoral scans at block 806 and/or inputting data from the first intraoral scans, first 2D images and/or first 3D surface (e.g., which may include one or more projections of the first 3D surface onto one or more plane) into a trained ML model, which outputs a classification of the first dental arch at block 808.

At block 810, processing logic optionally generates a first 3D surface of the first dental arch by stitching together multiple intraoral scans. Alternatively, the first 3D surface may have been generated at block 806. At block 812, processing logic automatically determines when the first 3D surface of the first dental arch is complete and/or when a user has transitioned to scanning of a next dental arch (e.g., transitions from upper jaw to lower jaw or from lower jaw to upper jaw). In one embodiment, detection of transitions between scanning roles is facilitated by using inertial measurement data. For example, if an upper jaw role was determined for a first scan, and a rotation of the intraoral scanner about a horizontal axis (or a relatively or approximately horizontal axis) was detected between the first scan and a second scan, then this may be an indication that the second scan is of a lower jaw.

At block 814, processing logic may automatically generate a first 3D model of the first dental arch if the first 3D surface was determined to be complete.

At block 816, processing logic receives one or more second intraoral scans and/or associated 2D images of the patient's oral cavity. At block 818, processing logic determines that the second intraoral scan(s) and/or second 2D image(s) depict a second dental arch of the patient, and determines a second identity of the second dental arch (e.g., identifies the second dental arch as being the upper dental arch or the lower dental arch). This may include generating a second 3D surface from the intraoral scans at block 820 and/or inputting data from the second intraoral scans, second 2D images and/or second 3D surface (e.g., which may include one or more projections of the second 3D surface onto one or more plane) into a trained ML model, which outputs a classification of the second dental arch at block 822.

At block 824, processing logic optionally generates a second 3D surface of the second dental arch by stitching together multiple intraoral scans. Alternatively, the second 3D surface may have been generated at block 820. At block 830, processing logic automatically determines when the second 3D surface of the second dental arch is complete and/or when a user has transitioned to scanning of a patient bite. At block 832, processing logic may automatically generate a second 3D model of the second dental arch if the second 3D surface was determined to be complete.

At block 834, processing logic receives one or more third intraoral scans and/or associated 2D images of the patient's oral cavity. At block 836, processing logic determines that the third intraoral scan(s) and/or third 2D image(s) depict a patient bite. This may include generating a third 3D surface from the intraoral scans and/or inputting data from the third intraoral scans, third 2D images and/or third 3D surface (e.g., which may include one or more projections of the third 3D surface onto one or more plane) into a trained ML model, which outputs a classification of the patient bite role at block 838.

At block 840, processing logic determines a relative position and orientation of the first 3D model to the second 3D model using the third intraoral scans depicting the patient bite. This may include at block 842 determining a 3D surface of a bite depicting a relation of the upper dental arch to the lower dental arch.

At block 844, processing logic determines occlusal contact areas on the upper dental arch and the lower dental arch based on the 3D models of the upper and lower dental arches and/or the 3D surface determined at block 842. Processing logic may also determine a margin line on preparation teeth on the upper and/or lower dental arches (e.g., first and/or second 3D models of such dental arches). At block 846, processing logic may generate an occlusal map depicting the occlusal contact areas on the upper dental arch and the lower dental arch. This may be performed automatically without first receiving an instruction from a user to generate an occlusal map or to perform an occlusal contact analysis. For example, occlusal analysis may be carried out in the form of an occlusal map which may be presented in different colors (e.g., as a heat map) depending on the distance from the surface of the tooth to the opposing tooth in the opposing arch. Using this occlusal map, analysis of the occlusion and interference existing in the maxillo-mandibular complex can be carried out.

Methods 700 and 800 provide multiple advantages over the state of the art workflow for intraoral scanning. Traditionally, a user provides input that they are scanning an upper arch, scans the upper arch, then provides an input that they are done scanning the upper arch. Additionally, the user provides input that they are scanning a lower arch, scans the lower arch, then provides an input that they are done scanning the lower arch. Additionally, the user provides input that they are scanning a patient bite, scans the patient bite, then provides an input that they are done scanning the patient bite. Additionally, for each preparation tooth the user provides input that they are scanning that particular preparation tooth, scans that particular preparation tooth, then provides an input that they are done scanning the preparation tooth. The 3D model generated for the preparation tooth from the preparation tooth scanning pass may be higher resolution than the 3D model generated for the upper and lower jaws. This workflow results in multiple scanning passes of each preparation tooth (one associated with an upper or lower jaw scanning role and one associated with a preparation tooth scanning role), and further results in a separate segment or 3D model for each of the upper dental arch, the lower dental arch and each of the preparation teeth. Thus, duplicate segments/3D models are generated for each of the preparation teeth, one specific to that preparation tooth and one of a full dental arch that includes that preparation tooth. In contrast, in embodiments herein, such as described with reference to method 700, each preparation tooth is only scanned once (in a single scanning pass). For example, when a doctor scans a dental arch that includes a preparation tooth, processing logic automatically identifies the preparation tooth and uses a higher resolution for the preparation tooth than is used for a remainder of the dental arch. Additionally, a portion of the 3D model that depicts a margin line of the preparation tooth may be shown at an even higher resolution than is used for a remainder of the preparation tooth in embodiments. Accordingly, in some embodiments a multi-resolution 3D model may include three or more different resolutions, each associated with a different type of dental object or area. In some embodiments, smoothing or simplification is performed for some regions that are not designated as areas of interest to reduce the resolution of those areas.

Figure 9:
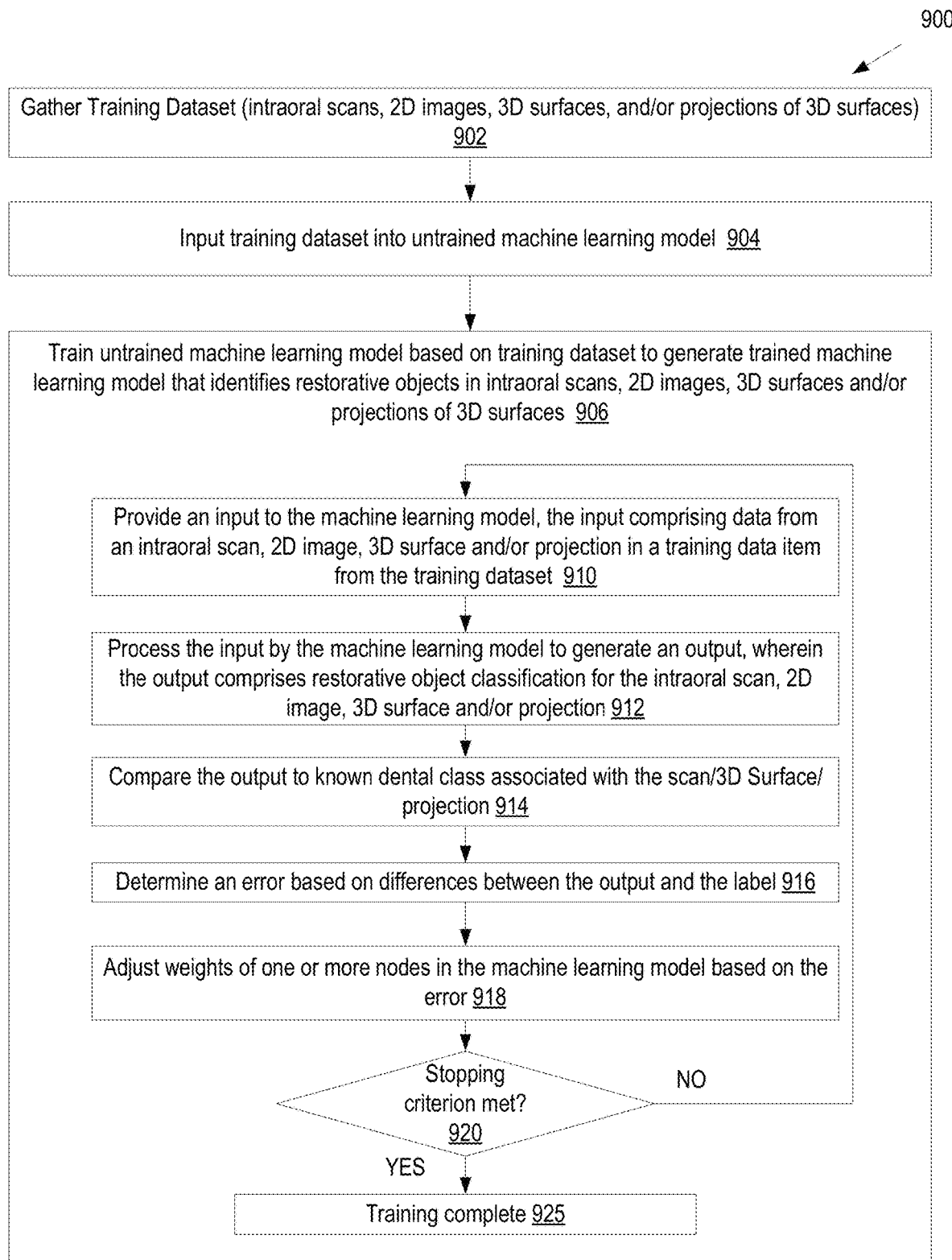
FIG. 9 is a flow chart illustrating an embodiment for a method of training a machine learning model to classify dental objects, including restorative objects.

FIG. 9 is a flow chart illustrating an embodiment for a method 900 of training a machine learning model to classify dental objects, including restorative objects. At block 902 of method 900, processing logic gathers a training dataset, which may include labeled intraoral scans, 2D images, 3D surfaces and/or projections of 3D surfaces. In embodiments, data items in the training dataset include point-level or pixel-level labels of dental classes. The dental classes may include, for example a teeth class, a gingiva class, a restorative object class, a palate class, and/or one or more other dental classes. The dental classes may additionally include different types of restorative object classes, such as one or more types of scan bodies (or a generic scan bodies class), a preparation tooth class, an implant class, and so on. Multiple other types of labels may also be associated with the data items in the training dataset, such as an excess material or moving tissue class. In embodiments, data items in the training dataset include image-level or input-level classifications. In one embodiment, input-level classifications include restorative object or no restorative object.

At block 904, processing logic inputs the training data into an untrained machine learning model. At block 906, processing logic trains the untrained ML model based on the training dataset to generate a trained ML model that identifies restorative objects in intraoral scans, 2D images, 3D surfaces and/or projections of 3D surfaces. In one embodiment, the ML model is trained to perform input-level or image-level/scan-level classification of inputs into one of a first class of "restorative object" or a second class of "no restorative object." In one embodiment, the machine learning model is trained based on the training dataset to generate a trained machine learning model that performs segmentation of intraoral scans, images and/or 3D surfaces (or projections of 3D surfaces) into dental classes. This may include performing pixel-level classification of intraoral scans, 3D surfaces, images, etc. into dental classes. The machine learning model may also be trained to output one or more other types of predictions, image-level classifications (e.g., role classifications), pixel-level classifications, patch-level classifications (where a patch is a group of pixels), decisions, and so on.

In one embodiment, at block 910 an input of a training data item is input into the machine learning model. The input may include data from an intraoral scan (e.g., a height map), a 3D surface, a 2D image and/or a projection of a 3D surface. At block 912, the machine learning model processes the input to generate an output. The output may include a classification of "restorative object" or "no restorative object." Alternatively, or additionally, the output may include, for each pixel from the input, a first probability that the pixel belongs to a teeth class, a second probability that the pixel belongs to a gingiva class, and a third probability that the pixel belongs to a restorative object class. The output may additionally include, for each pixel, a probability of the pixel belonging to a palate class, a probability of the pixel belonging to a preparation tooth class, a probability of the pixel belonging to a margin line class, a probability of the pixel belonging to an attachment class, a probability of the pixel belonging to a bracket class, a probability of the pixel belonging to a scan body class, and so on. In one embodiment, the ML model outputs a probability map having a size that is equal to a size of an input image and/or intraoral scan (e.g., height map).

At block 914, processing logic compares the output dental class probabilities for the input and/or for each of the pixels to known dental classes for the input and/or for the pixels/points of the input. At block 916, processing logic determines an error based on differences between the output(s) and the label(s) associated with the input. At block 918, processing logic adjusts weights of one or more nodes in the machine learning model based on the error.

Additionally, at block 914, processing logic may compare output probabilities of other predictions, classifications, etc. to one or more other labels associated with the input. At block 916, processing logic may determine errors for each of the comparisons. At block 918, processing logic may adjust weights of one or more nodes in the machine learning model based on these errors. Thus, the machine learning model may be trained to perform dental object classification as well as or one or more other classification, prediction and/or segmentation operations.

At block 920, processing logic determines if a stopping criterion is met. If a stopping criterion has not been met, the method returns to block 910, and another training data item is input into the machine learning model. If a stopping criterion is met, the method proceeds to block 925, and training of the machine learning model is complete.

Figure 10A:
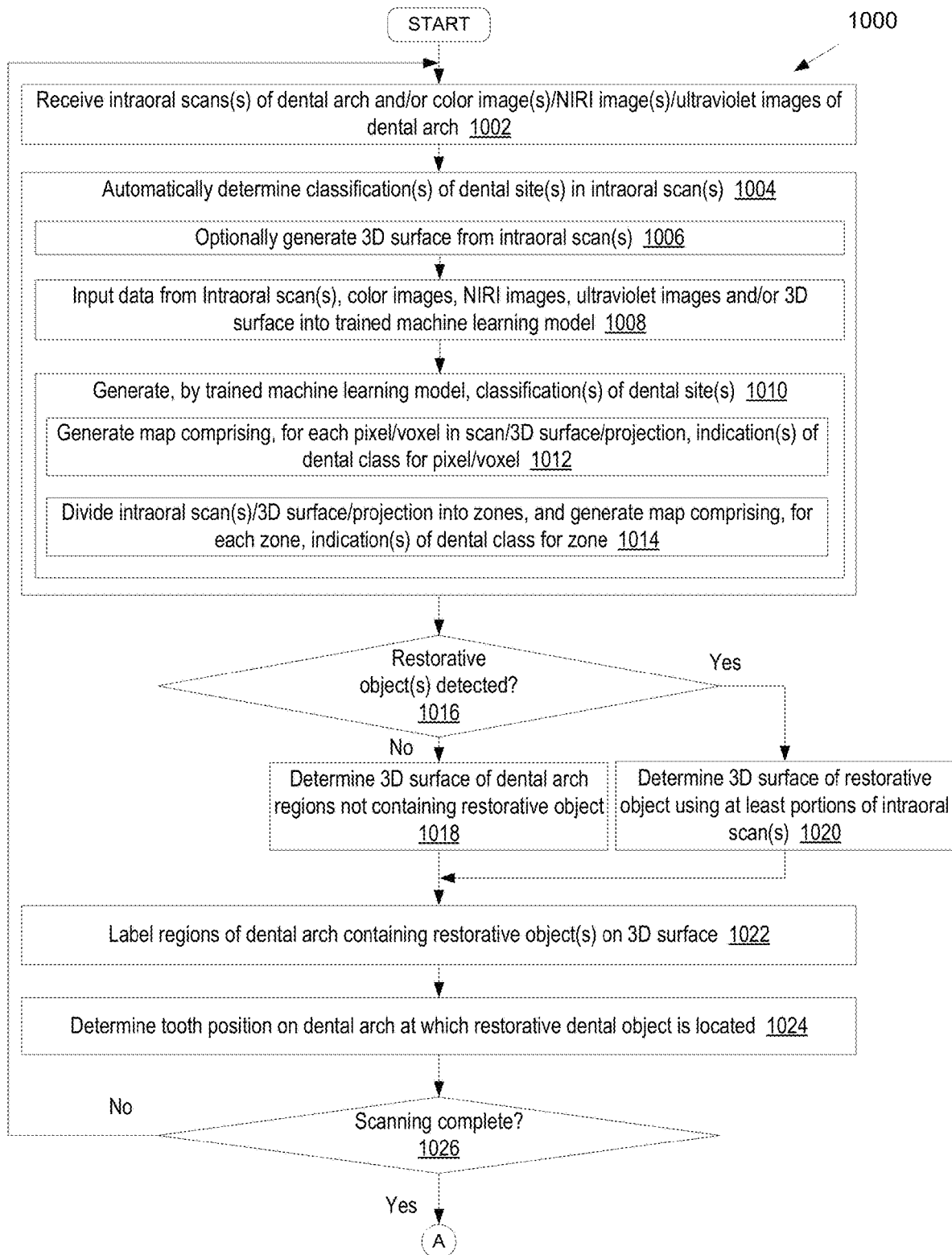
FIGS. 10A-B illustrate a flow chart of an embodiment for a method of automatically identifying restorative objects and of generating a 3D model of a dental arch including such restorative objects.
Figure 10B:
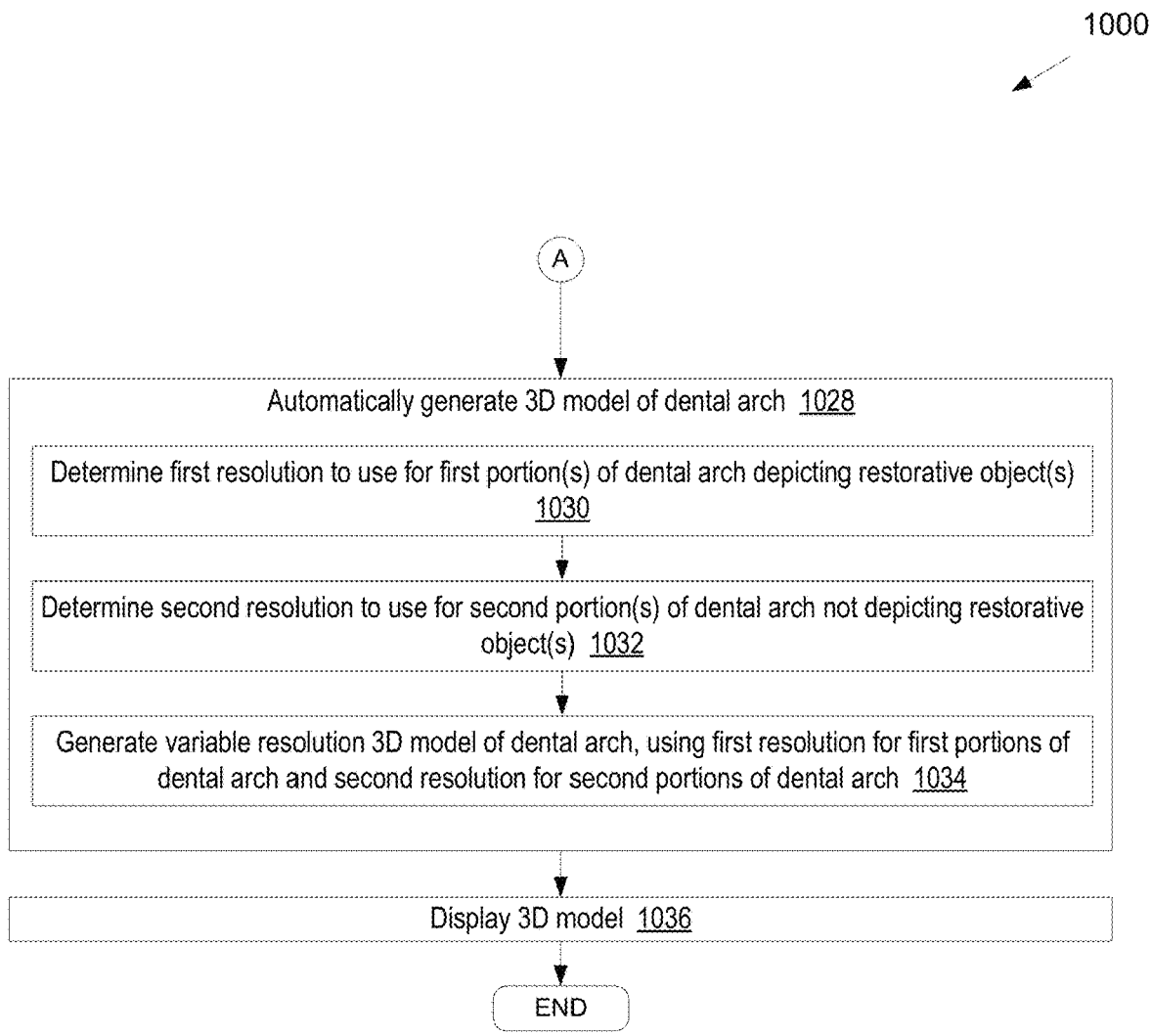

FIGS. 10A-B illustrate a flow chart of an embodiment for a method 1000 of automatically identifying restorative objects and of generating a 3D model of a dental arch including such restorative objects. At block 1002 of method 1000, processing logic receives one or more intraoral scans and/or associated images (e.g., color images and/NIRI images and/or ultraviolet images) of a dental arch.

At block 1004, processing logic automatically determines classifications of dental sites in the intraoral scans, in the images, and/or in 3D surfaces formed by stitching together the intraoral scans. Classifications of dental sites may be performed on an image/scan-level basis, on a point/voxel/pixel-level basis, or on an intermediate basis (e.g., for patches or zones containing 9 pixels or some other number of pixels). In one embodiment, processing logic classifies scans/images as containing a restorative object or as not containing a restorative object. Additionally, or alternatively, processing logic may classify scans/images as containing other types of dental objects and/or areas of interest that are designated to be represented using a high resolution. Such a classification or classifications may be made using a trained ML model or a rule-based approach. For example, processing logic may determine whether an input includes a representation of a restorative object (e.g., a preparation tooth) and/or a margin line based on processing of the second intraoral scan data using a machine learning model that has been trained to identify restorative objects and/or margin lines. Alternatively, one or more rule-based algorithms may be used to process the intraoral scan data and/or 3D surface, and may determine that the intraoral scan data and/or 3D surface depicts a restorative object and/or a margin line based on the intraoral scan data and/or 3D surface data satisfying criteria of the one or more rule-based algorithms. For example, preparation teeth and scan bodies may have a shape that does not naturally occur in the mouth. A shape of a dental site represented in the intraoral scan data and/or 3D surface data may be analyzed using the rule-based algorithm to determine that it meets the criteria for a preparation tooth or scan body.

In one embodiment, processing logic performs pixel-level classification or patch-level classification of dental sites to identify pixels or patches (e.g., groups of pixels) depicting restorative objects and to identify pixels or patches not depicting restorative objects. In one embodiment, processing logic performs pixel-level or patch-level classification (also referred to as zone-level classification) of dental sites to identify pixels or patches/zones depicting teeth, pixels or patches/zones depicting gingiva and pixels or patches/zones depicting restorative objects. In one embodiment, processing logic performs pixel-level or patch-level classification (also referred to as zone-level classification) of dental sites to identify pixels or patches/zones depicting an interproximal area between teeth, pixels or patches/zones depicting a border between gingiva and teeth, pixels or patches/zones depicting margin lines and/or pixels/patches otherwise associated with areas of interest. The pixel-level classification or patch-level classification may also be performed to identify pixels or patches/zones depicting other types of objects found in an oral cavity, such as an upper palate, attachments on teeth, brackets on teeth, preparation teeth, scan bodies, prosthodontics, and so on. Based on the classifications, processing logic may perform segmentation of the intraoral scans, images and/or 3D surfaces in some embodiments.

In one embodiment, at block 1006 processing logic generates a 3D surface by stitching together multiple intraoral scans. Processing logic may then project the 3D surface onto multiple different planes to provide multiple views of the 3D surface. For example, processing logic may project the 3D surface onto a lingual side plane, onto a buccal side plane, and onto an occlusal plane.

At block 1008, processing logic may input data from the intraoral scans (e.g., height maps) and/or color images associated with the intraoral scans into a trained ML model. Additionally, or alternatively, processing logic may input one or more projections of the 3D surface generated at block 1006 into a trained ML model, optionally with one or more color images. Additionally, or alternatively, processing logic may input the 3D surface or portions of the 3D surface into a trained ML model (e.g., for an ML model trained to operate on 3D data).

At block 1010, the trained ML model(s) may output one or more dental classification based on processing of the input data (e.g., intraoral scan(s), projections, images, 3D surface, etc.). The output dental classification(s) may include any of the dental classifications discussed herein above, for example. In one embodiment, at block 1012 processing logic (e.g., the ML model) generates a map comprising, for each pixel, voxel or point in the intraoral scan, the 3D surface, or the projection of the 3D surface that was input into the ML model, one or more indications of a dental class for the pixel. In one embodiment, the map includes for each pixel, voxel or point a value indicating a most likely dental class for that pixel/voxel/point. The map may also include, for each pixel/voxel/point, a confidence value indicating a confidence that the determined dental class for that pixel/voxel/point is correct. In one embodiment, the map is a probability map that includes, for each pixel, voxel or point a separate probability value for each of the types of dental classes.

In one embodiment, the ML model(s) further outputs a role classification associated with the intraoral scan data and/or 3D surface data.

In one embodiment, at block 1014 processing logic (e.g., the ML model) divides the intraoral scan(s), 3D surface and/or projection(s) of a 3D surface into zones or patches. Processing logic (e.g., the ML model) may then generate a map comprising, for each zone or patch, an indication of a dental class for that zone or patch. This technique essentially reduces a resolution of the input data, which reduces a computational load associated with processing the input data to perform dental classification and/or segmentation.

At block 1016, processing logic may determine whether one or more restorative objects have been detected. In one embodiment, processing logic determines whether one or more other type of dental objects or areas of interest that are designated to be represented with a high resolution are identified. Examples of such other types of dental objects or areas of interest include a margin line, a tooth to gingiva border, and a tooth to tooth border (e.g., interproximal area between teeth). If no restorative object (or no other object or area of interest to be represented with a higher resolution) has been detected, then at block 1018 processing logic may determine a 3D surface of a region of dental arch not containing a restorative object (and optionally not including any other dental object or area designated to be represented with a high resolution) based on the classifications determined at block 1004. This may include stitching an intraoral scan depicting the region of the dental arch to a 3D surface of the dental arch. In one embodiment, if an intraoral scan is determined to not depict a restorative object or other dental object or area designated to be represented with a high resolution, then the intraoral scan may be marked as not depicting a restorative object such as a preparation (and optionally as not containing any other dental object or area designated to be represented with a high resolution). The region of the 3D surface generated from the intraoral scan may have the low resolution. Other regions of the 3D surface may have the low resolution or a high resolution (where high and low are used herein as relative terms to one another).

If at block 1016 processing logic determines that one or more restorative objects have been detected and/or that one or more other types of dental objects or areas designated to be represented with a high resolution have been detected, then at block 1020 processing logic may determine a 3D surface of a region of a dental arch containing a restorative object and/or other type of dental object or area designated to be represented with a high resolution based on the classifications determined at block 1004. In one embodiment, if an intraoral scan is determined to depict a restorative object, then the intraoral scan may be marked as containing a restorative object such as a preparation. If an intraoral scan is determined to depict another dental object or area of interest to be represented using high resolution, then the intraoral scan may be marked as containing such an other dental object or area of interest. The 3D surface generated from the intraoral scan may have the high resolution. Other regions of the 3D surface may have the low resolution or the high resolution.

At block 1022, processing logic may label regions of the dental arch on the 3D surface based on the determined dental classifications. In one embodiment, processing logic labels regions containing restorative objects. Processing logic may additionally label regions associated with different dental classes. For example, processing logic may label teeth and gingiva as well. In other examples, processing logic may label a border between teeth and gingiva, may label interproximal regions between teeth, may label margin lines, and so on. If dental classifications were determined for intraoral scans or projections of a 3D surface onto a plane, then registration information of the intraoral scans or projections to the 3D surface may be used to determine points on the 3D surface that correspond to pixels in the intraoral scans or projections. These points on the 3D surface may then be assigned dental classes according to the dental classes of the corresponding pixels in the intraoral scans or projections.

Different intraoral scans and/or projections of 3D surfaces may have pixels that correspond to the same point on the 3D surface. In some instances these multiple pixels may have different determined dental classes and/or different dental class probabilities. In such instances, processing logic may use a voting function to determine a dental class for each point. For example, each set of probability values from an intraoral scan may indicate a particular dental class. Processing logic may determine the number of votes for each dental class for a point, and may then classify the point as having a dental class that receives the most votes.

Generally the majority vote of the highest probability value of a dental class represents the dental class for that point. However, further processing may be performed in some instances to select a dental class for a point even if that dental class was not a highest probability dental class for that point. For example, one or more cost functions may be applied to select a dental class other than a highest probability dental class for a point. In a further example, processing logic may compute one or more quality scores for a particular dental object, such as a restorative object, a tooth, and so on. Each quality score may be based on a cost value for the dental object (or a segment of the dental object) as computed using a cost function, and the dental object quality scores may be compared to a quality threshold to determine which dental class to assign to a point.

In one embodiment, processing logic generates a matrix that identifies, for each point (e.g., edge, vertex, voxel, etc. on a 3D surface), a probability that the point belongs to a restorative object class or other dental class. For example, entries in the matrix that have no chance of representing a restorative object may have an assigned 0% probability. Processing logic may also generate a matrix that identifies, for each point (e.g., edge, vertex, voxel, etc. on a 3D surface), a probability that the point belongs to a margin line, a gum to tooth border, or a tooth to tooth border (e.g., interproximal region between teeth)

Processing logic may use the cost function to create a closest contour going through points with high probabilities of representing the restorative object or other dental class. In one embodiment, a total cost of the contour that is drawn for the restorative object or other dental class is the sum of all edges (e.g., vertexes) included in the restorative object or other dental class, adjusted by weights associated with each of the vertexes. Each weight for a vertex may be a function of the probability assigned to that vertex. The cost for that vertex being included in the restorative object or other dental class may be approximately $1/(A+P)$, where A is a small constant and P is the probability of the vertex representing the restorative object or other dental class. The smaller the probability for a vertex, the larger the cost of that vertex being included in a region classified as the restorative object (or other dental class if being computed to determine a contour of another dental class). Costs may also be computed for segments of the restorative object based on a sum of the costs of the vertexes included those segments. When probability is close to 100%, then cost is approximately 1 adjusted by length.

In one embodiment, a path finding operation or algorithm is applied to the 3D model using values from the matrix as a cost basis. Any pathfinding algorithm may be used. Some examples of possible path finding algorithms to use include dynamic programming, Dijkstra's algorithm, A* search algorithm, an incremental heuristic search algorithm, and so on. A pathfinding algorithm may apply a cost function to determine a path of the restorative object.

A pathfinding algorithm that uses probability of representing the restorative object in the matrix as a cost basis may search for a path with a maximal cost or a path with a minimal cost. The cost function described above searches for minimum cost using a function that is based on an inverse of probability. Alternatively, a cost function may be used that is based directly on probability, where the maximum cost is searched for. If a pathfinding algorithm is run to maximize cost, then a path between vertexes will be determined that results in a maximum aggregate of probability values. The probability scores of the vertexes may be input into the pathfinding algorithm to find the path that has the maximal cost for the probability score. The path finding algorithm may be used to define a contour that represents the restorative object (or other dental object having another dental class), margin line, tooth to gum border, tooth to tooth border, and so on.

In one embodiment, at block 1024 processing logic determines a tooth position on the dental arch at which a restorative dental object has been identified. The 3D surface and/or intraoral scans may be updated to include the tooth position information associated with the restorative dental object.

Determination of the tooth position may be performed automatically using the application of machine learning or a rule-based image processing algorithm. In an example, a 3D surface of a partial or whole upper or lower jaw with point-level classification of points on the 3D surface may be projected onto an occlusal plane. The projection of the 3D surface onto the occlusal plane may result in an image or height map showing the partial or whole upper or lower jaw. The projected image or height map may include pixel-level classification of dental classes. The projected image or height map with the pixel-level classification may be input into a trained ML model, which may output tooth numbering of each tooth in the image or height map and/or of each restorative object in the image or height map.

In one embodiment, to determine the tooth position on the dental arch for the restorative object, processing logic prompts a user to input the tooth number. The user may input the tooth number, and the input tooth number may then be stored.

At block 1026, processing logic determines whether scanning of a dental arch (e.g., upper jaw or lower jaw) is complete. Such a determination may be made as discussed above, such as by using the outputs of one or more ML models, motion data, and so on. If scanning of the dental arch is not complete, the method returns to block 1002, and additional intraoral scans, color images and/or NIRI images of the dental arch are received. If scanning of the dental arch is complete, the method continues to block 1028. In addition to proceeding to block 1028, processing logic may in parallel also return to block 1002 to receive intraoral scans for another dental arch for which scanning is not complete. If scanning of both dental arches and optionally of a patient bite are complete, then processing logic may proceed to block 1028 without in parallel returning to block 1002.

At block 1028, processing logic automatically generates a 3D model of one or more dental arch based on intraoral scans associated with that dental arch (e.g., intraoral scans classified as having a scanning role associated with the dental arch). As mentioned above, the resolution of an intraoral scan may be based on whether or not a restorative object and/or other type of dental object that is to be represented with a high resolution was detected in that intraoral scan. In particular, intraoral scans that depict restorative objects and/or other types of dental objects designated to be represented with a high resolution may have higher resolution than intraoral scans that do not depict restorative objects and/or the other types of dental objects designated to be represented with a high resolution.

In one embodiment, at block 1030 processing logic determines a first resolution to use for first portions of the dental arch depicting restorative objects and/or the other types of dental objects designated to be represented with a high resolution (e.g., margin line, gum to tooth boundary, tooth to tooth boundary, etc.). In one embodiment, at block 1032 processing logic determines a second resolution to use for second portions of the dental arch not depicting restorative objects or the other types of dental objects designated to be represented with a high resolution. Notably, the second resolution is a lower resolution than the first resolution.

At block 1034, processing logic generates a variable resolution 3D model of the dental arch. In the variable resolution 3D model of the dental arch, the first resolution is used for the first portion of the dental arch (e.g., depicting restorative objects) and the second resolution is used for the second portion of the dental arch (e.g., not depicting restorative objects).

In one embodiment, the 3D model is initially generated at a high resolution, and based on the dental object classification information, processing logic then performs a smoothing or simplifying operation to reduce the resolution to a lower resolution for one or more regions of the 3D model that were determined not to depict restorative objects or to otherwise be areas of interest. In one embodiment, the 3D model is initially generated as a multi-resolution 3D model, and portions of the high resolution regions and/or low resolution regions are smoothed or simplified to reduce the resolution for those portions. In some embodiments, in addition to or instead of reducing a resolution of one or more areas to achieve a multi-resolution 3D model, the resolution of one or more areas of a 3D model may be increased to achieve a multi-resolution 3D model.

At block 1036, the 3D model may be displayed (e.g., output to a display of a GUI of intraoral scan application 115 of FIG. 1).

The intraoral site at which a prosthesis is to be implanted generally should be measured accurately and studied carefully, so that the prosthesis such as a crown, denture or bridge, for example, can be properly designed and dimensioned to fit in place. For this reason, it can be useful for preparation teeth to be represented at a higher resolution than other areas of a dental arch in a 3D model. A good fit enables mechanical stresses to be properly transmitted between the prosthesis and the jaw, and can prevent infection of the gums and tooth decay via the interface between the prosthesis and the intraoral site, for example. After the intraoral site has been scanned, a virtual 3D model (also referred to herein simply as a 3D model) of the dental site may be generated, and that 3D model may be used to manufacture a dental prosthetic. Accordingly, a variable resolution 3D model that includes a high resolution representation of a preparation tooth or other restorative object may be used.

Figure 11:
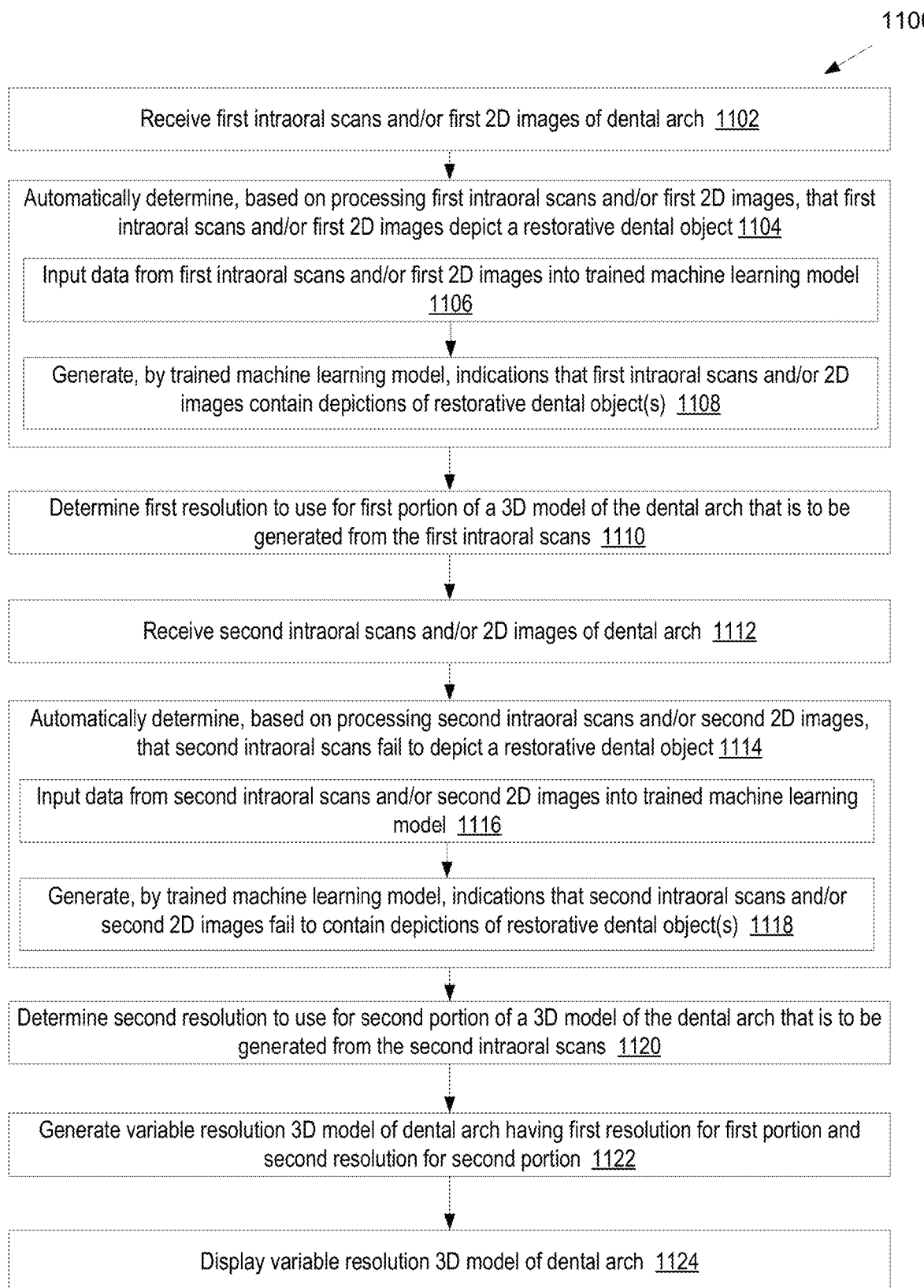
FIG. 11 illustrates a flow chart of an embodiment for a method of automatically identifying restorative objects and of generating a 3D model of a dental arch including such restorative objects.

FIG. 11 illustrates a flow chart of an embodiment for a method 1100 of automatically identifying restorative objects and of generating a 3D model of a dental arch including such restorative objects. Method 1100 is described with reference to identifying restorative objects. However, it should be understood that method 1100 may also be applied to other types of dental classes to be depicted using a higher resolution than a remainder of dental objects on a dental arch. For example, processing logic may access a list of types of objects or areas of interest (AOIs) to be represented with a high resolution. The list may be modified by a user or automatically by processing logic based on the user's practice. The user or processing logic may add any type of dental object class to the list and/or may remove any type of dental object class from the list. Those objects and/or AOIs on the list will then be represented with a higher resolution than other objects and/or AOIs. In one embodiment, the list automatically includes restorative objects (e.g., preparation teeth) as a default. In one embodiment, the list additionally includes margin lines, gum to tooth borders and/or interproximal areas as a default.

At block 1102 of method 1100, processing logic receives one or more first intraoral scans and/or first images (e.g., 2D color images and/or 2D NIRI images and/or 2D ultraviolet images) of a dental arch.

At block 1104, processing logic automatically determines, based on processing the first intraoral scans and/or the first images, that the first intraoral scans and/or first images depict a restorative object such as a preparation (or other type of object on the list). In one embodiment, at block 1106 processing logic inputs input data from the first intraoral scans (e.g., height maps) and/or first images associated with the first intraoral scans into a trained ML model. At block 1010, the trained ML model outputs an indication that the first intraoral scans and/or first images contain depictions of a restorative dental object such as a preparation (or other type of object on the list).

At block 1110, processing logic determines a first resolution to use for a first portion of a 3D model of the dental arch that is to be generated from the first intraoral scans. The 3D surface may include multiple faces, divided into connected triangles or other surface shapes. The resolution may be the number of such faces in a given unit area. Larger resolutions have a higher number of faces in a given unit area, and lower resolutions have a smaller number of faces in a given unit area.

At block 1112, processing logic, processing logic receives one or more second intraoral scans and/or second images (e.g., 2D color images and/or 2D NIRI images and/or 2D ultraviolet images) of a dental arch. At block 1114, processing logic automatically determines, based on processing the second intraoral scans and/or the second images, that the second intraoral scans and/or second images fail to depict a restorative object (or other type of object on the list). In one embodiment, at block 1116 processing logic inputs input data from the second intraoral scans (e.g., height maps) and/or second images associated with the second intraoral scans into the trained ML model. At block 1010, the trained ML model outputs an indication that the second intraoral scans and/or second images fail to contain depictions of a restorative dental object (or other type of object on the list).

At block 1120, processing logic determines a second resolution to use for a second portion of the 3D model of the dental arch that is to be generated from the second intraoral scans.

At block 1122, processing logic generates a variable resolution 3D model of the dental arch, where the variable resolution 3D model has a first resolution for the first portion of the 3D model and a lower second resolution for the second portion of the 3D model. At block 1124, processing logic displays the variable resolution 3D model of the dental arch.

In some embodiments, the list of dental objects and/or AOIs to be depicted with a higher resolution is divided into categories, where one category may be high resolution and another category may be ultra-high resolution. Regions associated with dental objects and/or AOIs included in the ultra-high resolution category may be represented with an even higher resolution than regions associated with dental objects and/or AOIs included in the high resolution category. For example, a margin line may be in the ultra-high category and a preparation tooth or other restorative object may be in the high resolution category.

Figure 12A:
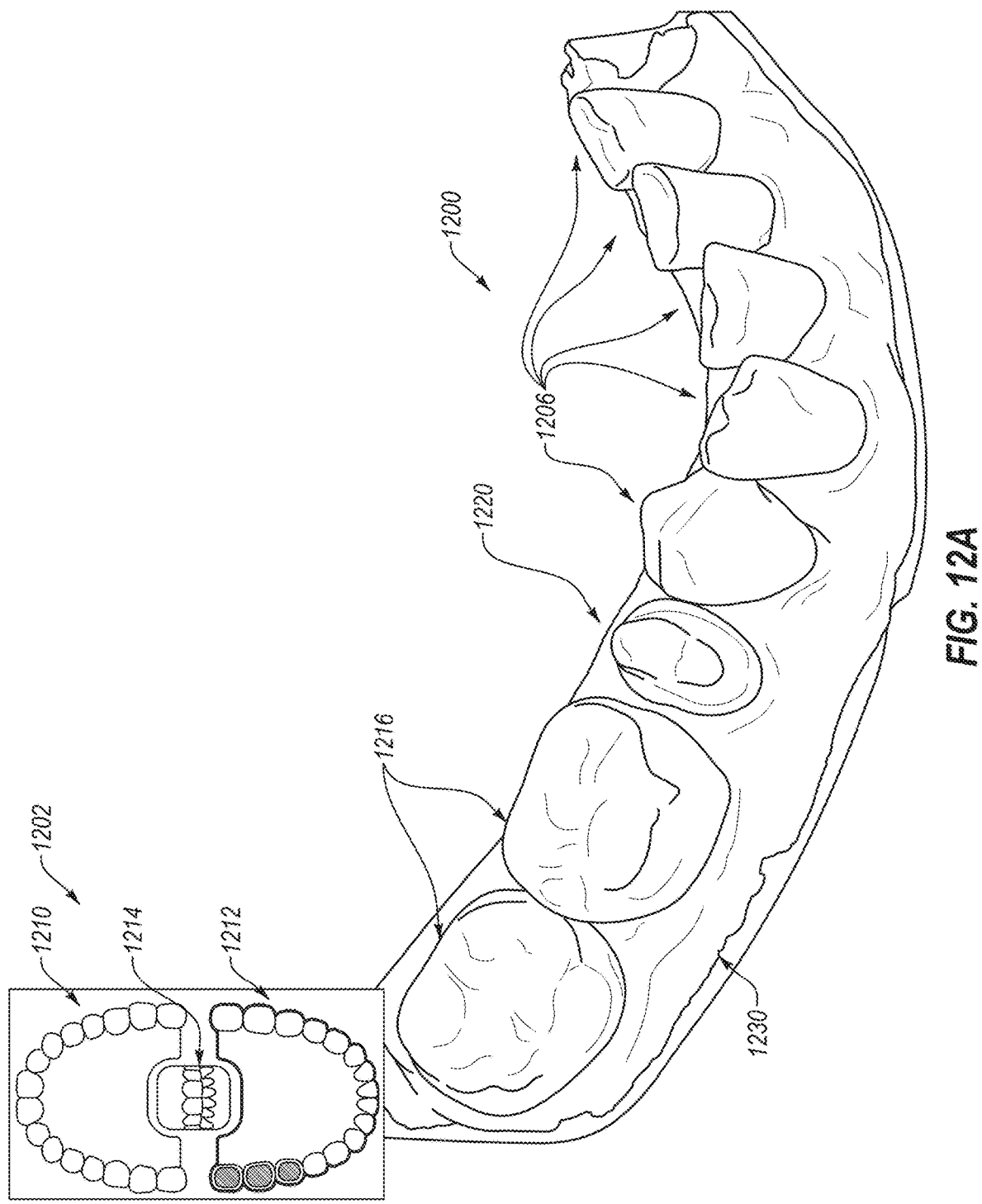
FIGS. 12A-B illustrate intraoral scans of restorative objects and dental objects naturally occurring in a patient mouth.

FIG. 12A illustrates a view of an intraoral scan application's GUI showing a 3D surface 1200 of a lower dental arch during scanning of the lower dental arch. As shown, during scanning processing logic has identified gingiva, a first type of restorative objects 1216, a second type of restorative objects 1220, and teeth 1206. The first type of restorative objects 1216 are gold crowns, and the second type of restorative object 1220 is a preparation tooth. The GUI may include a scanning role indicator 1202 that shows a first graphic 1210 for an upper dental arch scanning role, a second graphic 1212 for a lower dental arch scanning role and a third graphic 1214 for a bite scanning role. During scanning processing logic also determined that 3D surface 1200 is a lower dental arch, which is shown in scanning role indicator 1202 by highlighting the second graphic associated with the lower dental arch scanning role. Once scanning of the lower dental arch is complete and a user transitions to scanning an upper dental arch, the first graphic 1210 associated with the upper dental arch scanning role may be highlighted, and a visualization of the second graphic associated with the lower dental arch scanning role may be updated to indicate that scanning of the lower dental arch is complete. Similarly, once scanning of the upper dental arch is complete and a user transitions to scanning a patient bite, the third graphic 1214 associated with the bite scanning role may be highlighted, and a visualization of the first graphic 1210 associated with the upper dental arch scanning role may be updated to indicate that scanning of the upper dental arch is complete.

In one embodiment, the first graphic 1210 associated with the upper dental arch includes a separate tooth icon for each tooth on the upper dental arch. Similarly, the second graphic 1212 associated with the lower dental arch includes a separate icon for each tooth on the lower dental arch. Each icon of a tooth on may be associated with a tooth number. Processing logic may have identified the tooth numbers associated with the identified restorative objects. A visualization of the icons associated with those tooth numbers associated with restorative objects may be updated so that a user may see at a glance which teeth locations on the lower dental arch have restorative objects.

Figure 12B:
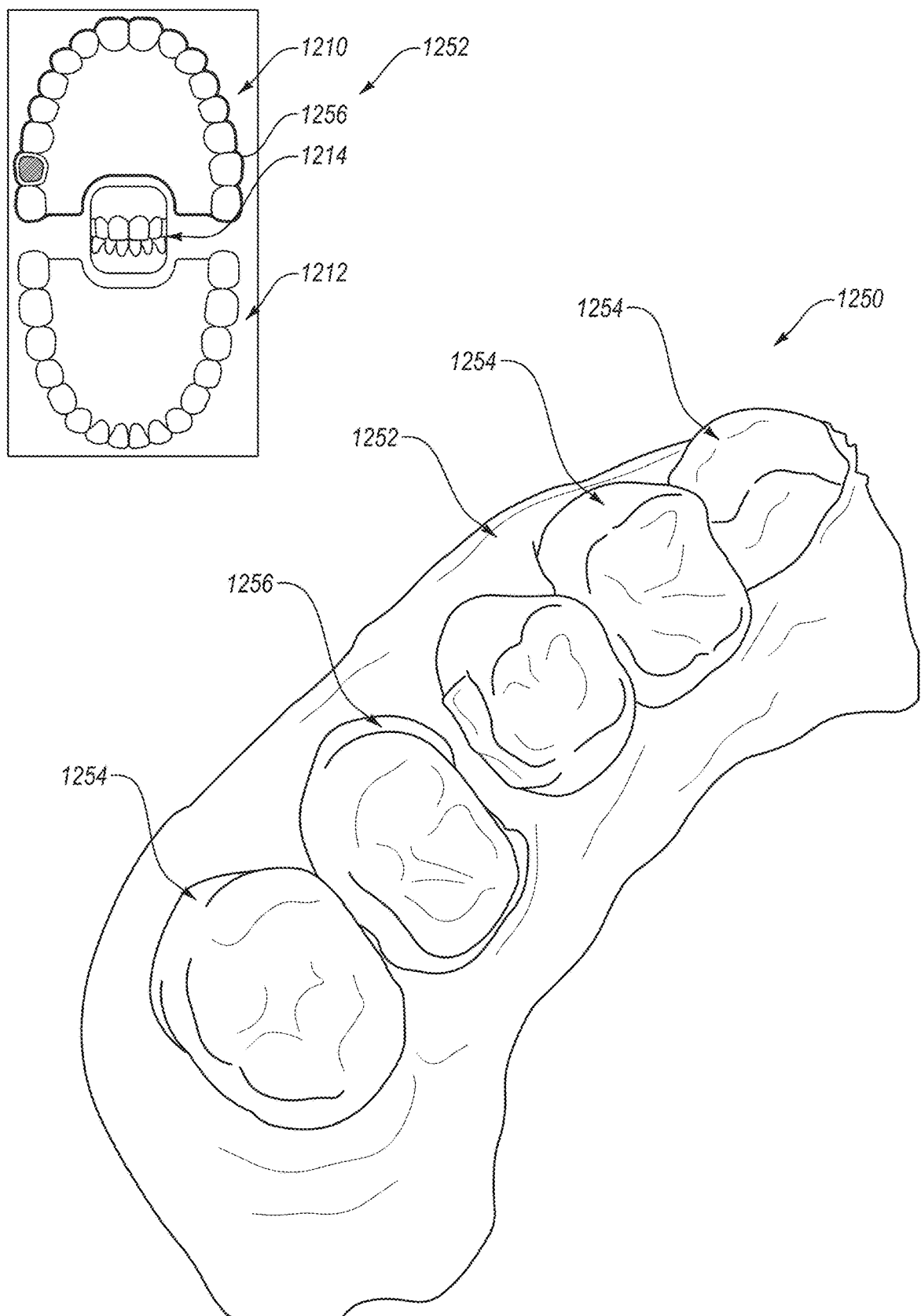

FIG. 12B illustrates a view of an intraoral scan application's GUI showing a 3D surface 1250 of an upper dental arch during scanning of the upper dental arch. As shown, during scanning processing logic has identified gingiva 1252, a restorative object 1256, and teeth 1254. The restorative object 1256 is a preparation tooth. The GUI may include scanning role indicator 1202 that shows a first graphic 1210 for an upper dental arch scanning role, a second graphic 1212 for a lower dental arch scanning role and a third graphic 1214 for a bite scanning role. During scanning processing logic also determined that 3D surface 1250 is an upper dental arch, which is shown in scanning role indicator 1202 by highlighting the first graphic 1210 associated with the upper dental arch scanning role. Once scanning of the upper dental arch is complete and a user transitions to scanning a lower dental arch, the second graphic 1212 associated with the upper dental arch scanning role may be highlighted, and a visualization of the first graphic 1210 associated with the upper dental arch scanning role may be updated to indicate that scanning of the upper dental arch is complete. Similarly, once scanning of the lower dental arch is complete and a user transitions to scanning a patient bite, the third graphic 1214 associated with the bite scanning role may be highlighted, and a visualization of the second graphic 1212 associated with the lower dental arch scanning role may be updated to indicate that scanning of the lower dental arch is complete.

In one embodiment, the first graphic 1210 associated with the upper dental arch includes a separate tooth icon for each tooth on the upper dental arch. Similarly, the second graphic 1212 associated with the lower dental arch includes a separate icon for each tooth on the lower dental arch. Each icon of a tooth on may be associated with a tooth number. Processing logic may have identified the tooth numbers associated with the identified restorative objects. A visualization of the icons associated with those tooth numbers associated with restorative objects may be updated so that a user may see at a glance which teeth locations on the lower dental arch have restorative objects.

Figure 13A:
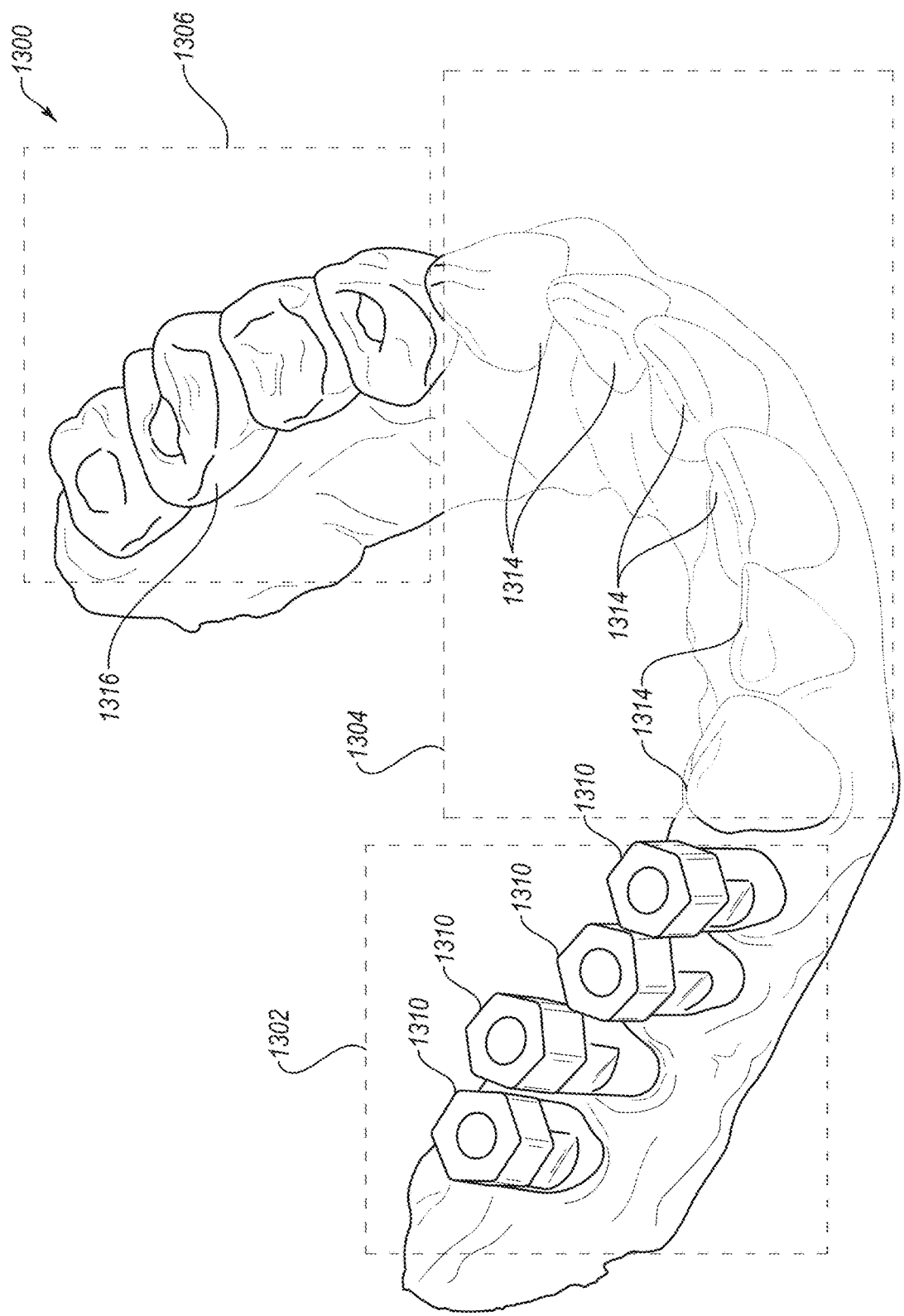
FIG. 13A illustrates a variable resolution 3D model of a dental arch.

FIG. 13A illustrates a variable resolution 3D model 1300 of a dental arch. The variable resolution 3D model includes three different regions. A first region 1302 includes scan bodies 1310, and is shown at a high resolution. A second region 1304 includes natural teeth 1314, and is shown at a lower resolution. A third region 1306 includes a bridge 1316 and may be shown at the high resolution or at the lower resolution, depending on a setting of an intraoral scan application. For the intraoral scan application, restorative dental objects such as scan bodies and preparations are represented at high resolution and natural teeth are represented at the lower resolution. The intraoral scan application may include a first setting to use the high resolution for dental prosthetics or a second setting to use the lower resolution for dental prosthetics. The setting may be user selectable. The user may also select to use the high resolution setting for natural teeth and/or to use the lower resolution setting for restorative dental objects in embodiments.

Figure 13C:
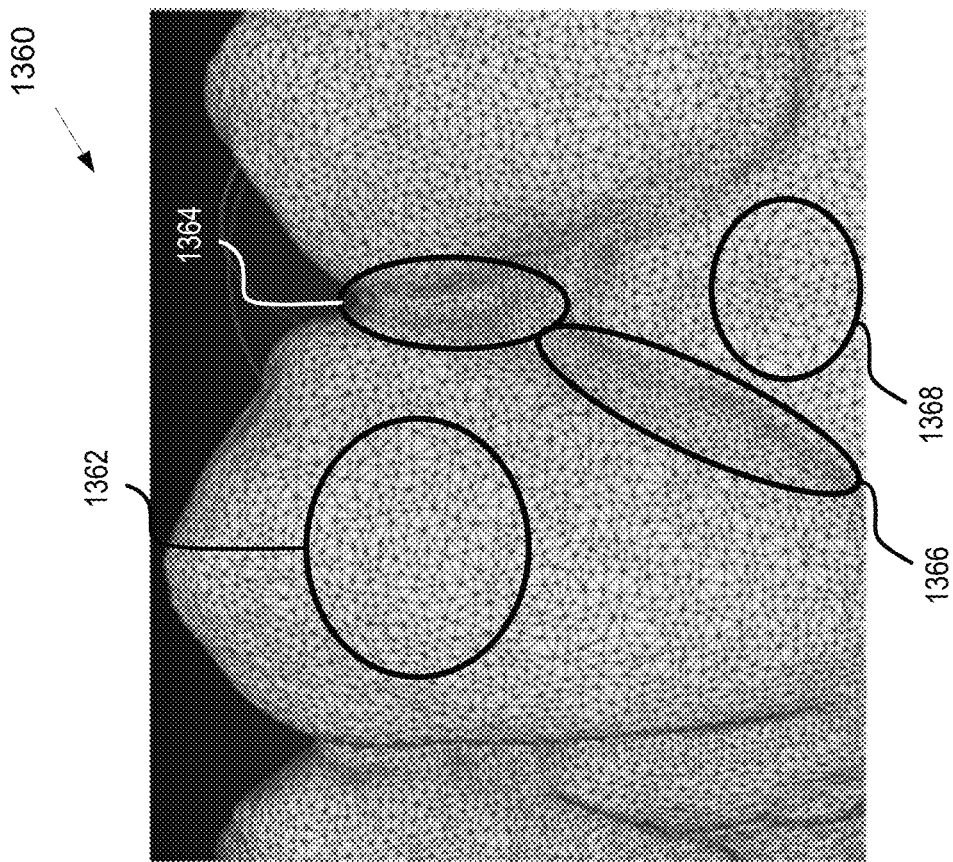
FIG. 13C illustrates a variable resolution version of the 3D model of the dental arch of FIG. 13B.
Figure 13B:
FIG. 13B illustrates a 3D model of a dental arch.

FIG. 13B illustrates a 3D model 1350 of a dental arch. The 3D model 1350 is a high resolution model with a uniform resolution for all regions of the 3D model 1350. As shown, a very high number of vertexes and/or polygons per unit area are included in the 3D model 1350.

FIG. 13C illustrates an updated 3D model 1360 that is a variable resolution version of the 3D model 1350. Multiple regions 1362, 1364, 1366, 1368 of the 3D model 1360 are depicted. A first region 1368 is of a gingiva, and has a first resolution that may be a lowest resolution of the 3D model 1360. A second region 1362 is of a natural tooth, and has a second resolution that may be slightly higher than the first resolution. A third region 1366 is of a tooth to gingiva border, and a fourth region 1364 is of a tooth to tooth border (interproximal region). The third and fourth regions 1364, 1366 may each have a third resolution, which may be a higher resolution than the second resolution. As shown, first region 1368 has a lowest number of vertexes and/or polygons per unit area, second region 1362 has a greater number of vertexes and/or polygons per unit area than first region 1368, and third and fourth regions 1364, 1366 have still a greater number of vertexes and/or polygons per unit area than second region 1362.

Figure 14B:
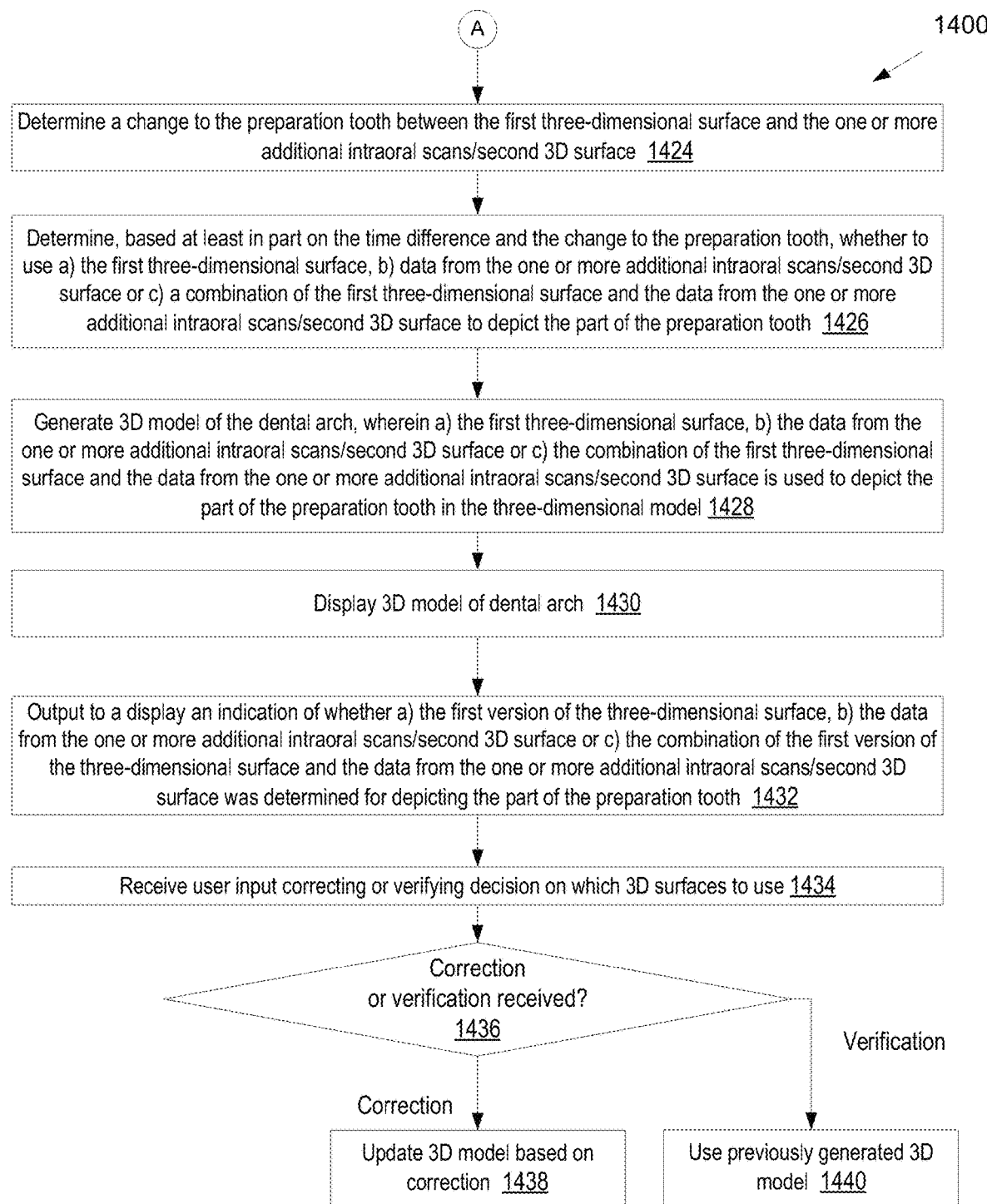

FIGS. 14A-B illustrate a flow chart of an embodiment for a method 1400 of automatically generating and updating a 3D model of a preparation tooth as the preparation tooth is modified. One of the most complex workflows associated with intraoral scanning for a dentist to learn is the restorative workflow. The restorative workflow generally involves the doctor scanning a tooth before grinding it and generating a pre-scan 3D model of the preparation tooth, then grinding the tooth to generate a preparation tooth, then inserting retraction cord around the preparation tooth, then scanning the tooth again before gingiva collapse back over a margin line of the preparation tooth and generating a 3D model of the preparation tooth. Then, if the preparation tooth needs to be modified, the doctor manually selects a region of 3D model of the preparation tooth to erase and replace, scans the preparation tooth again, and replaces the manually selected region of the 3D model based on the further scans that were generated. The doctor may need to perform additional grinding of the preparation tooth to increase a clearance between the preparation tooth and a tooth on an opposite jaw for example, or may need to repack dental cord, pull the dental cord, and rescan a region of the margin line around the preparation tooth that was obscured in the previous 3D model.

Method 1400 provides an automated restorative workflow in which processing logic automatically performs many of the operations that are traditionally manually performed by a doctor, such as identifying which areas of a 3D model of a preparation tooth to update. Processing logic can perform such operations automatically by understanding which regions of or around a preparation tooth have changed, and then determining which scans of the changed regions have better quality.

Method 1400 relates to automatically determining whether an orthodontic workflow or a restorative workflow is appropriate, and automatically following a restorative treatment workflow with minimal or no user input. In one embodiment, processing logic automatically determines based on analysis of one or more intraoral scans and/or 3D surfaces (or projections of 3D surfaces) generated from intraoral scans whether an orthodontic workflow or a restorative workflow is appropriate. In one embodiment, if a restorative object is detected, then a determination is made that a restorative workflow is appropriate. In one embodiment, if no restorative objects are detected, then a determination is made that an orthodontic workflow is appropriate. In some embodiments, processing logic may include historical information indicating whether a particular dental office in which scanning is being performed only provides orthodontic treatment, only provides restorative treatment, or provides orthodontic and restorative treatment. If processing logic determines that the dental office only provides restorative treatment, then a restorative workflow may be determined automatically based on such information. If processing logic determines that the dental office only provides orthodontic treatment, then an orthodontic workflow may be determined automatically based on such information. In embodiments, a combination of historical information about the dental office and analysis of intraoral scan data (or 3D surface data) is used to determine whether an orthodontic workflow or a restorative workflow is appropriate.

At block 1402 of method 1400, processing logic receives a first plurality of intraoral scans and/or 2D images (e.g., color images) of a dental arch that were generated by an intraoral scanner at a first time. The first plurality of intraoral scans may be received as they are generated by an intraoral scanner scanning a mouth after a doctor has ground a tooth to form a preparation tooth. At block 1404, processing logic determines a first 3D surface of at least a portion of a dental arch using the first plurality of intraoral scans (e.g., by stitching together the first plurality of intraoral scans).

At block 1406, processing logic automatically determines that the first 3D surface depicts at least a part of a preparation tooth and/or a part of a surrounding region of the preparation tooth. The depicted part of the preparation tooth and/or surrounding region may include a ground region of the preparation tooth, an unground region of the preparation tooth, gingiva surrounding the preparation tooth, and so on. In one embodiment, an input based on one or more of the intraoral scans, the first 3D surface, and/or one or more projections of the 3D surface is provided to a trained ML model that outputs an indication as to whether or not the input includes a preparation tooth or does not include a preparation tooth. The trained ML model may output an image-level or surface-level indication as to whether the input includes a preparation tooth, or may output a pixel-level classification dividing the pixels or points of the input at least into a first class (preparation tooth) and a second class (not a preparation tooth). The trained ML model may alternatively output a zone-level classification.

A pre-treatment scanning operation may have been performed to generate a pre-treatment 3D model of the patient's dental arch. In one embodiment, processing logic compares the 3D surface to the pre-treatment 3D model. Based on the comparison, processing logic may determine that one of the teeth in the 3D surface differs from a corresponding tooth in the pre-treatment 3D model. Processing logic may determine differences between the 3D surface and the pre-treatment 3D model, and based on such differences may determine that the tooth associated with the differences is a preparation tooth.

In one embodiment, at block 1408 processing logic inputs data from the first intraoral scan(s), a first 3D surface generated from the first intraoral scans, one or more projections of the first 3D surface and/or one or more 2D images into a trained ML model. At block 1410, the trained ML model generates a pixel-level classification of the 3D surface, classifying pixels as representing a preparation tooth or as representing something other than a preparation tooth. In one embodiment, pixels may be classified as a preparation tooth, as a gingiva, as a natural tooth, and/or as other types of restorative objects. At block 1411, processing logic may segment the first 3D surface into gums, a preparation tooth and additional teeth based on the pixel-level classification output by the ML model.

At block 1412, processing logic receives one or more additional intraoral scans and/or 2D images (e.g., color images) of the dental arch that were generated by an intraoral scanner at a second time. Between the first time and the second time a doctor may have reviewed the first 3D surface and determined that one or more modification needed to be made to the first 3D surface. This may include inserting and/or removing a dental wire around a preparation tooth, or further grinding a part of the preparation tooth, for example. To perform such an action, the doctor may have removed the intraoral scanner from the patient's mouth and set it down on a surface or in a cradle. The doctor may also have used a dental drill to grind the preparation tooth. The amount of elapsed time between the first time and the second time, motion data of the intraoral scanner between the first time and the second time, audio recorded between the first time and/or the second time, and/or other data may be used as clues to determine whether any changes might have been made to the preparation tooth between the first time and the second time.

At block 1414, processing logic determines a second 3D surface of at least a portion of a dental arch using the one or more additional intraoral scans (e.g., by stitching together the one or more additional intraoral scans).

At block 1416, processing logic automatically determines that the second 3D surface depicts at least the part of the preparation tooth and/or the part of the surrounding region of the preparation tooth that was represented in the first 3D surface and/or a different part of the preparation tooth that was not represented in the first 3D surface (e.g., a portion of the preparation tooth that was previously covered by gingiva) and/or a part of a region surrounding the preparation tooth (e.g., gingiva around the preparation tooth). In one embodiment, an input based on one or more of the additional intraoral scans, the second 3D surface, and/or one or more projections of the second 3D surface is provided to the trained ML model that outputs an indication as to whether or not the input includes a preparation tooth or does not include a preparation tooth.

In one embodiment, at block 1418 processing logic inputs data from the one or more additional intraoral scan(s), the second 3D surface generated from the one or more additional intraoral scans, one or more projections of the second 3D surface and/or one or more additional 2D images into the trained ML model. At block 1420, the trained ML model generates a pixel-level classification of the second 3D surface, classifying pixels as representing a preparation tooth or as representing something other than a preparation tooth. In one embodiment, pixels may be classified as a preparation tooth, as a gingiva, as a natural tooth, and/or as other types of restorative objects. At block 1421, processing logic may segment the second 3D surface into gums, a preparation tooth and additional teeth based on the pixel-level classification output by the ML model.

At block 1422 processing logic may determine a time difference between the first time and the second time.

At block 1424, processing logic may compare the second 3D surface to the first 3D surface to determine one or more differences between the second 3D surface and the first 3D surface. Additionally, or alternatively, processing logic may determine a change to the preparation tooth (e.g., a change in a shape of the preparation tooth, a change in exposed sub-gingival portions of the preparation tooth, and so on) and/or a change to a region surrounding the preparation tooth between the first 3D surface and the one or more additional intraoral scans based on comparison of the second 3D surface to the first 3D surface and/or comparison of the one or more additional intraoral scans to the first 3D surface.

In one embodiment, processing logic compares spatial information from the first plurality of intraoral scans and/or the first 3D surface with spatial information from the one or more additional intraoral scans and/or the second 3D surface. Spatial comparison of the plurality of intraoral scans and/or the first 3D surface with the one or more additional intraoral scans and/or the second 3D surface may include performing registration between these two sets of data. The registration involves determination of the transformations which align one image or surface with the other. Registration may involve identifying multiple points, point clouds, edges, corners, surface vectors, etc. in each image/surface of an image/surface pair, surface fitting to the points of each image/surface, and using local searches around points to match points of the two images/surfaces. For example, processing logic may match points of the one or more additional intraoral scans with the closest points interpolated on the first 3D surface, and iteratively minimize the distance between matched points. Processing logic may select the points based on a random sampling of surface vertices, based on binning of vertices to a voxel grid and averaging each voxel, based on feature detection (e.g., detecting tooth cusps), and/or based on other techniques.

Processing logic may validate the quality of detected matches with a suitable method and discard points that did not match well. One suitable method for validation includes computing a percentage of surface area on a tested part of the test surface that is less than a threshold distance (e.g., in millimeters) away from the reference surface after alignment. A match may be validated if the size of the surface area that matched is larger than a size threshold. Another suitable method for validation includes computing an average or median distance between vertices of a tested part of the test surface and the reference surface after alignment. If the average or median between vertices is less than a threshold distance, then validation may be successful.

Processing logic may compute a mean and/or median alignment of the entire set of matches. Processing logic may detect and remove outliers that suggest variants of alignment of the test surface and reference surface that are too different from the mean or median alignment of the entire set of matches by using an appropriate method. For example, surface patches for which the alignment of the test surface to the reference surface has an alignment value that differs from the mean or median by more than a threshold may be too different. One appropriate method that may be used is the random sample consensus (RANSAC) algorithm. If two surfaces are not comparable, then spatial comparator 168 will determine that the registration has failed because the number of surviving points would be too small to reasonably cover the entire test surface. This might happen, for example, if input data contained a mistake (e.g., a user tried to match an intraoral scan of one person to an intraoral scan of another person).

A result of the surface matching may be a dense set of pairs of matching points, with each pair corresponding to a region on the test surface and a matching region on the reference surface. Each such region is also associated with a point, so each pair can also be viewed as a pair of a point on the test surface and a matching point on reference surface. An ordered set of these points on a test surface is a point cloud on the test surface, and a set of matching points on a reference surface ordered in the same way is a matching point cloud on the reference surface.

A suitable algorithm may be used to compute an approximate alignment of a test point cloud to a reference point cloud. One example of such a suitable algorithm includes the least-squares minimization of distance between test and reference point clouds. After approximate alignment via a rigid transformation of the test surface, test and reference point clouds won't coincide exactly. A suitable algorithm may be used to compute a non-rigid transformation such as a piecewise-smooth warp space transformation that smoothly deforms a 3D space such that 1) this deformation is as smooth as possible and b) the test point cloud after application of the warp transformation is much better aligned with the reference point cloud. Possible implementation options include, but are not limited to, radial basis function interpolation, thin-plate splines (TPS) and estimating teeth movements and propagating them to a nearby space.

Accordingly, once corresponding point sets are determined between surface patches of the first 3D surface and the second 3D surface and/or one or more additional intraoral scans(s), determination of the transformation between the two sets of corresponding points in two coordinate frames can be solved. Essentially, a registration algorithm may compute a transformation between surfaces that will minimize the distances between points on one surface, and the closest points to them found in the interpolated region on the other surface can be used as a reference. The transformation may include rotations and/or translational movement in up to six degrees of freedom. Additionally, the transformation may include deformation of one or both of the images (e.g., warp space transformations and/or other non-rigid transformations). A result of the image registration may be one or more transformation matrix that indicates the rotations, translations and/or deformations that will cause the 3D surface to correspond to the other 3D surface.

A result of the spatial comparison may include an alignment transformation (e.g., rigid transformation in position and/or orientation to achieve a rigid body alignment) and a warp space transformation or other non-rigid transformation (e.g., smooth deformation of 3D space). Processing logic may use such information to determine differences between points, point clouds, features, etc. on first 3D surface and a second repr3D surface. Processing logic may then distinguish between differences that are attributable to scanner inaccuracy and differences that are attributable to clinical changes in the preparation tooth.

Differences between the 3D surface of the preparation tooth and the second 3D surface of the preparation tooth attributable to scanner error or noise and differences attributable to actual physical changes generally occur in different spatial frequency domains. Scanner errors may have a very high spatial frequency or a very fine scale. This may be noise introduced by the scanner, and may be filtered out with a low pass filter. Spatial differences with a very high spatial frequency (a very small scale) may be those spatial differences with a spatial frequency that exceeds a frequency threshold. Spatial differences attributable to clinical changes may have a spatial frequency that is lower than the frequency threshold.

At block 1426, processing logic determines based at least in part on the time difference and the change to the preparation tooth and/or the change to the region surrounding the preparation tooth whether to use a) the first three-dimensional surface, b) data from the one or more additional intraoral scans and/or the second 3D surface, or c) a combination of the first 3D surface and the data from the one or more additional intraoral scans and/or second 3D surface to depict the part of the preparation tooth that was changed. Various different rules may be applied to determine which portions of the first and/or second 3D surfaces to use for different parts of the preparation tooth and/or surrounding regions of the preparation tooth. Examples of such rules are set forth with reference to FIGS. 15A-F. Processing logic may apply one or a combination of these rules to determine which portions of the first and/or second 3D surfaces to use for different parts of the preparation tooth.

In some instances, the change to the preparation tooth and/or surrounding region is small enough that it can be obscured or drowned out by noise and/or to scanner inaccuracy. In embodiments, processing logic performs one or more operations to distinguish between changes attributable to noise or scanner inaccuracy and changes attributable to physical changes to a tooth made by a doctor.

For example, processing logic may determine a plurality of spatial differences between a first representation of the preparation tooth in the first 3D surface and a second representation of the preparation tooth in the second 3D surface and/or additional intraoral scans. Processing logic may determine that a first spatial difference of the plurality of spatial differences is attributable to scanner inaccuracy and that a second spatial difference of the plurality of spatial differences is attributable to a clinical change to the preparation tooth. In one embodiment, processing logic performs one or more operations described in U.S. Pat. No. 10,499,793, entitled "Longitudinal analysis and visualization under limited accuracy system," to distinguish between changes attributable to noise/scanner inaccuracy and changes attributable to actual physical changes to the preparation tooth. U.S. Pat. No. 10,499,793 is incorporated by reference herein.

At block 1428, processing logic generates a 3D model of the dental arch. In the 3D model, the region that depicts the part of the preparation tooth and/or the part of the surrounding region that was changed (e.g., part that was exposed, part that was further ground, etc.) may be generated using a) the first three-dimensional surface, b) data from the one or more additional intraoral scans and/or the second 3D surface, or c) a combination of the first 3D surface and the data from the one or more additional intraoral scans and/or second 3D surface, as determined at block 1426. At block 1430, processing logic may display the 3D model of the dental arch (e.g., in a GUI of a dental scan application).

At block 1432, processing logic outputs to a display (e.g., via the GUI of the dental scan application) an indication of whether a) the first three-dimensional surface, b) data from the one or more additional intraoral scans and/or the second 3D surface, or c) a combination of the first 3D surface and the data from the one or more additional intraoral scans and/or second 3D surface was used to generate the part of the 3D model of the dental arch. Processing logic may additionally show what the original part of the preparation tooth and/or the part of the surrounding region of the preparation tooth looked like in the display (e.g., via a visualization such as a partially transparent surface, a mesh, dashed lines, and so on). Processing logic may additionally optionally display what the preparation tooth and/or surrounding region (e.g., gingiva) in the 3D model would look like if a different option had been selected between using a) the first three-dimensional surface, b) data from the one or more additional intraoral scans and/or the second 3D surface, or c) a combination of the first 3D surface and the data from the one or more additional intraoral scans and/or second 3D surface in the 3D model.

At block 1434, processing logic may receive user input correcting or verifying the decision of which 3D surface or surfaces to use in the 3D model of the dental arch. At block 1436, processing logic may determine whether the user input was a correction or a verification of the automatic selection that was performed. If a correction is received, the method continues to block 1438 and the 3D model is updated in accordance to the correction (e.g., using a user selected one of) the first three-dimensional surface, b) data from the one or more additional intraoral scans and/or the second 3D surface, or c) a combination of the first 3D surface and the data from the one or more additional intraoral scans and/or second 3D surface. If a verification is received, the method may continue to block 1440, at which the previously generated 3D model may be used for further operations and/or may be stored.

FIGS. 15A-F illustrate flow charts of embodiments for methods of determining which 3D surfaces to use to represent a restorative object for a 3D model. One or more of the methods of FIGS. 15A-F may be performed alone or together at block 1426 of method 1400.

Figure 15A:
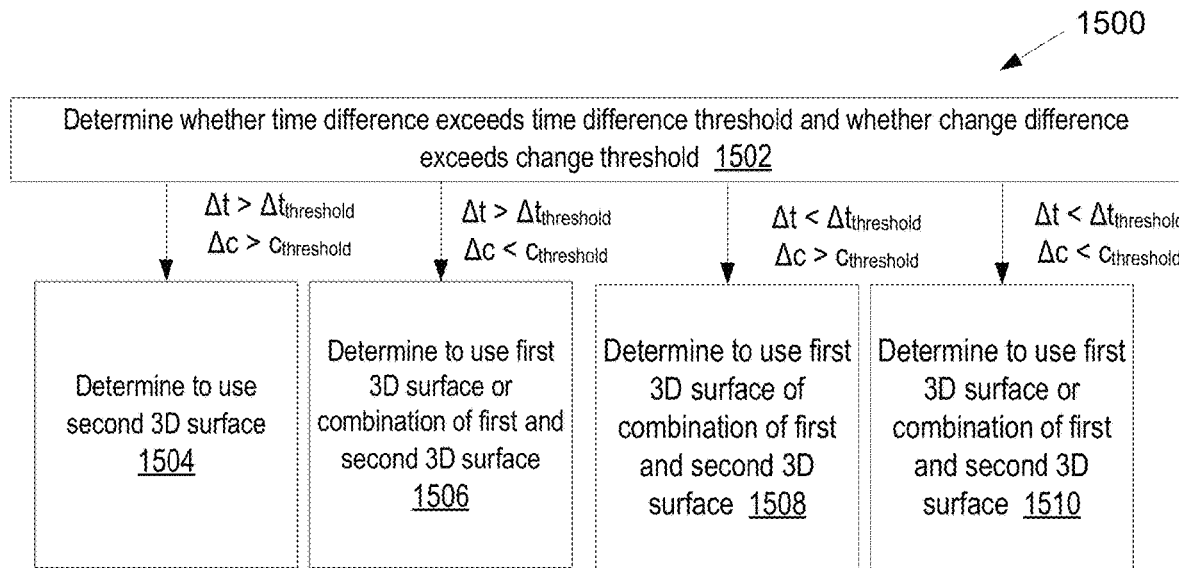
FIG. 15A-F illustrate flow charts of embodiments for methods of determining which 3D surfaces to use to represent a restorative object for a 3D model.

FIG. 15A illustrates a flow chart depicting a method 1500 that applies a first rule for determining which 3D surfaces to use to represent a restorative object (e.g., a preparation tooth). At block 1502 of method 1500, processing logic determines whether a time difference between a plurality of first intraoral scans taken at a first time and one or more additional intraoral scans taken at a second time exceeds a time difference threshold. In one embodiment, processing logic groups scans that are generated during continuous scanning (e.g., between a doctor pushing a start and stop scanning button or processing logic automatically determining to start and stop scanning). In one embodiment, processing logic groups scans that are a) generated during continuous scanning and b) that are associated with a same scanning role. In one embodiment, processing logic groups scans that were generated at times that are within a threshold time difference from scans generated before and/or after the scans. If the plurality of first intraoral scans are in a same group as the one or more additional intraoral scans, then a time difference between the first time and the second time may be less than the time difference threshold. If the plurality of first intraoral scans are in a different group from the one or more additional intraoral scans, then a time difference between the first time and the second time may be greater than the time difference threshold.

Additionally, processing logic determines whether a change between a first 3D surface associated with the first plurality of intraoral scans and a second 3D surface associated with the one or more second intraoral scans exceeds a change threshold. If the time difference exceeds the time difference threshold and the change difference exceeds the change difference threshold, then the method proceeds to block 1504 and processing logic determines to use the second 3D surface to represent a portion of a preparation tooth. If the time difference exceeds the time difference threshold and the change difference is below the change difference threshold, then the method proceeds to block 1506 and processing logic determines to use the first 3D surface or a combination of the first 3D surface and the second 3D surface to represent the portion of the preparation tooth. If the time difference is below the time difference threshold and the change difference is above the change difference threshold, then the method proceeds to block 1508 and processing logic determines to use the first 3D surface or a combination of the first 3D surface and the second 3D surface to represent the portion of the preparation tooth. If the time difference is below the time difference threshold and the change difference is below the change difference threshold, then the method proceeds to block 1510 and processing logic determines to use the first 3D surface or a combination of the first 3D surface and the second 3D surface to represent the portion of the preparation tooth.

Figure 15B:
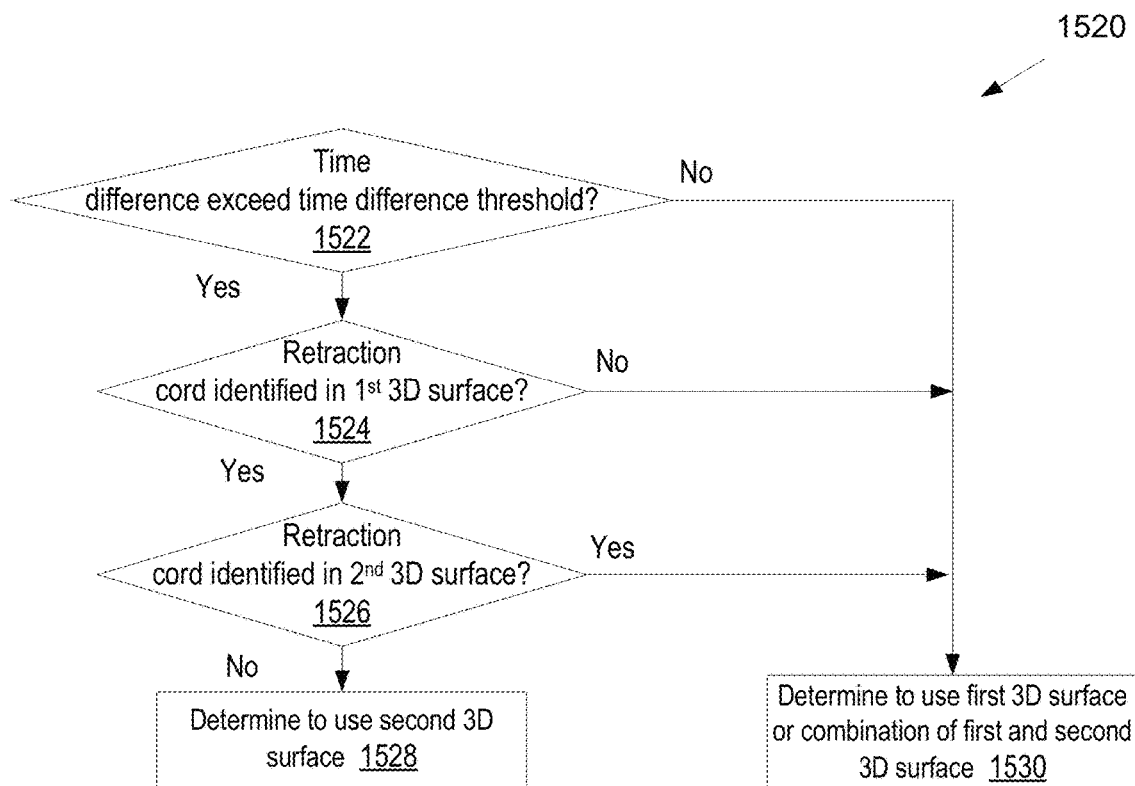

FIG. 15B illustrates a flow chart depicting a method 1520 that applies a second rule for determining which 3D surfaces to use to represent a preparation tooth. The second rule determines which 3D surface to use to represent a preparation tooth (or a portion of a preparation tooth) based on whether or not a retraction cord is identified in the first and/or second 3D surfaces.

If a retraction cord is identified in the first 3D surface and not in the second 3D surface, this may indicate that a retraction cord was pulled between generation of the intraoral scans used for the first 3D surface and generation of the intraoral scans used for the second 3D surface. For restorative dental work such as crowns and bridges, one or more intraoral scans may be generated of a preparation tooth and/or surrounding teeth on a patient's dental arch using an intraoral scanner. In cases of sub-gingival preparations, the gingiva covers at least portions of the margin line (also referred to herein as a finish line) and is retracted in order to fully expose the margin line. Thus, intraoral scans are generally created after a doctor packs a dental retraction cord under the gums around the preparation tooth and then withdraws the retraction cord, briefly exposing a sub-gingival margin line. For scans that show the retraction cord, the margin line may be covered by the retraction cord. For scans taken after the retraction cord has been pulled, the sub-gingival margin line may be shown.

At block 1522 of method 1520, processing logic determines whether a time difference between a plurality of first intraoral scans taken at a first time and one or more additional intraoral scans taken at a second time exceeds a time difference threshold. If the time difference meets or exceeds the time difference threshold, then the method proceeds to block 1524. Otherwise the method proceeds to block 1530.

At block 1524, processing logic determines whether a retraction cord (dental wire) is identified in the first 3D surface. The presence or absence of a retraction cord may be identified by inputting the first plurality of intraoral scans, the first 3D surface and/or one or more projections of the first 3D surface onto one or more planes into a trained ML model. The Trained ML model may be trained to perform image/surface level classification to identify the presence or lack of a retraction cord around a preparation tooth in an intraoral scan (e.g., an image such as a height map) or 3D surface. Alternatively, the trained ML model may perform pixel-level (also referred to as point-level) classification to identify specific points/pixels that are of a retraction cord. If a retraction cord is identified in the first 3D surface, the method continues to block 1526. Otherwise, the method proceeds to block 1530.

At block 1526, processing logic determines whether a retraction cord (dental wire) is identified in the second 3D surface. If a retraction cord is not identified in the second 3D surface, the method continues to block 1528. Otherwise, the method proceeds to block 1530.

At block 1528, processing logic determines to use the second 3D surface for the portion of the preparation tooth (e.g., the portion of the preparation tooth showing the margin line).

At block 1530, processing logic determines to use the first 3D surface of a combination of the first 3D surface and the second 3D surface.

Figure 15C:
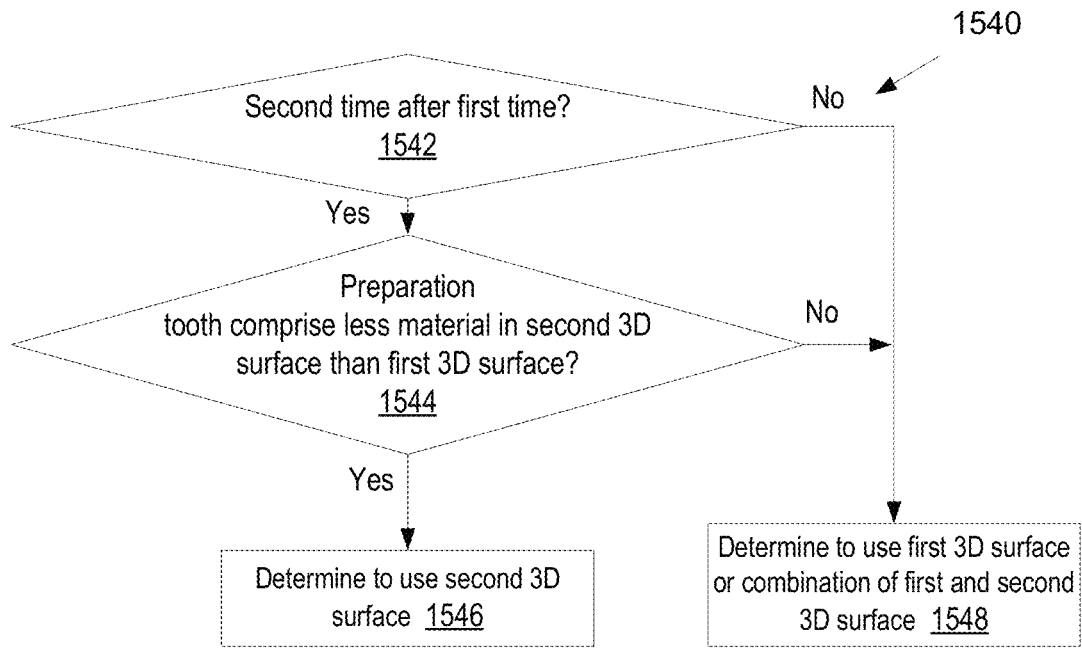

FIG. 15C illustrates a flow chart depicting a method 1540 that applies a third rule for determining which 3D surfaces to use to represent a restorative object (e.g., a preparation tooth). Method 1540 determines which 3D surface to use to depict a preparation tooth based on an amount of material in the preparation tooth. Often during generation of a preparation tooth, a doctor may determine that further material needs to be removed from the preparation tooth after generation of a 3D surface or 3D model. The doctor may then grind the preparation tooth to remove the further material, and generate another scan of the preparation tooth. Processing logic may take advantage of this workflow to determine which 3D surface to use to depict at least a portion of a preparation tooth.

At block 1542 of method 1540, processing logic determines whether a second time at which the one or more additional intraoral images used to generate the second 3D surface is later than the first time at which the plurality of intraoral images used to generate the first 3D image. If so, the method continues to block 1544. Otherwise, the method proceeds to block 1548.

At block 1544, processing logic determines whether the preparation tooth comprises less material in the second 3D surface than the first 3D surface. This determination may be made based on a comparison between the first and second 3D surfaces, and a determination of any differences between the preparation in the first and second 3D surfaces from the comparison. If the preparation tooth comprises less material in the second 3D surface than in the first 3D surface, this indicates that material was removed from the preparation tooth between the generation of the first plurality of intraoral scans and the one or more additional intraoral scans. If the preparation tooth comprises less material in the second 3D surface than in the first 3D surface, the method continues to block 1546. Otherwise the method proceeds to block 1548.

At block 1546, processing logic determines to use the second 3D surface for at least the portion of the preparation tooth (e.g., the portion of the preparation tooth showing the margin line) that is different between the first and second 3D surfaces.

At block 1548, processing logic determines to use the first 3D surface of a combination of the first 3D surface and the second 3D surface.

Figure 15D:
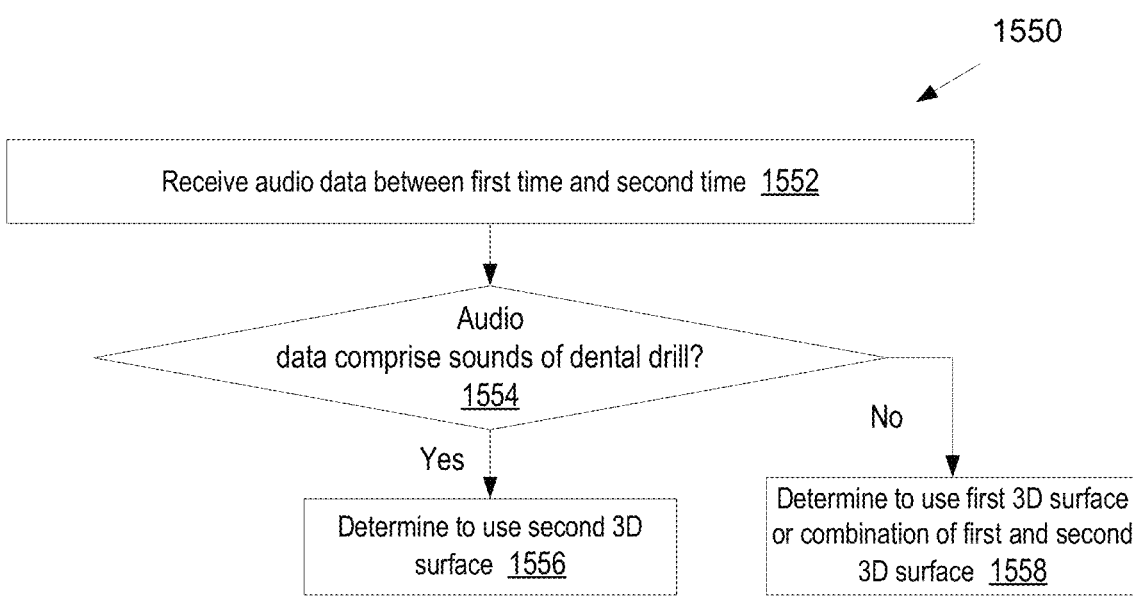

FIG. 15D illustrates a flow chart depicting a method 1550 that applies a fourth rule for determining which 3D surfaces to use to represent preparation tooth. Method 1550 determines which 3D surface to use to depict a preparation tooth based on audio data received between generation of the plurality of intraoral scans used to generate the first 3D surface and the one or more intraoral scans used to generate the second 3D surface. Often during generation of a preparation tooth, a doctor may determine that further material needs to be removed from the preparation tooth after generation of a 3D surface or 3D model. The doctor may then grind the preparation tooth to remove the further material, and generate another scan of the preparation tooth. The tool (e.g., dental drill) used to grind the tooth generates a distinctive sound. A microphone may record audio during and/or between generation of intraoral scans, and such audio data may be analyzed to determine whether it includes sounds of a dental drill.

At block 1552 of method 1550, processing logic receives audio data between a first time at which the first plurality of intraoral scans were generated and a second time at which the one or more additional intraoral scans were generated. At block 1554, processing logic determines whether the audio data comprises sounds of a dental drill. This may include comparing the audio data to a recording of a dental drill. In one embodiment, processing logic generates an audio fingerprint of the received audio data and compares it to an audio fingerprint of a recording of an audio drill in use. If there is a match between the received audio data and the stored audio data, processing logic may determine that the audio data comprises sounds of a dental drill.

If the audio data is determined to include sounds of a dental drill, the method proceeds to block 1556. If the audio does not comprises sounds of a dental drill, the method continues to block 1558.

A dental office may include multiple doctors working in parallel at different chairs. Accordingly, in some instances a dental drill sound may be recorded even if a doctor did not further grind a preparation tooth between scans. However, the sounds of distant dental drills will generally be fainter or less loud than sounds of a dental drill used on a patient associated with 3D surfaces under analysis. Accordingly, in embodiments a volume level of the detected dental drill needs to exceed a volume threshold in order to proceed to block 1556.

At block 1556, processing logic determines to use the second 3D surface for at least the portion of the preparation tooth (e.g., the portion of the preparation tooth showing the margin line) that is different between the first and second 3D surfaces.

At block 1558, processing logic determines to use the first 3D surface of a combination of the first 3D surface and the second 3D surface.

Figure 15E:
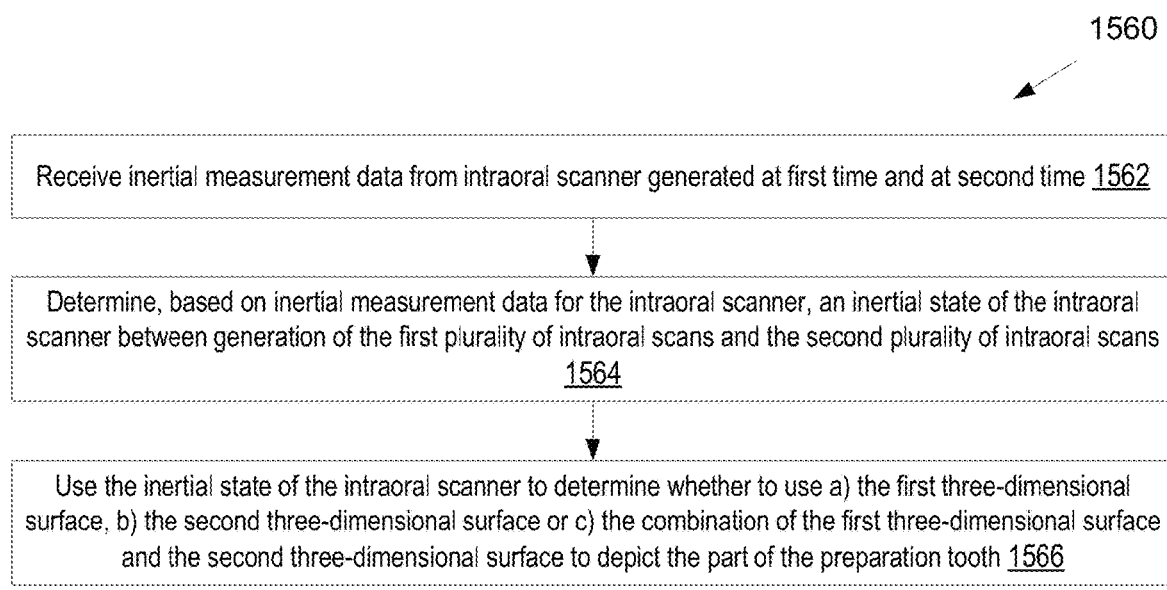

FIG. 15E illustrates a flow chart depicting a method 1560 that applies a fifth rule for determining which 3D surfaces to use to represent a restorative object (e.g., a preparation tooth). The fifth rule uses inertial measurement data to determine which 3D surfaces to use for the preparation tooth. At block 1562, processing logic receives inertial measurement data from an intraoral scanner. Processing logic may receive inertial measurement data generated at a first time at which a first plurality of intraoral scans were generated, second inertial measurement data generated at a second time at which one or more additional intraoral scans were generated, and/or third inertial measurement data generated between the first and second time.

At block 1564, processing logic determines an inertial state of the intraoral scanner between the generation of the first plurality of intraoral scans and the one or more second intraoral scans based on the received inertial measurement data.

At block 1566, processing logic uses the determined inertial state of the intraoral scanner between the first and second times to determine whether to use a) the first 3D surface, b) the second 3D surface, or c) a combination of the first 3D surface and the second 3D surface to depict a part of the preparation tooth. For example, if the inertial state indicates that there as little movement of the intraoral scanner between the first and second times, this may indicate that the doctor merely rested between scans and did not perform any actions that would change the preparation tooth. On the other hand, if the inertial state is indicative of removal of the intraoral scanner from the oral cavity, then this may provide a clue that further actions were performed on the preparation tooth in a manner that could change the preparation tooth.

Figure 15F:
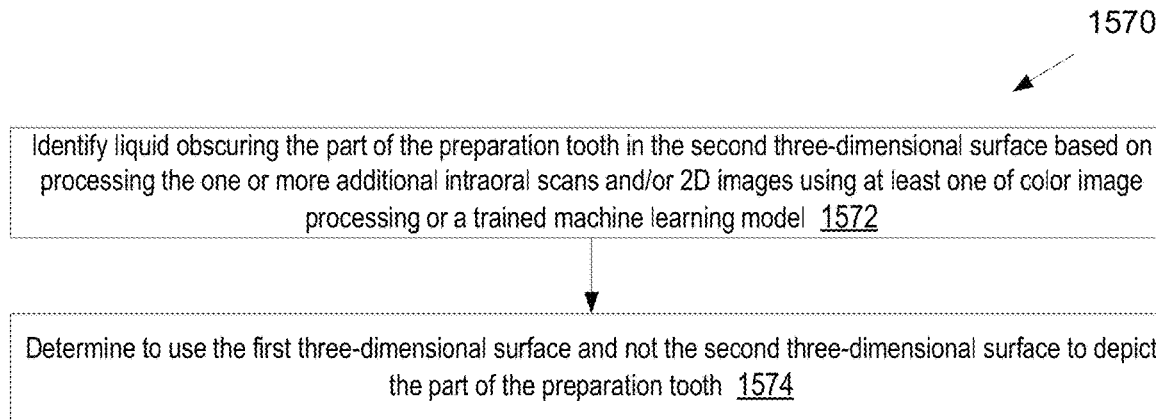

FIG. 15F illustrates a flow chart depicting a method 1570 that applies a seventh rule for determining which 3D surfaces to use to represent a restorative object (e.g., a preparation tooth). At block 1572, processing logic identifies a liquid (e.g., blood or saliva) obscuring part of the preparation tooth in the second 3D surface based on processing the one or more additional intraoral scans (or the second 3D surface or projection(s) of the second 3D surface onto one or more planes) and/or one or more associated 2D color images using color image processing and/or a trained machine learning model trained to identify liquid on a preparation tooth.

At block 1574, processing logic determines to use the first 3D surface and not the second 3D surface if liquid obscuring the preparation tooth was detected in the second 3D surface. Similarly, if an obscuring liquid was identified in the first 3D surface and not in the second 3D surface (e.g., which may be the case if the doctor wipes or washes the preparation tooth between scans), then processing logic determines to use the second 3D surface.

An eighth rule for determining which 3D surfaces to use to represent a restorative object may use determinations of whether or not the intraoral scanner was removed from the patient's mouth between scans as a clue as to whether changes were made to the preparation tooth. For example, a trained ML model may process color images of generated by the intraoral scanner to identify when the scanner is inserted into and/or withdrawn from a patient mouth. If the intraoral scanner was detected to have been removed from a patient mouth between intraoral scans, then processing logic may determine to use a second 3D surface for at least a part of the preparation tooth.

A ninth rule for determining which 3D surfaces to use to represent a restorative object may determine quality ratings for the first 3D surface and the second 3D surface, and use the quality ratings to determine which 3D surface to use in generating a 3D model or in updating a previously generated 3D model. Quality ratings may be determined for different regions or parts of the first 3D surface and the second 3D surface. Quality ratings may be determined using multiple criteria, such as number of data points (e.g., density of a point cloud), existence, number and/or size of voids, angle of scanner to 3D surface, uncertainty associated with registration between scans in a 3D surface, amount of moving tissue, gum tissue and/or other objects obscuring the preparation tooth (e.g., obscuring the margin line), a cost function value, and so on.

In one embodiment, processing logic divides the first 3D surface and the second 3D surface into superpixels (or other equivalent structure in 3D). A superpixel is a group of pixels that share common characteristics (e.g., like pixel intensity). In one embodiment, each superpixel may be assigned a quality score. Superpixels associated with the first 3D surface may be compared to overlapping superpixels from the second 3D surface, and superpixels with a highest quality value may be selected.

In one embodiment, intraoral scans, 3D surfaces and/or projections of 3D surfaces are input into a machine learning model that has been trained to select and/or grade areas of dental sites. In one embodiment, one or more scores are assigned to each input of the ML model, where each score may be associated with a particular dental site and indicate a quality of a representation of that dental site in the input.

Each of the first through ninth rules for determining which surface to use are merely examples of rules that can be applied to determine which surface to use for a preparation tooth in a 3D model. These rules may be combined and the outputs of two or more of these rules may be applied to a voting or weighted voting algorithm to determine which surface to use. For example, if multiple rules indicate that a particular 3D surface should be used, then processing logic may determine to use that particular 3D surface. In some embodiments, if any of the rules indicate to use the second 3D surface, then the second 3D surface is used.

Additionally, or alternatively, regions a first 3D surface and a second 3D surface for which the two 3D surfaces differ at may be assigned weights based on scores assigned to those regions of those 3D surfaces. The scores may be determined based on the output of one or more of the first through ninth rules above and/or one or more other selection rules. During model updating, conflicting data from the first and second 3D surfaces may be combined using a weighted average to depict a preparation tooth. The weights that are applied may be those weights that were assigned based on quality scores and/or the number of rules that voted for a particular 3D surface for the preparation tooth. For example, processing logic may determine that data for a particular overlapping region from the first 3D surface is superior in quality to data for the particular overlapping region of the second 3D surface. The first 3D surface may then be weighted more heavily than the second 3D surface when averaging the differences between the image data sets. For example, the first 3D surface assigned the higher rating may be assigned a weight of 70% and the second 3D surface may be assigned a weight of 30%. Thus, when the data is averaged, the merged result will look more like the depiction from the first 3D surface and less like the depiction from the second 3D surface.

Figure 16:
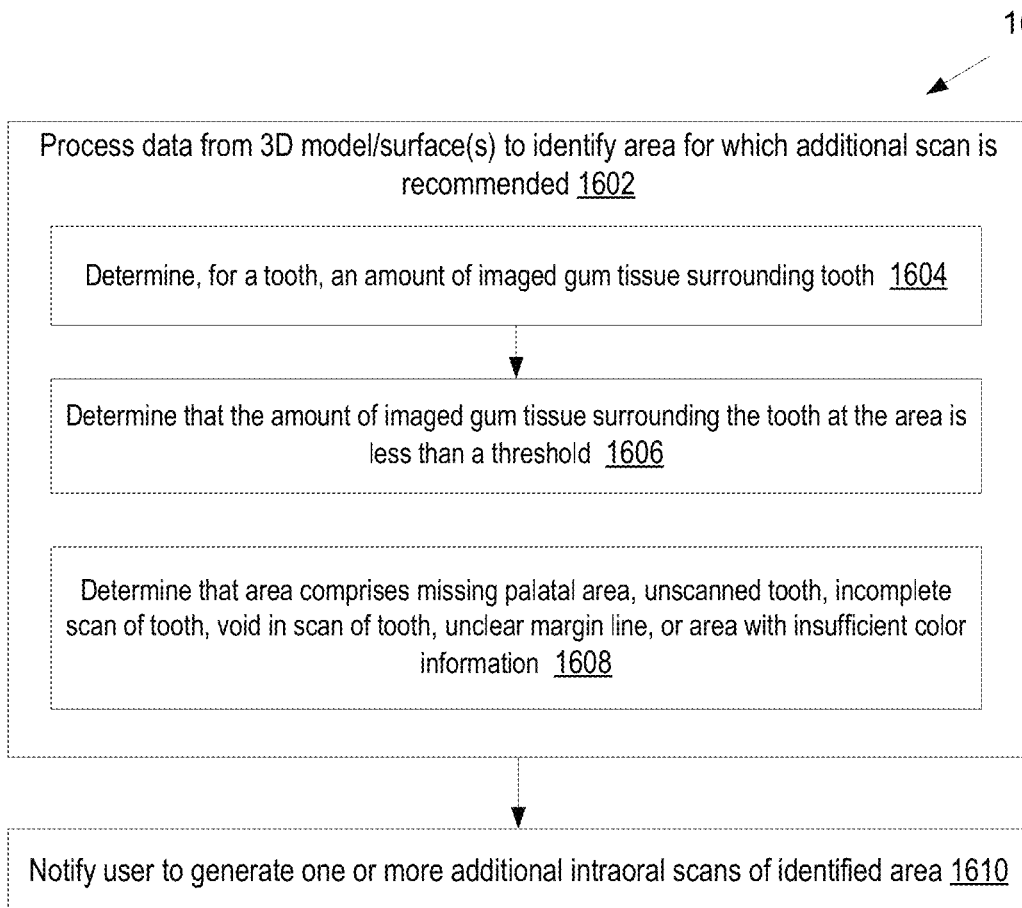
FIG. 16 is a flow chart illustrating an embodiment for a method of determining whether additional scans of a tooth are recommended.

FIG. 16 is a flow chart illustrating an embodiment for a method 1600 of determining whether additional scans of a tooth are recommended. After intraoral scanning is performed for a particular scanning role (e.g., for an upper dental arch, a lower dental arch, a patient bite, etc.), processing logic may automatically determine whether one or more additional intraoral scans are recommended to be generated. For example, if the area of a preparation tooth containing the margin line lacks definition, it may not be possible to properly determine the margin line, and thus the margin of a restoration may not be properly designed. In another example, if not enough gum tissue is imaged around a tooth, then aligners and/or dental prosthesis associated with that tooth may be designed that interfere with the gum tissue around the tooth. Additionally, the quality of one or more automatic determinations, the quality of a generated 3D model of a dental arch and/or the quality of a manufactured dental prosthesis can be affected by the presence or lack of a palatal area, voids, an amount of color information, one or more unclear or conflicting areas, and so on. Method 1600 may detect these and other issues that can negatively impact treatment, and can recommend rescanning of areas where these issues are identified.

At block 1602 of method 1600, processing logic processes data from a 3D model and/or a 3D surface to identify one or more area for which additional scans are recommended. Processing of the data may be performed using image processing and/or the application of machine learning. In one embodiment, one or more portions of the 3D model or 3D surface or one or more projections of the 3D model or 3D surface onto one or more surfaces are input into a trained machine learning model. The trained machine learning model may output a map with two different pixel-level or point-level classifications, where one classification indicates that no further scanning is recommended and another classification indicates that further scanning is recommended. In further embodiments, the ML model may output different classes associated with why further scanning is recommended. For example, the ML model may output an indication of a void, an unclear area, an obscured area, a low confidence area, and so on.

In an example, a part of a margin line of a scanned preparation tooth or a part of another dental object may not be sufficiently clearly defined in the 3D model. For example, during the initial 3D data collection step, for example via scanning, that resulted in the first 3D virtual model being generated, a part of the physical dental surface may have been covered with foreign material, such as for example saliva, blood, or debris. The part of the physical dental surface may also have been obscured by another element such as for example part of the gums, cheek, tongue, dental instruments, artifacts, etc. Alternatively, for example, during the initial 3D data collection step (e.g., via scanning) that resulted in the first virtual 3D model being generated, the region may have been distorted or otherwise defective and may not properly correspond to a physical dental surface (e.g., due to some defect in the actual scanning process). These situations may lead to an unclear or low quality region of the 3D model.

In one embodiment, at block 1604 processing logic determines, for one or more teeth in the 3D model, an amount of imaged gum tissue surrounding the one or more teeth. Such a determination may be made by performing image processing to measure a distance from an outer edge of scanned gingiva around each of the one or more teeth. Processing logic may then compare the determined distances to a distance threshold. If any of the distances are less than the distance threshold, this may be an indication that further scanning of gingiva around a tooth would be beneficial. Accordingly, at block 1606 responsive to determining that an amount of imaged gum tissue around a tooth is less than a threshold (e.g., that a detected distance between an edge of the tooth and a nearest outer edge of scanned gingiva is less than a distance threshold), processing logic may identify the tooth and/or the gingiva around the tooth for further scanning.

In one embodiment, at block 1608 processing logic determines that the identified area comprises a missing palatal area, an incomplete surface of a tooth, a void in a surface of a tooth, an unclear margin line, and/or an area with insufficient color information. These determinations may be made by inputting the 3D surface, a 3D model, a portion of a 3D surface or 3D model, intraoral scans associated with a 3D surface or 3D model, 2D images (e.g., color images) associated with the 3D surface or 3D model and/or one or more projections of the 3D surface or 3D model into a trained ML model, which may output an indication as to whether the 3D surface or 3D model has a missing palatal area, an incomplete surface of a tooth, a void in a surface of a tooth, an unclear margin line, and/or an area with insufficient color information. Additionally, or alternatively, processing logic may perform one or more image processing operations to detect insufficient color information, voids, incomplete surface of a tooth, missing palatal area, and so on.

In one embodiment, processing logic computes a margin line quality score for one or more segments of the margin line. Each margin line quality score may be based on the cost value for the margin line (or a segment of the margin line) as computed using a cost function. In one embodiment, a margin line quality score is determined for the entirety of the margin line. In one embodiment, multiple additional margin line quality scores are computed, where each margin line quality score is for a particular segment of the margin line. Those segments of the margin line that have a margin line quality score below a margin line quality score threshold may be identified for further scanning.

In some embodiments, processing logic may additionally or alternatively determine a clarity value and/or quality value for surfaces that do not include or are not associated with a margin line. Processing logic may mark such surfaces (or portions of surfaces) that have low quality values on the 3D model. For example, the surface quality scores for one or more surface portions may be compared to a quality threshold. Any surfaces (or surface portions) having surface quality scores that are below the quality threshold may be marked or highlighted.

In one embodiment, processing logic 1600 determines which areas to rescan using the techniques set forth in US Publication No. 2021/0059796, which is incorporated by reference herein.

Figure 17:
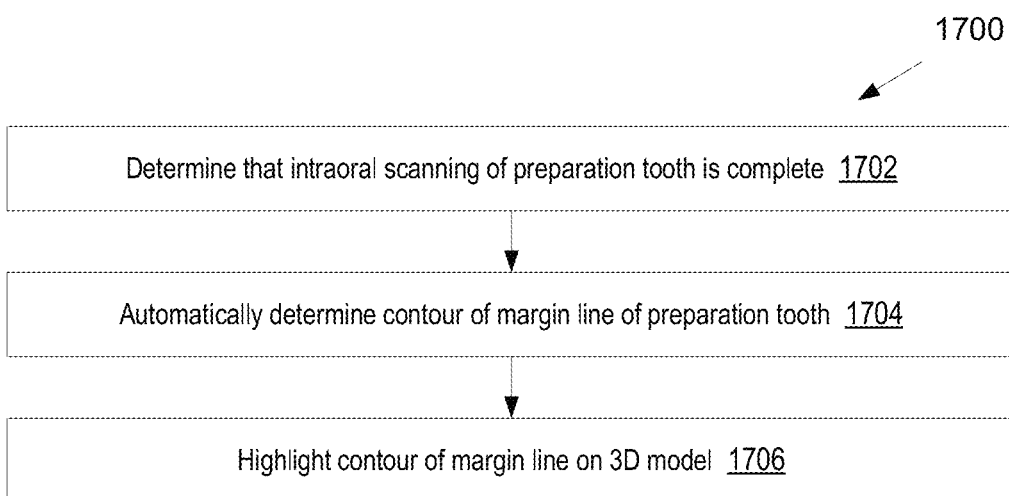
FIG. 17 is a flow chart illustrating an embodiment for a method of determining a contour of a preparation tooth's margin line.

FIG. 17 is a flow chart illustrating an embodiment for a method 1700 of determining a contour of a preparation tooth's margin line. Method 1700 may automatically be performed once a 3D model of a dental arch is generated. At block 1702, processing logic determines that intraoral scanning of a preparation tooth is complete, and generates a 3D surface or 3D model that includes the preparation tooth. This may include determining that intraoral scanning of a dental arch that includes the preparation tooth is complete. Once scanning of the dental arch is complete, a 3D model of the dental arch, including the preparation tooth, may automatically be generated. The 3D model of the dental arch may be a variable resolution 3D model in which the preparation tooth has a higher resolution in the 3D model than other regions of the 3D model. Processing logic may automatically identify the preparation tooth on the 3D model using one or more of the techniques for restorative object identification discussed herein.

At block 1704, processing logic automatically determines a contour of a margin line of the preparation tooth using machine learning and a cost function. The 3D model may be segmented into natural teeth, preparation teeth, and gingiva, as described above. For example, each point on the 3D model may include probability information on probabilities of the point belonging to one or more dental classes. In one embodiment, each point includes a probability of that point belonging to a natural tooth dental class, a gingiva dental class, a preparation dental class, and a margin line dental class. In one embodiment, once the 3D model of the preparation tooth (e.g., of a dental arch including the preparation tooth) is complete, the 3D model or projections of the 3D model onto one or more planes may be input into a trained ML model that outputs at least a first class indicating a representation of a margin line and a second class indicating a representation of something other than a margin line. Processing logic may compute a margin line by applying a cost function to the points on the 3D model using the probabilities of those points depicting a margin line. In one embodiment, processing logic generates a matrix that identifies, for each point (e.g., edge, vertex, voxel, etc. on a surface of the 3D model), a probability that the point represents a margin line. For example, entries in the matrix that have no chance of representing the margin line have an assigned 0% probability.

Processing logic uses the cost function to create a closest contour going through points with high probabilities of representing the margin line. In one embodiment, a total cost of the contour that is drawn for the margin line is the sum of all edges (e.g., vertexes) included in the margin line, adjusted by weights associated with each of the vertexes. Each weight for a vertex may be a function of the probability assigned to that vertex. The cost for that vertex being included in the margin line may be approximately 1/(A+P), where A is a small constant and P is the probability of the vertex representing the margin line. The smaller the probability for a vertex, the larger the cost of that vertex being included in the margin line. Costs may also be computed for segments of the margin line based on a sum of the costs of the vertexes included those segments. When probability is close to 100%, then cost is approximately 1 adjusted by length.

In one embodiment, a path finding operation or algorithm is applied to the 3D model using values from the matrix as a cost basis. Any pathfinding algorithm may be used. Some examples of possible path finding algorithms to use include dynamic programming, Dijkstra's algorithm, A* search algorithm, an incremental heuristic search algorithm, and so on. A pathfinding algorithm may apply a cost function to determine a path of the margin line.

A pathfinding algorithm that uses probability of representing the margin line in the matrix as a cost basis may search for a path with a maximal cost or a path with a minimal cost. The cost function described above searches for minimum cost using a function that is based on an inverse of probability. Alternatively, a cost function may be used that is based directly on probability, where the maximum cost is searched for. If a pathfinding algorithm is run to maximize cost, then a path between vertexes will be determined that results in a maximum aggregate of probability values. The probability scores of the vertexes may be input into the pathfinding algorithm to find the path that has the maximal cost for the probability score. The path finding algorithm may be used to define a contour that represents the margin line.

At block 1706, processing logic highlights or otherwise marks a contour of the margin line on the 3D model. In one embodiment, processing logic computes separate costs for different segments of the margin line. For example, processing logic may determine multiple segments of the margin line, each segment including a collection of connected or adjacent vertexes. For each segment, processing logic may use the cost function to compute a cost for the segment. Cost values may be computed for overlapping and/or non-overlapping segments. Processing logic may determine whether any of the segments has a cost value/score that fails to satisfy a cost criterion. For example, processing logic may determine whether any of the segments has a cost that exceeds a cost threshold (if the cost function optimizes for minimal cost). Alternatively, processing logic may determine whether any segment has a cost value/score that is below a cost threshold (if the cost function optimizes for maximal cost). Processing logic optionally highlights segments of the margin line that failed to satisfy the cost criterion and/or that satisfied the cost criterion, but that came close to failing the cost criterion. Such segments of the margin line may be identified as having an unacceptable level of uncertainty or clarity.

In one embodiment, processing logic applies the techniques of U.S. Publication No. 2021/0059796 to determine the contour of the margin line.

Processing logic may automatically determine whether there are any issues with the margin line, such as regions of the margin line that are unclear or obscured. Processing logic may then recommend one or more additional intraoral scans of the regions of the margin line for which issues were detected.

Figure 18:
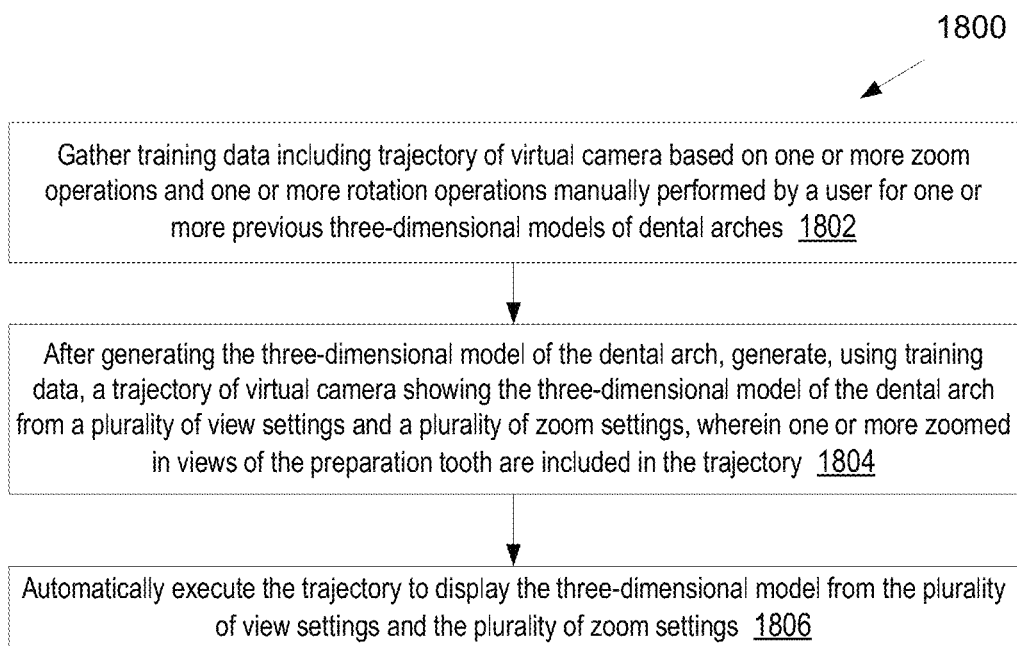
FIG. 18 is a flow chart illustrating an embodiment for a method of determining trajectory to display a 3D model of a dental arch.

FIG. 18 is a flow chart illustrating an embodiment for a method of determining trajectory to display a 3D model of a dental arch. At block 1802, processing logic gathers training data including a trajectory of a virtual camera based on one or more zoom operations, panning operations, pause operations, play operations, rotation operations, and so on performed by a user for one or more previous 3D models of dental arches. Such data may be generated by recording viewing sessions in which a doctor at hand and/or other doctors viewed 3D models of dental arches. From the viewing sessions processing logic may determine each of the views of the 3D model that the doctor manually cycled through. For example, processing logic may determine that a doctor zoomed in on 3D surfaces of preparation teeth, that they rotated around the dental arch about a vertical axis, and so on. The training data may include different trajectories associated with different types of treatments. For example, the training data may include treatments with one preparation tooth, with multiple preparation teeth, with preparation teeth in different tooth numbers, with no preparation teeth, with different types of malocclusion, and so on.

At block 1804, after generating a 3D model of a dental arch, processing logic generates, using the training data, a trajectory of a virtual camera showing the 3D model of the dental arch from a plurality of view settings and a plurality of zoom settings. One or more zoomed in views of the preparation tooth (or of multiple preparation teeth) are included in the trajectory.

In one embodiment, a machine learning model is trained on the training dataset to receive a 3D model and to output a trajectory for the 3D model. In another embodiment, processing logic includes a set of rules that are applied to automatically generate a trajectory. For example, a trajectory may be generated based on whether an upper or lower dental arch is depicted, whether or not there are any preparation teeth on the dental arch, the locations of the preparation teeth, whether any malocclusions have been detected on the dental arch, the locations and/or types of the malocclusions, whether attachments have been identified, whether brackets have been identified, and so on.

In one embodiment, a doctor may manually record a standard virtual camera trajectory by inputting a record trajectory request. The doctor may then manually perform one or more zoom, rotation, pan, etc. operations, each of which may be recorded. Processing logic may additionally record the spacing in time between operations to determine how long to display a particular view of the 3D model. The doctor may then input a stop recording command when finished. The recorded trajectory may then automatically be applied to other 3D models viewed by the doctor. In embodiments, the doctor may record different trajectories for different types of patient cases. The doctor may then select which trajectory they would like to use to view a particular 3D model. Alternatively, processing logic may compare patient case details (e.g., existence of preparation tooth, location or preparation tooth, upper or lower jaw, etc.) of a current 3D model to patient case details associated with multiple stored virtual camera trajectories. Processing logic may then automatically select the virtual camera trajectory associated with patient case details that most closely match current patient case details.

At block 1806, processing logic automatically executes the determined virtual camera trajectory to display the 3D model from the plurality of view settings and the plurality of zoom settings.

Figure 19A:
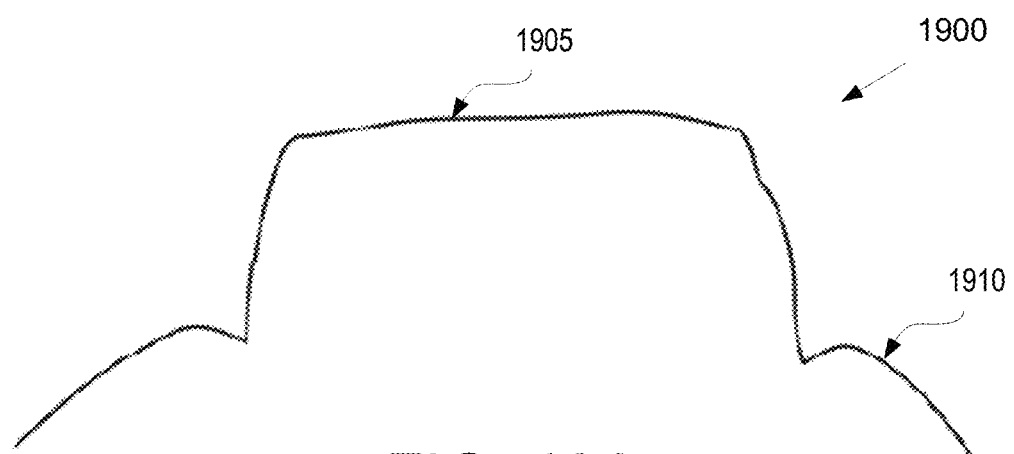
FIGS. 19A-C illustrate a side view of a 3D surface of a preparation tooth at various stages of the preparation tooth.
Figure 19B:
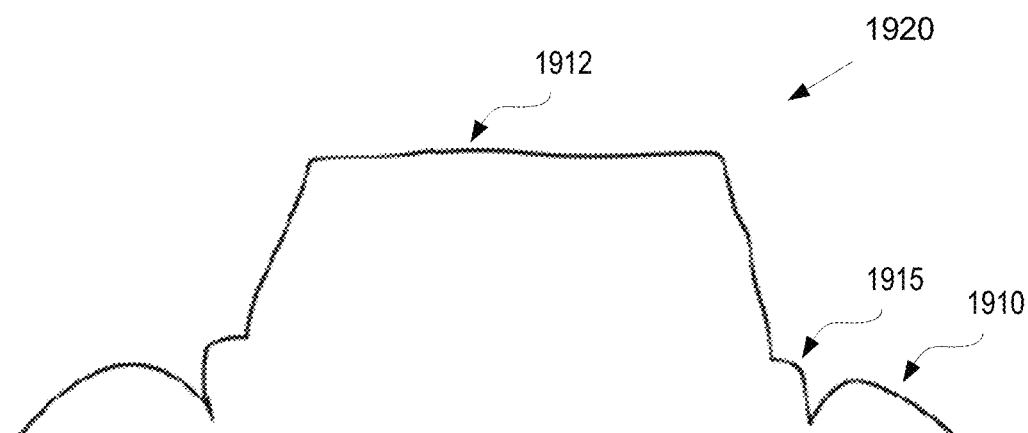
Figure 19C:
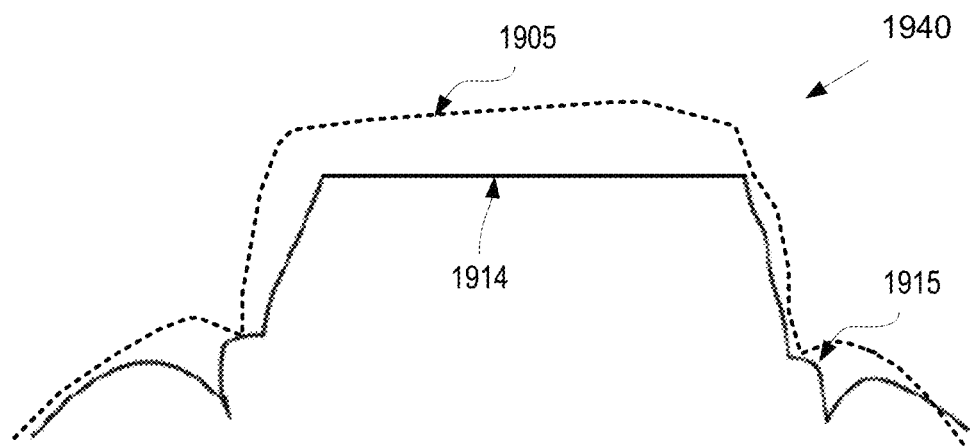

FIGS. 19A-C illustrate a side view of a 3D surface of a preparation tooth at various stages of the preparation tooth 1905. FIG. 19A illustrates first side view 1900 of a first 3D surface of the preparation tooth 1905 after grinding has been performed to form the preparation tooth 1905. However, the first 3D surface was generated while gingiva 1910 obscured a margin line of the preparation tooth 1905. Accordingly, the margin line is not shown in FIG. 19A.

FIG. 19B illustrates second side view 1920 of a second 3D surface of the preparation tooth 1912 after further grinding has been performed to change a shape of the preparation tooth and after a retraction cord was packed around the preparation tooth and removed to expose the margin line 1915. As shown, both the shape of the preparation tooth and the shape of the gums around the preparation tooth have changed between the first side view 1900 and the second side view 1920.

FIG. 19C illustrates third side view 1940 of a third 3D surface of the preparation tooth 1914 after further grinding has been performed to change a shape of the preparation tooth. Also shown is first side view 1905 of the first 3D surface of the preparation tooth superimposed over the third side view 1914 of the third 3D surface of the preparation tooth. Processing logic may show the change between the current 3D surface and a past 3D model (e.g., the immediate prior version of the 3D surface or one or more earlier versions of the 3D surface) of a preparation tooth to indicate to a doctor what has changed and/or to show which 3D surface is being used to update a preparation tooth in a 3D model of a dental arch or to update a 3D model of a preparation tooth. The doctor may override an automatic selection of which 3D surface to use, resulting in a different 3D model.

Figure 20:
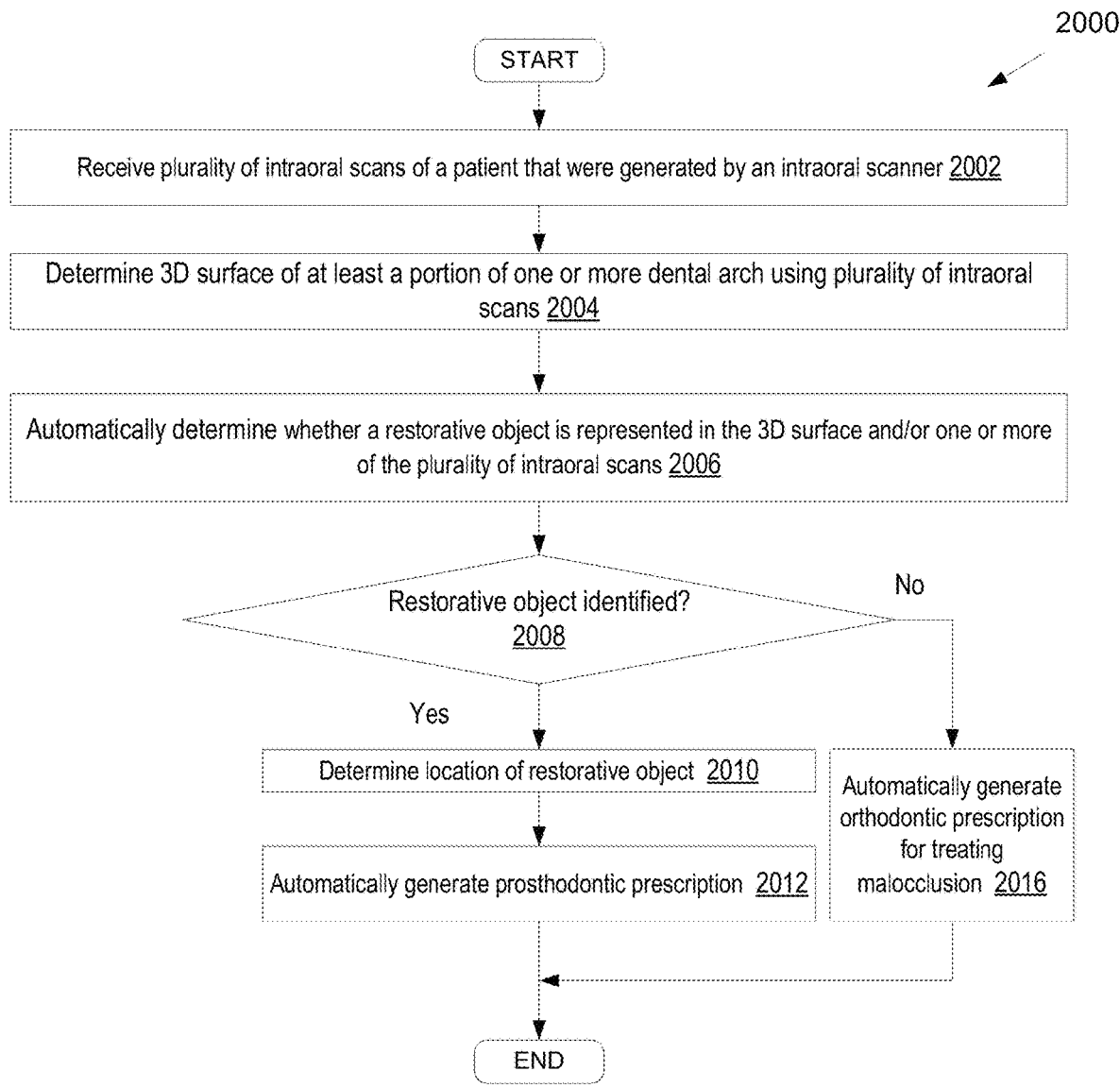
FIG. 20 is a flow chart illustrating an embodiment for a method of automatically generating a prescription for a dental prosthesis or orthodontia.

FIG. 20 is a flow chart illustrating an embodiment for a method 2000 of automatically generating a prescription for a dental prosthesis or orthodontia. At block 2002 of method 2000, processing logic receives a plurality of intraoral scans of a patient that were generated by an intraoral scanner. At block 2004, processing logic determines a 3D surface of at least a portion of one or more dental arch using the plurality of intraoral scans. At block 2006, processing logic automatically determines whether a restorative object is represented in the 3D surface and/or one or more of the plurality of intraoral scans. This may be achieved using any of the techniques described herein above (e.g., by inputting the intraoral scans into a machine learning model trained to identify restorative objects).

At block 2006, processing logic determines whether a restorative object was detected. If no restorative object (e.g., no preparation tooth or scan body) was detected, the method proceeds to block 2016. If one or more restorative object is detected, processing logic proceeds to block 2010.

At block 2010, processing logic determines a location of the restorative object. This may include determining a tooth number associated with the restorative object. At block 2012, processing logic automatically generates a prosthodontic prescription. Generating the prosthodontic prescription may include adding a 3D model of a preparation tooth and/or surrounding teeth to the prescription, inputting an indication of a tooth number to be treated to the prescription, determining and inputting a type of dental prosthesis to be manufactured (e.g., an inlay, an only, a bridge, a crown, a denture, and so on), determining and inputting a type of material to be used for the dental prosthesis, determining and inputting a dental lab to manufacture the dental prosthesis, and so on. Each of these prescription details may be automatically determined using the techniques set forth above. Once the restorative prescription is generated, it may automatically be sent to a dental lab indicated in the prescription. Alternatively, the prescription may be sent to the dental lab after the doctor has reviewed and approved the prescription (and optionally made one or more changes to the prescription).

At block 2016, processing logic automatically generates a prescription for treating a malocclusion using the 3D model. This may include determining a treatment goal including a final arrangement of patient teeth, determining one or more intermediate arrangements of patient teeth, and generating a final 3D model for the final arrangement of patient teeth and intermediate 3D models for each of the intermediate arrangements of patient teeth. Each of the 3D models may be used to manufacture a clear plastic aligner.

Once the virtual 3D model of the patient's dental arch is generated, a dental practitioner may determine a desired treatment outcome, which includes final positions and orientations for the patient's teeth. Alternatively, a treatment outcome may automatically be determined by processing logic. Processing logic may then determine a number of treatment stages to cause the teeth to progress from starting positions and orientations to the target final positions and orientations. The shape of the final virtual 3D model and each intermediate virtual 3D model may be determined by computing the progression of tooth movement throughout orthodontic treatment from initial tooth placement and orientation to final corrected tooth placement and orientation. For each treatment stage, a separate virtual 3D model of the patient's dental arch at that treatment stage may be generated. The shape of each virtual 3D model will be different. The original virtual 3D model, the final virtual 3D model and each intermediate virtual 3D model is unique and customized to the patient.

Accordingly, multiple different virtual 3D models may be generated for a single patient. A first virtual 3D model may be a unique model of a patient's dental arch and/or teeth as they presently exist, and a final virtual 3D model may be a model of the patient's dental arch and/or teeth after correction of one or more teeth and/or a jaw. Multiple intermediate virtual 3D models may be modeled, each of which may be incrementally different from previous virtual 3D models.

Each virtual 3D model of a patient's dental arch may be used to generate a unique customized physical mold of the dental arch at a particular stage of treatment. The shape of the mold may be at least in part based on the shape of the virtual 3D model for that treatment stage. The virtual 3D model may be represented in a file such as a computer aided drafting (CAD) file or a 3D printable file such as a stereolithography (STL) file. The virtual 3D model for the mold may be sent to a third party (e.g., clinician office, laboratory, manufacturing facility or other entity). The virtual 3D model may include instructions that will control a fabrication system or device in order to produce the mold with specified geometries.

Figure 21:
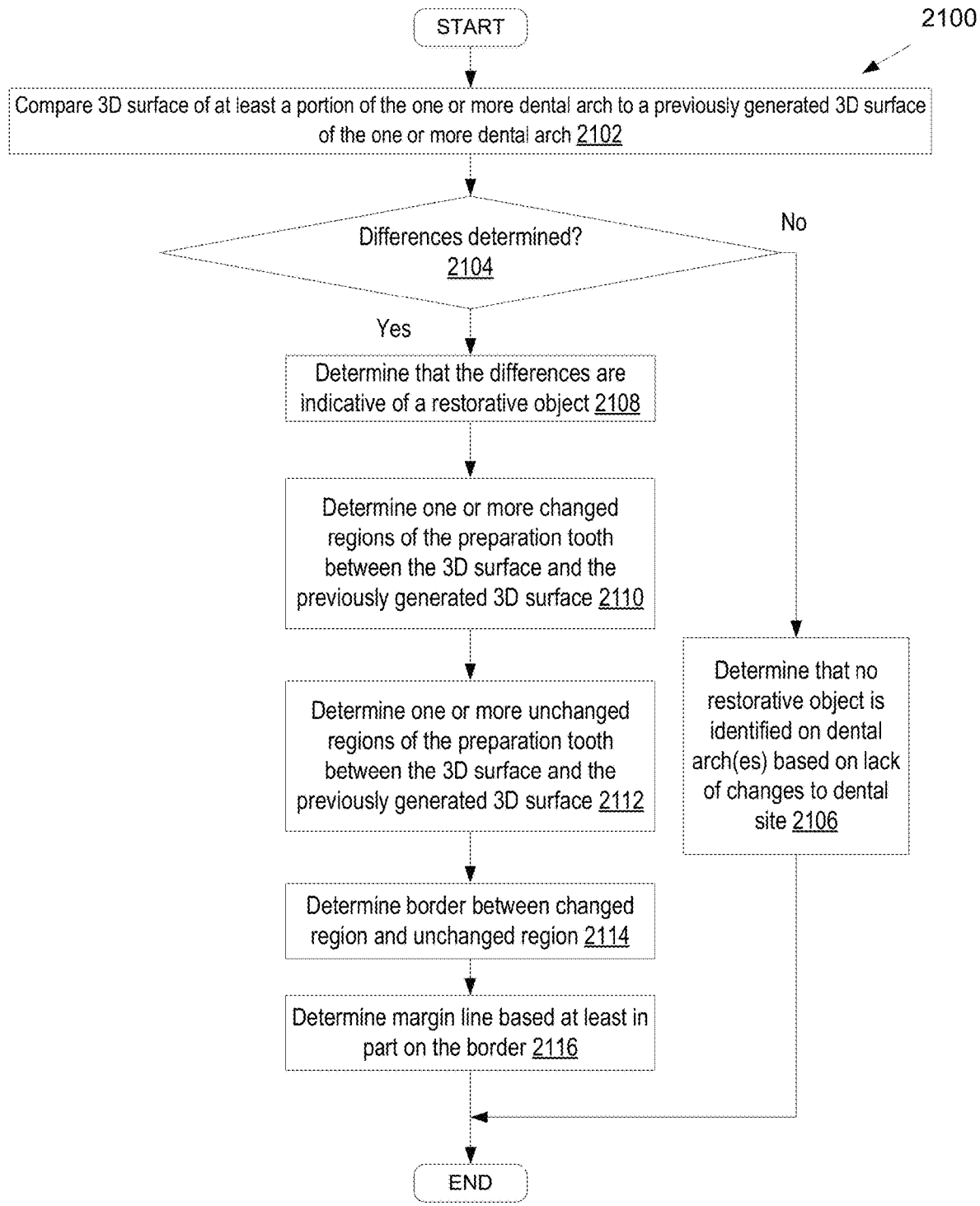
FIG. 21 is a flow chart illustrating an embodiment for a method of automatically determining a 3D model of a dental prosthesis.

FIG. 21 is a flow chart illustrating an embodiment for a method 2100 of automatically determining a 3D model of a dental prosthesis. At block 2102 of method 2100, processing logic compares a 3D surface of at least a portion of one or more dental arch to a previously generated 3D surface of the one or more dental arch. At block 2104, processing logic determines whether one or more differences are determined. If one or more differences are determined, the method continues to block 2018. If no differences are determined, the method proceeds to block 2106, and processing logic determines that no restorative object is identified one the one or more dental arches based on lack of changes to a dental site.

At block 2018, processing logic determines that the determined differences are indicative of a restorative object (e.g., a preparation tooth). At block 2110, processing logic determines one or more changed regions of the preparation tooth between the 3D surface and the previously generated 3D surface. At block 2112, processing logic determines one or more unchanged regions of the preparation tooth between the 3D surface and the previously generated 3D surface.

At block 2114, processing logic determines a border between the changed region and the unchanged region. At block 2116, processing logic determines a margin line based at least in part on the border between the changed region and the unchanged region. One or more of the other aforementioned techniques for determining the margin line may also be applied and combined with the technique set forth in method 2100 for a more accurate determination of the margin line.

Figure 22A:
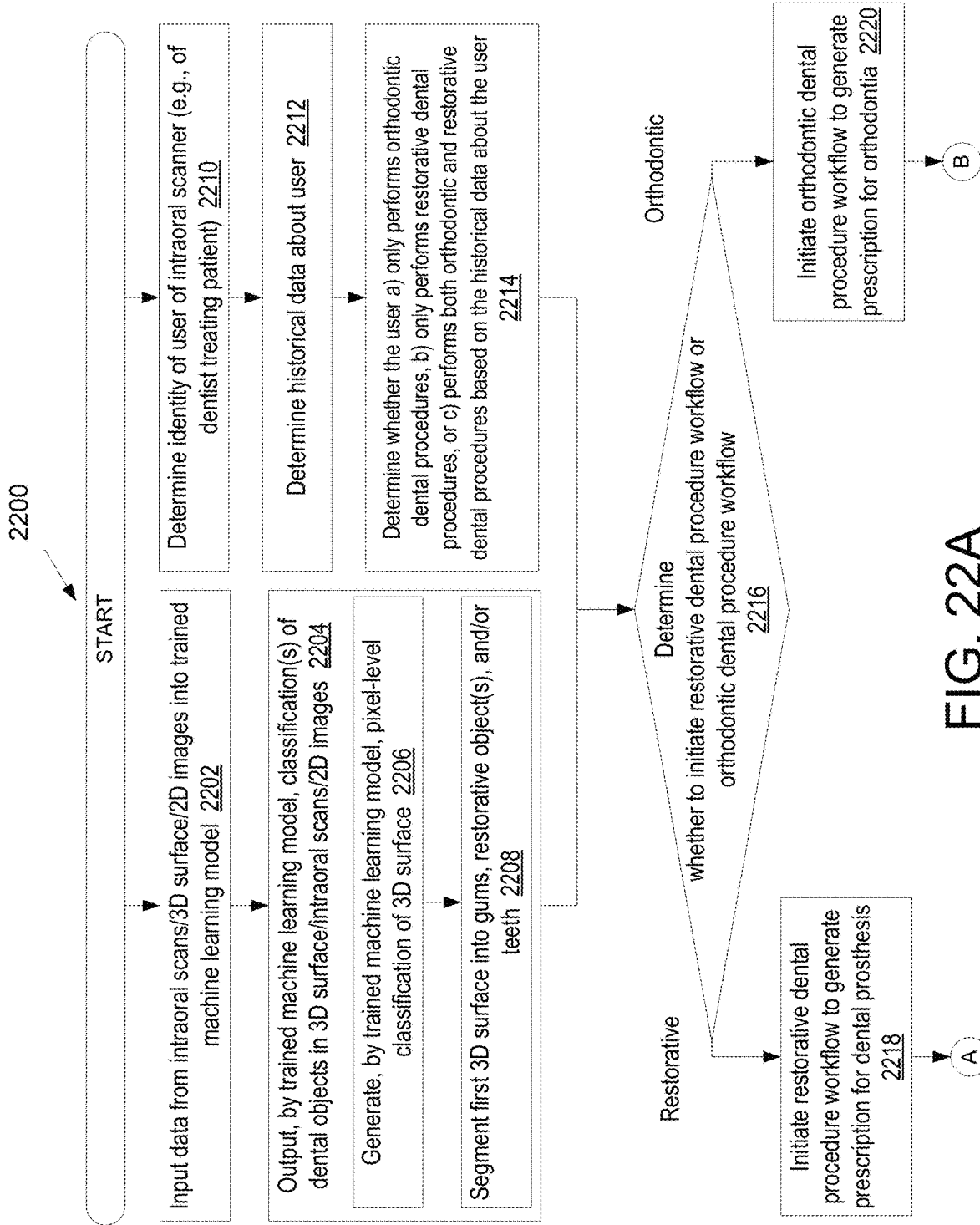
FIGS. 22A-C illustrate a flow chart of an embodiment for a method of automatically generating one or more prescription for a dental prosthesis and/or orthodontia for a patient.
Figure 22B:
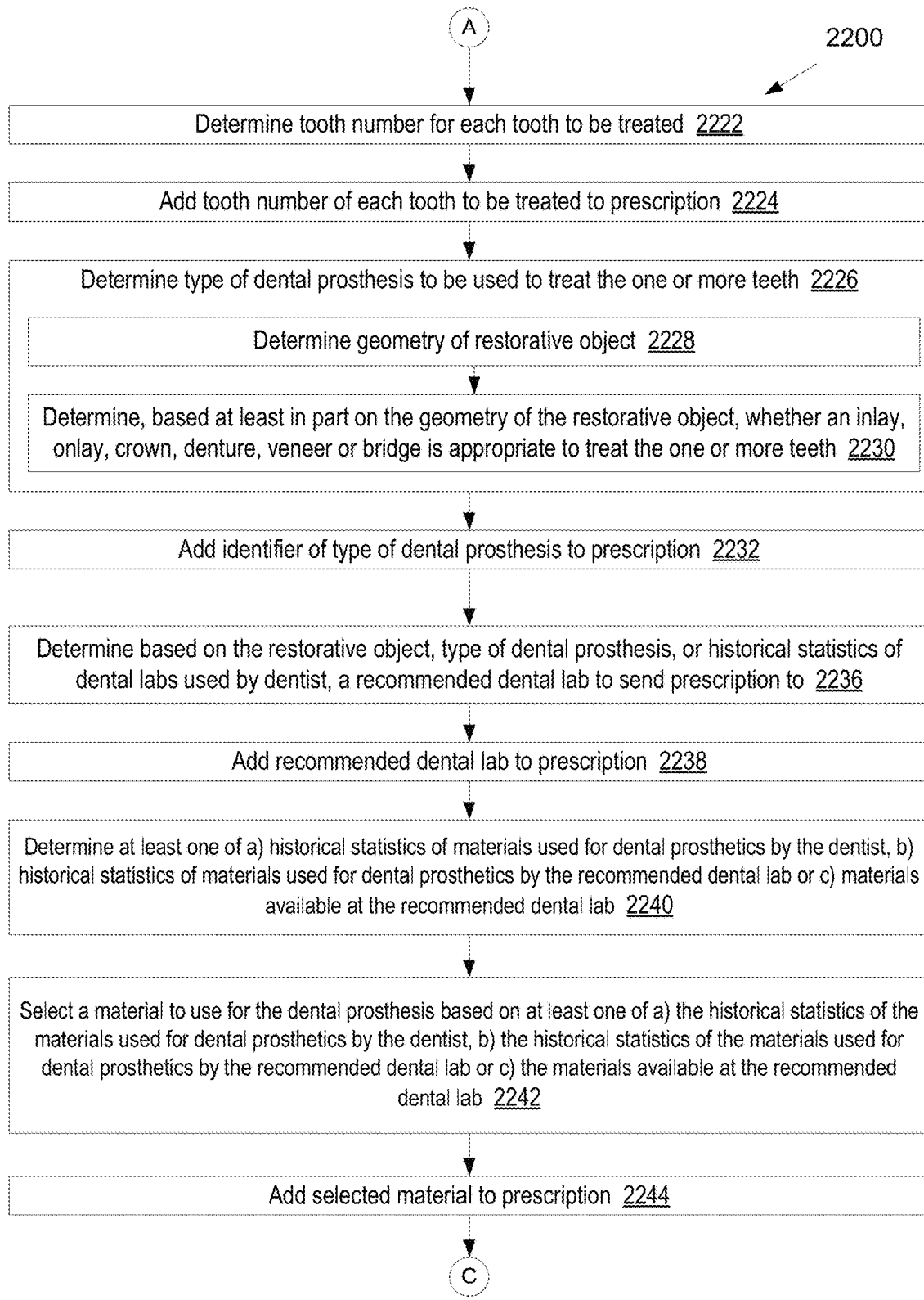
Figure 22C:
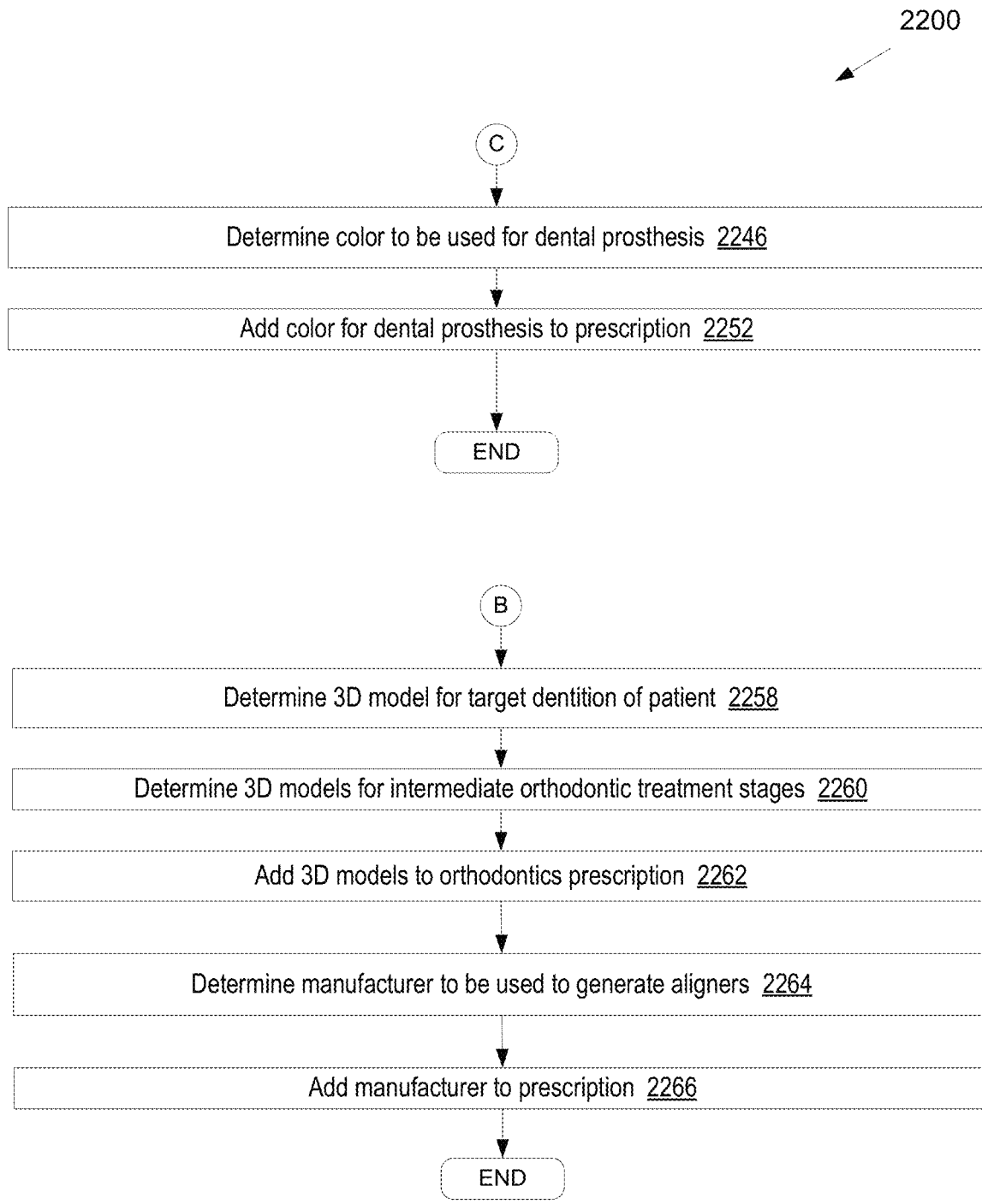

FIGS. 22A-C illustrate a flow chart of an embodiment for a method 2200 of automatically generating one or more prescription for a dental prosthesis and/or orthodontia for a patient. At block 2202 of method 2200, processing logic inputs data from intraoral scans, a 3D surface (e.g., which may include projections of the 3D surface onto one or more planes) and/or 2D images into a trained ML model. At block 2204, the ML model outputs classifications of dental objects in the 3D surface, intraoral scans and/or 2D images. This may include outputting a pixel-level or point-level classification of points on the 3D surface at block 2206 and segmenting the 3D surface into gums, restorative objects, natural teeth and/or other dental objects in an embodiment.

At block 2210, processing logic determines an identity of a user of an intraoral scanner used to generate the intraoral scans, optionally using one of the automated techniques discussed herein above. At block 2212, processing logic determines historical data about the user of the intraoral scanner. This may include determining dental labs to which prescriptions have been sent, materials used for dental prosthetics, whether the user has performed restorative and/or orthodontic treatments in the past, and so on. At block 2214, processing logic determines whether the user a) only performs orthodontic dental procedures, b) only performs restorative dental procedures, or c) performs both orthodontic and restorative dental procedures based on the historical data about the user.

At block 2216, processing logic uses the determinations made to block 2204 and at block 2214 to determine whether to initiate a restorative dental procedure workflow or an orthodontic procedure workflow. If processing logic determines to initiate a restorative dental procedure workflow, the method continues to block 2218, and processing logic initiates a restorative dental procedure workflow to generate a prescription for a dental prosthesis. If processing logic determines to initiate an orthodontic dental procedure workflow, the method continues to block 2220, and processing logic initiates an orthodontic dental procedure workflow to generate a prescription for orthodontia.

From block 2218 the method continues to block 2222. At block 2222, processing logic determines a tooth number for each tooth to be treated. For example, processing logic may determine a tooth number associated with each identified preparation tooth and/or other restorative object. At block 2224, processing logic adds the determined tooth number(s) to the prescription.

At block 2226, processing logic determines a type of dental prosthesis to be used to treat the one or more teeth. In one embodiment, this includes determining a geometry of the restorative object at block 2228. At block 2230, processing logic may then determine, based at least in part on the geometry of the restorative object, whether an inlay, onlay, crown, denture, veneer or bridge is appropriate for the one or more teeth. In one embodiment, processing logic inputs data of the 3D surface of the restorative object(s) and/or surrounding teeth into a trained ML model, which outputs a prediction of a type of dental prosthesis to be used. Alternatively, processing logic may apply one or more rules based on a size of the restorative object, a tooth position of the restorative object, tooth positions of other restorative objects, whether an edentulous region is between the restorative object and another restorative object, and so on to determine which type of dental prosthesis to be used. At block 2232, processing logic adds an identifier of the type of dental prosthesis to be used for each of the detected restorative objects to the prescription.

At block 2236, processing logic determines based on the restorative object (e.g., including the placement and/or geometry of the restorative object and/or surrounding teeth), the type of dental prosthesis to be used, and/or historical statistics of dental labs used by the dentist, a recommended lab to send the prescription to. At block 2238, processing logic adds the recommended dental lab to the prescription. The historical statistics of used dental labs may include restorative prescriptions sent to those dental labs, which may include details such as the type of dental prosthetic to be manufactured, the teeth to which the dental prosthetic will be applied, surface shape of the preparation tooth or preparation teeth and/or surface shape of surrounding teeth, whether an edentulous region is present, a size of the edentulous region, whether the patient's mouth is large, medium or small, and so on. Processing logic may determine which prescriptions with which case details were sent to which dental labs in the past. Based on this information, processing logic may determine which of the dental labs to which the doctor has sent prescriptions to in the past should be sent the current prescription. This may include classifying restorative dental prescriptions as simple, medium and complex, and assigning simple cases to a first dental lab, medium cases to a second dental lab, and complex cases to a third dental lab. In one embodiment, processing logic inputs the data on prescriptions and/or patient case details with associated assigned dental labs into an ML model to train the ML model to receive patient case details and/or a prescription and to output a prediction of a dental lab to assign the prescription to.

At block 2240, processing logic determines at least one of a) historical statistics of materials used for dental prosthetics by the dentist, b) historical statistics of materials used for dental prosthetics by the recommended dental lab, or c) materials available at the recommended dental lab. At block 2242, processing logic selects a material to be used for the dental prosthesis based on at least one of a) the historical statistics of materials used for dental prosthetics by the dentist, b) the historical statistics of materials used for dental prosthetics by the recommended dental lab, or c) the materials available at the recommended dental lab. At block 2244, processing logic adds the selected material to the prescription.

At block 2246, processing logic determines a color to use for the dental prosthesis. In one embodiment, processing logic determines the color to use for the dental prosthesis based on a color of a tooth that the dental prosthesis will be replacing. The color of the tooth to be replaced may be determined based on color images generated of the tooth prior to grinding of the tooth and/or removal of the tooth to form a preparation. Additionally, or alternatively, the color of the tooth may be determined based on colors of surrounding teeth, which may be determined from color images generated of the surrounding teeth. At block 2252, processing logic adds the color information for the dental prosthesis to the prescription. Once the prescription is generated, it may be reviewed by the doctor and then sent to the specified dental lab once approved.

From block 2220 the method continues to block 2258. At block 2258, processing logic determines a 3D model for a target dentition of the patient. At block 2260, processing logic determines 3D models for intermediate orthodontic treatment stages. At block 2262, processing logic adds the 3D models generated at block 2258 and 2260 to the orthodontic treatment prescription.

At block 2264, processing logic determines a manufacturer to be used to generate aligners for the orthodontic treatment. At block 2266, processing logic adds the manufacturer to the prescription. Once the prescription is generated, it may be reviewed by the doctor and then sent to the specified dental lab once approved.

Figure 23:
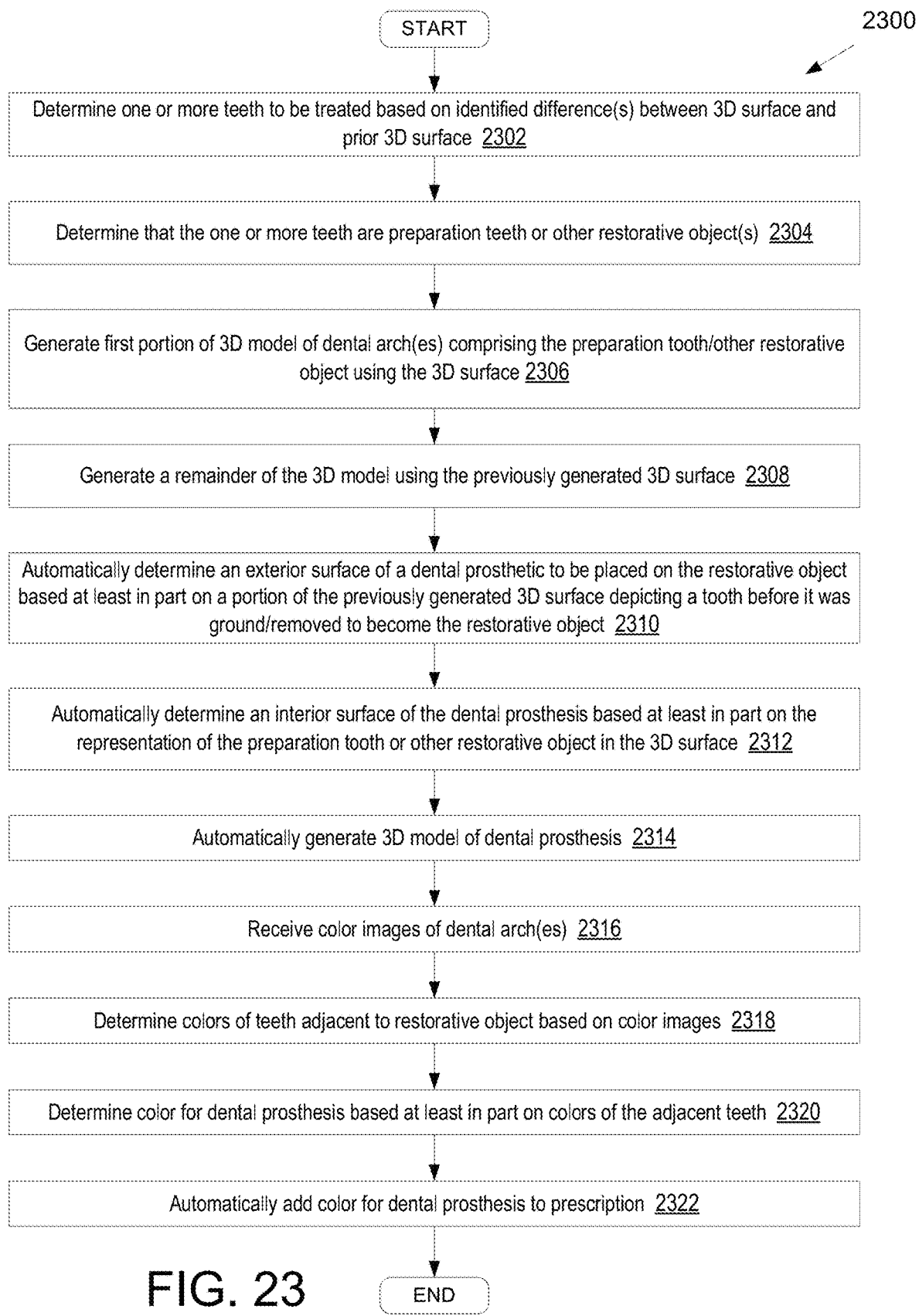
FIG. 23 is a flow chart illustrating an embodiment for a method of automatically generating a prescription for a dental prosthesis.

FIG. 23 is a flow chart illustrating an embodiment for a method 2300 of automatically generating a prescription for a dental prosthesis. Method 2300 may be performed to reduce an amount of scanning that a doctor needs to perform before generating a prescription for a dental prosthesis. Generally, a doctor scans an entire dental arch that contains a restorative object in order to generate an accurate 3D model of the restorative object and a remainder of the dental arch. However, embodiments leverage one or more previously generated 3D models that were generated before the preparation tooth was created or before another type of restorative object was installed to generate a 3D model. This enables the doctor to only scan the preparation tooth or other restorative object and portions of surrounding teeth after the restorative object/preparation are added to the dental arch and still obtain an accurate 3D model of the dental arch.

At block 2302 of method 2300, processing logic determines one or more teeth to be treated based on identified differences between a current 3D surface of a dental arch and a prior 3D surface of the dental arch and/or based on an identification of restorative objects. At block 2304, processing logic determines that the one or more teeth are preparation teeth or other restorative objects. In some embodiments, the operations of blocks 2302 and 2304 may be reversed such that restorative objects are first identified, and that identification is used to determine which teeth are to be treated.

At block 2306, processing logic generates a first portion of a 3D model of a dental arch comprising the preparation tooth and/or other restorative object using the current 3D surface. At block 2308, processing logic generates a remainder of the 3D model using the previously generated 3D surface, which may be a pre-scan 3D model or a 3D model generated from intraoral scanning performed at a prior patient visit.

At block 2310, processing logic automatically determines an exterior surface of a dental prosthetic to be placed on the restorative object based at least in part on a portion of the previously generated 3D surface depicting a tooth before the tooth was ground or removed. At block 2312, processing logic automatically determines an interior surface of the dental prosthesis based at least in part on the representation of the preparation tooth or other restorative object in the current 3D surface. At block 2414, processing logic automatically generates a 3D model of the dental prosthesis using the determined exterior surface and interior surface.

At block 2318, processing logic determines colors of teeth adjacent to the restorative object based on color images. Processing logic may additionally or alternatively determine a color of the tooth that will be replaced from the prior 3D model and/or color images associated with the prior 3D model depicting the tooth to be replaced. At block 2320, processing logic determines a color of the dental prosthesis based on the colors of the adjacent teeth and/or the color of the tooth to be replaced. At block 2322, processing logic automatically adds the determined color for the dental prosthesis to the prescription.

Figure 24:
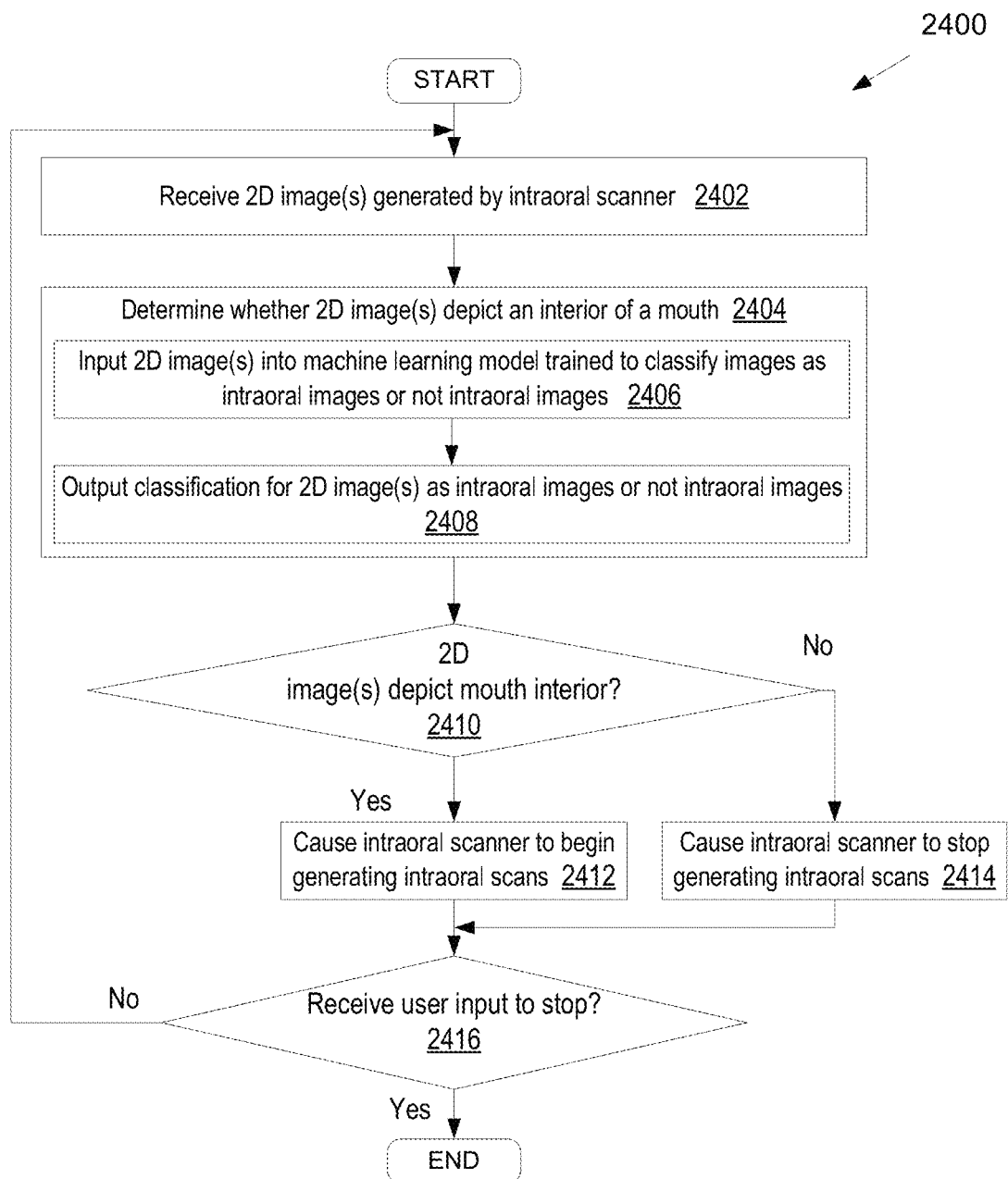
FIG. 24 is a flow chart illustrating an embodiment for a method of automatically determining when to start and/or stop generating intraoral scans.

FIG. 24 is a flow chart illustrating an embodiment for a method 2400 of automatically determining when to start and/or stop generating intraoral scans. At block 2402 of method 2400, processing logic receives 2D images generated by an intraoral scanner. These may be, for example, 2D color images. At block 2404, processing logic determines whether the 2D images depict an interior of a mouth. In one embodiment, at block 2406 processing logic inputs the 2D images into a ML model trained to classify images as intraoral images or not intraoral images. At block 2408 the ML model may then output a classification for the 2D images indicating whether those 2D images are intraoral images or not intraoral images.

At block 2410, processing logic determines whether the 2D images depict an interior of a mouth based on the determination based at block 2410. If the 2D images depict the interior of a mouth, the method continues to block 2412. Otherwise the method continues to block 2414.

At block 2412, processing logic causes the intraoral scanner to begin generating intraoral scans. Processing logic may also cause the intraoral scanner to start outputting light patterns (e.g., structured light), which may assist with determining height information for some types of scanners).

At block 2414, processing logic causes the intraoral scanner to stop generating intraoral scans. Processing logic may also cause the intraoral scanner to stop outputting light patterns.

At block 2416, processing logic determines whether a user input to stop has been received (e.g., via a user pressing a button on the scanner to stop determining whether to generate scans). If no such user input is received, the method returns to block 2404. If a user input to stop is received, the method ends.

Figure 25:
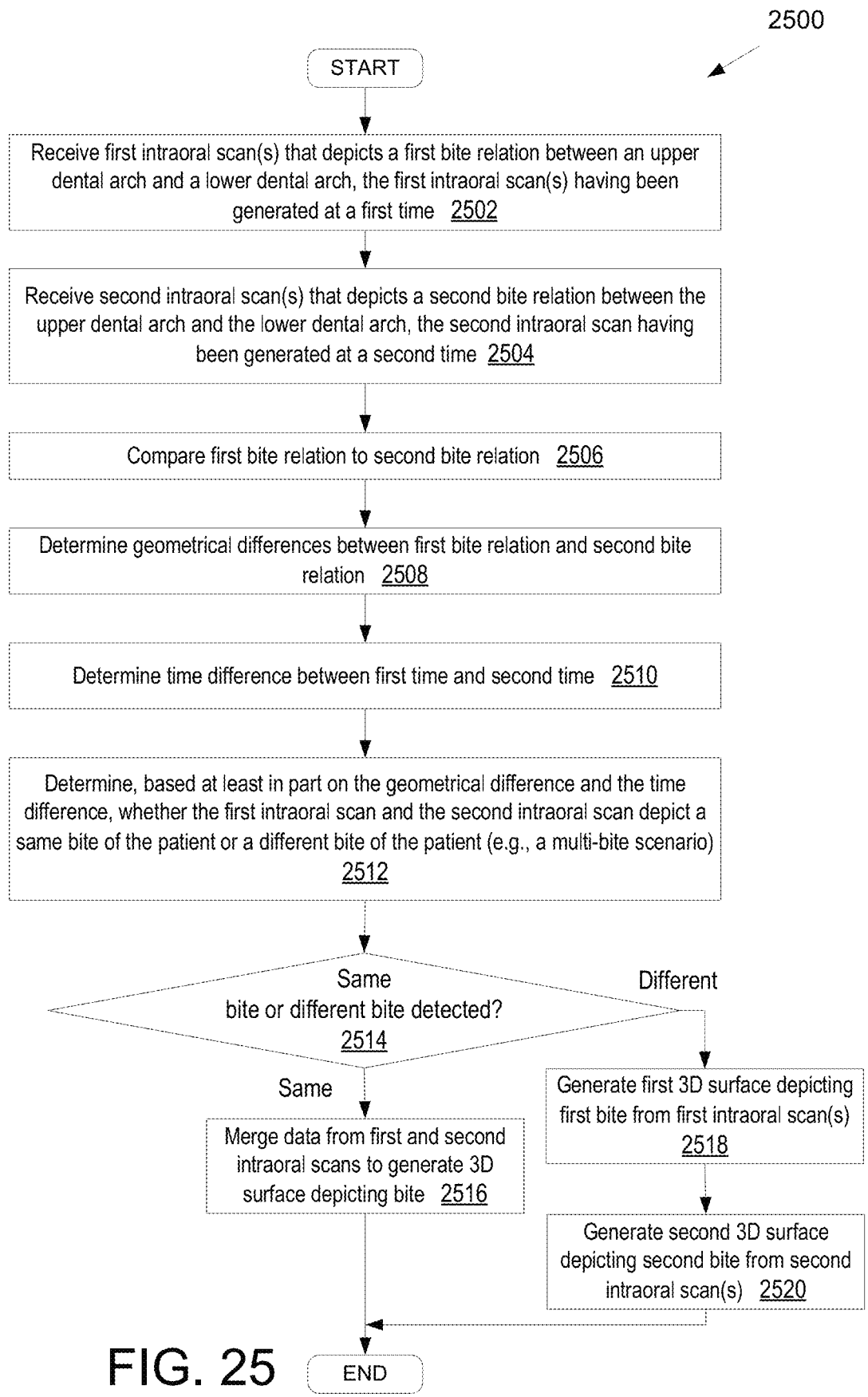
FIG. 25 is a flow chart illustrating an embodiment for a method of automatically detecting an multi-bite scanning scenario.

FIG. 25 is a flow chart illustrating an embodiment for a method 2500 of automatically detecting a multi-bite scanning scenario. At block 2502, processing logic receives one or more first intraoral scans (or first 3D surface generated from the first intraoral scans and/or a one or more first projections of the first 3D surface) that depict a first bite relation between an upper dental arch and a lower dental arch, where the first intraoral scans were generated at a first time. At block 2504, processing logic receives one or more second intraoral scans (or second 3D surface generated from the second intraoral scans and/or a one or more second projections of the second 3D surface) that depict a second bite relation between the upper dental arch and the lower dental arch, where the second intraoral scans were generated at a second time. At block 2506, processing logic compares the first bite relation to the second bite relation. At block 2508, processing logic determines one or more geometrical differences between the first bite relation and the second bite relation.

At block 2510, processing logic determines a time difference between the first time and the second time.

At block 2512, processing logic determines, based at least in part on the geometrical difference and the time difference, whether the first intraoral scan and the second intraoral scan depict a same bite of the patient or a different bite of the patient (e.g., multi-bite scenario). For example, if the time difference is less than a time difference threshold, then the first and second bite relations are likely for the same bite. However, if the time differences are greater than or equal to the time threshold, then there is an increased likelihood that the first and second bite relations depict different bites. Additionally, the greater the difference between the first and second bite relations, the higher the probability that they detect difference patient bites. Processing logic determine whether the geometrical differences between the first bite relation and the second bite relation exceed one or more geometrical difference thresholds. If the geometrical differences exceed a threshold, then there is an increased likelihood that the different bite relations are for different bites. In one embodiment, if the geometrical differences exceed a geometrical difference threshold, processing logic determines that the two bite relations are for different patient bites.

In one embodiment, the time difference threshold and/or the geometrical difference threshold are variable thresholds. For example, a value of the time difference threshold may be dependent on the measured geometrical difference between the bite relations. Similarly, a value of the geometrical difference threshold may be dependent on the measured time difference. In one embodiment, if the time difference exceeds the time difference threshold and the bite difference exceeds the bite difference threshold, processing logic determines that the two bite relations are for different patient bites. In one embodiment, if the time difference is less than the time difference threshold and the geometrical difference is less than the geometrical difference threshold, then processing logic determines that the two bite relations are for the same patient bite.

In an embodiment, processing logic uses a trained ML model to determine whether two bite relations are for the same patient bite or for different patient bites. The ML model may have been trained based on pairs of intraoral scans of patient bites, pairs of 3D surfaces of patient bites and/or pairs or projections of such 3D surfaces. Each pair may include a label indicating whether the two scans or surfaces are for the same patient bite or for different bites of a patient. Accordingly, the ML model may be trained to receive a pair of scans, 3D surfaces and/or projection(s) of 3D surfaces, and to determine for the pair whether they represent the same patient bite or a different patient bite. The first intraoral scans and the second intraoral scans (or 3D surfaces generated from those intraoral scans and/or projections of such 3D surfaces) may be input into the trained ML model, which may output a prediction as to whether the first and second intraoral scans (or first and second 3D surfaces) are for the same patient bite or a separate patient bites.

At block 2514, processing logic determines whether the two bite relations are for the same patient bite or for different patient bites. If the two bite relations are for the same patient bite, the method continues to block 2516. If the two bite relations are for different patient bites, the method proceeds to block 2518.

At block 2516, processing logic merges data from the first and second intraoral scans (or from the first and second 3D surfaces) to generate a single 3D surface depicting the patient bite.

At block 2518, processing logic may generate a first 3D surface depicting a first patient bite from the first intraoral scans. At block 2520, processing logic may generate a second 3D surface depicting a second patient bite from the second intraoral scans.

Figure 26:
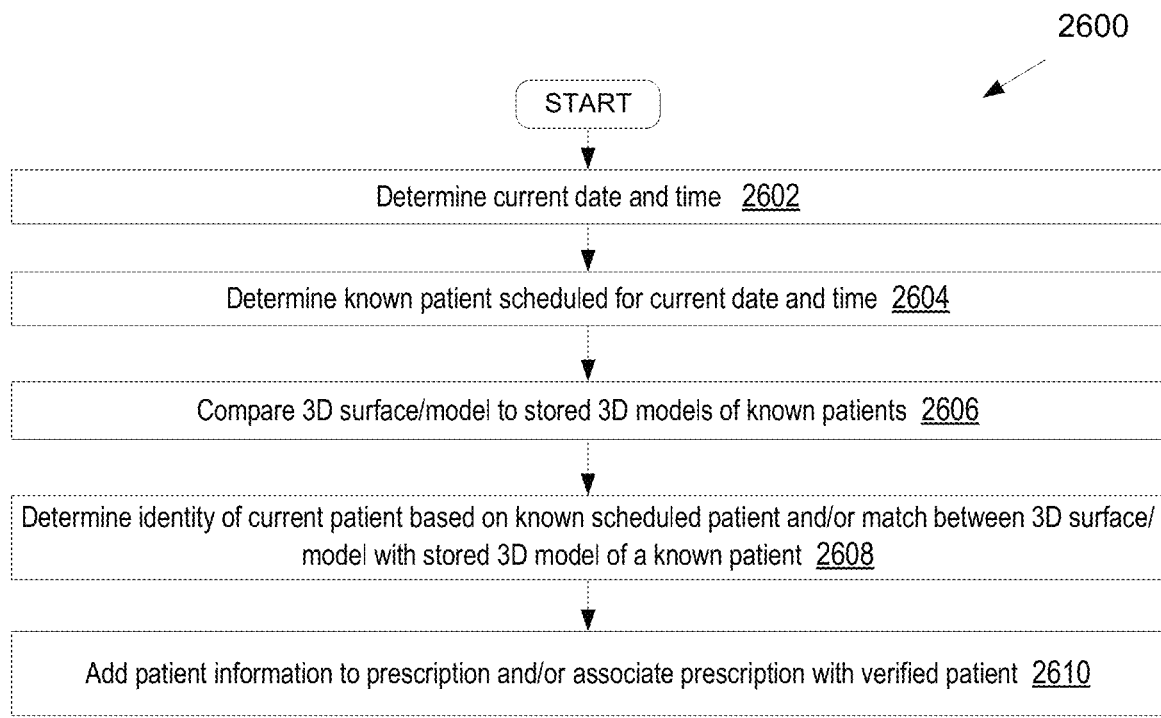
FIG. 26 is a flow chart illustrating an embodiment for a method of automatically determining an identity of a patient.

FIG. 26 is a flow chart illustrating an embodiment for a method 2600 of automatically determining an identity of a patient. At block 2602, processing logic may determine a current date and time. Processing logic may also determine a current dental chair at which scanning is being performed. At block 2604, processing logic may determine a known patient scheduled for the current date and time (and/or the current chair) by accessing calendar software, office management software and/or other software. Such software may contain patient details such as a patient name, age, gender, allergies, and/or other information.

At block 2606, processing logic may compare a 3D surface or 3D model generated from received intraoral scans generated during a current scanning session to stored 3D models of known patients. Based on such comparisons, processing logic may determine whether there is a match between the current 3D surface or 3D model and one or more stored 3D model. If such a match is found, then there is a high likelihood that the known patient associated with the stored 3D model is also the patient currently being scanned.

At block 2608, processing logic may determine an identity of the current patient based on known scheduled patient and/or a match between the current 3D surface or 3D model and a stored 3D model associated with a known patient.

At block 2610, processing logic may add patient information to a prescription for orthodontic treatment and/or a prescription for restorative treatment and/or associate the prescription(s) with the identified patient.

Figure 27:
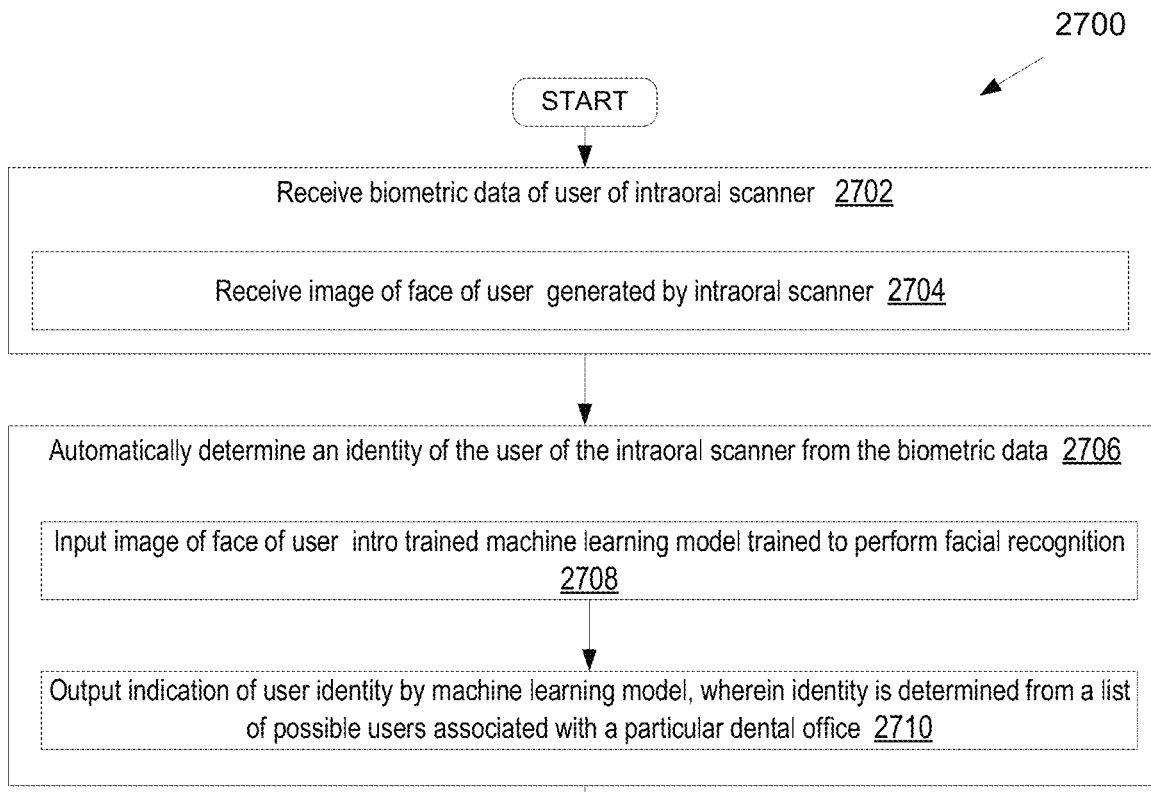
FIG. 27 is a flow chart illustrating an embodiment for a method of automatically determining an identity of a user of an intraoral scanner.

FIG. 27 is a flow chart illustrating an embodiment for a method 2700 of automatically determining an identity of a user of an intraoral scanner. At block 2702 of method 2700, processing logic receives biometric data of a user of the intraoral scanner. Such biometric data may include audio data of the user speaking, an image of the user's face, an image or scan of the user's fingerprint, an image or scan of the user's retina, and so on. For example, at block 2704 processing logic may receive an image of a face of the user generated by the intraoral scanner or by a camera of a computing device connected to the intraoral scanner by a wired or wireless connection.

At block 2706, processing logic automatically determines an identity of the user of the intraoral scanner from the biometric data. This may include at block 2708 inputting the image of the face of the user into a trained ML model trained to perform facial recognition (e.g., of doctors at a particular dental office), and at block 2710 outputting by the ML model an indication of a user identity. The output may be determined from a list of possible users associated with the dental office. If no match to a user is identified, then the ML model may output an unknown user indication.

Figure 28:
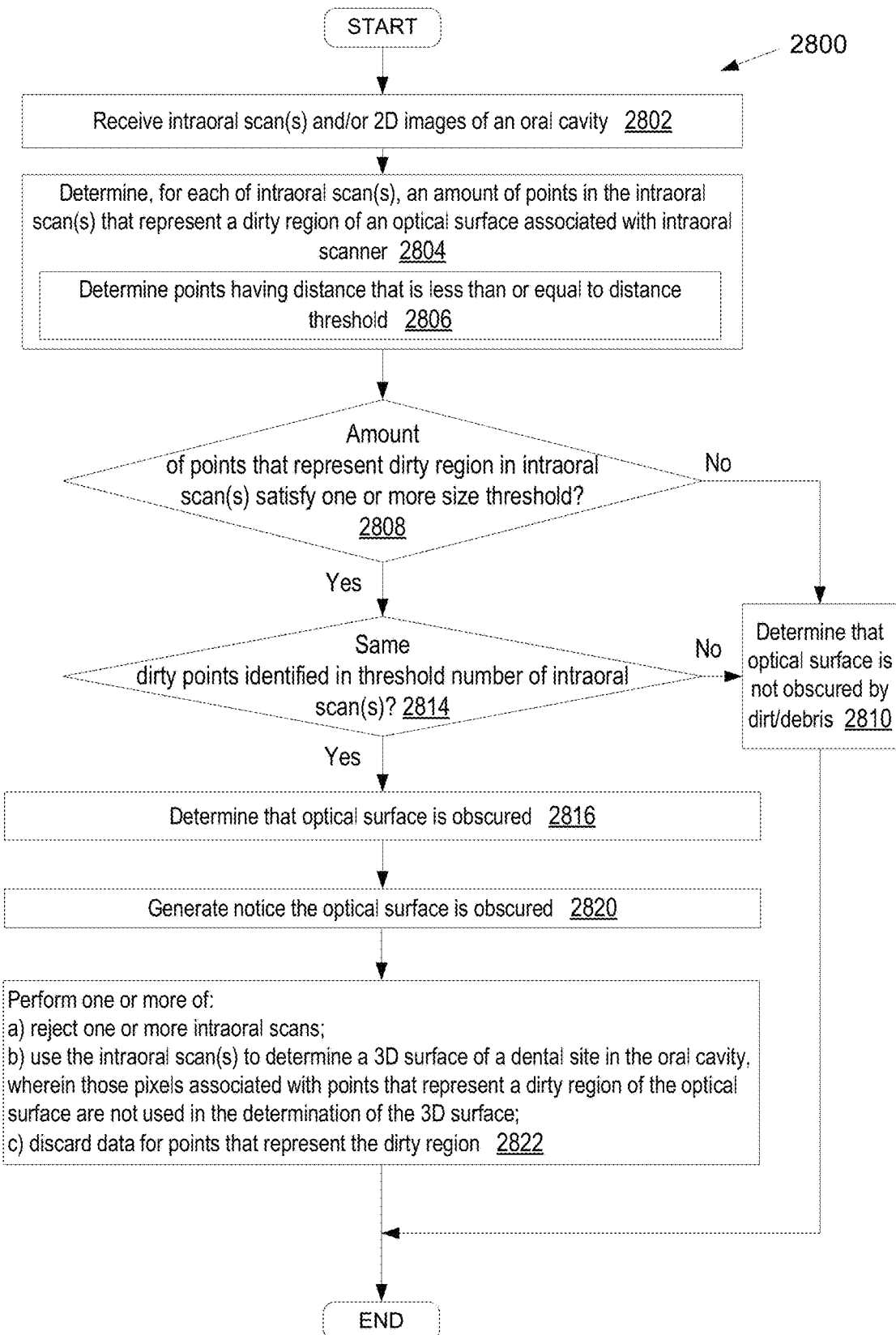
FIG. 28 is a flow chart illustrating an embodiment for a method of automatically detecting a dirty optical surface of an intraoral scanner or protective sleeve on the intraoral scanner.

FIG. 28 is a flow chart illustrating an embodiment for a method 2800 of automatically detecting a dirty optical surface of an intraoral scanner or protective sleeve or attachment on the intraoral scanner. At block 2802 of method 2800, processing logic receives intraoral scans and/or 2D images of an oral cavity, where the scans and/or images were generated by an intraoral scanner. The scans may be generated by generating coherent light or non-coherent light by an intraoral scanner, which is reflected off of an intraoral object back into the intraoral scanner and detected to generate the intraoral scans and/or 2D images. The light may include structured light and/or unstructured light. The intraoral scanner may be inserted into a disposable sleeve, which may act as a protective sleeve to protect the intraoral scanner from contact with the patient's oral cavity.

At block 2804, processing logic determines, for each of the intraoral scans, an amount of points in the intraoral scans that represent a dirty region of an optical surface associated with the intraoral scanner. Such optical surfaces may include lenses, windows, mirrors, and so on of the scanner and/or of a protective sleeve or protective attachment of the intraoral scanner.

In one embodiment, the intraoral scans include height information (e.g., the intraoral scans may be height maps, which may be 2D monochrome images in which each pixel includes a height value), and at block 2806 processing logic identifies points representing dirty regions of an optical surface based on the height information. For example, processing logic may compare heights detected for pixels with one or more height thresholds (or depth thresholds). If a height is greater than a height threshold (or a depth is less than a depth threshold), then this may indicate that the detected surface is not a point on an intraoral surface but is instead a dirty point on an optical surface associated with the scanner. Thus, points that have a height greater than a height threshold (or depths less than a depth threshold) may be identified as dirty points.

In one embodiment, processing logic identifies unmoving points between multiple intraoral scans and/or images. As the intraoral scanner is moved and multiple scans and/or images are generated, all of the points or pixels on the scans/images should have changing values. For example, a video of the scans/images played in sequence should show movement of intraoral objects relative to the scanner. However, a dirty surface is going to be the same between the scans and/or images. Accordingly, unmoving surfaces may be indicative of dirty pixels. Accordingly, processing logic may compare multiple scans together to identify unmoving pixels between those scans. If a majority of pixels between scans show movement, then those pixels that do not show movement may be identified as dirty pixels.

In some embodiments, distance and non-moving pixel information may be used together to determine which pixels are associated with dirty regions of the scanner.

In one embodiment, processing logic inputs the intraoral scan(s) and/or 2D image(s) into a trained ML model trained to identify dirty optical surfaces of scanners. The ML model may output a map (e.g., a probability map) that includes pixel-level classification of each pixel as being a dirty point or a clean point.

At block 2808, processing logic determines whether an amount of points that represent a dirty region in the intraoral scan(s) satisfy one or more size threshold. One size threshold may be an overall dirty pixel count threshold. If the total number of dirty points exceeds the overall dirty count threshold, this may indicate that an optical surface of the scanner is dirty. The overall dirty pixel count threshold may be, for example 5000 to 10000 pixels in an embodiment. In one embodiment, the overall dirty pixel count threshold is expressed as a percentage of a total number of pixels, and is about ⅛ to about ¼ (or about ⅙ to about ⅓) of the total number of pixels of the intraoral scanner. One size threshold may be a contiguous dirty region threshold. Processing logic may determine one or more dirty regions in the intraoral scan(s) and/or 2D images, where a dirty region is a region of all adjacent dirty pixels that together form a contiguous dirty region. If a size of any contiguous dirty region exceeds the contiguous dirty region threshold, then this may indicate that the scanner is dirty. In some embodiments, different contiguous dirty region thresholds are associated with different regions of the intraoral scans and/or 2D images. For example, if a large dirty region is in the center of the scans (i.e., in the center of the field of view of the scanner), then this may impair scanning more than if the large dirty region is at a periphery of the scans. Thus, a first dirty region size threshold may be applied to dirty regions in a first region of the intraoral scans and/or 2D images (e.g., near a center of the scans/images), and a second dirty region size threshold may be applied to dirty regions in a second region of the intraoral scans and/or 2D images (e.g., ear a periphery of the scans/images). In one embodiment, the first dirty region size threshold is smaller (fewer dirty pixels) than the second dirty region size threshold.

If the number of points that represent a dirty region in the intraoral scan(s) and/or 2D images does not satisfy any of the size thresholds, the method continues to block 2810. If the number of points that represent a dirty region in the intraoral scan(s) and/or 2D images satisfies one or more of the size thresholds, the method continues to block 2814.

At block 2814, processing logic may determine whether the same dirty points or same dirty regions have been identified for at least a threshold number of intraoral scans and/or images. As intraoral scans are generated and the intraoral scanner is moved within a patient's mouth, the surfaces detected at each scan should be different. However, dirty optical surfaces will generally show the same dirty surfaces for each of the scans. Accordingly, by comparing dirty pixels and/or dirty regions across multiple intraoral scans and/or images, the accuracy of dirty region determination can be increased. In one embodiment, processing logic determines whether the same dirty region or regions are detected in a majority of images or scans within a moving window. For example, processing logic may determine if at least 7 of 10 most recent scans or images include the same dirty regions. Processing logic may also determine a median or average of dirty regions between multiple scans, and determine dirty regions based on the average or median. If the same dirty points and/or regions are identified for a threshold number of intraoral scans and/or images, or one of the other conditions for dirty regions based on a combination of images are satisfied, the method continues to block 2816. If the same dirty points and/or regions are not identified for at least the threshold number of scans, or one or more other conditions for dirty regions based on a combination of images are not satisfied, the method proceeds to block 2810.

At block 2810, processing logic determines that the intraoral scanner does not include any optical surfaces that are obscured by dirt, grime or debris.

At block 2816, processing logic determines that an optical surface of the intraoral scanner is obscured by dirt, grime or debris. In some embodiments, processing logic can determine specifically which optical surface is dirty based on the measured heights/depths. For example, a window of a protective sleeve may be at a known first height, a window of the scanner may be at a known second height, a folding mirror may be at a known third height, and a lens may be at a known fourth height. The measured heights of the dirty regions may be compared to the known heights of each of the optical surfaces, and the optical surface with the height that matches or is close to the measured height may be determined to be the dirty optical surface.

At block 2820, processing logic generates a notice that an optical surface of the scanner is obscured. This may include generating a notice of a particular optical surface that is obscured if such information is known. For example, processing logic may output a notice that a protective sleeve or protective attachment is dirty and to replace the protective sleeve or protective attachment.

At block 2822, processing logic may perform one or more of a) reject one or more of the intraoral scans that were taken while the optical surface was dirty, b) use the intraoral scans to determine a 3D surface of the dental site in the oral cavity, where those pixels associated with points that represent a dirty region of the optical surface are not used in the determination of the 3D surface, or c) discard data for points that represent the dirty region. For example, once pixels associated with dirty regions are identified, it is still possible to use intraoral scans that include those dirty regions by excluding data from those regions. This may effectively reduce a field of view of the scanner. For some scanner designs, dirty regions can also negatively impact the accuracy of depth information determined by adjacent non-dirty regions.

In some instances, if the optical surfaces are too dirty to generate a high quality 3D surface, then processing logic may prevent a 3D model generated from these scans from being sent to a dental lab and/or may prevent further scanning until the dirty scanner is cleaned and/or a dirty protective sleeve is replaced.

In one embodiment, processing logic determines which action to perform based on a size of the dirty region or dirty regions and/or a location of the dirty region or dirty regions. For example, processing logic may determine whether number of dirty pixel regions exceeds a dirty region size threshold. If the number of dirty pixel regions exceeds the dirty region size threshold, then processing logic may determine that accurate scanning is no longer possible, and may stop further scanning. In one embodiment, the dirty region size threshold is about ¼ to ½ of the total number of pixels of the intraoral scanner.

The method then ends. Method 2800 may be repeated as further intraoral scans and/or 2D images are received.

Figure 29:
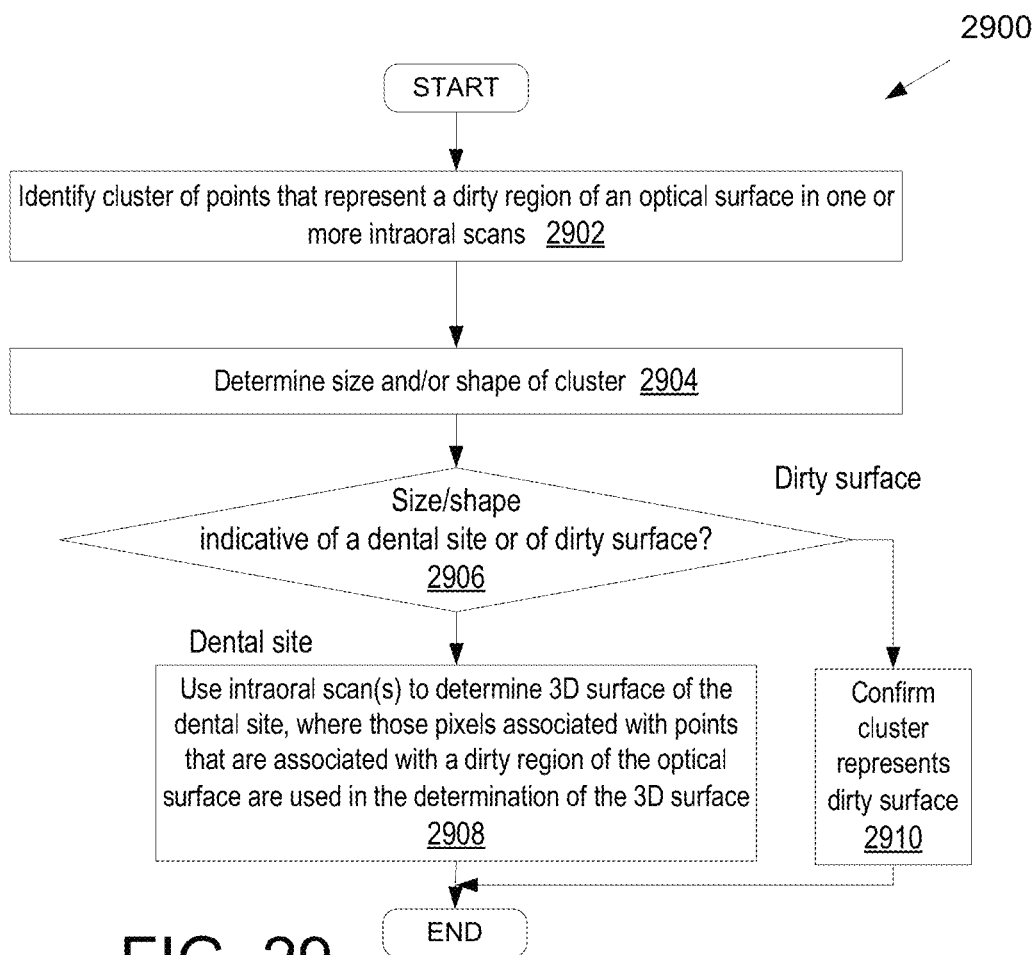
FIG. 29 is a flow chart illustrating an embodiment for a method of determining how to use pixels of intraoral scans associated with dirty regions of an optical surface.

FIG. 29 is a flow chart illustrating an embodiment for a method 2900 of determining how to use pixels of intraoral scans associated with dirty regions of an optical surface. Even if an optical surface of a scanner is dirty, the scanner may still be used to generate usable intraoral scans. However, it can be more efficient to simply clean the scanner, to clean a protective sleeve or attachment of the scanner, or replace a protective sleeve or attachment of the scanner.

At block 2902 of method 2900, processing logic identifies a cluster of points that represent a dirty region of an optical surface of the intraoral scanner from one or more intraoral scans and/or 2D images generated by the intraoral scanner. At block 2904, processing logic determines a size and/or shape of the cluster of points that represent the dirty region. In some instances, processing logic may incorrectly identify a dirty region of a dental site. Accordingly, in one embodiment processing logic performs a shape assessment of the dirty region to determine whether the dirty region has a shape of a dental object or a shape associated with dirt or grime (e.g., blood) on an optical surface. For example, dirt and grime may have a random shape or a splat or droplet-like shape. Additionally, dental object may have a predefined range of sizes.

At block 2906, processing logic determines whether the size or shape is indicative of a dental site or of a dirty surface. If the size and/or shape of the cluster is indicative of a dirty surface, then the method continues to block 2910, and processing logic confirms the cluster as a dirty surface. Processing logic may then perform one or more of a) reject one or more of the intraoral scans that were taken while the optical surface was dirty, b) use the intraoral scans to determine a 3D surface of the dental site in the oral cavity, where those pixels associated with points that represent a dirty region of the optical surface are not used in the determination of the 3D surface, or c) discard data for points that represent the dirty region.

At block 2906, if the size and/or shape of the cluster is indicative of a dental object, then the method continues to block 2908. At block 2908, processing logic may user the intraoral scans to determine a 3D surface of a dental site. Those pixels associated with points that were associated with a dirty region may be used in the determination of the 3D surface.

Figure 30:
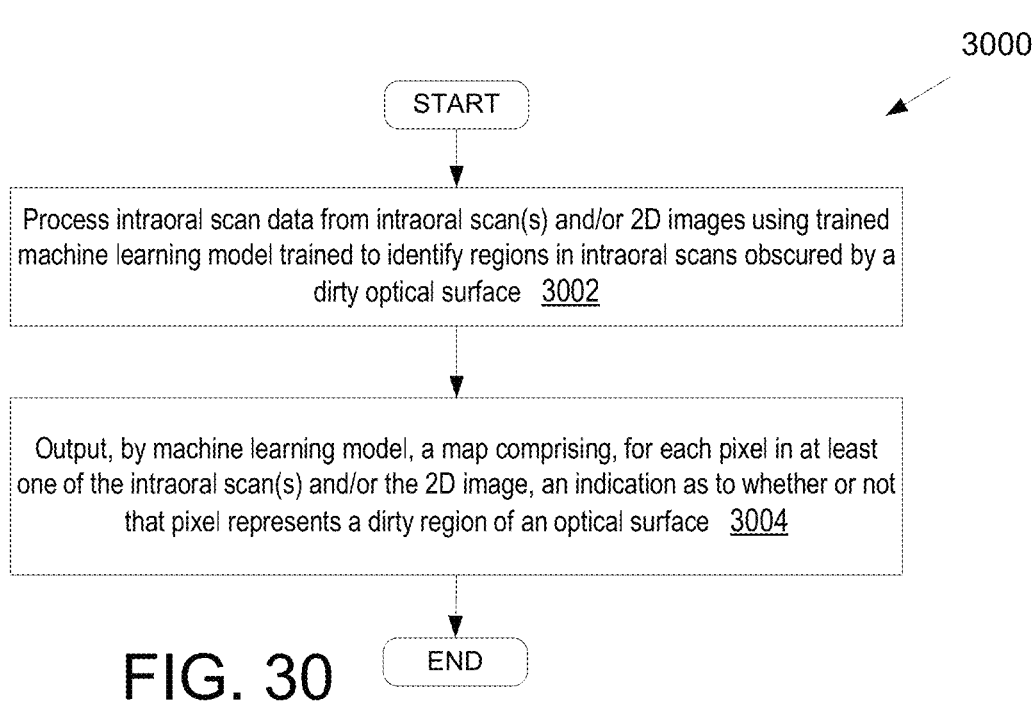
FIG. 30 is a flow chart illustrating an embodiment for a method of using a trained machine learning model to identify a dirty region of an optical surface of an intraoral scanner or protective sleeve on the intraoral scanner.

FIG. 30 is a flow chart illustrating an embodiment for a method 3000 of using a trained machine learning model to identify a dirty region of an optical surface of an intraoral scanner or protective sleeve on the intraoral scanner. At block 3002, processing logic inputs intraoral scans and/or 2D images into a trained ML model that has been trained to identify dirty regions in the input data (e.g., regions in intraoral scans that are obscured due to a dirty optical surface). Processing logic may input a single scan or multiple scans into the ML model. At block 3004, the ML model may output a map comprising, for each pixel/point in the intraoral scan(s) and/or image(s) an indication as to whether or not that pixel represents a dirty region of the optical surface. Alternatively, the ML model may output an indication of a dirty optical surface or a clean optical surface (e.g., a scan or image-level classification of clean vs. dirty optical scanners). In one embodiment, the ML model outputs a dirtiness score, where the higher the score the more dirty the intraoral scanner is.

Figure 31:
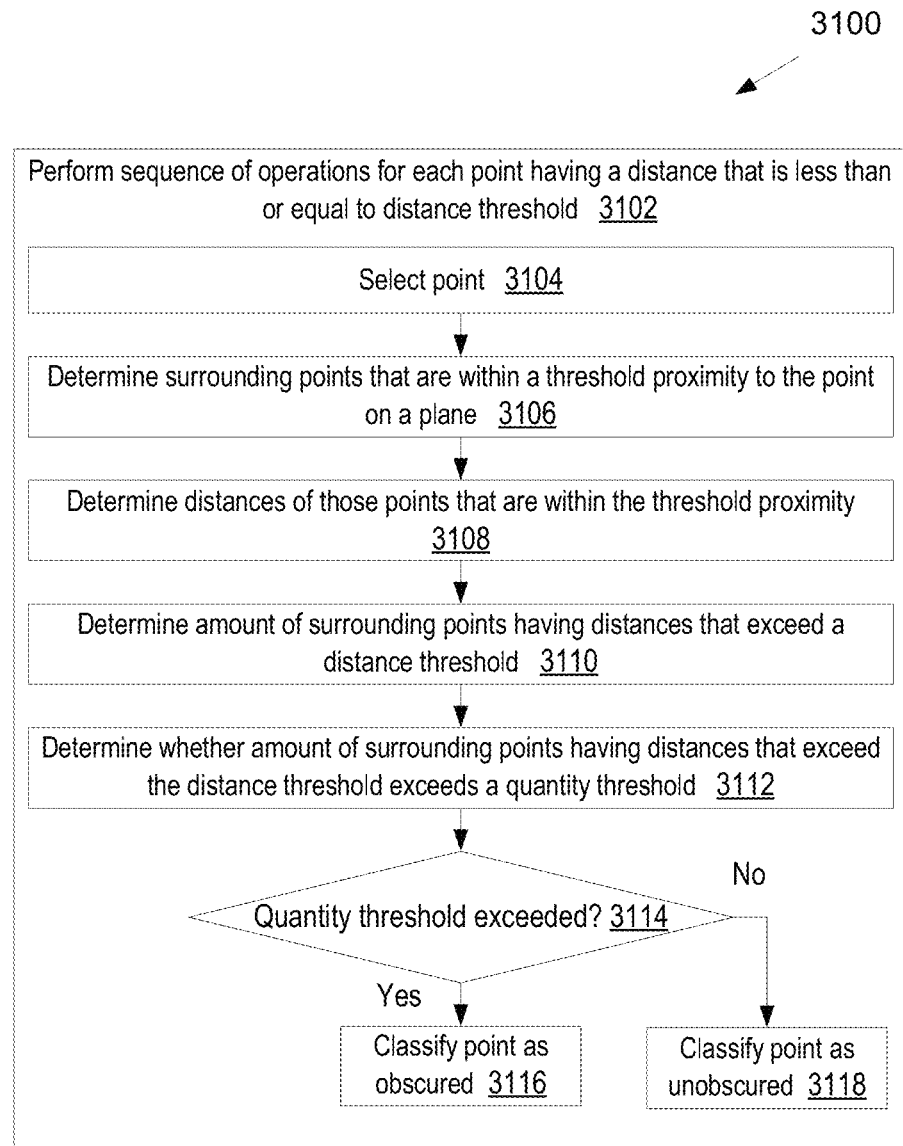
FIG. 31 is a flow chart illustrating an embodiment for a method of determining which pixels in an intraoral scan or image represent a dirty region of an optical surface of an intraoral scanner or protective sleeve on the intraoral scanner.

FIG. 31 is a flow chart illustrating an embodiment for a method 3100 of determining which pixels in an intraoral scan or image represent a dirty region of an optical surface of an intraoral scanner or protective sleeve on the intraoral scanner. In one embodiment, method 3100 is performed at block 2804 of method 2800. At block 3102, processing logic performs a sequence of operations for each point in an intraoral image having a distance that is less than or equal to a distance threshold.

In one embodiment, at block 3104, processing logic selects a point (e.g., a pixel). At block 3106, processing logic determines surrounding points that are within a threshold proximity to the point on a plane. At block 3108, processing logic determines distances of those points that are within the threshold proximity. At block 3110, processing logic determines an amount of surrounding points having distances that are less than the distance threshold.

At block 3112, processing logic determines whether the amount of surrounding pixels having distances the exceed the distance threshold exceeds a quantity threshold. At block 3114, if the number of surrounding points having distances that exceed the distance threshold exceeds a quantity threshold, the method continues to block 3116 and the selected point is classified as obscured. At block 3114, if the number of surrounding points having distances that exceed the distance threshold is less than the quantity threshold, the method continues to block 3118 and the selected point is classified as unobscured.

Figure 32A:
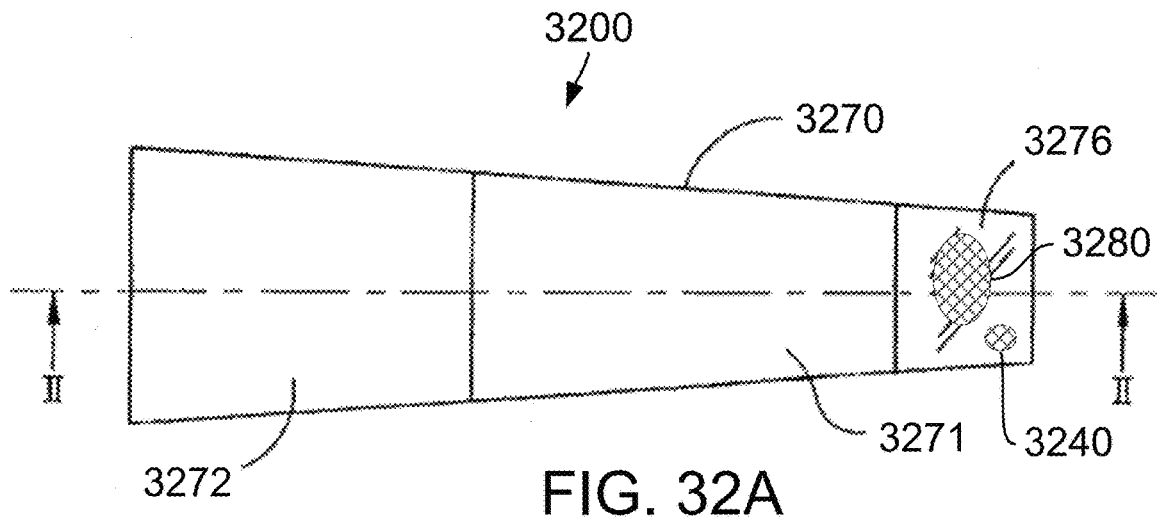
FIGS. 32A-B illustrate a probe of an intraoral scanner with a dirty optical surface, in accordance with an embodiment of the present disclosure.
Figure 32B:
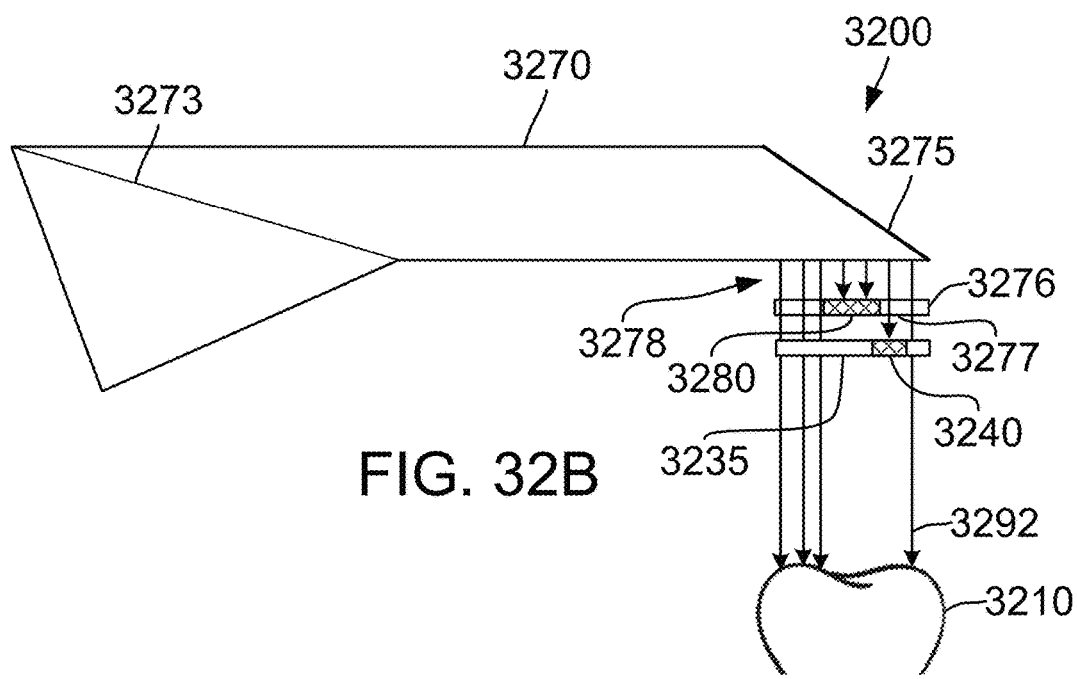

FIGS. 32A-B illustrate a probe (also referred to as a probing member) 3200 of an intraoral scanner with a dirty optical surface, in accordance with an embodiment of the present disclosure. In one embodiment, the probing member 3200 is made of a light transmissive material such as glass or plastic. In one embodiment, the probing member 3200 acts as a prism. Probing member 3200 may include an anterior segment 3271 and a posterior segment 3272, tightly bonded (e.g., glued) in an optically transmissive manner at 3273. Probing member 3200 may additionally include a slanted face covered by a reflective mirror layer 3275, which may be a folding mirror. A window 3276 defining a sensing surface 3277 may be disposed at a bottom end of the anterior segment 3271 in a manner optionally leaving an air gap 3278. The window 3276 may be fixed in position by a holding structure which is not shown. Light 3292 such as an array of light rays or beams may be projected through the probe 3200, off of the mirror 3275, through window 3276 and onto an imaged object such as tooth 3210. The light 3292 can be reflected back through the window 3276, off of mirror 3275, back through probe 3200 and onto a detector (not shown). In one embodiment, the light 3292 is reflected at the walls of the probing member at an angle in which the walls are totally reflective and finally reflect on mirror layer 305 out through the sensing face 307. The light 3292 may focus on a non-flat focal surface or a flat focal surface, the position of which can be changed by focusing optics (not shown in this figure) of the intraoral scanner.

In some embodiments, a protective sleeve is disposed over a head of the intraoral scanner (e.g., over at least a portion of probe 3200). The protective sleeve may include an additional window 3235 that may line up with (align with) window 3277 of intraoral probe 3200. Window 3277, mirror 3275 and/or window 3235 may each be an optical surface of the intraoral scanner that may become dirty over time. For example, window 3235 may become soiled with patient blood and/or saliva. This may introduce an occlusion to one or more regions of generated intraoral scans and/or images (e.g., 2D color images and/or NIRI images). As shown, window 3277 includes a first dirty region 3280 and window 3235 includes a second dirty region 3240. Together (or individually) these dirty regions 3280, 3235 cause some of the light output by probe 3200 to be blocked or obscured. This can interfere with scans generated by the intraoral scanner and reduce an accuracy of such intraoral scans.

In embodiments, the distances of the optical surface(s) (e.g., of mirror 3275, window 3277 and/or window 3235) from a detector and/or focusing lens(es) may be known. Accordingly, points that are detected to be at the known distances of the optical surface(s) may be indicative of dirty or an obstruction on the optical surface(s).

During measurement, light (e.g., an array of light rays or beams) may be projected out of the anterior segment 3271. As can be seen, the dirty regions 2380, 3235 are in the path of light beams 3292. Accordingly, the light beams 3992 are reflected off of the dirty regions 3280, 3240, which provides a depth (z-axis) measurement of the points on the dirty regions 3280, 3240. The optical surfaces are generally significantly closes to the probe than a dental object being scanned. Accordingly, points that have distances/depths that are less than a threshold may be identified as dirty points in embodiments.

Figure 33:
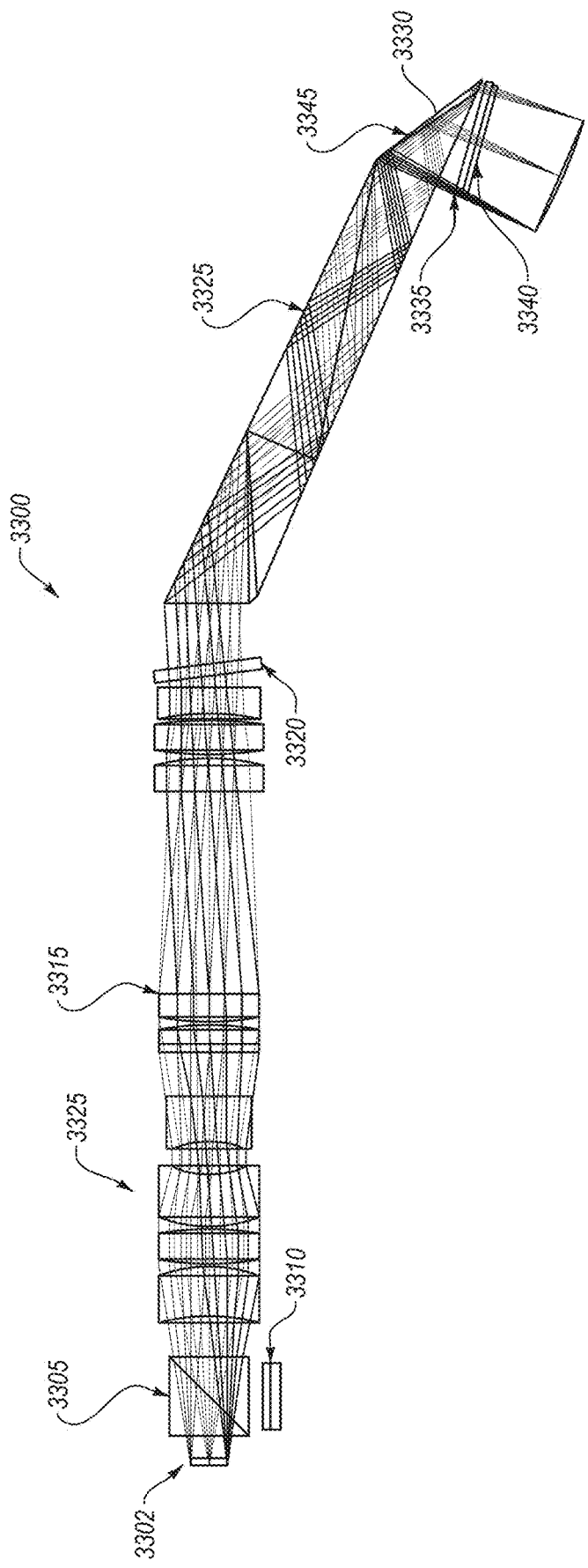
FIG. 33 illustrates an intraoral scanner with a dirty surface, in accordance with an embodiment of the present disclosure.

FIG. 33 illustrates an intraoral scanner 3300 with a dirty surface, in accordance with an embodiment of the present disclosure. Intraoral scanner 3300 includes a light source and/or illumination module 3302 that emits light (e.g., a focused light beam or array of focused light beams). The light passes through a polarizer (not shown) and through a unidirectional mirror or beam splitter (e.g., a polarizing beam splitter) 3305 that passes the light. The light may pass through a pattern before or after the beam splitter to cause the light to become patterned light.

Along an optical path of the light after the unidirectional mirror or beam splitter 3305 are optics, which may include one or more lens groups such as lens group 3325, lens group 3315 and lens group 3320. Any of the lens groups may include only a single lens or multiple lenses. One of the lens groups (e.g., lens group 3315) may include at least one moving lens.

The light may pass through an endoscopic probing member 3325, which may include a rigid, light-transmitting medium, which may be a hollow object defining within it a light transmission path or an object made of a light transmitting material, e.g. a glass body or tube. In one embodiment, the endoscopic probing member 3325 includes include a prism such as a folding prism. At its end, the endoscopic probing member 3325 may include a mirror 3330 of the kind ensuring a total internal reflection. Thus, the mirror 3345 may direct the array of light beams towards a teeth segment or other object. The endoscope probing member 3325 thus emits light, which optionally passes through one or more windows 3335, 3340 and then impinges on to surfaces of intraoral objects.

The light may include an array of light beams arranged in an X-Y plane, in a Cartesian frame, propagating along a Z axis. As the surface on which the incident light beams hits is an uneven surface, illuminated spots are displaced from one another along the Z axis, at different $(X_i, Y_i)$ locations, Thus, while a spot at one location may be in focus of the confocal focusing optics, spots at other locations may be out-of-focus. Therefore, the light intensity of returned light beams of the focused spots will be at its peak, while the light intensity at other spots will be off peak. Thus, for each illuminated spot, multiple measurements of light intensity are made at different positions along the Z-axis. For each of such $(X_i, Y_i)$ location, the derivative of the intensity over distance (Z) may be made, with the $Z_1$ yielding maximum derivative, $Z_0$, being the in-focus distance.

The light reflects off of intraoral objects and passes back through windows 3340, 3335 (if they are present), reflects off of mirror 3330, passes through the optical system (e.g., lens groups 3320, 3315, 3325, and is reflected by beam splitter 3305 onto a detector 3310. The detector 3310 is an image sensor having a matrix of sensing elements each representing a pixel of the scan or image. In one embodiment, the detector is a charge coupled device (CCD) sensor. In one embodiment, the detector is a complementary metal-oxide semiconductor (CMOS) type image sensor. Other types of image sensors may also be used for detector 3310. In one embodiment, the detector 3310 detects light intensity at each pixel, which may be used to compute height or depth.

Any of the optical surfaces of the intraoral scanner 3300 may become dirty, such as windows 3335, 3340 mirror 3330, lenses of lens groups 3320, 3315, 3325, beam splitter 3305, and so on. Most often one or more of windows 3335, 3340 (e.g., a window 3335 of intraoral scanner or a window 3340 of a protective sleeve on intraoral scanner 3300) or mirror 3330 becomes dirty. For example, in FIG. 33 a dirty point 3345 is shown on mirror 3330.

FIG. 33 illustrates one type of intraoral scanner (e.g., a confocal intraoral scanner) that can be used in embodiments. However, other types of intraoral scanners may alternatively be used, such as an intraoral scanner that does not apply confocal scanning. One such intraoral scanner is described in U.S. Publication No. 2019/0388193, entitled "Intraoral 3D Scanner Employing Multiple Miniature Cameras and Multiple Miniature Pattern Projectors," which is incorporated by reference herein.

Figure 34B:
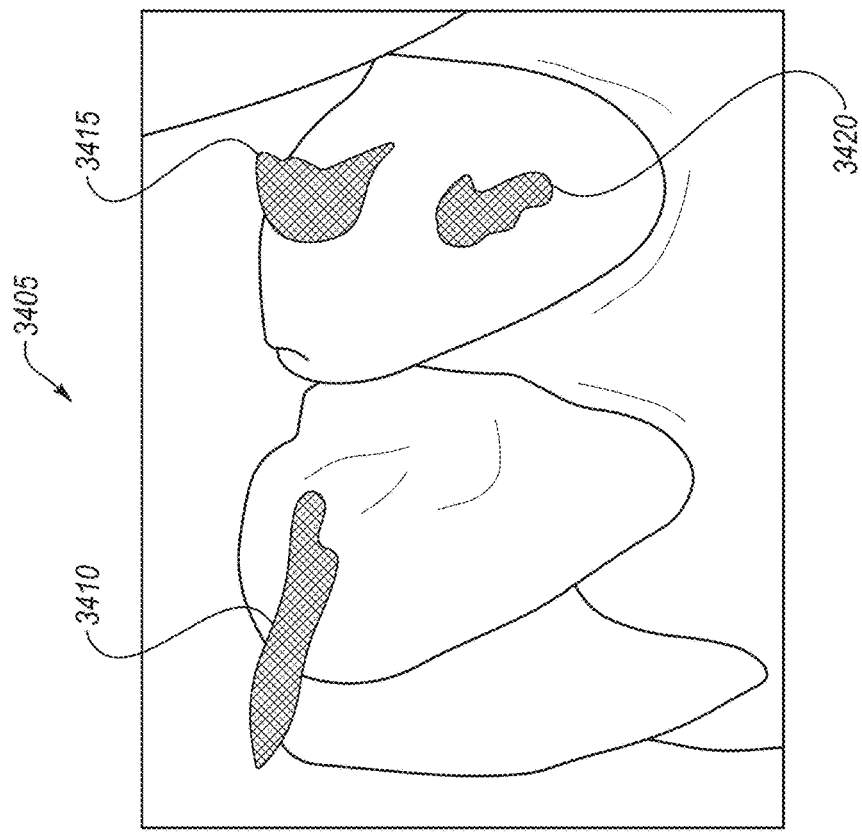
FIGS. 34A-B illustrate images taken by an intraoral scanner with a dirty surface.
Figure 34A:
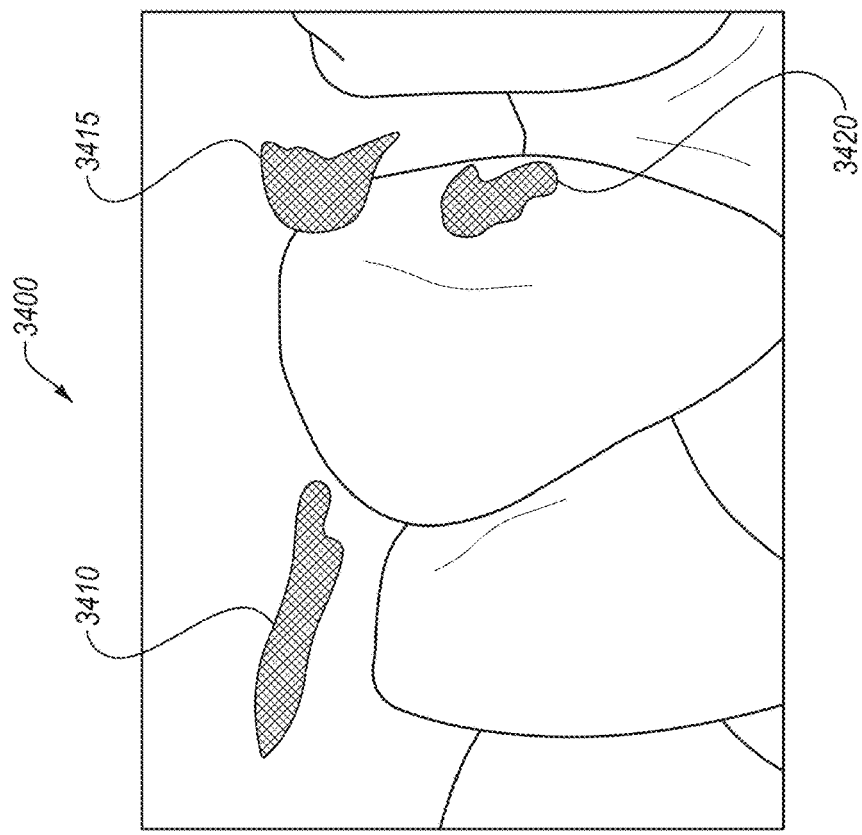

FIGS. 34A-B illustrate images taken by an intraoral scanner with a dirty surface and/or dirty sleeve. FIG. 34A illustrates a first image 3400 taken by the dirty intraoral scanner, and FIG. 34B illustrates a second image 3405 taken by the dirty intraoral scanner. As shown, each of the images 3400, 3405 shows different teeth of a patient. However, both images 3400, 3405 show the same dirty regions 3410, 3415, 3420. Such matching dirty regions between the images 3400, 3405 may be used to automatically identify the dirty regions with high accuracy as discussed herein above.

Figure 35:
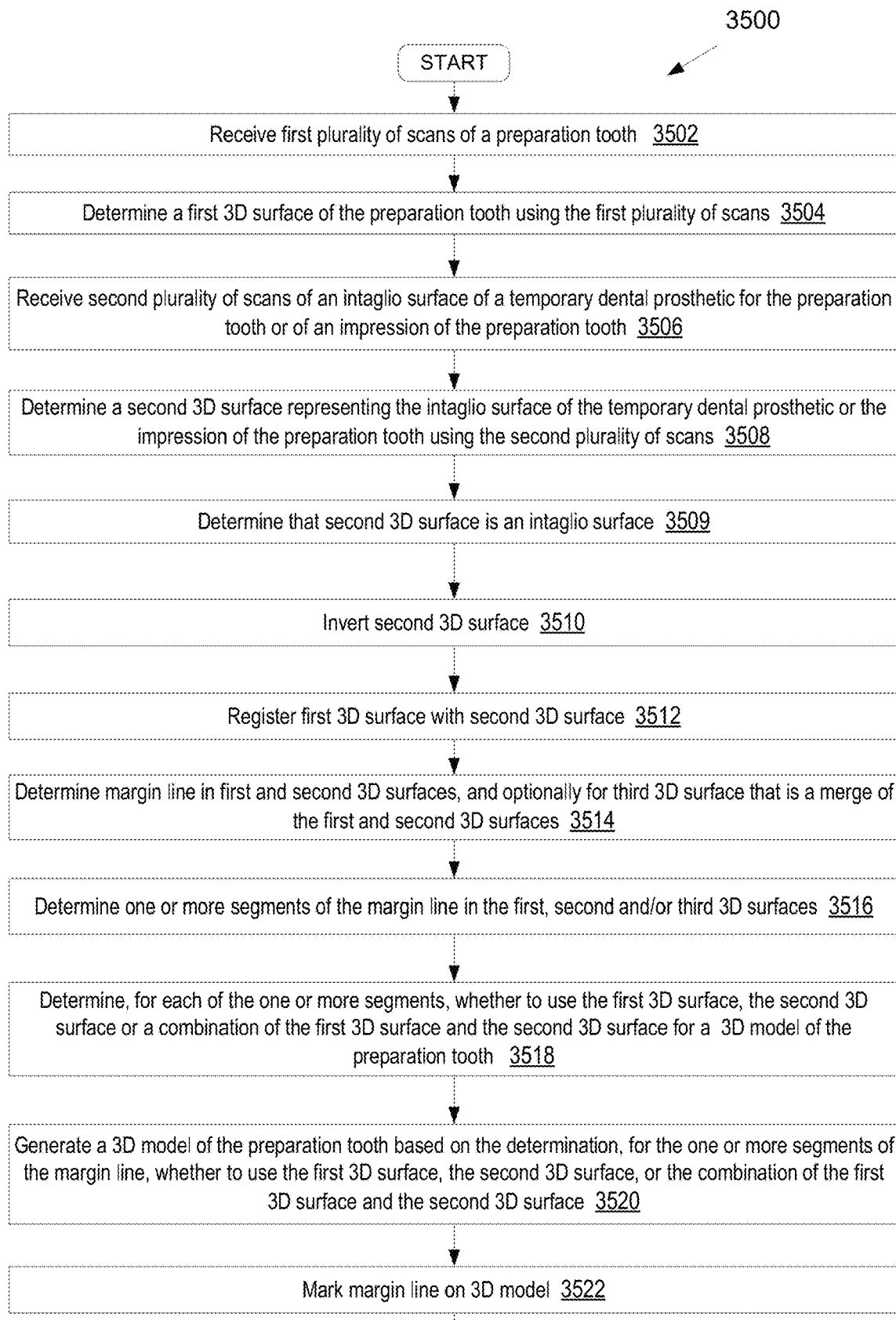
FIG. 35 is a flow chart illustrating an embodiment for a method of determining a 3D model of a dental prosthesis using a scan of a dental site that will receive the dental prosthesis and a scan of an intaglio surface of impression of the dental site, or a preexisting dental prosthesis.

FIG. 35 is a flow chart illustrating an embodiment for a method 3500 of determining a 3D model of a dental prosthesis using a scan of a dental site that will receive the dental prosthesis and a scan of an intaglio surface of an impression of the dental site, or a preexisting dental prosthesis. At block 3502, processing logic receives a first plurality of scans (e.g., intraoral scans) of a preparation tooth. At block 3504, processing logic determines a first 3D surface of the preparation tooth using the first plurality of scans (e.g., by stitching together the first plurality of scans).

At block 3506, processing logic receives a second plurality of scans of an intaglio surface of a temporary dental prosthetic (e.g., a temporary crown) for the preparation tooth or of an impression of the preparation tooth. The impression may include an elastomeric impression material that was placed over the preparation tooth and then hardened while in place. At block 3508, processing logic determines a second 3D surface representing the intaglio surface of the temporary dental prosthetic or the impression of the preparation tooth using the second plurality of scans.

At block 3509, processing logic determines that the second 3D surface is an intaglio surface. Intaglio surfaces may have a distinct geometry that is distinguishable from a geometry of dental sites in a patient's mouth. For example, intaglio surfaces may have a generally concave surface (e.g., where on average the intaglio surface is concave), and surfaces of teeth (including preparation teeth) and restorative objects may have a generally convex surface (e.g., where on average the surface of the tooth/restorative object is convex). In one embodiment, the second 3D surface or one or more projections of the second 3D surface are input into a trained ML model, which outputs a classification indicating that the second 3D surface is an intaglio surface. Similarly, the first 3D surface or projections of the first 3D surface may be input into the ML model, which may output a classification that the first 3D surface is not an intaglio surface.

At block 3510, processing logic may invert the intaglio surface. The inverted intaglio surface should approximately match the first 3D surface.

At block 3512, processing logic registers the first 3D surface with the second 3D surface. Such registration may be performed using any of the registration techniques discussed herein and/or other registration techniques. The registration may be performed to determine overlapping regions between the first 3D surface and the second 3D surface. In one embodiment, processing logic knows to attempt registration between the first 3D surface and the second 3D surface based on user input and/or some clues that indicate that the first 3D surface and the second 3D surface are associated with the same preparation tooth.

In one embodiment, processing logic knows which patient is associated with the first 3D surface and the second 3D surface, but does not have information on which of the patient's teeth is represented by the second 3D surface. Accordingly, processing logic may compare the inverted second 3D surface to 3D surfaces of multiple preparations of the patient until a match is found. Once a match is found, processing logic may determine a specific tooth associated with the second 3D surface.

In one embodiment, processing logic does not know which patient is associated with the second 3D surface, but does know what patient is associated with the first 3D surface. Processing logic may compare the inverted second 3D surface to 3D surfaces of preparations of multiple patients until a match is found between the second 3D surface and the first 3D surface. Once the match is found, processing logic may determine a patient associated with the second 3D surface and optionally a tooth number associated with the second 3D surface.

At block 3514, processing logic determines a margin line in the first and second 3D surfaces. Additionally, processing logic may generate a third 3D surface by merging together data from the first 3D surface and the second 3D surface. Processing logic may then determine a margin line in the third 3D surface. In one embodiment, the margin line for the first 3D surface is determined by inputting the first 3D surface or one or more projections of the first 3D surface into a trained ML model, which outputs pixel-level or point-level classification of one or more dental classes for points on the first 3D surface, one of which is a margin line dental class. Similarly, the margin line for the second 3D surface may be determined by inputting the inverted second 3D surface or one or more projections of the second 3D surface into the trained ML model, which outputs pixel-level or point-level classification of one or more dental classes for points on the second 3D surface, one of which is a margin line dental class. Alternatively, the margin line of the non-inverted second 3D surface may be determined by inputting the second 3D surface or one or more projections of the second 3D surface onto one or more planes into a trained ML model. The ML model may have been trained on scans of intaglio surfaces of dental prosthetics and/or elastomeric impressions. Additionally, training data for training the ML model may include inversions of scans of preparation teeth. The margin line for the third 3D surface may be determined by inputting the third 3D surface or one or more projections of the third 3D surface into the trained ML model, which outputs pixel-level or point-level classification of one or more dental classes for points on the third 3D surface, one of which is a margin line dental class. In one embodiment, processing logic applies one or more operations of method 1700 to determine the margin line.

In one embodiment, processing logic generates appropriate data inputs from the first, second and/or third 3D models (e.g., one or more images or height maps of the 3D model). These inputs may include any information produced during scanning that is useful for margin line detection. Inputs may include image data, such as 2D height maps that provide depth values at each pixel location, and/or color images that are actual or estimated colors for a given 2D model projection. 3D inputs may also be used and include Cartesian location and connectivity between vertices (i.e. mesh). Each image may be a 2D or 3D image generated by projecting a portion of the 3D model that represents a particular tooth onto a 2D surface. Different images may be generated by projecting the 3D model onto different 2D surfaces. In one embodiment, one or more generated images may include a height map that provides a depth value for each pixel of the image. Alternatively, or additionally, intraoral images that were used to generate the 3D model may be used. The generated images and/or the received intraoral images may be processed by a machine learning model that has been trained to identify margin lines on preparation teeth. The machine learning model may output a probability map that indicates, for each pixel of the image or 3D data input into the machine learning model, a probability that the pixel or surface represents a margin line. In the case of images, the probability map may then be projected back onto the 3D model to assign probability values to points on the 3D model. A cost function may then be applied to find the margin line using the probability values assigned to the points on the 3D model. Other techniques may also be used to compute the margin line based on the assigned probability values.

At block 3516, processing logic may determine one or more segments of the margin line in each of the first 3D surface, the second 3D surface and/or the third 3D surface. A segment may be a contiguous portion of the margin line. At block 3518, processing logic determines, for each of the one or more segments, whether to use the first 3D surface, the second 3D surface, or a combination of the first 3D surface and the second 3D surface (e.g., the third 3D surface). In one embodiment, the operations of block 3516 and 3518 are performed together, and the segments are determined as a result of operations performed at block 3518.

In one embodiment, processing logic determines, for each segment of the margin line in the first 3D surface and for each segment of the margin line in the second 3D surface, one or more margin line quality scores. Processing logic may also determine margin line quality scores for each segment of the third 3D surface. Each margin line quality score may be based on the cost value for the margin line (or a segment of the margin line) as computed using the cost function. In one embodiment, a margin line quality score is determined for the entirety of the margin line. In one embodiment, multiple additional margin line quality scores are computed, where each margin line quality score is for a particular segment of the margin line.

The selected segments may be those segments that result in a lowest combined cost value. For example, a first segment from the first 3D surface, a second segment from the second 3D surface and a third segment from the third 3D surface may combine to result in a margin line with an optimal cost function value, and so may be selected.

Figure 38:
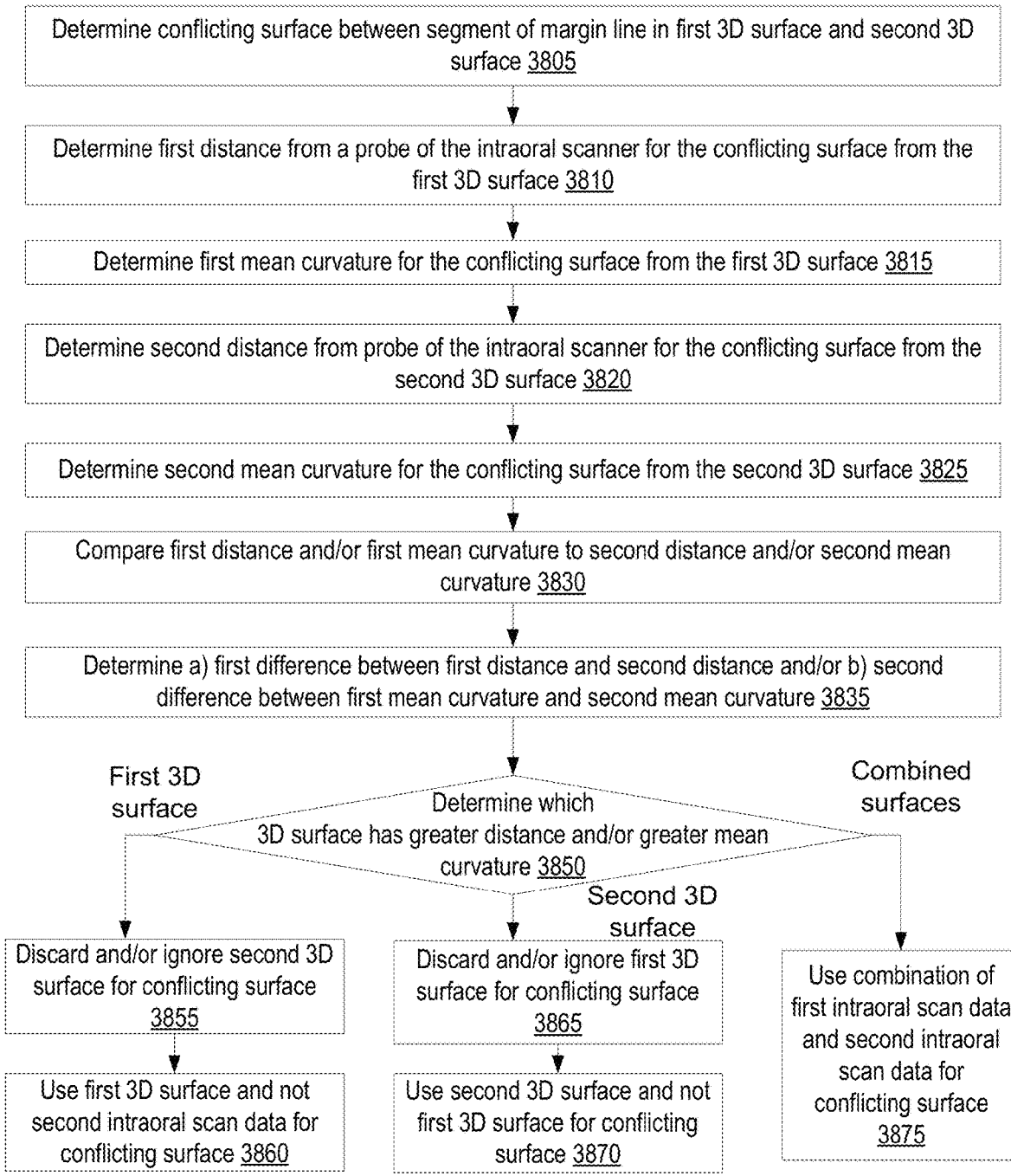
FIG. 38 is a flow chart illustrating an embodiment for a method of determining which 3D surfaces to use to generate segments of a margin line in a 3D model of a preparation tooth.

In one embodiment, processing logic determines, for each segment of the margin line, which 3D surface to use based on depths of points on those 3D surfaces and/or curvatures of the 3D surfaces at those points. FIG. 38 sets forth one method for using depth and/or curvature to select which surfaces to use for segments of a margin line.

At block 3520, processing logic generates a 3D model of the preparation tooth based on the determination, for the one or more segments of the margin line, whether to use the first 3D surface, the second 3D surface, or the combination of the first 3D surface and the second 3D surface. At block 3522, processing logic may mark the margin line in the 3D model.

In embodiments, processing logic may combine the use of machine learning (e.g., as set forth above and with reference to FIG. 37) and one or more rules that take into account distance and/or curvature (e.g., as set forth with reference to FIG. 38) to select which 3D surfaces to use for segments of the margin line.

Figure 36:
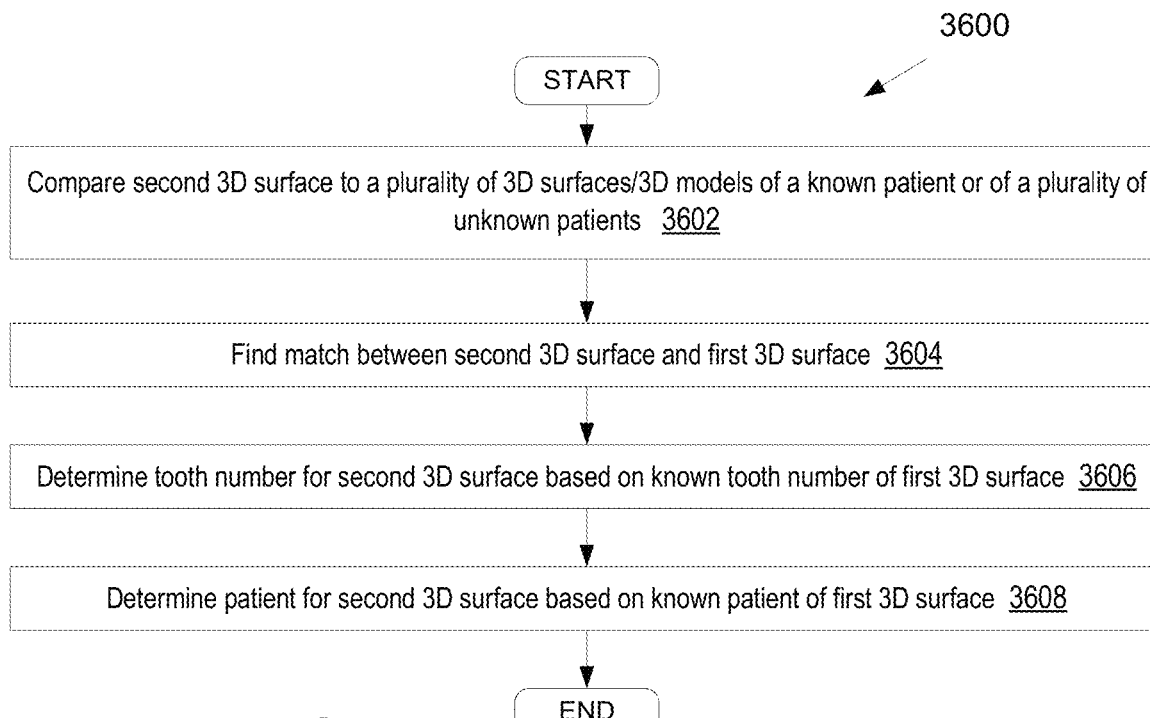
FIG. 36 is a flow chart illustrating an embodiment for a method of automatically determining a 3D surface of a preparation tooth that registers to a 3D surface of an intaglio surface of a dental site.

FIG. 36 is a flow chart illustrating an embodiment for a method 3600 of automatically determining a 3D surface of a preparation tooth that registers to a 3D surface of an intaglio surface of a dental site. At block 3600, processing logic compares a second 3D surface of an intaglio surface of a dental prosthetic or an impression of a preparation tooth to a plurality of 3D models of a single patient (if the patient associated with the second 3D surface is known) or to 3D models of a plurality of patients (if the patient associated with the second 3D surface is not known). At block 3604, processing logic finds a match between the second 3D surface and a first 3D surface in a first 3D model based on the searching. At block 3606, processing logic may determine a tooth number for the second 3D surface based on a known tooth number of the first 3D surface to which the second 3D surface is a match. At block 3608, processing logic may determine a patient associated with the second 3D surface based on the patient associated with the first 3D surface.

Figure 37:
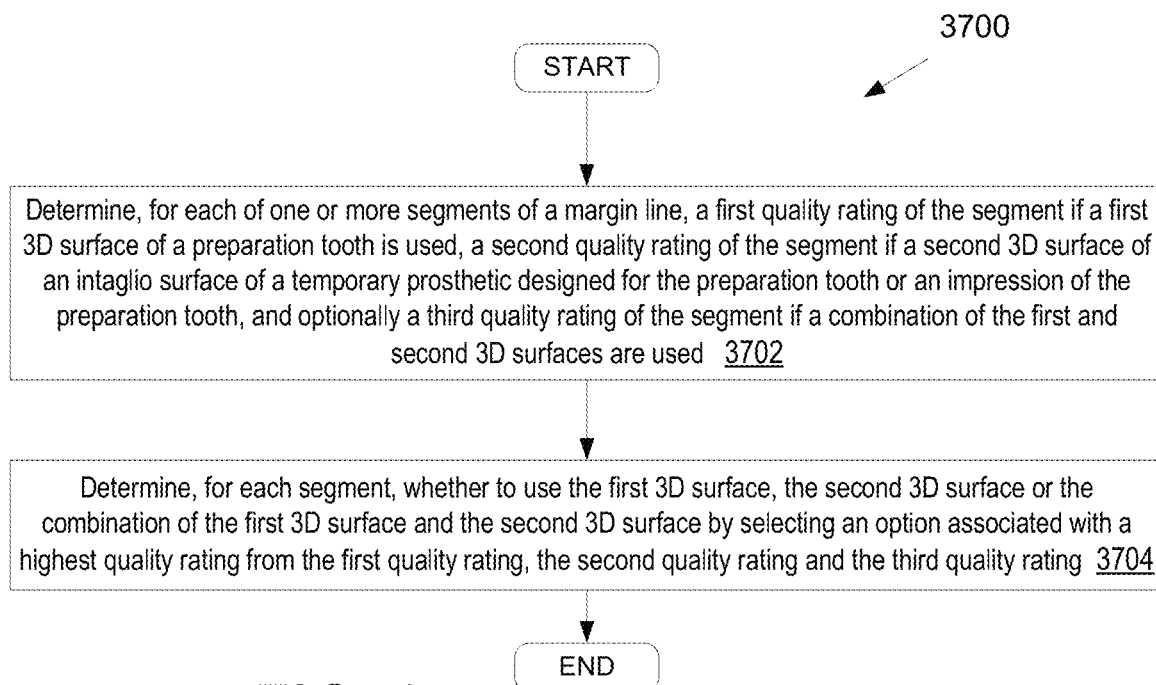
FIG. 37 is a flow chart illustrating an embodiment for a method of determining which 3D surfaces to use to generate segments of a margin line in a 3D model of a preparation tooth.

FIG. 37 is a flow chart illustrating an embodiment for a method 3700 of determining which 3D surfaces to use to generate segments of a margin line in a 3D model of a preparation tooth. At block 3702, processing logic determines, for each of one or more segments of a margin line, a first quality rating of the segment if a first 3D surface of the preparation tooth is used, a second quality rating of the segment if a second 3D surface of an intaglio surface of a temporary prosthetic designed for the preparation tooth or an impression of the preparation tooth is used, and optionally a third quality rating of the segment if a combination of the first 3D surface and the second 3D surface is used. The selection may be made using one or more machine learning model and a cost function as described above. A different cost value may be associated with each of the first option (using first 3D surface for segment), the second option (using second 3D surface for segment) and the third option (using combination of first and second 3D surfaces for segment), where each cost value represents a quality rating. The option that results in a lowest combined value of the cost function, when including the costs of all segments of the margin line, may be selected. At block 3704, processing logic determines, for each segment of the margin line, whether to use the first 3D surface, the second 3D surface or the combination of the first 3D surface and the second 3D surface by selecting an option associated with a highest quality rating (e.g., lowest cost function value) from the first quality rating, the second quality rating and the third quality rating.

FIG. 38 is a flow chart illustrating an embodiment for a method 3800 of determining which 3D surfaces to use to generate segments of a margin line in a 3D model of a preparation tooth. At block 3805 of method 3800, processing logic determines a conflicting surface for a pair of 3D surfaces, where a first one of the 3D surfaces was generated from scanning a preparation tooth and a second one of the 3D surfaces was generated from scanning an intaglio surface of a dental prosthetic (e.g., a temporary crown) for the preparation tooth or an elastomeric impression of the preparation tooth. At block 3810, processing logic determines a first distance from a probe of an intraoral scanner (also referred to as a first depth and/or first height) for the conflicting surface for the first 3D surface. The first depth may be a combined depth value (e.g., an average depth or median depth) based on the depths of some or all pixels of the first 3D surface or a projection of the 3D surface onto a plane. At block 3815, processing logic determines a first mean curvature (or a first Gaussian curvature) for the conflicting surface for the first 3D surface.

At block 3820, processing logic determines a second distance from the probe of the intraoral scanner (also referred to as a second depth and/or second height) for the conflicting surface for the second 3D surface. The second depth may be a combined depth value (e.g., an average depth or media depth) based on the depths of some or all pixels of the second 3D surface or a projection of the second 3D surface onto the same plane that the first 3D surface may have been projected onto. At block 3825, processing logic determines a second mean curvature (or a second Gaussian curvature) for the conflicting surface for the second 3D surface.

At block 3830, processing logic compares the first distance and/or the first mean curvature (or first Gaussian curvature) to the second distance and/or the second mean curvature (or second Gaussian curvature). At block 3835, processing logic determines a) a first difference between the first distance and the second distance and/or b) a second difference between the first mean curvature (or second Gaussian curvature) and the second mean curvature (or second Gaussian curvature).

At block 3850, processing logic determines one or more of the following: a) whether the first difference is greater than a first difference threshold, or b) whether the second difference is greater than a second difference threshold. If the first difference is less than the first difference threshold and/or the second difference is less than the second difference threshold, then the method may proceed to block 3875.

At block 3875, processing logic uses a combination of the first 3D surface and the second 3D surface for the conflicting surface. This may include, for example, averaging the first 3D surface with the second 3D surface for the conflicting surface. The first and second 3D surfaces may be averaged with a weighted or non-weighted average. For example, the 3D surface with the greater distance measurement (e.g., greater height measurement or lesser depth measurement) may be assigned a higher weight than the 3D Surface with the lesser distance measurement (e.g., lesser height measurement or greater depth measurement).

At block 3850, processing logic may determine which of the 3D surfaces has a greater distance and/or a greater mean curvature (or greater Gaussian curvature) for the conflicting surface. If the first 3D surface has a greater distance and/or a greater mean curvature than the second 3D surface for the conflicting surface, then the method continues to block 3855. If the second 3D surface has a greater distance and/or a greater mean curvature than the first 3D surface for the conflicting surface, then the method continues to block 3865.

At block 3855, processing logic discards and/or ignores the second 3D surface data for the conflicting surface. At block 3860, processing logic uses the first 3D surface data and not the second 3D surface data for the conflicting surface when generating a virtual 3D model of the preparation tooth.

At block 3865, processing logic discards and/or ignores the first 3D surface data for the conflicting surface. At block 3870, processing logic uses the second 3D surface data and not the first 3D surface data for the conflicting surface when generating the 3D surface for the virtual 3D model of the preparation tooth.

Figure 39:
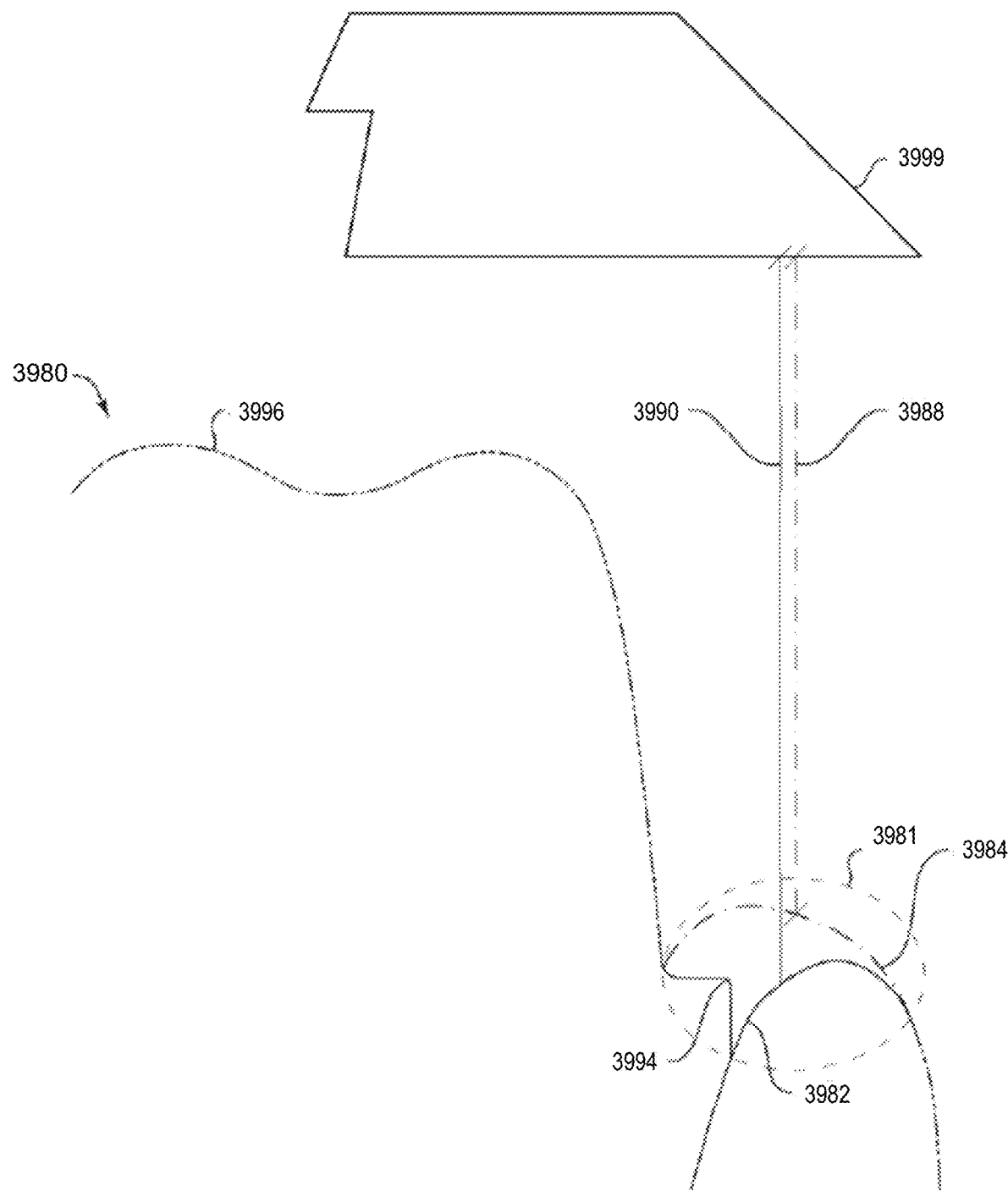
FIG. 39 illustrates selection of points from two different 3D surfaces to generate a 3D model of a preparation tooth with a clear margin line.

FIG. 39 illustrates selection of points from two different 3D surfaces to generate a 3D model of a preparation tooth with a clear margin line. FIG. 39 shows resolution of conflicting scan data of a dental site that includes a preparation tooth and surrounding gingiva, in accordance with an embodiment. In FIG. 39, a first 3D surface is generated of a preparation tooth, and a second 3D surface is generated of an intaglio surface of a dental prosthetic for the preparation tooth or of an impression of the preparation tooth. The second 3D surface is inverted, and then registered with the first 3D surface 3981. The 3D surface of the intaglio surface of the dental prosthetic or impression includes a representation of a margin line 3994 that was exposed. The first 3D surface was generated from scans that were taken while the margin line 3994 was covered by gingiva. The second 3D surface shows surfaces 3982, 3996, which includes exposed margin line 3994. The first 3D surface includes surfaces 3996, 3984, which includes gingiva that overlies the margin line. The margin line is therefore not shown in the second 3D surface. A conflicting surface 3981 may be determined based on comparison between the two 3D surfaces.

For the second 3D surface, a first distance 3990 from a probe of an intraoral scanner is determined for the conflicting surface 3981. The first distance may be an average distance from the probe for surface 3982 in one embodiment. However, a first distance 3990 for a particular point on surface 3982 is illustrated for the purposes of clarity. For the first 3D surface, a second distance 3988 from the probe is determined for surface 3984. The second distance may be an average distance of the first 3D surface for the surface 3984. However, a second distance 3988 for a particular point is illustrated for the purposes of clarity. As described with reference to FIG. 38, the first and second distances may be compared, and a difference between these distances may be computed. Processing logic may determine that the first difference is greater than a difference threshold, and that the first distance 3990 is greater than the second distance 3988. The first 3D surface may then be used to generate a portion of a 3D model that includes the margin line.

A first mean curvature may also be computed for the first surface 3982 of the conflicting surface 3981 and a second mean curvature may be computed for the second surface 3984 of the conflicting surface 3981. As shown, the first surface 3982 would have a greater mean curvature than the second surface 3984. The first and second mean curvatures may be compared, and the result of the comparison may be used as an additional data point to determine which of the 3D surfaces should be used to depict the conflicting surface, as described with reference to FIG. 38.

Figure 40A:
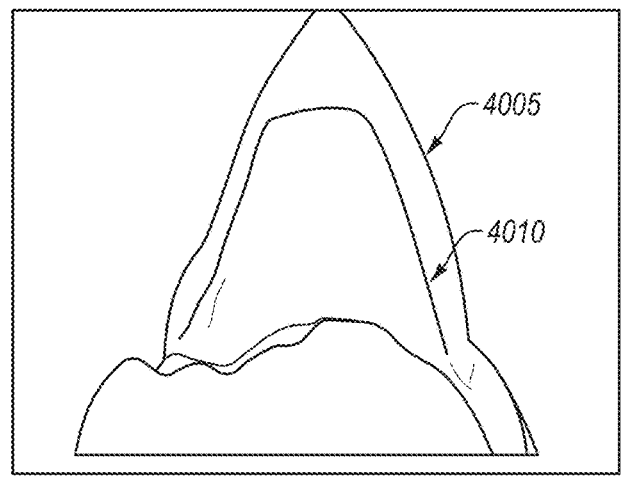
FIG. 40A illustrates a crown disposed over a preparation tooth.

FIG. 40A illustrates a crown 4005 disposed over a preparation tooth 4010.

Figure 40B:
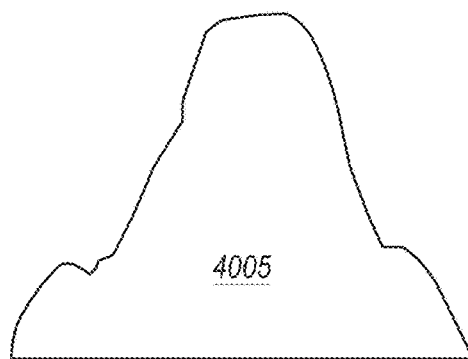
FIG. 40B illustrates side view of a 3D surface of the preparation tooth of FIG. 40A.

FIG. 40B illustrates side view of a 3D surface 4015 of the preparation tooth 4010 generated by performing intraoral scanning of the preparation tooth.

Figure 40C:
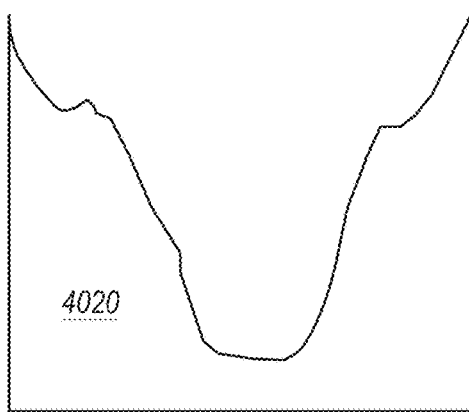
FIG. 40C illustrates side view of a 3D surface of an intaglio surface of the crown of FIG. 40A.

FIG. 40C illustrates side view of a 3D surface of an intaglio surface of the crown 4005 generated by performing intraoral scanning of the intaglio surface of the crown 4005.

As shown, the 3D surface 4015 of the preparation tooth 4010 closely matches the 3D surface 4020 of the intaglio surface of the crown 4005. Accordingly, the 3D surface 4020 of the intaglio surface of the crown 4005 may be inverted and then registered to the 3D surface 4025 of the preparation tooth 4010. Once the two surfaces are registered, one or more of the aforementioned techniques for determining a margin line and/or generating a 3D model may be performed.

Figure 41:
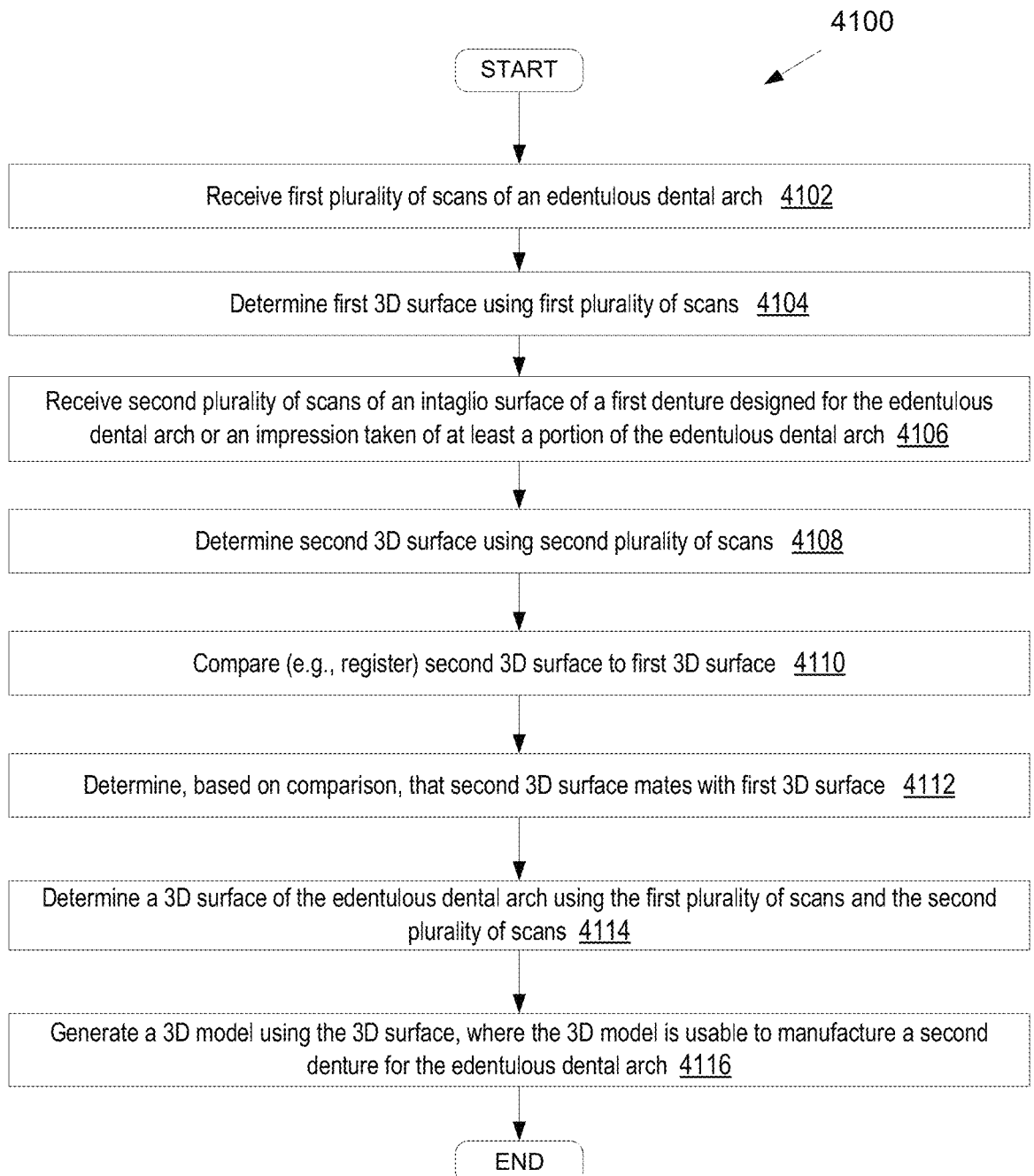
FIG. 41 is a flow chart illustrating an embodiment for a method of generating a 3D model of an edentulous dental arch for the manufacture of a denture.

FIG. 41 is a flow chart illustrating an embodiment for a method 4100 of generating a 3D model of an edentulous dental arch for the manufacture of a denture. At block 4102 of method 4100, processing logic receives a first plurality of scans of an edentulous dental arch. These scans may be of the entire edentulous dental arch or of just a portion of the edentulous dental arch. In embodiments, a doctor may instruct the patient to move their jaw in various positions during the scan and/or may press on the gingiva in one or more manners during the scanning to capture the muccal-dynamic borders of the edentulous dental arch. At block 4104, processing logic determines a first 3D surface using the first plurality of scans of the edentulous dental arch. The scans may include scans of an upper palate of the patient to improve registration and stitching between scans.

At block 4106, processing logic receives a second plurality of scans of an intaglio surface of a first denture for the edentulous dental arch or of an impression taken of at least a portion of the edentulous dental arch. The impression may be of all of the dental arch or of only a region of the dental arch. In embodiments, a doctor may not need to generate an impression of the entire dental arch due to use of intraoral scans of the edentulous dental arch. In embodiments, a doctor may have instructed the patient to move their jaw in various positions during forming of the elastomeric impression to capture the muccal-dynamic borders of the edentulous dental arch. At block 4108, processing logic determines a second 3D surface using the second plurality of scans of the intaglio surface of the first denture and/or of the intaglio surface of the elastomeric impression.

At block 4110, processing logic compares the second 3D surface to the first 3D surface. This may include inverting the second 3D surface and registering the inverted second 3D surface to the first 3D surface. At block 4112, processing logic determines, based on the comparison, that the second 3D surface mates with the first 3D surface (e.g., that the inverted second 3D surface registers with the first 3D surface).

At block 4114, processing logic determines a 3D surface of the edentulous dental arch using the first plurality of scans and the second plurality of scans. This may include merging the first 3D surface of the dental arch to the inverted second 3D surface of the intaglio surface of the first denture and/or impression. In one embodiment, points on the first 3D surface are averaged with points on the second 3D surface. In one embodiment, a weighted average is performed to merge the points on the first 3D surface to the points on the second 3D surface. In one embodiment, the second 3D surface is weighted more heavily than the first 3D surface. In one embodiment, the first 3D surface is weighted more heavily than the second 3D surface. Additionally, the first 3D surface may be weighted more heavily for some regions and the second 3D surface may be weighted more heavily for other regions.

At block 4116, processing logic generates a 3D model using the 3D surface generated at block 4114. The 3D model is usable to manufacture a second denture for the edentulous dental arch.

Figure 42:
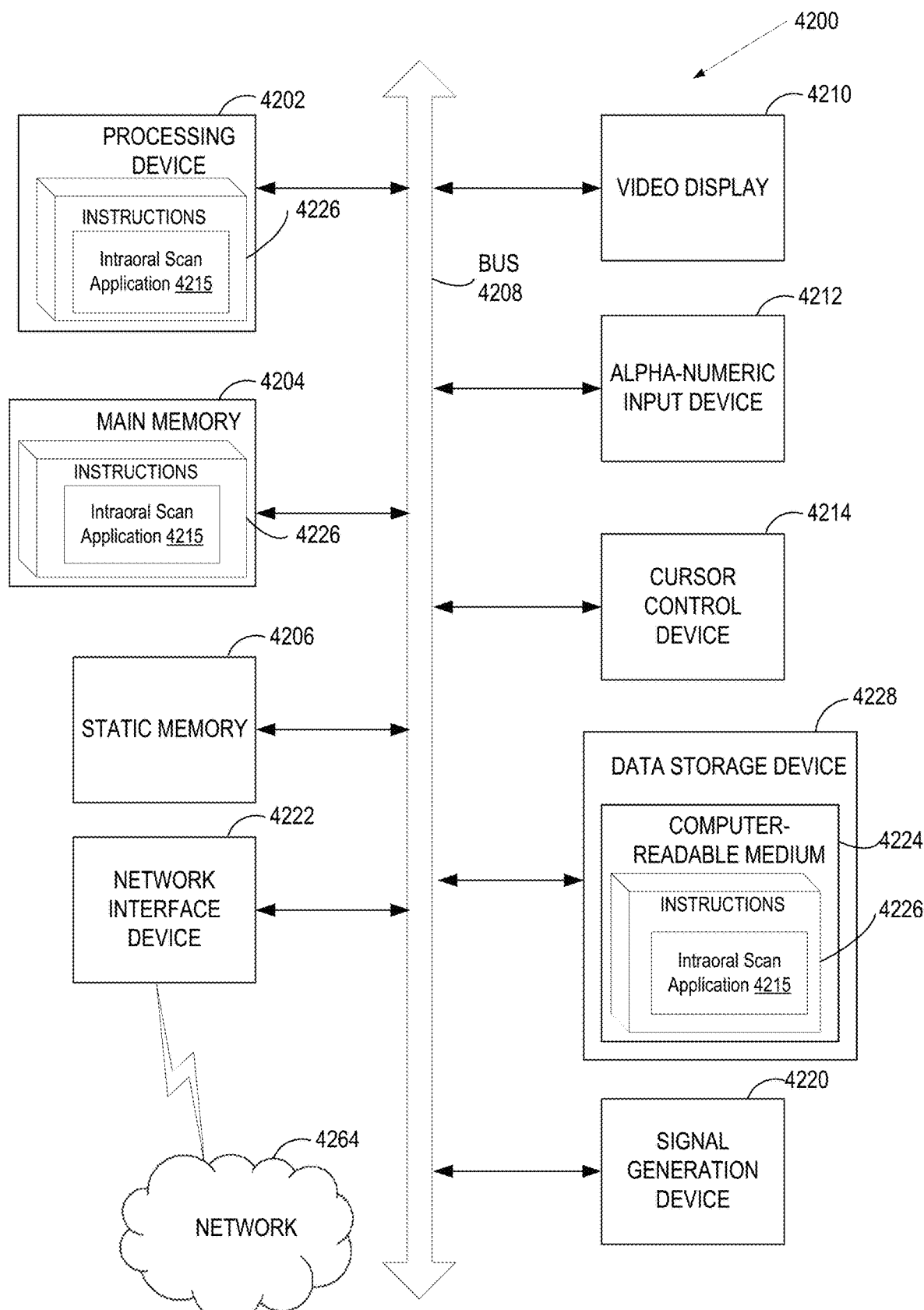
FIG. 42 illustrates a block diagram of an example computing device, in accordance with embodiments of the present disclosure.

FIG. 42 illustrates a diagrammatic representation of a machine in the example form of a computing device 4200 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The computing device 4200 may correspond, for example, to computing device 105 and/or computing device 106 of FIG. 1. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 4200 includes a processing device 4202, a main memory 4204 (e.g., read-only memory (ROM), flash memory, dynamic random access memory (DRAM) such as synchronous DRAM (SDRAM), etc.), a static memory 4206 (e.g., flash memory, static random access memory (SRAM), etc.), and a secondary memory (e.g., a data storage device 4228), which communicate with each other via a bus 4208.

Processing device 4202 represents one or more general-purpose processors such as a microprocessor, central processing unit, or the like. More particularly, the processing device 4202 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 4202 may also be one or more special-purpose processing devices such as an application specific integrated circuit (ASIC), a field programmable gate array (FPGA), a digital signal processor (DSP), network processor, or the like. Processing device 4202 is configured to execute the processing logic (instructions 4226) for performing operations and steps discussed herein.

The computing device 4200 may further include a network interface device 4222 for communicating with a network 4264. The computing device 4200 also may include a video display unit 4210 (e.g., a liquid crystal display (LCD) or a cathode ray tube (CRT)), an alphanumeric input device 4212 (e.g., a keyboard), a cursor control device 4214 (e.g., a mouse), and a signal generation device 4220 (e.g., a speaker).

The data storage device 4228 may include a machine-readable storage medium (or more specifically a non-transitory computer-readable storage medium) 4224 on which is stored one or more sets of instructions 4226 embodying any one or more of the methodologies or functions described herein, such as instructions for intraoral scan application 4215, which may correspond to intraoral scan application 115 of FIG. 1. A non-transitory storage medium refers to a storage medium other than a carrier wave. The instructions 4226 may also reside, completely or at least partially, within the main memory 4204 and/or within the processing device 4202 during execution thereof by the computer device 4200, the main memory 4204 and the processing device 4202 also constituting computer-readable storage media.

The computer-readable storage medium 4224 may also be used to store dental modeling logic 4250, which may include one or more machine learning modules, and which may perform the operations described herein above. The computer readable storage medium 4224 may also store a software library containing methods for the intraoral scan application 115. While the computer-readable storage medium 4224 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A system comprising:
   an intraoral scanner to generate a first plurality of intraoral scans of a dental arch and a second plurality of intraoral scans of the dental arch; and
   a computing device connected to the intraoral scanner via a wired or wireless connection, the computing device to: a
   receive the first plurality of intraoral scans of the dental arch;
   automatically determine, based on processing of the first plurality of intraoral scans using a trained machine learning model that has been trained to identify restorative dental objects, that the first plurality of intraoral scans depict a restorative dental object, wherein for each intraoral scan the trained machine learning model generates an output classifying the intraoral scan as containing a restorative dental object or as not containing a restorative dental object;
   receive the second plurality of intraoral scans of the dental arch;
   automatically determine, based on processing of the second plurality of intraoral scans, that the second plurality of intraoral scans fail to depict a restorative dental object; and
   generate a three-dimensional model of the dental arch having a first portion corresponding to the restorative dental object and a second portion that does not correspond to the restorative dental object, wherein the first portion is generated from the first plurality of intraoral scans at a first resolution in response to determining that the first plurality of intraoral scans depict the restorative dental object, and wherein the second portion is generated from the second plurality of intraoral scans at a second resolution in response to determining that the second plurality of intraoral scans fail to depict a restorative dental object, wherein the first resolution is greater than the second resolution.

2. The system of claim 1, wherein the three-dimensional model comprises a single variable resolution three-dimensional surface, wherein the first portion of the single variable resolution three-dimensional surface has the first resolution and the second portion of the single variable resolution three-dimensional surface has the second resolution.

3. The system of claim 1, wherein the computing device is to:
   receive the first plurality of intraoral scans and the second plurality of intraoral scans based on an uninterrupted continuous scan of the dental arch, wherein no user input is received that indicates a transition from scanning of the dental arch to scanning of the restorative dental object or that indicates a transition from scanning of the restorative dental object to scanning of the dental arch.

4. The system of claim 1, wherein for each intraoral scan the trained machine learning model outputs a map comprising, for each pixel in the intraoral scan, an indication as to whether or not that pixel depicts a restorative dental object.

5. The system of claim 1, wherein the computing device is further to:
   determine a first region of the second portion that depicts a tooth to gum boundary or a tooth to tooth boundary;
   determine a second region of the second portion that fails to depict the tooth to gum boundary or the tooth to tooth boundary; and
   update the three-dimensional model to cause the second portion of the second region to have a third resolution that is lower than the second resolution.

6. The system of claim 1, wherein the computing device is further to:
   automatically determine, based on processing of the first plurality of intraoral scans, whether the first plurality of intraoral scans depict an upper dental arch, a lower dental arch or a bite; and
   automatically determine, based on processing of the second plurality of intraoral scans, whether the second plurality of intraoral scans depict the upper dental arch, the lower dental arch, or the bite.

7. The system of claim 1, wherein the computing device is further to:
   automatically determine, based on processing of the first plurality of intraoral scans, a first scanning role associated with the first plurality of intraoral scans, wherein the first scanning role is a first one of an upper dental arch role, a lower dental arch role or a bite role.

8. The system of claim 1, wherein the computing device is further to:
   automatically determine, based on processing of the first plurality of intraoral scans, that the first plurality of intraoral scans depict the dental arch and an identity of the dental arch.

9. The system of claim 8, wherein the computing device is further to:
   receive a third plurality of intraoral scans;
   automatically determine, based on processing of the third plurality of intraoral scans, that the third plurality of intraoral scans depict a second dental arch and an identity of the second dental arch; and
   generate a second three-dimensional model of the second dental arch using the third plurality of intraoral scans.

10. The system of claim 1, wherein the computing device is further to:
classify the restorative dental object as a preparation, a scan body or a dental implant.

11. The system of claim 1, wherein the computing device is further to:
process the first plurality of intraoral scans and the second plurality of intraoral scans during an intraoral scanning session as the first plurality of intraoral scans and the second plurality of intraoral scans are received and while additional intraoral scans are being generated.

12. The system of claim 1, wherein the computing device is further to:
determine, from an intraoral scan of the first plurality of intraoral scans or of the second plurality of intraoral scans, an area in the intraoral scan that represents a dirty region of an optical surface associated with the intraoral scanner.

13. The system of claim 12, wherein the computing device is further to:
determine whether the area that represents a dirty region of the optical surface satisfies one or more criteria; and
responsive to determining that the area that represents a dirty region of the optical surface satisfies the one or more criteria, perform the following:
determine that the optical surface is obscured; and
generate a notification indicating that the optical surface is obscured.

14. The system of claim 1, wherein the restorative dental object comprises a preparation tooth, and wherein the computing device is further to:
receive a third plurality of intraoral scans of an intaglio surface of a temporary dental prosthetic designed for the preparation tooth or of an impression of the preparation tooth;
determine a three-dimensional surface representing the intaglio surface of the temporary dental prosthetic or of the impression of the preparation tooth using the third plurality of intraoral scans; and
automatically make a determination, for one or more segments of a margin line of the preparation tooth, whether to use the first portion of the three-dimensional model of the dental arch, the three-dimensional surface, or a combination of the first portion of the three-dimensional model of the dental arch and the three-dimensional surface for a three-dimensional model of the preparation tooth.

15. The system of claim 1, wherein the intraoral scanner is further to generate a plurality of two-dimensional images, and wherein the computing device is further to:
receive the plurality of two-dimensional images; and
determine whether a two-dimensional image of the plurality of two-dimensional images depicts an interior of a mouth.

16. The system of claim 15, wherein the computing device is further to:
cause the intraoral scanner to begin generating intraoral scans responsive to determining that the two-dimensional image depicts an interior of a mouth.

17. The system of claim 15, wherein the computing device is further to:
cause the intraoral scanner to stop generating intraoral scans responsive to determining that the two-dimensional image does not depict an interior of a mouth.

18. The system of claim 1, wherein the computing device is further to:
determine, for the restorative dental object, an amount of imaged gum tissue surrounding the restorative dental object;
determine that the amount of imaged gum tissue surrounding the restorative dental object is less than a threshold; and
output a notice to generate one or more additional intraoral scans of the restorative dental object.

19. The system of claim 1, wherein the computing device is further to:
compare the three-dimensional model of the dental arch to a plurality of previously generated three-dimensional models of one or more patients;
find a match between the three-dimensional model of the dental arch and a previously generated three-dimensional model of the plurality of previously generated three-dimensional models; and
determine a patient based on the match.

20. A non-transitory computer readable medium comprising instructions that, when executed by a processing device, cause the processing device to perform operations comprising:
receiving a plurality of intraoral scans of a dental arch;
determining, from the plurality of intraoral scans, a first set of intraoral scans that depict a restorative dental object and a second set of intraoral scans that fail to depict any restorative dental object using a trained machine learning model that has been trained to identify restorative dental objects, wherein for each intraoral scan the trained machine learning model generates an output classifying the intraoral scan as containing a restorative dental object or as not containing a restorative dental object; and
generating a multi-resolution three-dimensional model of the dental arch, wherein a first portion of the multi-resolution three-dimensional model is generated from the first set of intraoral scans, has a first resolution and represents the restorative dental object, and wherein a second portion of the multi-resolution three-dimensional model is generated from the second set of intraoral scans, has a second resolution and represents a remainder of the dental arch, wherein the first resolution is greater than the second resolution.

21. The non-transitory computer readable medium of claim 20, wherein the instructions further cause the processing device to perform operations comprising:
receiving the plurality of intraoral scans based on an uninterrupted continuous scan of the dental arch, wherein no user input is received that indicates a transition from scanning of the dental arch to scanning of the restorative dental object or that indicates a transition from scanning of the restorative dental object to scanning of the dental arch.

22. The non-transitory computer readable medium of claim 21, wherein for each intraoral scan the trained machine learning model outputs a map comprising, for each pixel in the intraoral scan, an indication as to whether or not that pixel depicts a restorative dental object.

* * * * *